United States Patent [19]
Unger et al.

[11] Patent Number: 6,123,923
[45] Date of Patent: Sep. 26, 2000

[54] OPTOACOUSTIC CONTRAST AGENTS AND METHODS FOR THEIR USE

[75] Inventors: Evan C. Unger; Yunqiu Wu, both of Tucson, Ariz.

[73] Assignee: Imarx Pharmaceutical Corp., Tucson, Ariz.

[21] Appl. No.: 08/993,165

[22] Filed: Dec. 18, 1997

[51] Int. Cl.$^7$ .......................... A61K 49/00; A61K 49/22
[52] U.S. Cl. .......................... 424/9.52; 424/9.6; 424/9.2; 424/9.3; 424/450; 424/9.1; 514/410
[58] Field of Search ........................... 424/9.1, 9.2, 9.3, 424/9.52, 450, 9.6; 514/410

[56] References Cited

U.S. PATENT DOCUMENTS

| | | |
|---|---|---|
| 3,015,128 | 1/1962 | Sommerville et al. ............... 18/2.6 |
| 3,291,843 | 12/1966 | Fritz et al. ....................... 260/614 |
| 3,293,114 | 12/1966 | Kenaga et al. .................... 162/168 |
| 3,401,475 | 9/1968 | Morehouse et al. ................. 40/306 |
| 3,479,811 | 11/1969 | Walters ............................. 57/153 |
| 3,488,714 | 1/1970 | Walters et al. .................... 161/161 |
| 3,532,500 | 10/1970 | Priest et al. ........................ 96/91 |
| 3,557,294 | 1/1971 | Dear et al. ........................ 424/342 |
| 3,594,326 | 7/1971 | Himmel et al. .................... 252/316 |
| 3,615,972 | 10/1971 | Morehouse et al. ................ 156/79 |
| 3,650,831 | 3/1972 | Jungermann et al. .............. 134/27 |
| 3,732,172 | 5/1973 | Herbig et al. ..................... 252/316 |
| 3,873,564 | 3/1975 | Schneider et al. ............... 270/309.6 |
| 3,945,956 | 3/1976 | Garner ........................... 270/2.5 B |
| 3,960,583 | 6/1976 | Netting et al. .................... 106/122 |
| 3,968,203 | 7/1976 | Spitzer et al. ....................... 424/47 |
| 4,027,007 | 5/1977 | Messina ............................. 424/46 |
| 4,089,801 | 5/1978 | Schneider ......................... 252/316 |
| 4,108,806 | 8/1978 | Cohrs et al. ........................ 521/54 |
| 4,138,383 | 2/1979 | Rembaum et al. ............... 270/29.7 H |
| 4,162,282 | 7/1979 | Fulwyler et al. ..................... 274/9 |
| 4,179,546 | 12/1979 | Garner et al. ...................... 521/56 |
| 4,192,859 | 3/1980 | Mackaness et al. ................ 424/5 |
| 4,224,179 | 9/1980 | Schneider ......................... 252/316 |
| 4,229,360 | 10/1980 | Schneider et al. ................. 270/403 |
| 4,265,251 | 5/1981 | Tickner ............................. 128/660 |
| 4,276,885 | 7/1981 | Tickner et al. ..................... 128/660 |
| 4,310,505 | 1/1982 | Baldeschwieler et al. ............. 424/1 |
| 4,310,506 | 1/1982 | Baldeschwieler et al. ............. 424/1 |
| 4,315,514 | 2/1982 | Drewes et al. .................... 128/653 |
| 4,331,654 | 5/1982 | Morris .............................. 424/38 |
| 4,342,826 | 8/1982 | Cole .................................. 435/7 |
| 4,344,929 | 8/1982 | Bonsen et al. ..................... 424/15 |
| 4,420,442 | 12/1983 | Sands ............................... 274/13 |
| 4,421,562 | 12/1983 | Sands et al. ...................... 106/75 |
| 4,427,330 | 1/1984 | Sears .............................. 270/403 |
| 4,427,649 | 1/1984 | Dingle et al. ...................... 424/38 |
| 4,428,924 | 1/1984 | Millington .......................... 424/4 |
| 4,442,843 | 4/1984 | Rasor et al. ...................... 128/660 |
| 4,466,442 | 8/1984 | Hilmann et al. ................... 128/653 |
| 4,530,360 | 7/1985 | Duarte ........................... 128/419 F |
| 4,533,254 | 8/1985 | Cook et al. ........................ 366/176 |
| 4,534,899 | 8/1985 | Sears .............................. 270/403 |
| 4,540,629 | 9/1985 | Sands et al. ...................... 428/402 |
| 4,544,545 | 10/1985 | Ryan et al. ........................ 424/1.1 |
| 4,549,892 | 10/1985 | Baker et al. ....................... 65/21.4 |
| 4,569,836 | 2/1986 | Gordon . | |
| 4,572,203 | 2/1986 | Feinstein ......................... 128/661 |
| 4,586,512 | 5/1986 | Do-huu et al. .................... 128/660 |
| 4,603,044 | 7/1986 | Geho et al. ......................... 424/9 |
| 4,615,879 | 10/1986 | Runge et al. ....................... 424/9 |
| 4,620,546 | 11/1986 | Aida et al. ........................ 128/660 |
| 4,646,756 | 3/1987 | Watmough et al. ................ 128/804 |
| 4,657,756 | 4/1987 | Rasor et al. ........................ 424/9 |
| 4,658,828 | 4/1987 | Dory .............................. 128/660 |
| 4,663,161 | 5/1987 | Mannino et al. ................... 424/89 |
| 4,675,310 | 6/1987 | Chapman et al. ................... 514/6 |
| 4,681,119 | 7/1987 | Rasor et al. ...................... 128/660 |
| 4,684,479 | 8/1987 | D'Arrigo .......................... 252/307 |
| 4,689,986 | 9/1987 | Carson et al. ....................... 73/19 |
| 4,693,999 | 9/1987 | Axelsson et al. .................. 514/174 |
| 4,718,433 | 1/1988 | Feinstein ......................... 128/660 |
| 4,728,575 | 3/1988 | Gamble et al. ................... 428/402.2 |
| 4,728,578 | 3/1988 | Higgins et al. .................... 428/462 |
| 4,731,239 | 3/1988 | Gordon .............................. 424/9 |
| 4,737,323 | 4/1988 | Martin et al. ...................... 274/4.3 |
| 4,774,958 | 10/1988 | Feinstein ........................ 128/660.01 |
| 4,775,522 | 10/1988 | Clark, Jr. ............................. 424/9 |
| 4,776,991 | 10/1988 | Farmer et al. ...................... 274/4.3 |
| 4,781,871 | 11/1988 | West, III et al. .................... 274/4.3 |
| 4,789,501 | 12/1988 | Day et al. ......................... 252/645 |
| 4,790,891 | 12/1988 | Halliday et al. ..................... 149/2 |
| 4,822,534 | 4/1989 | Lencki et al. ...................... 274/4.3 |
| 4,830,858 | 5/1989 | Payne et al. ...................... 424/450 |
| 4,834,964 | 5/1989 | Rosen .............................. 424/9 |
| 4,844,882 | 7/1989 | Widder et al. ...................... 424/9 |
| 4,863,717 | 9/1989 | Keana ............................... 424/9 |
| 4,865,836 | 9/1989 | Long, Jr. ............................ 424/5 |
| 4,877,561 | 10/1989 | Iga et al. .......................... 274/4.3 |
| 4,893,624 | 1/1990 | Lele ................................. 128/399 |
| 4,895,719 | 1/1990 | Radhakrishnan ................... 424/45 |
| 4,898,734 | 2/1990 | Mathiowitz et al. ................ 424/427 |
| 4,900,540 | 2/1990 | Ryan et al. ......................... 424/9 |
| 4,918,065 | 4/1990 | Stindl et al. ....................... 514/179 |
| 4,919,895 | 4/1990 | Heldebrant et al. ................ 422/129 |
| 4,921,706 | 5/1990 | Roberts et al. ................... 424/450 |
| 4,927,623 | 5/1990 | Long, Jr. ............................ 424/5 |

(List continued on next page.)

FOREIGN PATENT DOCUMENTS

| | | |
|---|---|---|
| 641363 | 3/1990 | Australia . |
| B-30351/89 | 3/1993 | Australia . |
| 2047969 | 2/1992 | Canada . |
| 0 052 575 | 5/1982 | European Pat. Off. . |
| 0 107 559 | 5/1984 | European Pat. Off. . |

(List continued on next page.)

OTHER PUBLICATIONS

Nakakjima S, et al 5th International Photodynamic Association Biennial Meeting ;2371:495–500, 1994.

Warren S, et al Proceedings of the International Conference on Lasers ; 15: 795–801, 1993.

(List continued on next page.)

*Primary Examiner*—Jose' G. Dees
*Assistant Examiner*—Shahnam Sharareh
*Attorney, Agent, or Firm*—Woodcock Washburn Kurtz Mackiewcz & Norris LLP

[57] ABSTRACT

The present invention generally relates to optoacoustic contrast agents and methods of diagnostic and therapeutic imaging using optoacoustic contrast agents.

54 Claims, 11 Drawing Sheets

U.S. PATENT DOCUMENTS

| | | | |
|---|---|---|---|
| 4,933,121 | 6/1990 | Law et al. | 264/4.3 |
| 4,938,947 | 7/1990 | Nicolau et al. | 424/1.1 |
| 4,957,656 | 9/1990 | Cerny et al. | 252/311 |
| 4,981,692 | 1/1991 | Popescu et al. | 424/422 |
| 4,984,573 | 1/1991 | Leunbach | 128/653 |
| 4,985,550 | 1/1991 | Charpiot et al. | 536/18.4 |
| 4,987,154 | 1/1991 | Long, Jr. | 514/772 |
| 4,993,415 | 2/1991 | Long | 128/653 A |
| 4,996,041 | 2/1991 | Arai et al. | 424/9 |
| 5,000,960 | 3/1991 | Wallach | 424/450 |
| 5,004,611 | 4/1991 | Leigh | 424/450 |
| 5,008,050 | 4/1991 | Cullis et al. | 274/4.3 |
| 5,008,109 | 4/1991 | Tin | 424/422 |
| 5,013,556 | 5/1991 | Woodle et al. | 424/450 |
| 5,019,370 | 5/1991 | Jay et al. | 424/4 |
| 5,045,304 | 9/1991 | Schneider et al. | 424/9 |
| 5,049,388 | 9/1991 | Knight et al. | 424/450 |
| 5,078,994 | 1/1992 | Nair et al. | 424/501 |
| 5,088,499 | 2/1992 | Unger | 128/662.2 |
| 5,107,842 | 4/1992 | Levene et al. | 128/662.02 |
| 5,114,703 | 5/1992 | Wolf et al. | 424/5 |
| 5,123,414 | 6/1992 | Unger | 128/654 |
| 5,135,000 | 8/1992 | Akselrod et al. | 128/662.02 |
| 5,137,928 | 8/1992 | Erbel et al. | 521/56 |
| 5,141,738 | 8/1992 | Rasor et al. | 424/2 |
| 5,147,631 | 9/1992 | Glajch et al. | 424/9 |
| 5,149,319 | 9/1992 | Unger | 604/22 |
| 5,162,519 | 11/1992 | Bonnett et al. | 540/145 |
| 5,171,755 | 12/1992 | Kaufman | 514/759 |
| 5,186,922 | 2/1993 | Shell et al. | 128/654 |
| 5,190,766 | 3/1993 | Ishihara | 424/489 |
| 5,190,982 | 3/1993 | Erbel et al. | 521/56 |
| 5,192,549 | 3/1993 | Barenolz et al. | 424/450 |
| 5,194,266 | 3/1993 | Abra et al. | 424/450 |
| 5,195,520 | 3/1993 | Schlief et al. | 128/660.02 |
| 5,196,183 | 3/1993 | Yudelson et al. | 424/9 |
| 5,196,348 | 3/1993 | Schweighardt et al. | 436/173 |
| 5,198,225 | 3/1993 | Meybeck et al. | 424/450 |
| 5,205,287 | 4/1993 | Erbel et al. | 128/632 |
| 5,205,290 | 4/1993 | Unger | 128/653.4 |
| 5,209,720 | 5/1993 | Unger | 604/22 |
| 5,213,804 | 5/1993 | Martin et al. | 424/450 |
| 5,214,036 | 5/1993 | Allison et al. | 514/185 |
| 5,215,680 | 6/1993 | D'Arrigo | 252/307 |
| 5,219,538 | 6/1993 | Henderson et al. | 428/402.2 |
| 5,228,446 | 7/1993 | Unger et al. | 128/662.02 |
| 5,230,882 | 7/1993 | Unger | 424/9 |
| 5,234,680 | 8/1993 | Rogers, Jr. et al. | 424/9 |
| 5,247,935 | 9/1993 | Cline et al. | 128/653.2 |
| 5,271,928 | 12/1993 | Schneider et al. | 424/9 |
| 5,276,146 | 1/1994 | Breillatt, Jr. et al. | 530/413 |
| 5,281,408 | 1/1994 | Unger | 424/4 |
| 5,283,255 | 2/1994 | Levy et al. | 514/410 |
| 5,305,757 | 4/1994 | Unger et al. | 128/662.02 |
| 5,310,540 | 5/1994 | Giddey et al. | 424/9 |
| 5,312,617 | 5/1994 | Unger et al. | 424/9 |
| 5,315,997 | 5/1994 | Widder et al. | 128/653.3 |
| 5,315,998 | 5/1994 | Tachibana et al. | 128/660.01 |
| 5,316,771 | 5/1994 | Barenholz et al. | 424/450 |
| 5,334,381 | 8/1994 | Unger | 424/9 |
| 5,339,814 | 8/1994 | Lasker | 128/653.4 |
| 5,344,930 | 9/1994 | Riess et al. | 544/84 |
| 5,350,571 | 9/1994 | Kaufman et al. | 424/9 |
| 5,352,435 | 10/1994 | Unger | 424/9 |
| 5,354,549 | 10/1994 | Klaveness et al. | 424/3 |
| 5,358,702 | 10/1994 | Unger | 424/9 |
| 5,362,477 | 11/1994 | Moore et al. | 424/9 |
| 5,362,478 | 11/1994 | Desai et al. | 424/9 |
| 5,380,519 | 1/1995 | Schneider et al. | 424/9 |
| 5,393,524 | 2/1995 | Quay | 424/9 |
| 5,409,688 | 4/1995 | Quay | 424/9 |
| 5,410,516 | 4/1995 | Uhlendorf et al. | 367/7 |
| 5,413,774 | 5/1995 | Schneider et al. | 424/9.51 |
| 5,425,366 | 6/1995 | Reinhardt et al. | 128/662.02 |
| 5,433,204 | 7/1995 | Olson | 128/661.08 |
| 5,445,813 | 8/1995 | Schneider et al. | 424/9.51 |
| 5,456,900 | 10/1995 | Unger | 424/9.4 |
| 5,460,800 | 10/1995 | Walters | 424/9.6 |
| 5,466,467 | 11/1995 | Singh | 424/450 |
| 5,469,854 | 11/1995 | Unger et al. | 128/662.02 |
| 5,470,582 | 11/1995 | Supersaxo et al. | 424/489 |
| 5,485,839 | 1/1996 | Aida et al. | 128/653.1 |
| 5,487,390 | 1/1996 | Cohen et al. | 128/662.02 |
| 5,496,535 | 3/1996 | Kirkland | 424/9.37 |
| 5,498,421 | 3/1996 | Grinstaff et al. | 424/450 |
| 5,498,601 | 3/1996 | Sato et al. | 514/17 |
| 5,501,863 | 3/1996 | Rössling et al. | 424/489 |
| 5,502,094 | 3/1996 | Moore et al. | 524/145 |
| 5,505,932 | 4/1996 | Grinstaff et al. | 424/9.3 |
| 5,508,021 | 4/1996 | Grinstaff et al. | 424/9.322 |
| 5,527,521 | 6/1996 | Unger | 424/93 |
| 5,529,766 | 6/1996 | Klaveness et al. | 424/9.52 |
| 5,531,980 | 7/1996 | Schneider et al. | 424/9.52 |
| 5,536,489 | 7/1996 | Lohrmann et al. | 424/9.52 |
| 5,536,490 | 7/1996 | Klaveness et al. | 424/9.52 |
| 5,540,909 | 7/1996 | Schutt | 424/9.52 |
| 5,542,935 | 8/1996 | Unger et al. | 604/190 |
| 5,545,396 | 8/1996 | Albert et al. | 424/93 |
| 5,547,656 | 8/1996 | Unger | 424/9.4 |
| 5,552,133 | 9/1996 | Lambert et al. | 424/9.52 |
| 5,552,155 | 9/1996 | Bailey et al. | 424/450 |
| 5,556,372 | 9/1996 | Talish et al. | 601/2 |
| 5,556,610 | 9/1996 | Yan et al. | 424/9.52 |
| 5,558,092 | 9/1996 | Unger et al. | 128/660.03 |
| 5,558,094 | 9/1996 | Quay | 128/662.02 |
| 5,558,853 | 9/1996 | Quay | 424/9.5 |
| 5,558,854 | 9/1996 | Quay | 424/9.52 |
| 5,558,855 | 9/1996 | Quay | 424/9.5 |
| 5,558,856 | 9/1996 | Klaveness et al. | 424/9.37 |
| 5,560,364 | 10/1996 | Porter | 128/662.02 |
| 5,562,608 | 10/1996 | Sekins et al. | 604/20 |
| 5,562,893 | 10/1996 | Lohrmann | 424/9.52 |
| 5,565,215 | 10/1996 | Gref et al. | 424/501 |
| 5,567,413 | 10/1996 | Klaveness et al. | 424/9.51 |
| 5,567,414 | 10/1996 | Schneider et al. | 424/9.52 |
| 5,567,765 | 10/1996 | Moore et al. | 524/801 |
| 5,569,448 | 10/1996 | Wong et al. | 424/9.45 |
| 5,569,449 | 10/1996 | Klaveness et al. | 424/9.51 |
| 5,571,797 | 11/1996 | Ohno et al. | 514/44 |
| 5,573,751 | 11/1996 | Quay | 424/9.52 |
| 5,578,292 | 11/1996 | Schneider et al. | 424/9.51 |
| 5,580,575 | 12/1996 | Unger et al. | 424/450 |
| 5,585,112 | 12/1996 | Unger et al. | 424/450 |
| 5,593,680 | 1/1997 | Bara et al. | 424/401 |
| 5,595,723 | 1/1997 | Quay | 424/9.5 |
| 5,605,673 | 2/1997 | Schutt et al. | 424/9.51 |
| 5,606,973 | 3/1997 | Lambert et al. | 128/662.02 |
| 5,612,057 | 3/1997 | Lanza et al. | 424/450 |
| 5,612,318 | 3/1997 | Weichselbaum et al. | 514/44 |
| 5,614,169 | 3/1997 | Klaveness et al. | 424/9.52 |
| 5,620,689 | 4/1997 | Allen et al. | 424/178.1 |
| 5,626,833 | 5/1997 | Schutt et al. | 424/9.52 |
| 5,639,443 | 6/1997 | Schutt et al. | 424/9.52 |
| 5,643,553 | 7/1997 | Schneider et al. | 424/9.52 |
| 5,648,095 | 7/1997 | Illum et al. | 424/489 |
| 5,672,585 | 9/1997 | Pierschbacher et al. | 514/11 |
| 5,676,928 | 10/1997 | Klaveness et al. | 424/9.32 |
| 5,679,459 | 10/1997 | Riess et al. | 428/402.2 |
| 5,686,060 | 11/1997 | Schneider et al. | 424/9.52 |
| 5,686,102 | 11/1997 | Gross et al. | 424/450 |
| 5,707,352 | 1/1998 | Sekins et al. | 604/56 |
| 5,707,606 | 1/1998 | Quay | 424/9.52 |

| | | |
|---|---|---|
| 5,707,607 | 1/1998 | Quay ........................................ 424/9.52 |
| 5,711,933 | 1/1998 | Bichon et al. ........................... 424/9.52 |
| 5,716,597 | 2/1998 | Lohrmann et al. ....................... 424/9.5 |
| 5,732,707 | 3/1998 | Widder et al. ...................... 128/661.08 |
| 5,733,527 | 3/1998 | Schutt ..................................... 424/9.52 |
| 5,740,807 | 4/1998 | Porter ................................. 128/662.02 |
| 5,804,162 | 9/1998 | Kabalnov et al. ...................... 424/9.51 |
| 5,840,023 | 11/1998 | Oraevsky et al. ....................... 600/407 |
| 5,846,517 | 12/1998 | Unger ..................................... 424/9.52 |
| 5,855,865 | 1/1999 | Lambert et al. ........................ 424/9.52 |
| 5,858,399 | 1/1999 | Lanza et al. ............................. 424/450 |
| B1 4,229,360 | 11/1991 | Schneider et al. ....................... 270/403 |

FOREIGN PATENT DOCUMENTS

| | | |
|---|---|---|
| 0 077 752 B1 | 3/1986 | European Pat. Off. . |
| 0 243 947 | 4/1987 | European Pat. Off. . |
| 0 231 091 | 8/1987 | European Pat. Off. . |
| 0 272 091 | 6/1988 | European Pat. Off. . |
| 0 320 433 A2 | 12/1988 | European Pat. Off. . |
| 0 324 938 | 7/1989 | European Pat. Off. . |
| 0 338 971 | 10/1989 | European Pat. Off. . |
| 357163 A1 | 3/1990 | European Pat. Off. . |
| 0 361 894 | 4/1990 | European Pat. Off. . |
| 0 368 486 A2 | 5/1990 | European Pat. Off. . |
| 0 382 451 A2 | 8/1990 | European Pat. Off. . |
| 0 216 730 | 1/1991 | European Pat. Off. . |
| 0 467 031 A2 | 5/1991 | European Pat. Off. . |
| 441468 A2 | 8/1991 | European Pat. Off. . |
| 0 357 164 B1 | 10/1991 | European Pat. Off. . |
| 0 451 103 A1 | 10/1991 | European Pat. Off. . |
| 0 458 745 A1 | 11/1991 | European Pat. Off. . |
| 0 314 764 B1 | 9/1992 | European Pat. Off. . |
| 0 554 213 A1 | 8/1993 | European Pat. Off. . |
| 0 586 875 | 3/1994 | European Pat. Off. . |
| 0 614 656 A1 | 9/1994 | European Pat. Off. . |
| 0 422 938 B1 | 2/1995 | European Pat. Off. . |
| 0 727 225 A2 | 8/1996 | European Pat. Off. . |
| 2 700 952 | 8/1994 | France . |
| 25 21 003 | 8/1976 | Germany . |
| 62-286534 | 12/1987 | Japan . |
| 63-60943 | 3/1988 | Japan . |
| 1044680 | 10/1966 | United Kingdom . |
| 2193095 | 2/1988 | United Kingdom . |
| WO 80/02365 | 11/1980 | WIPO . |
| WO 82/01642 | 5/1982 | WIPO . |
| WO 85/01161 | 3/1985 | WIPO . |
| WO 86/00238 | 1/1986 | WIPO . |
| WO 86/01103 | 2/1986 | WIPO . |
| WO 89/05040 | 6/1989 | WIPO . |
| WO 90/01952 | 3/1990 | WIPO . |
| WO 90/04384 | 5/1990 | WIPO . |
| WO 90/04943 | 5/1990 | WIPO . |
| WO 91/00086 | 1/1991 | WIPO . |
| WO 91/03267 | 3/1991 | WIPO . |
| WO 91/12823 | 9/1991 | WIPO . |
| WO 91/15244 | 10/1991 | WIPO . |
| WO 92/10166 | 6/1992 | WIPO . |
| WO 92/11873 | 7/1992 | WIPO . |
| WO 92/15284 | 9/1992 | WIPO . |
| WO 92/17212 | 10/1992 | WIPO . |
| WO 92/17213 | 10/1992 | WIPO . |
| WO 92/17436 | 10/1992 | WIPO . |
| WO 92/17514 | 10/1992 | WIPO . |
| WO 92/21382 | 10/1992 | WIPO . |
| WO 92/22249 | 12/1992 | WIPO . |
| WO 92/22298 | 12/1992 | WIPO . |
| WO 93/00933 | 1/1993 | WIPO . |
| WO 93/05819 | 1/1993 | WIPO . |
| WO 93/06869 | 4/1993 | WIPO . |
| WO 93/13809 | 7/1993 | WIPO . |
| WO 93/17718 | 9/1993 | WIPO . |
| WO 93/20802 | 10/1993 | WIPO . |
| WO 93/23085 | 11/1993 | WIPO . |
| WO 93/25244 | 12/1993 | WIPO . |
| WO 94/00110 | 1/1994 | WIPO . |
| WO 94/06477 | 3/1994 | WIPO . |
| WO 94/07539 | 4/1994 | WIPO . |
| WO 94/07918 | 4/1994 | WIPO . |
| WO 94/09829 | 5/1994 | WIPO . |
| WO 84/02909 | 8/1994 | WIPO . |
| WO 94/16739 | 8/1994 | WIPO . |
| WO 94/19024 | 9/1994 | WIPO . |
| WO 94/21240 | 9/1994 | WIPO . |
| WO 94/21302 | 9/1994 | WIPO . |
| WO 94/28780 | 12/1994 | WIPO . |
| WO 94/28873 | 12/1994 | WIPO . |
| WO 94/28942 | 12/1994 | WIPO . |
| WO 95/06518 | 3/1995 | WIPO . |
| WO 95/07072 | 3/1995 | WIPO . |
| WO 95/23615 | 9/1995 | WIPO . |
| WO 95/24184 | 9/1995 | WIPO . |
| WO 96/04018 | 2/1996 | WIPO . |
| WO 96/09793 | 4/1996 | WIPO . |
| WO 96/23524 | 8/1996 | WIPO . |
| WO 96/36286 | 11/1996 | WIPO . |
| WO 96/40281 | 12/1996 | WIPO . |
| WO 98/00172 | 1/1998 | WIPO . |

OTHER PUBLICATIONS

Fitzpatrick, et al., "Metal Ion Catalyzed Decarboxylation: Kinetics and Mechanism of the Oxidative Decarboxylation of Copper (II) Complexes of Aminomalonic Acid in Aqueous Solution", *Inorganic Chemistry*, vol. 13, No. 3, pp. 568–574 (1974).

Thanassi, "Aminomalonic Acid: Spontaneous Decarboxylation and Reaction with 5–Deoxypyridoxal", *Biochemistry*, vol. 9, No. 3, pp. 525–532 (1970).

Stelmashok et al., *Koordinatsionnaya Khimiya*, vol. 3, No. 4, pp. 524–527 (1977) (Russian and English language versions).

Mayhew et al., "High–Pressure Continuous–Flow System for Drug Entrapment in Liposomes", *Methods in Enzymology*, vol. 149, pp. 64–77 (1987).

Mayhew et al., "Characterization of Liposomes Prepared Using a Microemulsifier", *Biochimica et Biophysica Acta*, vol. 775, pp. 169–174 (1984).

Hope et al., "Production of Large Unilamellar Vesicles by a Rapid Extrusion Procedure: Characterization of Size Distribution, Trapped Volume, and Ability to Maintain a Membrane Potential", *Biochimica et Biophysica Acta*, 812: 55–65 (1985).

Mayer et al., "Vesicles of Variable Size Produced by a Rapid Extrusion Procedure", *Biochimica et Biophysica Acta*, vol. 858, pp. 161–168 (1986).

Cheng, et al., "The Production and Evaluation of Contrast-–Carrying Liposomes Made with an Automatic High Pressure System", *Investigative Radiology*, vol. 22, pp. 47–55 (1987).

Jain, et al., *Introduction to Biological Membranes*, Ch. 9, pp. 192–231 (J. Wiley and Sons, N.Y. 1980).

Sigel, H., ed., *Metal Ions in Biological Systems: Antibiotics and Their Complexes*, vol. 19 (Marcel Dekker, N.Y. 1985).

Nayar et al., "Generation of Large Unilamellar Vesicles From Long–chain Saturated Phosphatidylcholines by Extrusion Technique", *Biochimica et Biophysica Acta*, vol. 986, pp. 200–206 (1989).

Hope et al., "Generation of Multilamellar and Unilamellar Phospholipid Vesicles", *Chemistry and Physics of Lipids*, vol. 40, pp. 89–107 (1986).

Mattrey et al., "Perfluorochemicals as US Contrast Agents for Tumor–Imaging and Hepatosplenography: Preliminary Clinical Results", *Radiology*, vol. 163, pp. 339–343 (1987).

Mattrey et al., "Perfluoroctylbromide: A Liver/Spleen–Specific and Tumor Imaging Ultrasound Contrast Material", *Radiology*, vol. 145, pp. 759–762 (1982).

Keller et al., "Successful Left Ventricular Opacification Following Peripheral Venous Injection of Sonicated Contrast Agent: An Experimental Evaluation", *LV Contrast Echocardiography*, vol. 114, No. 3, pp. 570–575 (1987).

Feinstein et al., "Two–Dimensional Contrast Echocardiography, I. In Vitro Development and Quantitative Analysis of Echo Contrast Agents", *JACC*, vol. 3, No. 1, pp. 14–20 (1984).

Ten Cate et al., "Two–Dimensional Contrast Echocardiography, II: Transpulmonary Studies", *JACC*, vol. 3, No. 1, pp. 21–27 (1984).

Unger et al., "Hepatic Metastases: Liposomal Gd–DTPA–enhanced MR Imaging", *Radiology*, vol. 171, pp. 81–85 (1989).

Deamer et al., "Permeability of Lipid Bilayers to Water and Ionic Solutes", *Chemistry and Physics of Lipids*, vol. 40, pp. 167–188 (1986).

Gutknecht et al., "Diffusion of Carbon Dioxide Through Lipid Bilayer Membrane: Effect of Carbonic Anhydrase, Bicarbonate, and Unstirred Layers", *Chemical Abstracts*, 87:34772q (1977).

Scarpa et al., "Cation Permeability of Liposomes as a Function of the Chemical Composition of the Lipid Bilayers", *Biochimica et Biophysica Acta*, vol. 241, pp. 789–797 (1971).

MacNaughton et al., "Effects of Gaseous Anesthetics and Inert Gases on the Phase Transition in Smectic Mesophases of Dipalmitoyl Phosphatidylcholine", *Biochimica et Biophysica Acta*, vol. 597, pp. 193–198 (1980).

Tilcock et al., "Liposomal Gd–DTPA: Preparation and Characterization of Relaxivity", *Radiology*, vol. 171, pp. 77–80 (1989).

Mann et al., "Formation of Iron Oxides in Unilamellar Vesicles", *Journal of Colloid and Interface Science*, vol. 122, No.2, pp. 326–335 (1988).

Anderson et al., "Manganese (III) Complexes in Oxidative Decarboxylation of Acids", *J. Am. Chem. Soc.*, vol. 92, No.8, pp. 2450–2460 (1970).

Muhlradt et al., "Vitamin B6 Analogs: An Improved Synthesis of 5–Deoxypyridoxal", *New Compounds*, vol. 10, pp. 129–130 (1967).

Chapman D., "Physiochemical Properties of Phospholipids and Lipid Water Systems", *Liposomes Technology*, Gregoriadis, G., ed., vol. 1, pp. 1–18 (CRC Press, Boca Raton, FL, 1984).

Violante et al., "Particulate Suspensions as Ultrasonic Contrast Agents for Liver and Spleen", *Inv. Rad.*, vol. 23, pp. S294–S297, Sep. 1988.

Fritzsch et al., "Preclinical and Clinical Results with an Ultrasonic Contrast Agent", *Inv. Rad.*, vol. 23, pp. S302–S305, Sep. 1988.

Brochure, *Experience*, Sonicator™, Heat Systems–Ultrasonics, Inc. (1987).

M. Ostro, "Liposomes", Marcel Dekker, New York, pp. 102–103 (1983).

Fukuda et al., "Polymer–Encased Vesicles Derived from Diotadecyldimethylammonium Methacrylate", *J. Am. Chem. Soc.*, vol. 108, pp. 2321–2327 (1986).

Regen, "Polymerized Vesicles", *J. Am. Chem. Soc.*, vol. 102, pp. 6638–6640 (1989).

Rose, A. and Rose, E., "The Condensed Chemical Dictionary", Reinhold Publishing, New York, pp. 728 and 743 (1966).

A.G. Belykh, *Farmakol Toksikol. (MOSC)*, vol. 44(3), pp. 322–326 (1981) (abstract).

J. Vion–Dury et al., *J. Pharmacol. Exper. Ther.*, vol. 250(3), pp. 1113–1118 (1989) (abstract).

M.R. Zalutsky et al., *Invest. Radiol.*, vol. 22(2), pp. 141–147 (1987) (abstract).

Crowe et al., *Archives of Biochemistry and Biophysics*, vol. 242, pp. 240–247 (1985).

Crowe et al., *Archives of Biochemistry and Biophysics*, vol. 220, pp. 477–484 (1983).

Dorland's Illustrated Medical Dictionary, p. 946, 27th ed. (W.B. Saunders Company, Philadelphia 1988).

*Liposome Technology*, Gregoriadis, G., ed., vol. I, pp. 30–35, 51–65 and 79–107 (CRC Press Inc., Boca Raton, FL, 1984).

Madden et al., *Chemistry and Physics of Lipids*, vol. 53, pp. 37–46 (1990).

Sinkula et al., *J. Pharm. Sci.*, vol. 64, pp. 181–210 (1975).

Shiina et al., "Hyperthermiably Low–frequency Synthesized Ultrasound", *IEEE Engineering*, pp. 879–880, vol. 2 (1988) (abstract).

McAvoy et al., *IEEE Engineering, Ultrasonics Symposium Proceedings*, vol. 2, pp. 677–1248 (1989) (abstract).

Chapman et al., "Biomembrane Phase Transitions", *J. Biol. Chem.*, 1974, 249:2512–2521.

Hug et al., "Liposomes for the Transformation of Eukaryotic Cells", *Biochimica et Biophysica Acta*, 1991, 1097:1–17.

Marsh, *CRC Handbook of Lipid Bilayers* (CRC Press, Boca Raton, FL 1990) pp. 139–141.

Szoka et al., "Procedure for Preparation of Liposomes With Large Internal Aqueous Space . . . ", *Proc. Natl. Acad. Sci.* 1978, 75:4194–4198.

Acoustic Imaging; AI5200; Convex Curved Linear Array Ultrasound Transducers Operator's Manual, Nov. 20, 1989, 4700–0003–1C, p. 4.

Bangham et al., "Diffusion of Univalent Ions across the Lamellae of Swollen Phospholipids", *J. Mol. Biol.*, 1965, 13:238–252.

Carson et al., *Ultrasound in Med. & Biol. 3*, 1978, 341–350.

Kost et al., *Polymers in Medicine II: Biomedical and Pharmaceutical Applications*, "Ultrasonic Modulated Drug Delivery Systems", Chiellini et al., ed., (Plenum Press, New York and London), pp. 387–396 (1985).

deGier et al., "Relations Between Liposomes and Biomembranes", *Annals of The New York Academy of Sciences*, 1978, 308:85–99.

Felgner et al., "Lipofection: A highly efficient, lipid–mediated DNA–transfection procedure", *Proc. Natl. Acad. Sci.*, 1987, 84:7413–7417.

Gabizon et al., "Liposome formulations with prolonged circulation time in blood and enhanced uptake by tumors", *Proc. Natl. Acad. Sci.*, 1988, 85:6949–6953.

Garelli, et al., *Biochimica et Biophysica Acta*, vol. 1127:41–48 (1992).

Kawai et al., "New Procedure for DNA Transfection with Polycation and Dimethyl Sulfoxide", *Molecular and Cellular Biology*, 1984, 4:1172–1174.

Kuo et al., "Metallocene Antitumor Agents. Solution and Solid–State Molybdenocene Coordination . . . ", *J. Am. Chem. Soc.*, 1991, 113:9027–9045.

MacDonald, *Mammalian Cell Biotechnology: A Practical Approach*, M. Butler, ed., 1991 (Oxford University Press, New York), p. 57–70.

Mathiowitz et al., "Photochemical Rupture of Microcapsules: A Model System", *Journal of Applied Polymer Science*, 1981, 27:809–822.

May et al., "Cationic Liposomes Enable Bovine Herpesvirus Type 2 DNA to Infect Cells", *Acta virol.*, 1991, 35:107.

Poznansky et al., "Biological Approaches to the Controlled Delivery of Drugs: A Critical Review", *Pharmacol, Rev.*, 1984, 36:277–336.

Sato et al., "Recent Aspects in the Use of Liposomes in Biotechnology and Medicine", *Prog. Lipid Res.* 1992, 4:345–372.

Simons et al., "Antisense c–myb oligonucleotides inhibit intimal arterial smooth muscle cell accumulation in vivo", *Nature*, 1992, 359:67–70.

Thompson, Larry, "At Age 2, Gene Therapy Enters a Growth Phase", *Science* 1992, 258:744–746.

Trubetskoy et al. "Cationic liposomes enhance targeted delivery and expression of exogenous DNA . . . ", Biochimica et Biophysica Acta 1992, 131:311–313.

Umemura et al., "Studies on Sonodynamic Cancer Therapy", *IEEE*, 1992, O–7803–0785, pp. 354–355.

Williams, "Human Gene Therapy: Searching for Better Vectors", *ASM News* [American Society for Microbiology] 1992, 58:67–69.

Woodle et al., "Versatility in lipid compositions showing prolonged circulation . . . ", *Biochimica et Biophysica Acta* 1992, 1105:193–200.

Zhou et al., "Targeted delivery of DNA by liposomes and polymers", *J. of Controlled Release* 1992, 19:269–274.

Mathiowitz et al., "Polyanhydride Microspheres as Drug Carriers", *Journal of Applied Polymer Science*, vol. 35, pp. 755–774 (1988).

Sankaram et al., "Cholesterol–Induced Fluid–Phase Immiscibility in Membranes", *Proc. Natl. Acad. Sci.*, vol. 88, pp. 8686–8690 (1991).

*Scientific Apparatus Catalog 92/93* (VWR Scientific, 1991), "Syringes", pp. 1511–1513; "Filtration, Syringe Filters", pp. 766–768; "Filtration, Membranes", pp. 750–753; "Filtration, Filter Holders", p. 744.

Gramiak et al., *Radiology*, "Detection of Intracardiac Blood Flow by Pulsed Echo–Ranging", pp. 415–418 (1971).

Santaella, et al., *FEBS 13463*, "Extended In Vivo Blood Circulation Time of Fluorinated Liposomes", vol. 336, No. 3, pp. 481–484 (1993).

Brown and Langer, *Annual Review Medicine*, 1988, 39:221 29, Annual Review, Inc., "Transdermal Delivery of Drugs", pp. 221–229.

Moseley, et al., *Microbubbles: A Novel MR Susceptibility Contrast Agent*, abstract, 1991 Napa, California Meeting of the Society for Magnetic Resonance in Medicine.

Ter–Pogossian *Tomography*, Kee, et al., n, "Physical Principles and Instrumentation", *Computed Body* eds., Raven Press, New York, Chapter 1, pp. 1–7 (1988).

Aronberg, "Techniques", *Computed Body Tomography*, Kee, et al., eds., Raven Press, New York, Chapter 2, pp. 9–36 (1988).

Miller, *Ultrasonics* (Sep. 1981), "Ultrasonic detection of resonant cavitation bubbles in a flow tube by their second-–harmonic emissions," pp. 217–224.

Dittrich, "Cardiac Muscle Ischemia and Infarction", *The Second Annual International Symposium on Contrast Agents in Diagnostic Ultrasound*, Atlantic City, NJ (May 7, 1996) (abstract).

Pantely, "Intravenous Contrast Echocardiography—Tissue Imaging & Quantification of Coronary Blood Flow", *The Second Annual International Symposium on Contrast Agents in Diagnostic Ultrasound*, Atlantic City, NJ (May 7, 1996) (abstract).

Schutt et al., "Osmotically Stabilized Microbubble Sonographic Contrast Agents", *Acad. Radiol.*, vol. 3, Suppl. 2, pp. S188–S190 (Aug. 1996).

Frézard, et al., "Permeability and stability in buffer and in human serum of fluorinated phospholipid–based liposomes", *Biochimica et Biophysica Acta*, 1192, pp. 61–70 (1994).

Freézard, et al., "Fluorinated Phospholipid–Based Vesicles as Potential Drug Carriers: Encapsulation/Sustaining of Drugs and Stability in Human Serum", *Art, Cells, Blood Subs., and Immob. Biotech.*, 22(4), pp. 1403–1408 (1994).

Chang et al., "Semipermeable Aqueous Microcapsules", *Canadian J. Of Phys. And Pharm.*, 1966, 44, 115–128.

Chang, "Semipermeable Microcapsules", *Science*, 1964, 146, 524–525.

Deasy, *Microencapsulation and Related Drug Processes*, 1983, vol. 20, Chs. 9 and 10, 195–240 (Marcel Dekker, Inc., NY).

Yeung et al., "Preparation of Microencapsulated Liposomes", *J. Microencapsulation*, 1988, 5, 331–337.

Mattrey et al., "Gas Emulsions as Ultrasound Contrast Agents; Preliminary Results in Rabbits and Dogs", *Investigative Radiology*, vol. 29, Jun. Supp. 2, pp. S139–S141, 1994.

Meltzer et al., "Transmission of Ultrasonic Contrast Through the Lungs", *Ultrasound in Med. & Biol.*, vol. 7, No. 4, 377–384, 1981.

PR Newswire, Apr. 1, 1986.

Swanson et al., Chapter 22, "Enhancement Agents for Ultrasound: Fundamentals", *Pharmaceuticals In Medical Imaging*, pp. 682–687 (1990).

Ophir et al., "Contrast Agents in Diagnostic Ultrasound", *Ultrasound in Med. & Biol.*, vol. 15, No. 4, pp. 319–333 (1989).

Jacobs, "Intraocular gas measurement using A–scan ultrasound", *Current Eye Research*, vol. 5, No. 8, pp. 575–578 (1986).

Lincoff et al., "Intravitreal Expansion of Perfluorocarbon Bubbles", *Arch. Ophthalmol.*, vol. 98, p. 1646, Sep. 1980.

Lincoff et al., "Intravitreal Longevity of Three Perfluorocarbon Gases", *Arch. Ophthalmol.*, vol. 98, pp. 1610–1611, Sep. 1980.

Lincoff et al., "The Perfluorocarbon Gases in the Treatment of Retinal Detachment", *Ophthalmology*, vol. 90, No. 5, pp. 546–551, May 1983.

Gardner et al., "A Survey of Intraocular Gas Use in North America", *Arch. Ophthalmol.*, vol. 106, pp. 1188–1189, Sep. 1988.

Unger et al., "liposomal MR Contrast Agents", *J. Liposome Research*, 4(2), pp. 811–834 (1994).

Feinstein, Steven B., "Myocardial Perfusion Imaging: Contrast Echocardiography Today and Tomorrow," *Journal of the American College of Cardiology*, 8(1):251–253 (1986).

Keller et al., "The Behavior of Sonicated Albumin Microbubbles Within the Microcirulation: A Basis for Their Use During Myocardial Contrast Echocardiography", *Circulation Res.*, 65(2):458–465 (1989).

Lincoff et al., "Perfluoro–n–butane: A Gas for Maximum Duration Retinal Tamponade," *Arch Ophthalmology*, 101:460–462 (1983).

*Remington's Pharmaceutical Sciences*, John Hoover, managing ed., Mack Publishing Company, Easton, PA, pp. 295–298; 736; 1242–1244 (1975).

*Handbook of Pharmaceutical Excipients*, American Pharmaceutical Association, Washington, D.C. and The Pharmaceutical Society of Great Britain, London, England, pp. 181–183 (1986).

Barnhart et al., "Characteristics of Albunex™: Air–Filled Microspheres for Echocardiography Contrast Enhancement," *Investigative Radiology*, 25:S162–164 (1990).

Levene et al., "Characterization of Albunex™," *J. Acoust. Soc. Am.*, 87(Suppl.1):569–70 (1990).

Miller et al., "Physiochemical Approaches to the Mode of Action of General Anesthetics," *J. Amer. Soc. Anesthesiologists*, 36(4):339–351 (1972).

"Properties and Applications of the 'Freon' Fluorocarbons" in DuPont Freon Technical Bulletin B–2 (E.I. DuPont de Nemours and Company, Wilmington, DE), pp. 1–11 (1964).

"'Freon' Fluorocarbons: Properties and Applications" in DuPont Technical Bulletin G–1 (E.I. DuPont de Nemours and Company, Wilmington, DE), pp. 1–10 (1987).

"Encyclopedia of Polymer Science and Engineering," John Wiley & Sons, New York, 1:164–169 (1985).

"Concise Encyclopedia of Polymer Science and Engineering," J. Kroschwitz, ed., John Wiley & Sons, New York, pp. 12–13 (1990).

Wheatley et al., "Contrast Agents for Diagnostic Ultrasound: Development and Evaluation of Polymer–Coated Microbubbles," *Biomaterials*, 11:713–717 (1990).

Villanueva et al., "Characterization of Spatial Patters of Flow Within the Reperfused Myocardium by Myocardial Contrast Echocardiography", *Circulation*, vol. 88, No. 6, pp. 2596–2606 (Dec. 1993).

Reexamination of U.S. Patent No. 5,527,521, Reexam Control No. 90/004,719.

Reexamination of U.S. Patent No. 5,547,656, Reexam Control No. 90/004,720.

Ahlers et al., "Quenching of fluorescein–conjugated lipids by antibodies", *Biophys. J.*, 1992, 63(3), 823–838.

Allcock, H.R., "Covalent Linkage of Proteins to Surface–Modified Poly(organophosphazenes): Immobilization of Glucose–6–Phosphate Dehydrogenase and Trypsin", *Macromolecules*, 1986, 19, 1502–1508.

Allcock, H.R., "Schiff Base Coupling of Cyclic and High–Polymeric Phosphazenes to Aldehydes and Amines: Chemotherapeutic Models", *Macromolecules*, 1981, 14, 1616–1622.

Bergstrom et al., "In–vitro photocytotoxicity of lysosomotropic immunoliposomes containing pheophorbide a with human bladder carcinoma cells", *J. Photochem. Photobiol. B: Biol.*, 1994, 24(1), 17–23.

Calzavara–Pinton et al., "Photodynamic therapy with systemic administration of photosensitizers in dermatology", *J. Photochem. Photobiol. B: Biol.*, 1996, 36, 225–231.

Canfield et al., "Incorporation of β–Carotene into Mixed Micelles", *Methods in Enzymology*, 1990, 189, 418–422.

"Concise Encyclopedia of Biochemistry", Second Edition, Walter de Gruyter & Co., 1988, 282–283.

De Jager, R. et al., "Current Status of Cancer Immunodetection with Radiolabeled Human Monoclonal Antibodies", *Semin. Nucl. Med.*, 1993, 23(2), 165–179.

Ebato et al., "Investigation of Specific Binding of Antifluorescyl Antibody and Fab to Fluorescein Lipids in Langmuir––Blodgett Deposited Films Using Quartz Crystal Microbalance Methodology", *Anal. Chem.*, 1994, 66(10), 1683–1689.

Elgorab et al., "Solubilization of β–Carotene and Retinol into Aqueous Solutions of Mixed Micelles", *Biochem. Biophys. Acta.*, 1973, 306, 58–66.

Fendler et al. (eds.), *Catalysis in Micellar and Macromolecular Systems*, Academic Press, NY, 1975.

Fremont et al., "Biophysical studies of T–cell receptors and their ligands", *Curr. Opin. Immunol.*, 1996, 8, 93–100.

Gatenby et al., "CT–guided Laster Therapy in Resistant Human Tumors: Phase I Clinical Trials", *Radiology*, 1987, 163(1), 172–175.

Gatenby et al., "Tumor Therapy with Hemotoporphyrin Derivative and Lasers Via a Percutaneous Fiberoptic Technique: Preclinical Experiments", *Radiology*, 1987, 163(1), 167–171.

Gèze et al., "Lysosomes, a key target of hydrophobic photosensitizers proposed for photochemotherapeutic applications", *J. Photochem. Photobiol. B: Biol.*, 1993, 20, 23–35.

Gioanni, J. et al., "Characterization of a New Surface Epitope Specific for Human Epithelial Cells Defined by a Monoclonal Antibody and Application to Tumor Diagnosis", *Cancer Res.*, 1987, 47, 4417–4424.

Greene, T.W. and Wuts, P.G.M., "Protective Groups in Organic Synthesis", John Wiley, New York, 2nd Edition, 1991.

Jori, "Tumour photosensitizers: approaches to enhance the selectivity and efficiency of photodynamic therapy", *J. Photochem. Photobiol. B: Biol.*, 1996, 36, 87–93.

Kawabata, K. et al., "Effect of second–harmonic superimposition on efficient induction and sonochemical effect", *Ultrasonics Sonochemistry*, 1996, 3, 1–5.

Leenhouts et al., "Membrane potential–driven translocation of a lipid–conjugated rhodamine", *Biochim. Biophys. Acta*, 1995, 1237(2), 121–126.

Lundblad, R.L., "The Chemical Cross–Linking of Peptide Chains", *Techniques in Protein Modification*, CRC Press, Chapter 15, 249–267.

MacDonald, "Characteristics of Self–quenching of the Fluorescence of Lipid–conjugated Rhodamine in Membranes", *J. Biol. Chem.*, 1990, 265(23), 13533–13539.

Marks et al., "A comprehensive approach to breast cancer detection using light; photon localization by ultrasound modulation and tissue characterization by spectral discrimination", *SPIE*, 1993, 1888, 500–510.

Matheson Company, Inc., *Matheson Gas Data Book*, 1996.

Merimsky, O. et al., "Antigens and Antibodies in Malignant Melanoma", *Tumor Biol.*, 1994, 15, 188–202.

Nicol, L. et al., "Immunoscintigraphie Des Mélanomes Malins", *Path. Biol.*, 1990, 38(8), 866–869 (Summary of article in English).

Peng et al., "Correlation of Subcellular and Intratumoral Photosensitizer Localization with Ultrastructural Features After Photodynamic Therapy", *Ultrastructural Path.*, 1996, 20, 109–129.

Reddi, "Role of delivery vehicles for photosensitizers in the photodynamic therapy of tumours", *J. Photochem. Photobiol. B: Biol.*, 1997, 37, 189–195.

Reddi et al., "Lipsome– or LDL–administered Zn(II)–phthalocyanine as a Photodynamic Agent for Tumours III. Effect of Cholesterol on Pharmacokinetic and Phototherapeutic Properties", *Lasers in Med. Sci.*, 1990, 5, 339–343.

Shahinian, S. et al.,"A novel strategy affords high–yield coupling of antibody Fab' fragments to liposomes", *Biochimica et Biophysica Acta*, 1995, 1239, 157–167.

Shinoda, K., et al., "The Formation of Micelles", *Colloidal Surfactant*, Academic Press, New York, 1963, Chapter 1, 1–88.

Siegall, "Targeted Toxins as Anticancer Agents", *Cancer*, 1994, 74(3), 1006–1012.

Spikes, "New Trends in Photobiology (Invited Review) Chlorins as Photosensitizers in Biology and Medicine", *J. Photochem. Photobiol. B: Biol.*, 1990, 6, 259–274.

Sutherland et al., "Color Doppler Myocardial Imaging: A New Technique for the Assessment of Myocardial Function", *J. Am. Soc. Echocardio.*, 1994, 7(5), 441–458.

Tagliaferri, P. et al., "Pharmacological modulation of peptide growth factor receptor expression on tumor cells as a basis for cancer therapy", *Anti–Cancer Drugs*, 1994, 5(4), 379–393.

Thorpe, P.E. et al., "Antibody–directed targeting of the vasculature of solid tumors", *Breast Cancer Res. and Treatment*, 1995, 36, 237–251.

Tsuji, Y. et al., "Identification of Two Different Surface Epitopes of Human Ovarian Epithelial Carcinomas by Monoclonal Antibodies", *Cancer Res.*, 1985, 45, 2358–2362.

Ulendorf, "Physics of Ultrasound Contrast Imaging: Scattering in the Linear Range", *IEEE Transactions on Ultrasonics, Ferroelectrics, and Frequency Control*, 1994, 41(1), 70–79.

Van Dongen et al., "Progress in radioimmunotherapy of head and neck cancer", *Oncology Reports*, 1994, 1, 259–264.

Wallner et al., "Primary Structure of Lymphocyte Function–Associated Antigen 3 (LFA-3): The Ligand of the T Lymphocyte CD2 Glycoprotein", *J. Experimental Med.*, 1987, 166, 923–932.

Weast, R.C. and Lide, D.R. (eds.), "Chemical Rubber Company Handbook of Chemistry and Physics", CRC Press, Inc., Boca Raton, Florida, 1989–1990.

Wu, T.Z., "Immunology of the human papilloma virus in relation to cancer", *Curr. Opin. Immunol.*, 1994, 6, 746–754.

Xueyong, Z. et al., "Use of MG Series Monoclonal Antibodies in the Diagnosis and Experimental Targeting Therapy of Gastric Cancer", *Chin. Med. Sci. J.*, 1991, 6(1), 56–59.

Desir et al., "Assessment of regional myocardial perfusion with myocardial contrast echocardiography in a canine model of varying degrees of coronary stenosis", *Am. Heart J.*, 1994, 127(1), 56–63.

Sekins et al., "Lung Cancer Hyperthermia via Ultrasound and PFC Liquids", Published in *Proceedings of the 5th International Symposium on Hyperthermic Oncology, Kyoto, Japan*, Aug. 29–Sep. 3, 1998, 3 pages.

Pietersen, "A New Warning System for Fires of Electrical Origin", *CERN European Organization for Nuclear Research, Health and Safety Division*, Mar., 1977, 1–5.

Nomura et al., "US Contrast Enhancement of Hepatic Tumor with Helium Gas Microbubbles: A Preliminary Report",*Jpn. J. Med. Ultrasonics*, 1991, 18(5), (Japanese with English language abstract).

Lindner et al., "Myocardial Perfusion Characteristics and Hemodynamic Profile of MRX–115, a Venous Echocardiographic Contrast Agent, During Acute Myocardial Infarction", *J. Am. Soc. Echocardiography*, 1998, 11(1), 36–46.

Regen et al., "Polymerized Phosphatidylcholine Vesicles. Synthesis and Characterization", *J. Am. Chem. Soc.*, 1982, 104(3), 191–195.

Wei et al., "Quantification of Myocardial Blood Flow with Ultrasound–Induced Destruction of Microbubbles Administered as a Constant Venous Infusion", *Circulation*, 1998, 97, 473–483.

Hynynen et al., "The Usefulness of a Contrast Agent and Gradient Recalled Acquisition in a Steady–State Imaging Sequence for Magnetic Resonance Imaging–Guided Noninvasive Ultrasound Surgery", *Investigative Radiology*, 1994, 29(10), 897–903.

Nakakjima, S. et al., "Acoustic, fluorescent diagnosis of malignant lesions using by HAT–DO1 and ATX–S10", *Proc. SPIE—Int. Soc. Opt. Eng.*, 1995, 2371, 495–500 (Abstract Only).

Warren, S. et al., "Combining Intravascular Ultrasound and Fluorescence Spectroscopy for Real Time Diagnosis of Atherosclerosis",*Proc. Int. Conf. Lasers*, 1993, 15, 795–801 (Abstract Only).

Lejbkowicz et al., "The response of normal and malignant cells to ultrasound in vitro", Database *BIOSIS*, No. 1993:95122245 (abstract only).

Jackson et al., "Effect of ultrasound therapy on the repair of Achilles tendon injuries in rats", *Med. Sci. Sports Exercise*, 1991, 23(2), 171–176.

Maxwell, "Therapeutic Ultrasound: Its Effects on the Cellular and Molecular Mechanisms of Inflammation and Repair", *Physiotherapy*, 1992, 78(6), 421–426.

Tuncay et al., "Expression of Genes Associated with Tissue Remodeling Upon Ultrasound Perturbation in the Gingival Fibroblast",*J. Dental Res.*, 1996, 75, 143, (abstract only).

Wang et al., "Low Intensity Ultrasound Treatment Increases Strength in a Rat Femoral Fracture Model",*J. Orthopaedic Res.*, 1994, 12(1), 40–47.

Yang et al., "Exposure to Low–Intensity Ultrasound Increases Aggrecan Gene Expression in a Rat Femur Facture Model",*J. Orthopaedic Res.*, 1996, 14(5), 802–809.

Young et al., "Effect of therapeutic ultrasound on the healing of full–thickness excised skin lesions", *Ultrasonics*, 1990, 28(3), 175–180.

Young et al., "The Effect of Therapeutic Ultrasound on Angiogenesis", *Ultrasound Med. Biol.*, 1990, 16(3), 261–269.

U.S. application No. 08/307,305, Unger et al., filed Sep. 16, 1994.

U.S. application No. 08/391,938, Unger et al., filed Feb. 21, 1995.

U.S. application No. 08/444,754, Unger, filed May 19, 1995.

U.S. application No. 08/465,868, Unger, filed Jun. 6, 1995.

U.S. application No. 08/851,780, Unger et al., filed May 6, 1997.

U.S. application No. 08/887,215, Unger et al., filed Jul. 2, 1997.

U.S. application No. 60/046,379, Unger, filed May 13, 1997.

cholesteryl 1-pyrenebutyrate n=3
cholesteryl 1-pyrenehexanoate n=5
cholesteryl 1-pyrenedecanoate n=9 cholesteryl 12-(N-methyl-N-(7-nitrobenz-2-oxa-1,3-diazol-4-yl)amino)dodecanate cholesteryl 4,4-difluoro-5,7-dimethyl-4-bora-3a,4a-diaza-s-indacene-3-dodecanoate cholesteryl cis-parinarate cholesteryl 3-((6-phenyl)-1,3,5-hexatrienyl)phenylproprionate 22-(N-(7-nitrobenz-2-oxa-1,3-diazol-4-yl)amino)-23,24-bisnor-5-cholen-3b-ol
R=H
22-(N-(7-nitrobenz-2-oxa-1,3-diazol-4-l(amino)-23,24-bisnor-5-cholen-3b-yl cis-9-octadecenoate 1-pyrenemethyl 3b-hydroxy-22,23-bisnor-5-cholenate
R=H
1-pyrenemethyl 3b-(cis-9-octadecenoylosy)-22,23-bisnor-5-cholenate acridine orange 10-dodecyl bromide n=11
acridine orange 10-nonyl bromide n=8

5-dodecanoylaminofluorescein n=10
5-hexadecanoylaminofluorescein n=14
5-octadecanoylaminofluorescein n=16

5-dodecanoylaminofluorescein-bis-4,5-dimethoxy-2-nitrobenzyl ether 2-dodecylresorufin fluorescein octadecyl ester 5-hexadecanoylaminoeosin octadecyl rhodamine B chloride N-octadecyl-N'-(5-(fluoresceinyl))thiourea

GAS, LIQUID, GASEOUS PRECURSOR, OIL OR CRYSTALS WITH GAS EMBEDDED THEREIN

OPTOACOUSTIC CONTRAST AGENTS AND METHODS FOR THEIR USE

FIELD OF THE INVENTION

The present invention generally relates to optoacoustic contrast agents and methods for diagnostic and therapeutic imaging using optoacoustic contrast agents.

BACKGROUND OF THE INVENTION

Optical imaging and acoustic imaging (e.g., ultrasound) have each been used as separate modalities for diagnostic imaging. However, optical imaging, and acoustic imaging each have limitations. For example, optical imaging is hampered by relatively poor penetrability and diffusion, while ultrasound imaging is hampered by its spatial and contrast resolution for defining the physiology of images.

New and improved contrast agents and methods of imaging are needed to overcome the limitations in the art. The present invention is directed to these, as well as other, important ends.

SUMMARY OF THE INVENTION

The present invention relates to methods of providing an image of a region of a patient comprising administering to the patient a composition comprising a stabilizing material and a photoactive agent and scanning the patient using optical imaging and ultrasound imaging to obtain visible images of the region of the patient. The compositions may comprise a wide variety of additional components, including, for example, one or more of gases, gaseous precursors, liquids, oils, stabilizing materials, diagnostic agents, photoactive agents, bioactive agents and/or targeting ligands.

The present invention also relates to methods of diagnosing the presence of diseased tissue in a patient comprising administering to the patient a composition comprising a stabilizing material and a photoactive agent and scanning the patient using optical imaging and ultrasound imaging to obtain visible images of any diseased tissue in the patient. The compositions may comprise a wide variety of additional components, including, for example, one or more of gases, gaseous precursors, liquids, oils, stabilizing materials, diagnostic agents, photoactive agents, bioactive agents and/or targeting ligands.

The present invention also relates to methods of delivering photoactive agents to a region of a patient comprising administering to the patient a composition comprising a stabilizing material and a photoactive agent, applying ultrasound to deliver the photoactive agent to the desired region, and applying light energy to activate the photoactive agent. If desired, the method may further comprise monitoring the location of the composition with ultrasound imaging and/or optical imaging to determine the location of the composition prior to applying ultrasound to deliver the photoactive agent to the desired region. The compositions may comprise a wide variety of additional components, including, for example, one or more of gases, gaseous precursors, liquids, oils, stabilizing materials, diagnostic agents, photoactive agents, bioactive agents and/or targeting ligands.

These and other aspects of the present invention will become more apparent from the following detailed description.

DETAILED DESCRIPTION OF THE INVENTION

Figure 1:
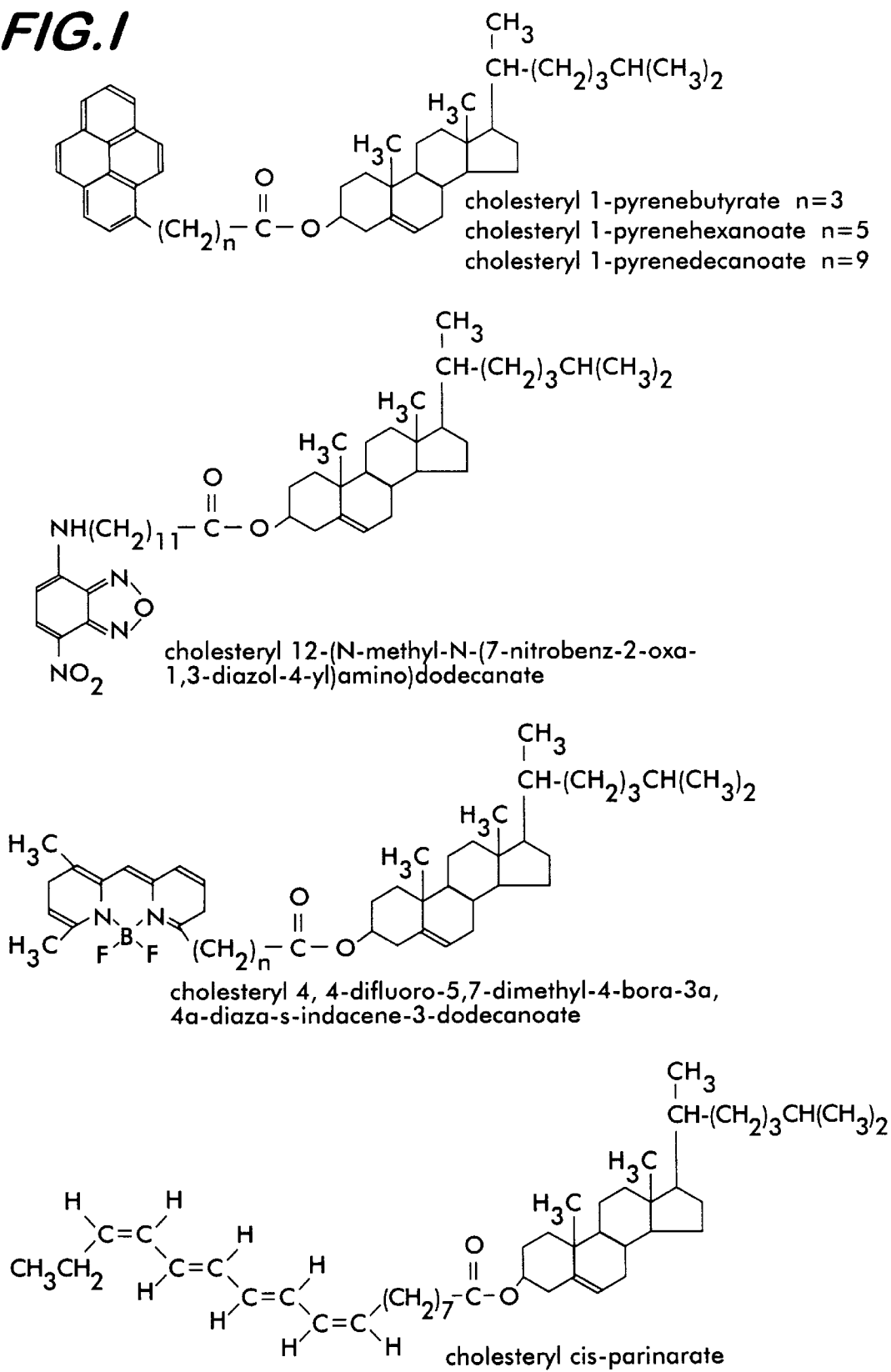
FIGS. 1 and 1A depict the chemical structures of photoactive agents that may be used in the compositions of the present invention.

As employed above and throughout the disclosure, the following terms, unless otherwise indicated, shall be understood to have the following meanings.

"Lipid" refers to a naturally-occurring, synthetic or semi-synthetic (i.e., modified natural) compound which is generally amphipathic. The lipids typically comprise a hydrophilic component and a hydrophobic component. Suitable lipids include, for example, fatty acids, neutral fats, fluorinated lipids, phosphatides, oils, fluorinated oils, glycolipids, surface active agents (surfactants and fluorosurfactants), aliphatic alcohols, waxes, terpenes and steroids. The phrase semi-synthetic (or modified natural) denotes a natural compound that has been chemically modified in some fashion.

"Surfactant" refers to a surface active agent, which is a compound that alters surface tension. Surface active agents include, for example, detergents, wetting agents, dispersing agents, foaming agents and emulsifiers. Preferable examples of surfactants are hydrophobic compounds, including phospholipids, oils, fluorinated oils and fluorosurfactants.

"Fluorosurfactant" refers to a surfactant in which at least one hydrogen atom of the surfactant is replaced with a fluorine atom.

"Polymer" or "polymeric" refers to molecules formed from the chemical union of two or more repeating units. Included within the term "polymer" may be, for example, dimers, trimers and oligomers. The polymer may be synthetic, naturally-occurring or semisynthetic. The polymer may be a "fluorinated polymer" in which at least one hydrogen atom of the polymer is replaced with a fluorine atom. "Polymer" preferably refers to molecules which comprise 10 or more repeating units.

"Protein" refers to molecules comprising, and preferably consisting essentially of, α-amino acids in peptide linkages. Included within the term "protein" are globular proteins such as albumins, globulins and histones, and fibrous proteins such as collagens, elastins and keratins. Also included within the term "protein" are "compound proteins," where a protein molecule is united with a nonprotein molecule, such as nucleoproteins, mucoproteins, lipoproteins and metalloproteins. The proteins may be naturally-occurring, synthetic or semi-synthetic.

"Amphiphilic moiety" or "amphiphile" refers to a synthetic, semi-synthetic (modified natural) or naturally-occurring compound having a water-soluble, hydrophilic portion and a water-insoluble, hydrophobic portion. Preferred amphiphilic compounds have a polar head group, for example, a phosphatidylcholine group, and one or more nonpolar, aliphatic chains, for example, palmitoyl groups. "Fluorinated amphiphilic moiety" refers to an amphiphilic compound in which at least one hydrogen atom of the amphiphilic compound is replaced with a fluorine atom. In a preferred form, the fluorinated amphiphilic compounds are polyfluorinated. "Polyfluorinated amphiphilic moiety" refers to amphiphilic compounds which contain two or more fluorine atoms. "Perfluorinated amphiphilic moiety" refers to amphiphilic compounds in which all the hydrogen atoms have been replaced with a fluorine atom. "Amphipathy" refers to the simultaneous attraction and repulsion in a single molecule or ion containing one or more groups having an affinity for the phase or medium in which they are dissolved, emulsified and/or suspended, together with one or more groups that tend to be expelled from the involved phase or medium.

"Vesicle" refers to an entity which generally has one or more walls or membranes which form one or more internal voids. Vesicles may be formulated, for example, from a stabilizing material such as a lipid, a protein, a polymer, a surfactant and/or a carbohydrate, including the various lipids, proteins, polymers, surfactants and carbohydrates described herein. The lipids, proteins, polymers, surfactants and/or other vesicle forming stabilizing materials may be natural, synthetic or semi-synthetic. Preferred vesicles are those which comprise walls or membranes formulated from lipids. The walls or membranes may be concentric or otherwise. The stabilizing compounds may be in the form of one or more monolayers or bilayers. In the case of more than one monolayer or bilayer, the monolayers or bilayers may be concentric. Stabilizing compounds may be used to form a unilamellar vesicle (comprised of one monolayer or bilayer), an oligolamellar vesicle (comprised of about two or about three monolayers or bilayers) or a multilamellar vesicle (comprised of more than about three monolayers or bilayers). The walls or membranes of vesicles may be substantially solid (uniform), or they may be porous or semi-porous. The internal void of the vesicles may be filled with a wide variety of materials including, for example, water, oils, fluorinated oils, gases, gaseous precursors, liquids, and fluorinated liquids, if desired, and/or other materials. The vesicles may also comprise a photoactive agent, a bioactive agent and/or a targeting ligand, if desired.

"Liposome" refers to a generally spherical or spheroidal cluster or aggregate of amphipathic compounds, including lipid compounds, typically in the form of one or more concentric layers, for example, bilayers. They may also be referred to as lipid vesicles or lipid microspheres. The liposomes may be formulated, for example, from ionic lipids and/or non-ionic lipids. Liposomes formulated from non-ionic lipids may be referred to as niosomes. Liposomes formulated, at least in part, from ionic lipids may be referred to as cochleates.

"Micelle" refers to colloidal entities formulated from lipids. In preferred embodiments, micelles comprise a monolayer, bilayer, or hexagonal H II phase structure.

"Aerogel" refers to generally spherical or spheroidal entities which are characterized by a plurality of small internal voids. The aerogels may be formulated from synthetic materials (for example, a foam prepared from baking resorcinol and formaldehyde), as well as natural materials, such as carbohydrates (polysaccharides) or proteins.

"Clathrate" refers to a solid, semi-porous or porous particle which may be associated with vesicles. In a preferred form, the clathrates may form a cage-like structure containing cavities which comprise one or more vesicles bound to the clathrate, if desired. A stabilizing material may, if desired, be associated with the clathrate to promote the association of the vesicle with the clathrate. Clathrates may be formulated from, for example, porous apatites, such as calcium hydroxyapatite, and precipitates of polymers and metal ions, such as alginic acid precipitated with calcium salts.

A "fluorinated compound" refers to a compound that contains at least one fluorine atom. More preferably, the fluorinated compound is a "polyfluorinated compound," which refers to a compound that contains at least two fluorine atoms. Even more preferably, the fluorinated compound is "perfluorinated," which means fully fluorinated, such as a compound where all hydrogen atoms have been replaced by fluorine atoms. The fluorinated compound may be in the form of a gas or a liquid (including a gaseous precursor). Preferably, the liquid is a gaseous precursor that can convert to a gas. A variety of fluorinated compounds may be used in this invention. Where the fluorinated compound is a carbon-based compound, the fluorinated compound preferably contains from 1 to about 30 carbon atoms, more preferably 1 to about 24 carbon atoms, even more preferably 1 to about 12 carbon atoms, still even more preferably about 5 to about 12 carbon atoms, and most preferably about 6 to about 10 carbon atoms. Thus, the number of carbon atoms in the fluorinated compound may be 1, 2, 3, 4, 5, 6, 7, 8, 9, 10, 11, 12, 13, 14, 15, 16, 17, 18, 19, 20, 21, 22, 23, 24 carbon atoms, and upwards. Alternatively, the fluorinated compound may be a sulfur or selenium based fluorinated compound, such as sulfur hexafluoride or selenium hexafluoride. The fluorinated compound may also, for example, have carbon atoms interrupted by one or more heteroatoms, such as —O— bonds (as in ether compounds) or have other substituents such as amines. Preferred fluorinated compounds of the present invention are fluorinated organic compounds, more preferably, perfluorocarbons and perfluoroethers.

"Gas filled vesicle" refers to a vesicle having a gas encapsulated therein. "Gaseous precursor filled vesicle"

refers to a vesicle having a gaseous precursor encapsulated therein. The vesicles may be minimally, partially, substantially, or completely filled with the gas and/or gaseous precursor. The term "substantially" as used in reference to the gas and/or gaseous precursor filled vesicles means that greater than about 30% of the internal void of the substantially filled vesicles comprises a gas and/or gaseous precursor. Preferably, greater than about 40%, about 50% or about 60% of the internal void of the substantially filled vesicles comprises a gas and/or gaseous precursor, with greater than about 70% or about 75% being more preferred. Even more preferably, greater than about 80%, about 85% or about 90% of the internal void of the substantially filled vesicles comprises a gas and/or gaseous precursor. In particularly preferred embodiments, greater than about 95% or about 99% of the internal void of the vesicles comprises a gas and/or gaseous precursor, with about 100% being especially preferred. Alternatively, the vesicles may contain no or substantially no gas or gaseous precursor.

"Emulsion" refers to a mixture of two or more generally immiscible liquids, and is generally in the form of a colloid. The mixture may be of lipids, for example, which may be homogeneously or heterogeneously dispersed throughout the emulsion.

Alternatively, the lipids may be aggregated in the form of, for example, clusters or layers, including monolayers or bilayers.

"Suspension" or "dispersion" refers to a mixture, preferably finely divided, of two or more phases (solid, liquid or gas), such as, for example, liquid in liquid, solid in solid, gas in liquid, and the like which can remain stable for extended periods of time.

"Hexagonal H II phase structure" refers to a generally tubular aggregation of lipids in liquid media, for example, aqueous media, in which the hydrophilic portion(s) of the lipids generally face inwardly in association with an aqueous liquid environment inside the tube.

The hydrophobic portion(s) of the lipids generally radiate outwardly and the complex assumes the shape of a hexagonal tube. A plurality of tubes is generally packed together in the hexagonal phase structure.

"Patient" refers to animals, including mammals, preferably humans.

"Region of a patient" refers to a particular area or portion of the patient and in some instances to regions throughout the entire patient. Exemplary of such regions are the pulmonary region, the gastrointestinal region, the cardiovascular region (including myocardial tissue), the renal region as well as other bodily regions, tissues, lymphocytes, receptors, organs and the like, including the vasculature and circulatory system, and as well as diseased tissue, including cancerous tissue. The "region of a patient" is preferably internal, although it may be external. The phrase "vasculature" denotes blood vessels, including arteries, veins and the like. The phrase "gastrointestinal region" includes the region defined by the esophagus, stomach, small and large intestines, and rectum. The phrase "renal region" denotes the region defined by the kidney and the vasculature that leads directly to and from the kidney, and includes the abdominal aorta. "Region to be imaged," "region of a patient" or "imaging region" denotes a region of a patient where diagnostic imaging is desired or where delivery of a therapeutic agent is desired.

"Optoacoustic contrast agent" refers to the compositions of the present invention, including, but not limited to, those which comprise a stabilizing material and a photoactive agent. "Optoacoustic contrast agent" also refers, for example, to delivery vehicles, vesicles, liposomes, micelles, emulsions, suspensions, dispersions, aerogels, clathrates, hexagonal H II phase structures and the like. Such contrast agents are capable of providing an image using both optical and acoustic imaging.

"Optical imaging" refers to the production of visible representations of tissue or regions of a patient produced by irradiating those tissues or regions of a patient with electromagnetic energy in the spectral range between ultraviolet and infrared, and analyzing either the reflected, scattered, absorbed and/or fluorescent energy produced as a result of the irradiation. Examples of optical imaging include, but are not limited to, visible photography and variations thereof, ultraviolet images, infrared images, fluorimetry, holography, visible microscopy, fluorescent microscopy, spectrophotometry, spectroscopy, fluorescence polarization and the like.

"Acoustic imaging" refers to the production of visible representations of tissue or regions of a patient produced by irradiating those tissues or regions of a patient with sound energy, and analyzing either the reflected, scattered and/or absorbed energy produced as a result of the irradiation. Examples of acoustic imaging include, but are not limited to, ultrasound imaging.

"Delivery vehicle" or "vehicle" refers to a composition, substance or material that can transport or carry in vivo or in vitro a photoactive agent, a bioactive agent and/or a targeting ligand. Suitable delivery vehicles include, for example, stabilizing materials, vesicles, liposomes, micelles, aerogels, clathrates, gas and/or gaseous precursor filled vesicles, emulsions, suspensions, dispersions, hexagonal H II phase structures, cochleates and the like.

"Photoactive agent" refers to any compound or material that is active in light or that responds to light, including, for example, chromophores (e.g., materials that absorb light at a given wavelength), fluorophores (e.g., materials that emit light at a given wavelength), photosensitizers (e.g., materials that can cause necrosis of tissue and/or cell death in vitro and/or in vivo), fluorescent materials, phosphorescent materials and the like, that may be used in diagnostic or therapeutic applications. "Light" refers to all sources of light including the ultraviolet (UV) region, the visible region and/or the infrared (IR) region of the spectrum.

"Bioactive agent" refers to a substance which may be used in connection with an application that is therapeutic or diagnostic, such as, for example, in methods for diagnosing the presence or absence of a disease in a patient and/or methods for the treatment of a disease in a patient. "Bioactive agent" refers to substances which are capable of exerting a biological effect in vitro and/or in vivo. The bioactive agents may be neutral, positively or negatively charged. Suitable bioactive agents include, for example, prodrugs, diagnostic agents, therapeutic agents, pharmaceutical agents, drugs, synthetic organic molecules, proteins, peptides, vitamins, steroids, steroid analogs and genetic material, including nucleosides, nucleotides and polynucleotides.

"Therapeutic agent," "pharmaceutical agent" or "drug" refers to any therapeutic or prophylactic agent which may be used in the treatment (including the prevention, diagnosis, alleviation, or cure) of a malady, affliction, condition, disease or injury in a patient. Therapeutically useful peptides, polypeptides and polynucleotides may be included within the meaning of the term pharmaceutical or drug.

"Diagnostic agent" refers to any substance which may be used in connection with methods for imaging an internal region of a patient and/or diagnosing the presence or absence of a disease or diseased tissue in a patient. Diagnostic agents include, for example, contrast agents for use in connection with ultrasound imaging, optical imaging, magnetic resonance imaging (MRI), nuclear magnetic resonance (NMR), computed tomography (CT), electron spin resonance (ESR), nuclear medical imaging, elastography, radiofrequency (RF), microwave laser and the like. Diagnostic agents may also include any other agents useful in facilitating diagnosis of a disease or other condition in a patient, whether or not imaging methodology is employed.

"Targeting ligand" refers to any material or substance which may promote targeting of tissues and/or receptors in vivo and/or in vitro with the compositions of the present invention. The targeting ligand may be synthetic, semi-synthetic, or naturally-occurring. Materials or substances which may serve as targeting ligands include, for example, proteins, including antibodies, antibody fragments, hormones, hormone analogues, glycoproteins and lectins, peptides, polypeptides, amino acids, sugars, saccharides, including monosaccharides and polysaccharides, carbohydrates, vitamins, steroids, steroid analogs, hormones, cofactors, and genetic material, including nucleosides, nucleotides, nucleotide acid constructs and polynucleotides. A "precursor" to a targeting ligand refers to any material or substance which may be converted to a targeting ligand. Such conversion may involve, for example, anchoring a precursor to a targeting ligand. Exemplary targeting precursor moieties include maleimide groups, disulfide groups, such as ortho-pyridyl disulfide, vinylsulfone groups, azide groups, and α-iodo acetyl groups.

"Genetic material" refers generally to nucleotides and polynucleotides, including deoxyribonucleic acid (DNA) and ribonucleic acid (RNA). The genetic material may be made by synthetic chemical methodology known in the art, or by the use of recombinant technology, or by a combination thereof. The DNA and RNA may optionally comprise unnatural nucleotides and may be single or double stranded. "Genetic material" also refers to sense and anti-sense DNA and RNA, which are nucleotide sequences that are complementary to specific sequences of nucleotides in DNA and/or RNA.

"Stabilizing material" or "stabilizing compound" refers to any material which can improve the stability of compositions containing the photoactive agents, gases, gaseous precursors, liquids, bioactive agents and/or targeting ligands described herein, including, for example, mixtures, suspensions, emulsions, dispersions, vesicles, or the like. The improved stability involves, for example, the maintenance of a relatively balanced condition, and may be exemplified by increased resistance of the composition against destruction, decomposition, degradation, and the like. In the case of preferred embodiments involving vesicles filled with photoactive agents, gases, gaseous precursors, liquids, bioactive agents and/or targeting ligands, the stabilizing compounds may serve to either form the vesicles or stabilize the vesicles, in either way serving to minimize or substantially (including completely) prevent the escape of photoactive agents, gases, gaseous precursors, bioactive agents and/or targeting ligands from the vesicles until release is desired. The term "substantially" as used in the context of preventing escape of photoactive agents, gases, gaseous precursors, bioactive agents and/or targeting ligands from the vesicles means greater than about 50% is maintained entrapped in the vesicles until release is desired, preferably greater than about 60%, about 70%, about 80% or about 85% is maintained entrapped in the vesicles until release is desired, with about 90% being even more preferred. In particularly preferred embodiments, greater than about 95%, about 99% or about 100% of the photoactive agents, gases, gaseous precursors, bioactive agents and/or targeting ligands are maintained entrapped until release is desired. Exemplary stabilizing materials include lipids, proteins, polymers, carbohydrates and surfactants. The resulting mixture, suspension, emulsion or the like may comprise walls (e.g., films, membranes and the like) around the photoactive agent, targeting ligand, bioactive agent, gases and/or gaseous precursors, or may be substantially devoid of walls or membranes, if desired. The stabilizing may, if desired, form droplets. The stabilizing material may also comprise salts and/or sugars. In other embodiments, the stabilizing materials may be substantially (including completely) crosslinked. The stabilizing material may be neutral, positively or negatively charged.

"Droplet" refers to a spherical or spheroidal entity which may be substantially liquid or which may comprise liquid and solid, solid and gas, liquid and gas, or liquid, solid and gas. Solid materials within a droplet may be, for example, particles, polymers, lipids, proteins, or surfactants.

"Crosslink," "crosslinked" and "crosslinking" generally refer to the linking of two or more stabilizing materials, including lipid, protein, polymer, carbohydrate, and/or surfactant materials, by one ore more bridges. The bridges may be composed of one or more elements, groups, or compounds, and generally serve to join an atom from a first stabilizing material molecule to an atom of a second stabilizing material molecule. The crosslink bridges may involve covalent and/or non-covalent associations. Any of a variety of elements, groups, and/or compounds may form the bridges in the crosslinks, and the stabilizing materials may be crosslinked naturally or through synthetic means. For example, crosslinking may occur in nature in material formulated from peptide chains which are joined by disulfide bonds of cystine residues, as in keratins, insulins and other proteins. Alternatively, crosslinking may be effected by suitable chemical modification, such as, for example, by combining a compound, such as a stabilizing material, and a chemical substance that may serve as a crosslinking agent, which may cause to react by, for example, exposure to heat, high-energy radiation, ultrasonic radiation and the like. Examples include crosslinking by sulfur to form disulfide linkages, crosslinking using organic peroxides, crosslinking of unsaturated materials by means of high-energy radiation, crosslinking with dimethylol carbamate, and the like. If desired, the stabilizing compounds may be substantially crosslinked. The term "substantially" means that greater than about 50% of the stabilizing compounds contain crosslinking bridges. If desired, greater than about 60%, 70%, 80%, 90%, 95% or even 100% of the stabilizing compounds contain such crosslinking bridges. Alternatively, the stabilizing materials may be non-crosslinked, i.e., such that greater than about 50% of the stabilizing compounds are devoid of crosslinking bridges, and if desired, greater than about 60%, 70%, 80%, 90%, 95% or even 100% of the stabilizing compounds are devoid of crosslinking bridges.

"Vesicle stability" refers to the ability of vesicles to retain the photoactive agent, gas, gaseous precursor, bioactive agent and/or targeting ligand entrapped therein after being exposed, for about one minute, to a pressure of about 100 millimeters (mm) of mercury (Hg). Vesicle stability is measured in percent (%), this being the fraction of the amount of gas which is originally entrapped in the vesicle and which is retained after release of the pressure. Vesicle stability also includes "vesicle resilience" which is the ability of a vesicle to return to its original size after release of the pressure.

"Covalent association" refers to an intermolecular association or bond which involves the sharing of electrons in the bonding orbitals of two atoms.

"Non-covalent association" refers to intermolecular interaction among two or more separate molecules which does not involve a covalent bond. Intermolecular interaction is dependent upon a variety of factors, including, for example, the polarity of the involved molecules, and the charge (positive or negative), if any, of the involved molecules. Non-covalent associations include ionic interactions, electrostatic interactions, dipole—dipole interactions, van der Waal's forces, and combinations thereof.

"Ionic interaction" or "electrostatic interaction" refers to intermolecular interaction among two or more molecules, each of which is positively or negatively charged. Thus, for example, "ionic interaction" or "electrostatic interaction" refers to the attraction between a first, positively charged molecule and a second, negatively charged molecule. Ionic or electrostatic interactions include, for example, the attraction between a negatively charged targeting ligand, for example, genetic material, and a positively charged lipid, for example, a cationic lipid, such as lauryltrimethylammonium bromide.

"Dipole—dipole interaction" refers generally to the attraction which can occur among two or more polar molecules. Thus, "dipole—dipole interaction" refers to the attraction of the uncharged, partial positive end of a first polar molecule, commonly designated as $\delta^+$, to the uncharged, partial negative end of a second polar molecule, commonly designated as $\delta^-$. Dipole—dipole interactions are exemplified by the attraction between the electropositive head group, for example, the choline head group, of phosphatidylcholine and an electronegative atom, for example, a heteroatom, such as oxygen, nitrogen or sulphur, which is present in a stabilizing material, such as a polysaccharide. "Dipole—dipole interaction" also refers to intermolecular hydrogen bonding in which a hydrogen atom serves as a bridge between electronegative atoms on separate molecules and in which a hydrogen atom is held to a first molecule by a covalent bond and to a second molecule by electrostatic forces. "Van der Waal's forces" refers to the attractive forces between non-polar molecules that are accounted for by quantum mechanics. Van der Waal's forces are generally associated with momentary dipole moments which are induced by neighboring molecules and which involve changes in electron distribution.

"Hydrogen bonding" refers to an attractive force, or bridge, which may occur between a hydrogen atom which is bonded covalently to an electronegative atom, for example, oxygen, sulfur, or nitrogen, and another electronegative atom. The hydrogen bonding may occur between a hydrogen atom in a first molecule and an electronegative atom in a second molecule (intermolecular hydrogen bonding). Also, the hydrogen bonding may occur between a hydrogen atom and an electronegative atom which are both contained in a single molecule (intramolecular hydrogen bonding).

"Hydrophilic interaction" refers to molecules or portions of molecules which may substantially bind with, absorb and/or dissolve in water. This may result in swelling and/or the formation of reversible gels.

"Hydrophobic interaction" refers to molecules or portions of molecules which do not substantially bind with, absorb and/or dissolve in water. "Biocompatible" refers to materials which are generally not injurious to biological functions and which will not result in any degree of unacceptable toxicity, including allergenic responses and disease states. Generally, the compositions described herein that are administered to patients are biocompatible.

"In combination with" refers to the incorporation of photoactive agents, bioactive agents and/or targeting ligands in stabilizing compositions of the present invention, including emulsions, suspensions, vesicles and the like. Photoactive agents, bioactive agents and/or targeting ligands can be combined with the stabilizing compositions in a variety of ways. For example, photoactive agents, bioactive agents and/or targeting ligands may be associated covalently and/or non-covalently with the compounds or stabilizing materials. In the case of vesicles, photoactive agents, bioactive agents and/or targeting ligands may be entrapped within the internal void of the vesicles. Photoactive agents, bioactive agents and/or targeting ligands may also be integrated within the layer(s) or wall(s) of the vesicle, for example, by being interspersed among stabilizing materials which form or are contained within the vesicle layer(s) or wall(s). In addition, photoactive agents, bioactive agents and/or targeting ligands may be located on the surface of vesicles or non-vesicular stabilizing materials. Photoactive agents, bioactive agents and/or targeting ligands may be concurrently entrapped within the internal void of the vesicle and/or integrated within the layer(s) or wall(s) of the vesicles and/or located on the surface of vesicles or non-vesicular stabilizing materials. Targeting ligands are preferably located on the surface of vesicles or non-vesicular stabilizing materials. In any case, photoactive agents, bioactive agents and/or targeting ligands may interact chemically with the walls of the vesicles, including, for example, the inner and/or outer surfaces of the vesicle and may remain substantially adhered thereto. Such interaction may take the form of, for example, non-covalent association or bonding, ionic interactions, electrostatic interactions, dipole—dipole interactions, hydrogen bonding, van der Waal's forces, covalent association or bonding, crosslinking or any other interaction, as will be apparent to one skilled in the art in view of the present disclosure. In some embodiments, the interaction may result in the stabilization of the vesicle. The photoactive agents, bioactive agents and/or targeting ligands may also interact with the inner or outer surface of the vesicles or non-vesicular stabilizing materials in a limited manner. Such limited interaction would permit migration of the photoactive agents, bioactive agents and/or targeting ligands, for example, from the surface of a first vesicle to the surface of a second vesicle, or from the surface of a first non-vesicular stabilizing material to a second non-vesicular stabilizing material. Alternatively, such limited interaction may permit migration of the photoactive agents, bioactive agents and/or targeting ligands, for example, from within the walls of a vesicle and/or non-vesicular stabilizing material to the surface of a vesicle and/or non-vesicular stabilizing material, and vice versa, or from inside a vesicle or non-vesicular stabilizing material to within the walls of a vesicle or non-vesicular stabilizing material and vice versa.

"Tissue" refers generally to specialized cells which may perform a particular function. The term "tissue" may refer to an individual cell or a plurality or aggregate of cells, for example, membranes, blood or organs. The term "tissue" also includes reference to an abnormal cell or a plurality of abnormal cells, such as cancerous cells. Exemplary tissues include myocardial tissue, including myocardial cells and cardiomyocites, membranous tissues, including endothelium and epithelium, laminae, connective tissue, including interstitial tissue, and tumors.

"Intracellular" or "intracellularly" refers to the area within the plasma membrane of a cell, including the protoplasm, cytoplasm and/or nucleoplasm. "Intracellular delivery" refers to the delivery of photoactive agents, bioactive agents and/or targeting ligands into the area within the plasma membrane of a cell. "Cell" refers to any one of the minute protoplasmic masses which make up organized tissue, comprising a mass of protoplasm surrounded by a membrane, including nucleated and unnucleated cells and organelles. "Receptor" refers to a molecular structure within a cell or on the surface of a cell which is generally characterized by the selective binding of a specific substance. Exemplary receptors include cell-surface receptors for peptide hormones, neurotransmitters, antigens, complement fragments, immunoglobulins and cytoplasmic receptors.

The optoacoustic contrast agents of the present invention may be used to improve and, indeed, make possible optoacoustic imaging. In the prior art, both optical imaging and acoustic imaging (e.g. ultrasound) have been used as separate modalities. In the present invention, ultrasound is used to resonate optoacoustic contrast agents in order to change the optical signals that are emitted therefrom. Using ultrasound, the phase, frequency and temporal modulation of the optical signals are altered to allow precise spatial mapping of the signals using optical imaging and ultrasound imaging. The acoustic and optical information may be integrated to produce a synthetic or hybrid image, i.e., a combined ultrasound and optical image.

The term "photoactive agent" includes fluorescent materials, phosphorescent materials, photosensitizers, chromophores, fluorophores and the like. Photoactive agents that are useful in optoacoustic contrast agents can be chosen from materials having relatively high molar absorptivities, such as greater than about $10^5$ $c^{-1}M^{-1}$, with absorption maxima preferably from about 500 nm to about 1400 nm, more preferably from about 730 nm to about 1300 nm. For photoactive materials used in imaging regions of a patient and/or diagnosing the presence of diseased tissue in a patient, fluorescence quantum yield is a critical consideration and is preferably maximized. Preferred photoactive agents are highly fluorometrically active and yield a high quantum percentage of light when energized at the appropriate wavelength. The photoactive agents may be active in the UV region, the visible region and/or the IR region of the spectrum, preferably in the IR region. For imaging regions of a patient and/or diagnosing the presence of diseased tissue in a patient, the photoactive material is preferably a fluorescent material.

In addition to imaging regions of a patient and/or diagnosing the presence of diseased tissue in a patient, the optoacoustic contrast agents of the present invention may be used for therapeutic applications. Optical therapy or phototherapy suffer from the same limitations as optical imaging, including poor penetration and signal diffusion. Moreover, high intensity ultraviolet light can cause skin damage, mutation and necrosis. In the present invention, therapeutic ultrasound is used to externally excite the optoacoustic contrast agents to induce rupture and release of the photoactive agents that have been incorporated into the optoacoustic contrast agents. At the release site, appropriate wavelengths of irradiation are applied to induce therapeutic photochemistry. Alternatively, ultrasound induced cavitation may be used to activate or stimulate the photoactive agents. Ultrasound and light energy may also be used at the same time to produce a synergistic effect.

Preferably, the photoactive agent that is used for therapeutic applications is a photosensitizer. Photosensitizers have shown great promise in cancer therapy. See, for example, Peng et al, *Ultrastructural Pathology*, 20:109 (1996), Reddi, *J. Photochem. Photobiol. B: Biol.*, 37:189 (1997), Jori, *J. Photochem. Photobiol. B: Biol.*, 36:87 (1996), Calzavara-Pinton et al, *J. Photochem. Photobiol. B: Biol.*, 36:225 (1996), Gèze et al, *J. Photochem. Photobiol. B: Biol.*, 20:23 (1993) and Spikes, *J. Photochem. Photobiol. B: Biol.*, 6:259 (1990), the disclosures of each of which are hereby incorporated by reference herein in their entirety. Upon application of the appropriate light, photosensitizers can photochemically (e.g., through photooxidation, photoreduction and the like) change into a form that is toxic to the surrounding tissue. For example, following excitation of a photosensitizer to a long-lived excited singlet and/or triplet state, a targeted tumor is destroyed either by the highly reactive singlet oxygen species (a Type II mechanism) and/or by free radical products (a Type I mechanism) generated by quantum energy transfer. Major biological target molecules of the singlet oxygen species and/or free radical products include nucleic acids, enzymes and cell membranes. A secondary therapeutic effect of the present methods involves the release of pathophysiologic products such as prostaglandins, thromboxanes and leukotrienes by tissue exposed to the effects of activated photosensitizers. Thus, it will be apparent to one skilled in the art that careful targeting of the photoactive agents is of paramount importance to achieve therapeutic effects without toxemias.

Irradiation of the photoactive agents, including fluorescent materials and therapeutic photosensitizers, may be applied interstitially, superficially, intravascularly and/or with the aid of light conductors, such as fiber optics. The wavelength and intensity of irradiation to be applied will depend upon the particular photoactive agents being used, since different photoactive agents have different optimal wavelengths of response. Thus, the requisite wavelength and intensity of irradiation may be readily determined by one skilled in the art based upon the particular photoactive agents being used.

Suitable photoactive agents that may be used in the present invention include, for example, fluoresceins, indocyanine green, rhodamine, triphenylmethines, polymethines, cyanines, fullerenes, oxatellurazoles, verdins, rhodins, perphycenes, sapphyrins, rubyrins, cholesteryl 4,4-difluoro-5,7-dimethyl-4-bora-3a,4a-diaza-s-indacene-3-dodecanoate, cholesteryl 12-(N-methyl-N-(7-nitrobenz-2-oxa-1,3-diazol-4-yl)amino)-dodecanate, cholesteryl cis-parinarate, cholesteryl 3-((6-phenyl)-1,3,5-hexatrienyl) phenyl-proprionate, cholesteryl 1-pyrenebutyrate, cholesteryl 1-pyrenedecanoate, cholesteryl 1-pyrenehexanoate, 22-(N-(7-nitrobenz-2-oxa-1,3-diazol-4-yl)amino)-23,24-bisnor-5-cholen-3β-ol, 22-(N-(7-nitrobenz-2-oxa-1,3-diazol-4-yl)amino)-23,24-bisnor-5-cholen-3β-yl cis-9-octadecenoate, 1-pyrenemethyl 3-(hydroxy-22,23-bisnor-5-cholenate, 1-pyrene-methyl 3β-(cis-9-octadecenoyloxy)-22,23-bisnor-5-cholenate, acridine orange 10-dodecyl bromide, acridine orange 10-nonyl bromide, 4-(N,N-dimethyl-N-tetradecylammonium)-methyl-7-hydroxycoumarin) chloride, 5-dodecanoylaminofluorescein, 5-dodecanoyl-aminofluorescein-bis-4,5-dimethoxy-2-nitrobenzyl ether, 2-dodecylresorufin, fluorescein octadecyl ester, 4-heptadecyl-7-hydroxycoumarin, 5-hexadecanoylaminoeosin, 5-hexadecanoylaminofluorescein, 5-octadecanoylaminofluorescein, N-octadecyl-N'-(5-(fluoresceinyl))thiourea, octadecyl rhodamine B chloride, 2-(3-(diphenylhexatrienyl)-propanoyl)-1-hexadecanoyl-sn-glycero-3-phosphocholine, 6-N-(7-nitrobenz-2-oxa-1,3-diazol-4-yl)amino)hexanoic acid, 1-hexadecanoyl-2-(1- pyrenedecanoyl)-sn-glycero-3-phosphocholine, 1,1'-dioctadecyl-3,3,3',3'-tetramethyl-indocarbocyanine perchlorate, 12-(9-anthroyloxy)oleic acid, 5-butyl-4,4-difluoro-4-bora-3a,4a-diaza-s-indacene-3-nonanoic acid, N-(lissamine™ rhodamine B sulfonyl)-1,2-dihexadecanoyl-sn-glycero-3-phosphoethanolamine, triethylammonium salt, phenylglyoxal monohydrate, naphthalene-2,3-dicarboxaldehyde, 8-bromomethyl-4,4-difluoro-1,3,5,7-tetramethyl-4-bora-3a,4a-diaza-s-indacene, o-phthaldialdehyde, lissamine™ rhodamine B sulfonyl chloride, 2 ',7'-difluorofluorescein, 9-anthronitrile, 1-pyrenesulfonyl chloride, 4-(4-(dihexadecylamino)-styryl)-N-methylpyridinium iodide, chlorins, such as chlorin, chlorin e6, bonellin, mono-L-aspartyl chlorin e6, mesochlorin, meso-tetraphenylisobacteriochlorin, and meso-tetraphenylbacteriochlorin, hypocrellin B, purpurins, such as octaethylpurpurin, zinc(II) etiopurpurin, tin(IV) etiopurpurin and tin ethyl etiopurpurin, lutetium texaphyrin, photofrin, metalloporphyrins, protoporphyrin IX, tin protoporphyrin, benzoporphyrin, haematoporphyrin, phthalocyanines, naphthocyanines, merocyanines, lanthanide complexes, silicon phthalocyanine, zinc phthalocyanine, aluminum phthalocyanine, Ge octabutyoxyphthalocyanines, methyl pheophorbide-α-(hexyl-ether), porphycenes, ketochlorins, sulfonated tetraphenylporphines, δ-aminolevulinic acid, texaphyrins, including, for example, 1,2-dinitro-4-hydroxy-5-methoxybenzene, 1,2-dinitro-4-(1-hydroxyhexyl)oxy-5-methoxybenzene, 4-(1-hydroxyhexyl)oxy-5 methoxy-1,2-phenylenediamine, and texaphyrin-metal chelates, including the metals Y(III), Mn(II), Mn(III), Fe(II), Fe(III) and the lanthanide metals Gd(III), Dy(III), Eu(III), La(III), Lu(III) and Tb(III), chlorophyll, carotenoids, flavonoids, bilins, phytochromes, phycobilins, phycoerythrins, phycocyanines, retinoic acids, retinoins, retinates, or combinations of any of the above. One skilled in the art will readily recognize or can readily determine which of the above compounds are, for example, fluorescent materials and/or photosensitizers. Lissamine™ is the trademark for N-ethyl-N-[4-[[4-[ethyl [(3-sulfophenyl)methyl]-amino]phenyl](4-sulfophenyl)-methylene]-2,5-cyclohexadien-1-ylidene]-3-sulfobenzene-methanaminium hydroxide, inner salt, disodium salt and/or ethyl[4-[p[ethyl(m-sulfobenzyl)amino]-α-(p-sulfophenyl)benzylidene]-2,5-cyclohexadien-1-ylidene](m-sulfobenzyl)ammonium hydroxide inner salt disodium salt (commercially available from Molecular Probes, Inc., Eugene, Oreg.).

Other suitable photoactive agents for use in the present invention include those described in U.S. Pat. No. 4,935,498, the disclosure of which is hereby incorporated by reference herein in its entirety, such as a dysprosium complex of 4,5,9,24-tetraethyl-16-(1-hydroxyhexyl)oxy-17-methoxypentaazapentacyclo-(20.2.1.1.sup.3,6.1. sup.8,11.0.sup. 14,19)-heptacosa-1,3,5,7,9,11(27),12,14,16,18,20,22(25),23-tridecaene and dysprosium complex of 2-cyanoethyl-N,N-diisopropyl-6-(4,5,9,24-tetraethyl-17-methoxypentaazapentacyclo-(20.2.1.1 .sup.3,6.1.sup.8,11.0.sup. 14,19)-heptacosa-1,3,5,7,9,11(27), 12,14,16,18,20,22(25),23-tridecaene-16-(1-oxy)hexylphosphoramidite.

Antibody-bound photoactive agents or photosensitizers may be used where an immune response to the presence of the antibody is desired, including those described, for example, by Ebato et al, Anal. Chem., 66:1683–1689 (1994), the disclosure of which is hereby incorporated by reference herein in its entirety.

Still other suitable photoactive agents for use in the present invention include those described, for example, in U.S. Pat. No. 5,214,036 (Allison et al), and U.S. Pat. No. 5,162,519 (Bonnett et al), Canadian Patent Application No. 2,047,969 (Madden), International Publication No. WO 96/23524 (Klaveness et al), Reddi et al, Lasers in Medical Science, 5:339 (1990), Spikes, J. Photochem. Photobiol. B: Biol., 6:259 (199), Jori, J. Photochem. Photobiol. B: Biol., 36:87 (1996), Gèze et al, J. Photochem. Photobiol. B: Biol., 20:23 (1993), Calzavara-Pinton et al, J. Photochem. Photobiol. B: Biol., 36: 225 (1996), Peng et al, Ultrastructural Pathology, 20:109 (1996), and Reddi, J. Photochem. Photobiol. B: Biol., 37:189 (1997), the disclosures of each of which are hereby incorporated by reference herein in their entirety. Still other suitable photoactive agents for use in the present invention will be apparent to one skilled in the art in view of the present disclosure.

The photoactive agents are used in the compositions of the present invention in an amount of about 0.01% to about 80% by weight, preferably about 0.1% to about 0% by weight, more preferably about 1% to about 50% by weight, based on the weight of the compositions.

Figure 1A:
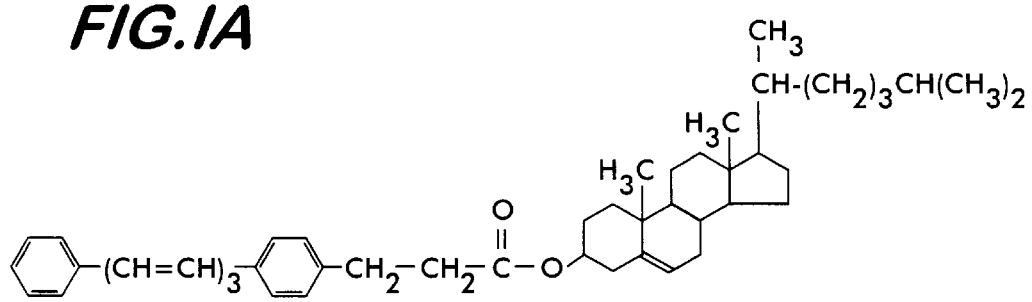
Figure 1A:
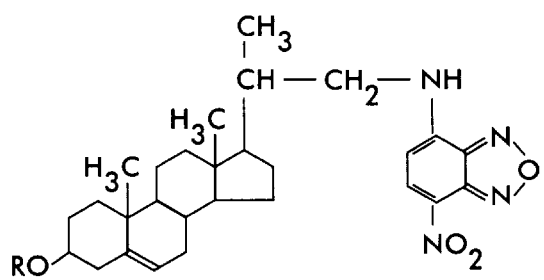
Figure 1A:
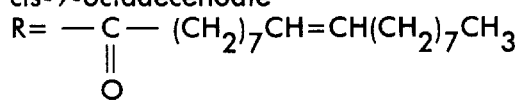
Figure 1A:
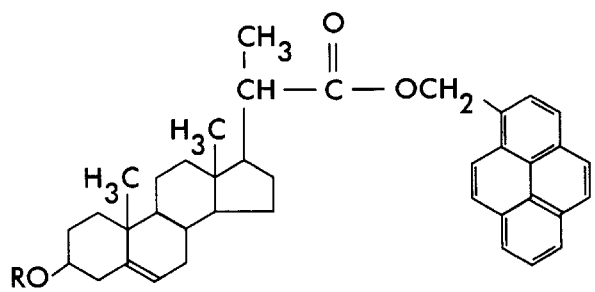
Figure 1A:
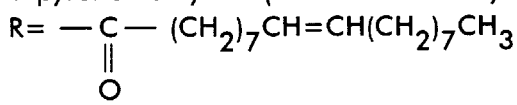

In some embodiments, the photoactive agents may be covalently bonded or conjugated to the stabilizing materials described herein, including lipids, polymers, proteins and surfactants, preferably lipids or surfactants, such as lipid conjugated rhodamine, lipid conjugated fluorescein, lipid conjugated N-(lissamine-rhodamine-β-sulfonyl), those described in FIGS. 1 and 1A, and those described by MacDonald, J. Biol. Chem., 265(23): 13533–9 (1990), Leenhouts et al, Biochim. Biophys. Acta, 1237(2):121–6 (1995), Ahlers et al, Biophys. J., 63(3):823–38 (1992) and Ebato et al, Anal. Chem., 66(10):1683–9 (1994), the disclosures of which are hereby incorporated by reference herein in their entirety. Alternatively, where a —OH group or —COO⁻ group is at the terminus of the photoactive agent, the photoactive agent may esterify with a lipid.

FIGS. 1 and 1A depict the chemical structures of the following photoactive agents that may be used in the compositions of the present invention: cholesteryl 1-pyrenebutyrate, cholesteryl 1-pyrenehexanoate, and cholesteryl 1-pyrenedecanoate; cholesteryl 12-(N-methyl-N-(7-nitrobenz-2-oxa-1,3-diazol-4-yl)amino)dodecanate; cholesteryl 4,4-difluoro-5,7-dimethyl-4-bora-3a,4a-diaza-s-indacene-3-dodecanoate; cholesteryl cis-parinarate; cholesteryl 3-((6-phenyl)-1,3,5-hexatrienyl) phenylproprionate; 22-(N-(7-nitrobenz-2-oxa-1,3-diazol-4-yl)amino-23,24-bisnor-5-cholen-3β-ol, 22-(N-(7-nitrobenz-2-oxa-1,3-diazol-4-yl)amino-23,24-bisnor-5-cholen-3β-yl cis-9-octadecenoate; 1-pyrenemethyl 3β-hydroxy-22,23-bisnor-5-cholenate, and 1-pyrenemethyl 3β-(cis-9-octadecenoyloxy)-22,23-bisnor-5-cholenate.

Figure 2:
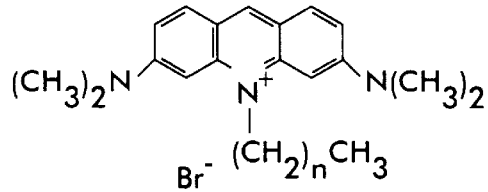
FIGS. 2 and 2A depict the chemical structures of photoactive agents that may be used in the compositions of the present invention.
Figure 2:
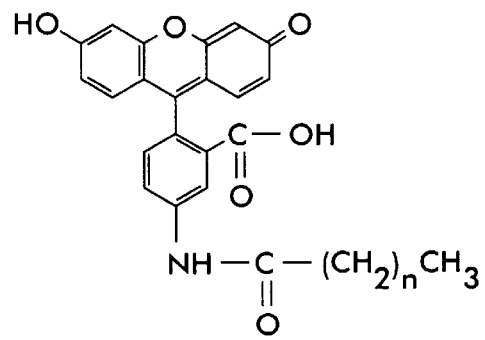
Figure 2:
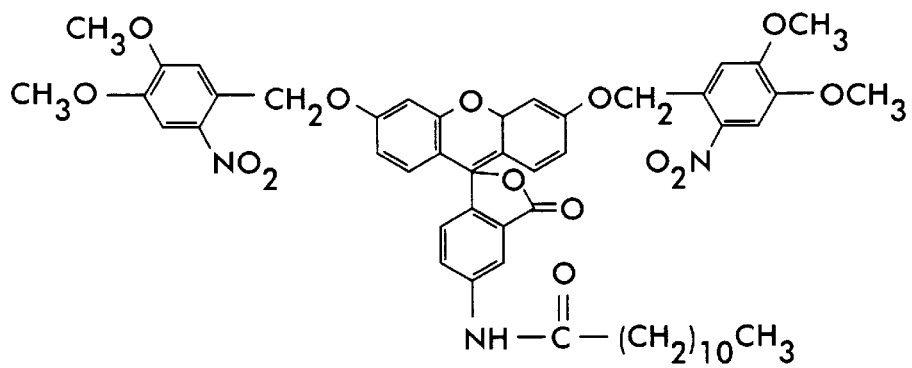
Figure 2:
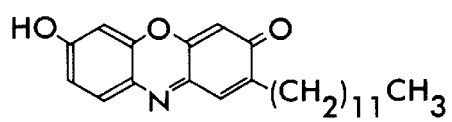
Figure 2A:
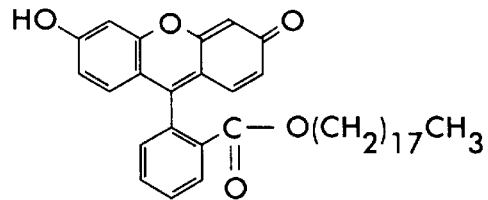
Figure 2A:
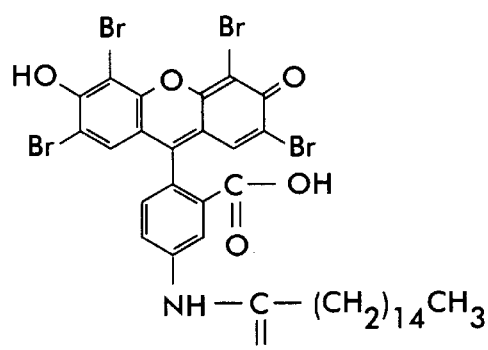
Figure 2A:
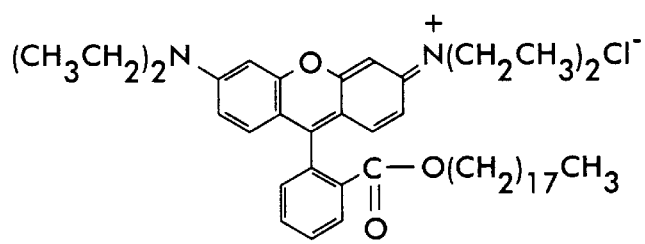
Figure 2A:
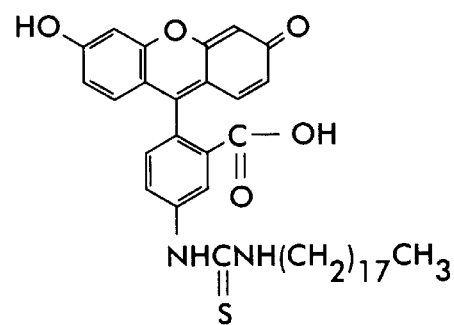

FIGS. 2 and 2A depict the chemical structures of the following photoactive agents that may be used in the compositions of the present invention: acridine orange 10-dodecyl bromide, and acridine orange 10-nonyl bromide; 5-dodecanoylaminofluorescein, 5-hexadecanoylaminofluorescein, and 5-octadecanoylaminofluorescein; 5-dodecanoylaminofluorescein-bis-4,5-dimethoxy-2-nitrobenzyl ether, 2-dodecylresorufin; fluorescein octadecyl ester; 5-hexadecanoylaminoeosin; octadecyl rhodamine B chloride; N-octadecyl-N'-(5-(fluoresceinyl))thiourea.

FIGS. 3–7 exemplify different embodiments of optoacoustic contrast agents of the present invention. One or more of a variety of different photoactive agents may be incorporated into a vesicular membrane(s). Optically active contrast agents that are also highly acoustically active may be produced by incorporating lipophilic, preferably amphipathic photoactive agents into the lipid compositions.

Figure 3:
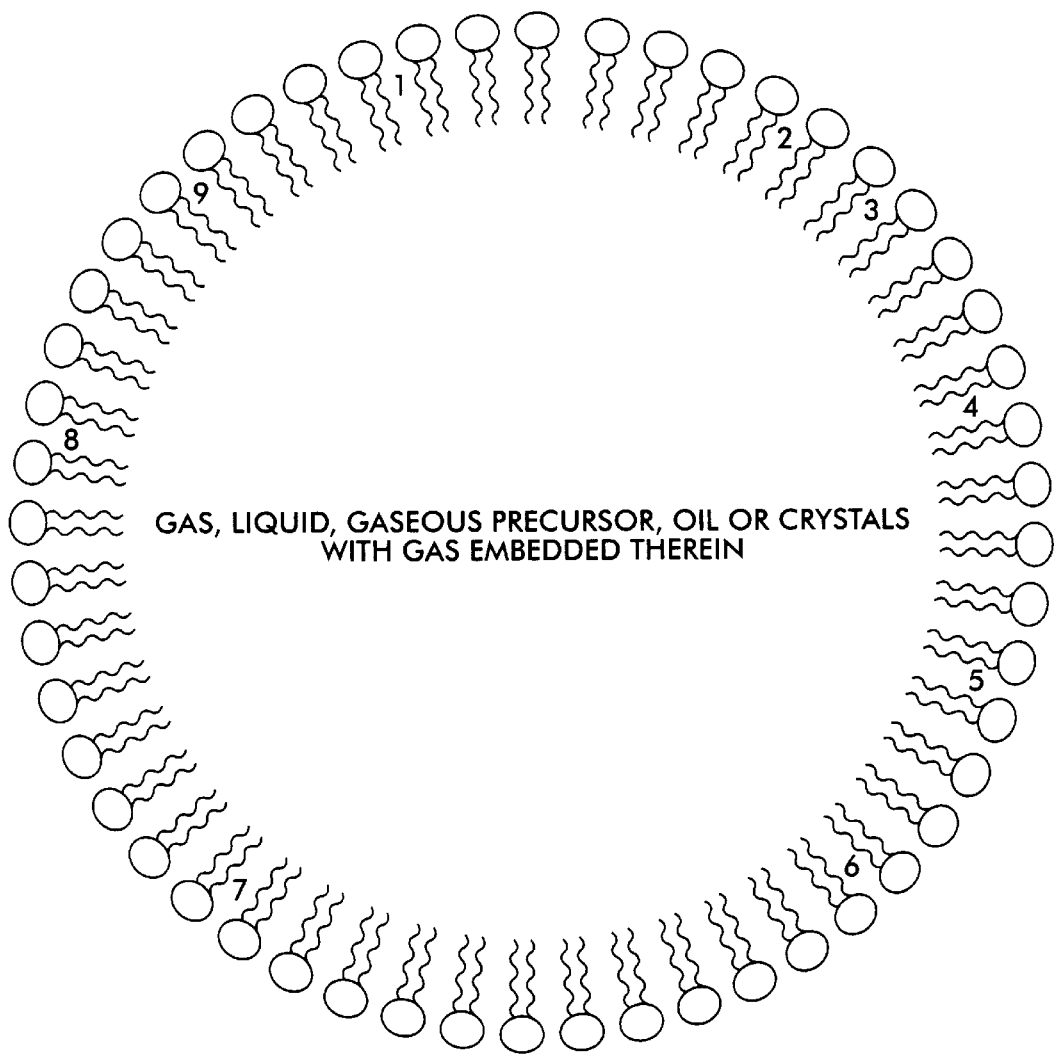
FIG. 3 is an embodiment of a composition of the present invention where photoactive agents are incorporated in the membrane(s) or wall(s) of the vesicle.

The optoacoustic contrast agents of the present invention are preferably flexible, i.e., have elastic membranes, such that the surface characteristics are readily modulated by ultrasound. The typical lipid-based optoacoustic contrast agent is highly elastic and readily deformable by ultrasound. FIG. 3 is an example of an optoacoustic contrast agent where the photoactive agents are located in the wall(s) of the vesicle and where the interior of the vesicle contains a gas, a liquid, a gaseous precursor, oil or crystals with gas embedded therein (e.g., solid porous matrix). The numbers in FIG. 3 represent the following photoactive agents: (1) 5-butyl-4,4-difluoro-4-boro-3a,4a-diaza-s-indacene-3-nonionic acid; (2) N-(lissamine rhodamine B sulfonyl)-1,2-dihexadecanoyl-sn-glycero-3-phosphoethanolamine (triethylammonium salt); (3) 12-(9-anthroyloxy)oleic acid; (4) 2-(3-(diphenylhexatrienyl)-propanoyl)-1-hexadecanoyl-sn-glycero-3-phospho-choline; (5) 5-dodecanoylaminofluorescein; (6) 4-(4-dihexadecyl-amino)styryl)-N-methylpyridinium iodide; (7) 1-hexadecanoyl-2-(-pyrenedecanoyl)-sn-glycero-3-phosphocholine; (8)1,1"-dioctadecyl-3,3,3',3'-tetramethylindocarbocyanine perchlorate; and (9) 6-N-(7-nitrobenz-2-oxa-1,3-diazol-4-yl)amino) hexanoic acid. Other variations of optoacoustic contrast agents can be designed for selected applications.

Figure 4:
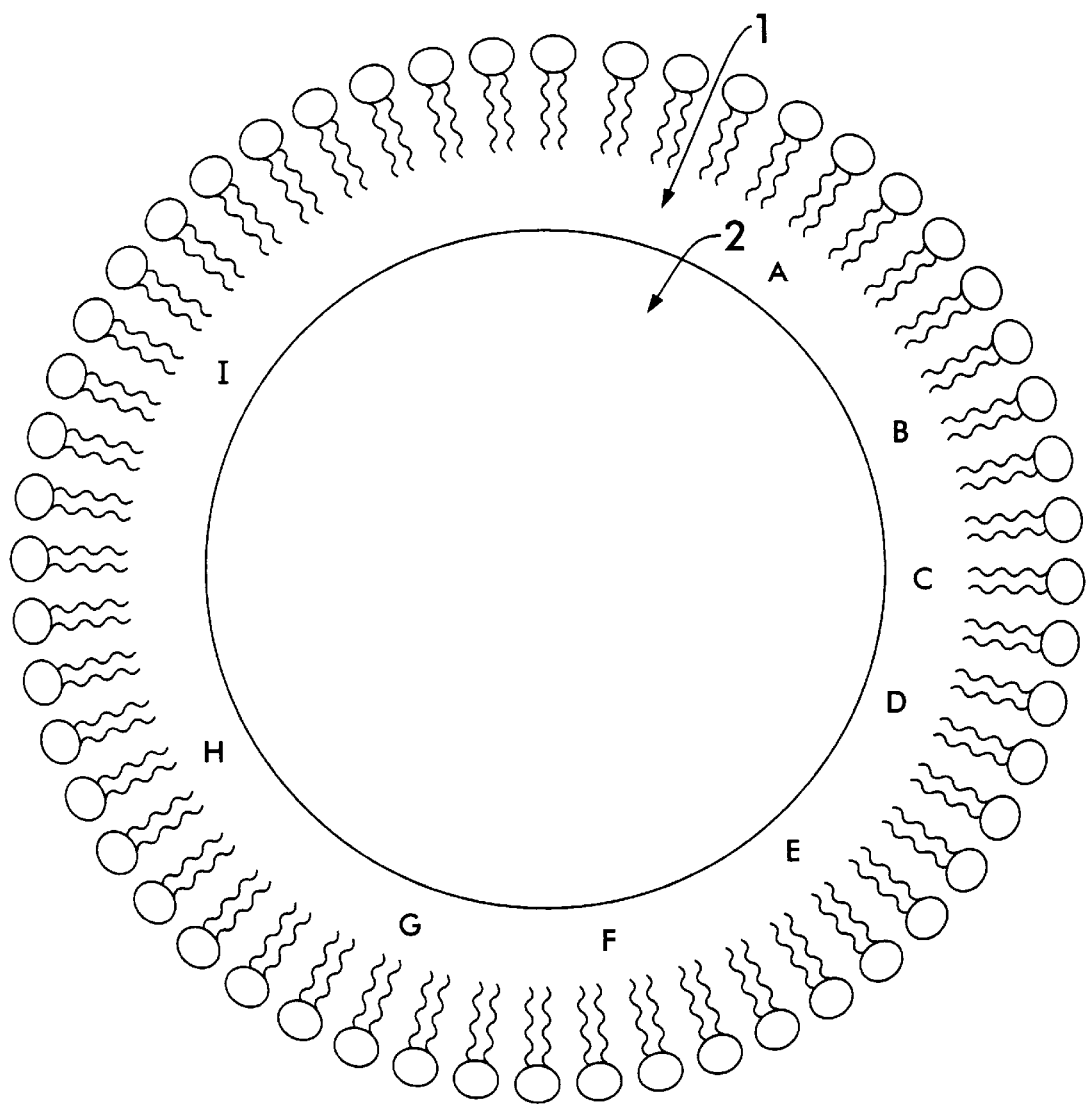
FIG. 4 is an embodiment of a composition of the present invention where photoactive agents are incorporated in an oily hydrophobic mantle (1) in the vesicles, and where a gas phase (2) is incorporated in the interior of the vesicle.

FIG. 4 is an example of an optoacoustic contrast agent of the present invention with an internal oil phase (1). A high concentration of hydrophobic photoactive agents (e.g., A–I) can be loaded into the interior of the oil phase within the vesicle by virtue of the oil phase. Using an internal oil phase, it is possible to prepare an optoacoustic contrast agent with a higher concentration of photoactive agent than lipid-based compositions which may have only a thin layer (e.g., monolayer or bilayer) of lipid surrounding a gas phase. Depending upon the solubility of the photoactive agents in the oil phase, it is possible to construct the optoacoustic contrast agent so that it emits an even higher optical signal. The letters in FIG. 4 represent the following photoactive agents: (A) phenyl-glyoxal monohydrate; (B) naphthalene-2,3-dicarboxaldehyde; (C) 8-bromo-methyl-4,4-difluoro-1,3,5,7-tetramethyl-4-boro-3a,4a-diaza-s-indacene; (D) o-phthaldi-aldehyde; (E) 2-(3-(diphenylhexatrienyl) propanoyl)-1-hexadecanoyl-sn-glycero-3-phosphocholine; (F) lissamine rhodamine B sulfonyl chloride; (G) 2',7'-difluorofluorescein; (H) 9-anthronitrile; (I) 1-pyrenesulfonyl chloride. The optoacoustic contrast agent exemplified in FIG. 4 also contains an internal gas phase (2).

Figure 5:
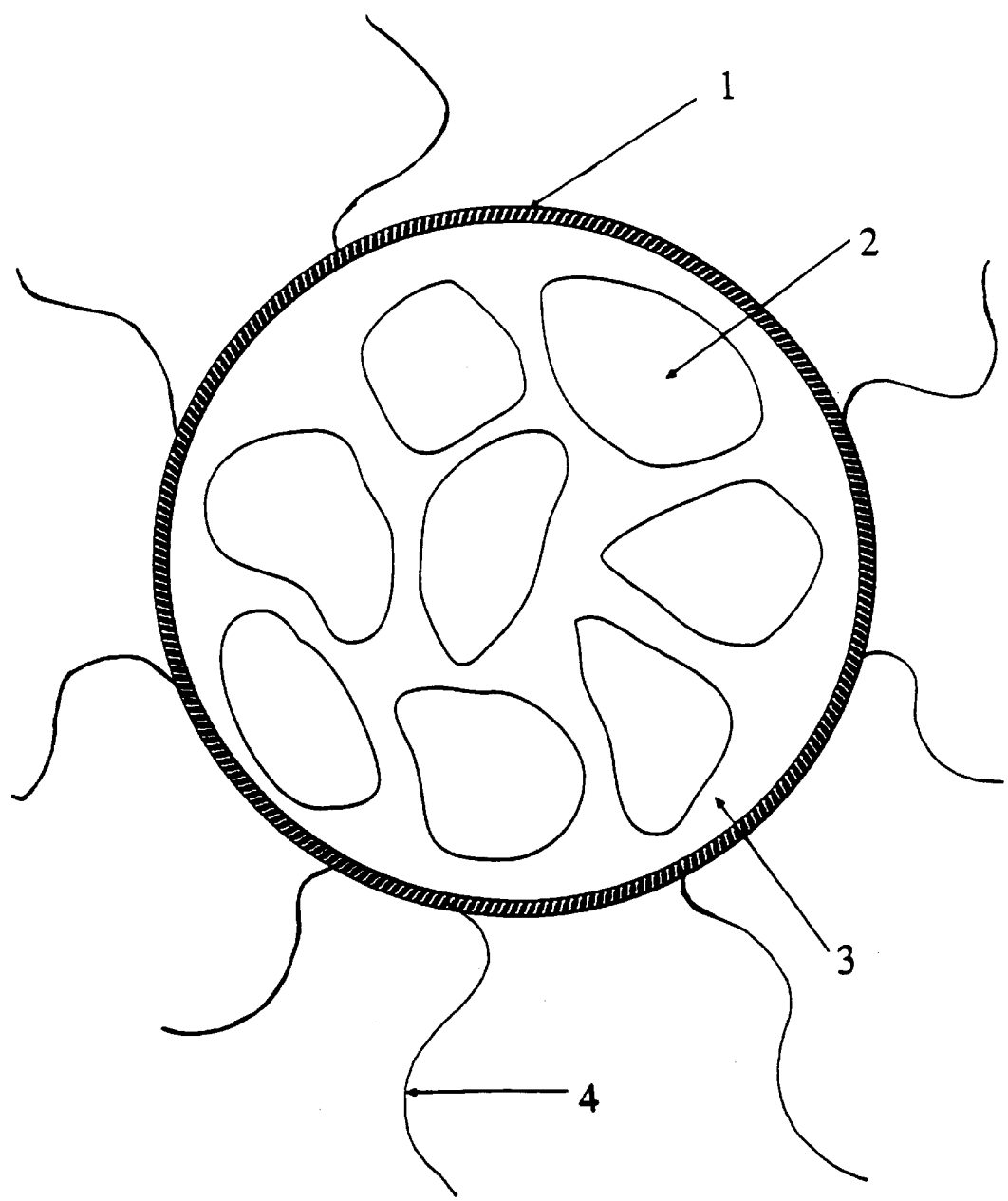
FIG. 5 is an embodiment of a composition of the present invention where photoactive agents are incorporated into solid matrices (2) in the composition. Gas (3) may also be present in the interstices of the composition. The composition may optionally comprise a film of a surfactant, a film forming material or a polymer at the surface (1) so as to maintain the stability of the gas (3) in association with the solid matrices (2). The composition may also optionally comprise a targeting ligand (4).

FIG. 5 provides an example of an optoacoustic contrast agent of the present invention comprising solid particles of photoactive agents (2). In this embodiment, the solid matrix is designed to be porous so that gases (3) can be incorporated into the voids surrounding the solid particles of photoactive agents. The composition may optionally comprise a film of a surfactant, a film forming material or a polymer at the surface (1) to maintain the stability of the gas in association with the solid porous matrix of photoactive agents. Optionally, the composition may also comprise targeting ligands (4).

Figure 6:
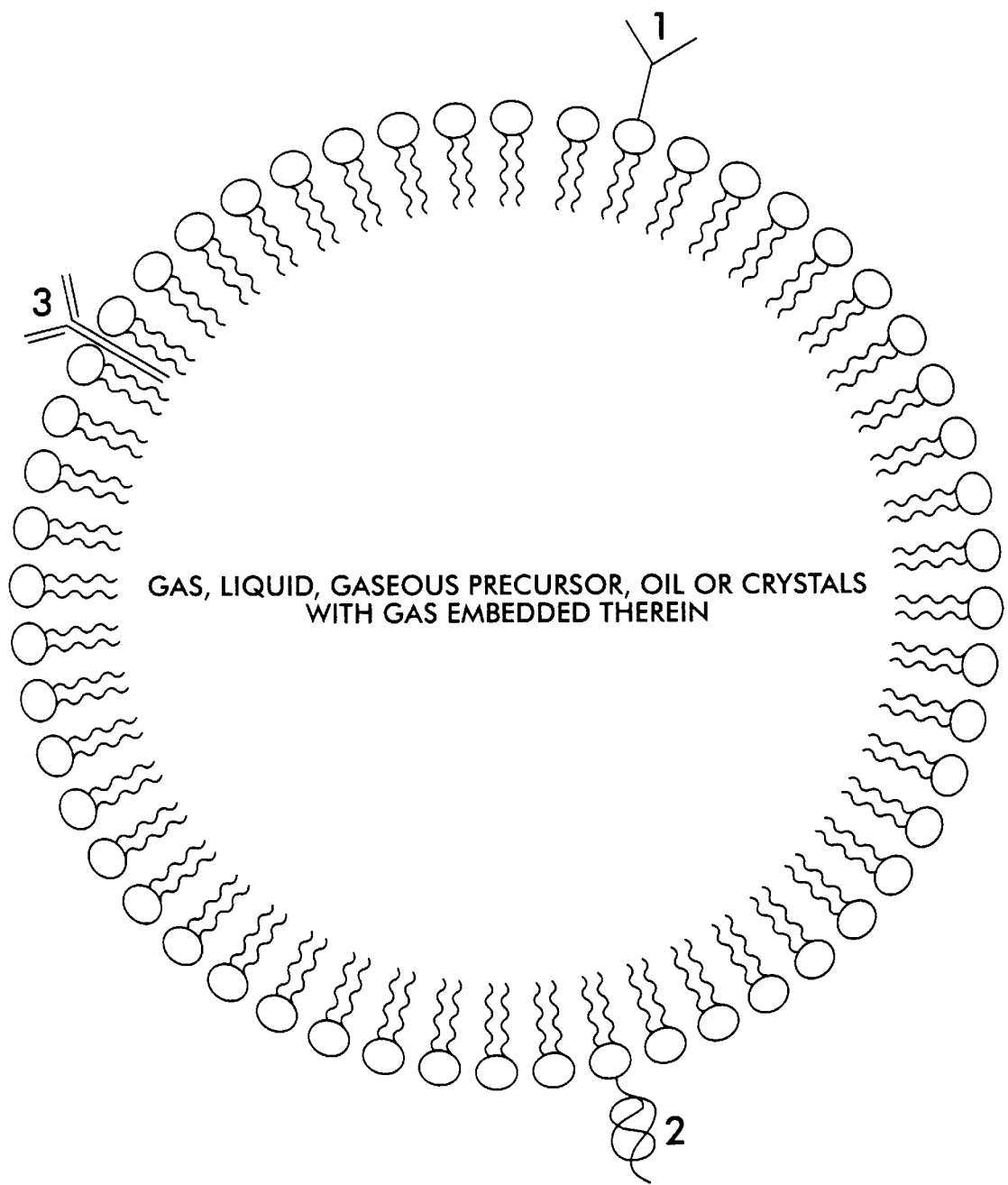
FIG. 6 is an embodiment of a composition of the present invention comprising photoactive agents and a plurality of targeting ligands (1, 2, 3) which provide cellular and tissue specific targeting for the composition.

FIG. 6 is an example of an optoacoustic contrast agent of the present invention comprising photoactive agents and targeting moieties, such as glycolipids (1), lipoproteins (2), and antibodies (3). Targeted optoacoustic contrast agents are useful for diagnostic imaging and for targeting and delivery of therapeutic photoactive agents. Because of the synergy of optoacoustic imaging, the methods of the present invention have superior sensitivity and contrast resolution than either technique alone (e.g., optical or ultrasound imaging). The sensitivity and accuracy are enhanced for detection of selected cells, tissue and subcellular targets with the new imaging technique of the present invention.

Figure 7:
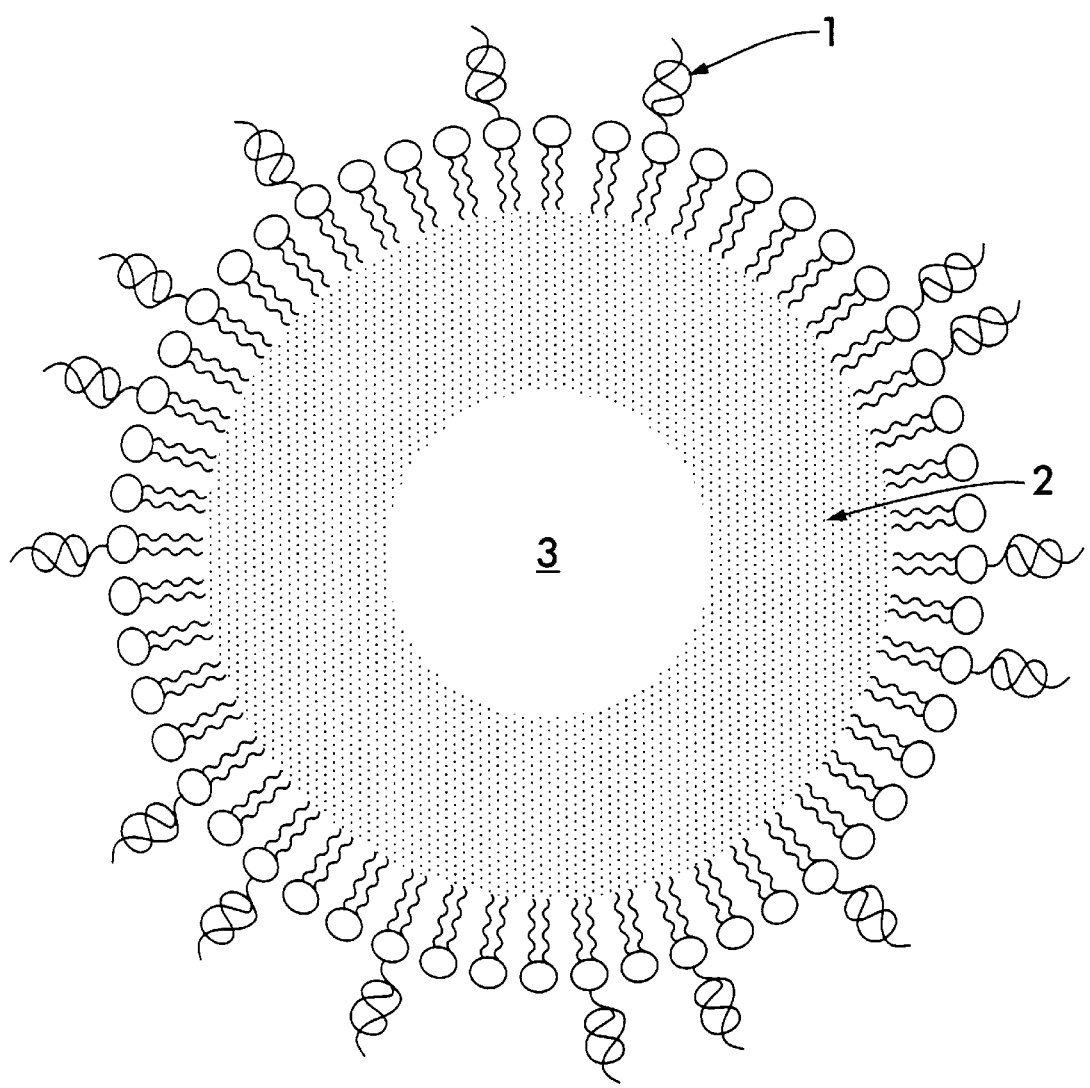
FIG. 7 is an embodiment of a composition of the present invention comprising a region for entrapment of photoactive agents (2), a gas (3), and targeting ligands covalently conjugated to lipids (1) which provide cellular and tissue specific targeting for the composition.

FIG. 7 is an embodiment of a composition of the present invention comprising a region for entrapment of photoactive agents (2), a gas (3), and targeting ligands covalently conjugated to lipids (1) which provide cellular and tissue specific targeting for the composition. The region for entrapment of photoactive agents (2) may be, for example, an oily hydrophobic region.

Generally, the size of optoacoustic contrast agents will depend on two factors. First, a consideration of echogenicity and ability to flow through arterioles and venules mandates that particle size be less than about 3 $\mu$m, preferably less than about 2 $\mu$m, in diameter for intravenous application. A second aspect of the size criterion is a consequence of the absorption characteristics of the photoactive agents. A range of about 0.06$\lambda$ to about 2.0, (where $\lambda$ is the wavelength of incident light in nm), preferably about $\lambda/2\pi$, is optimal for effective light scattering. Vesicles at sizes selected for wavelengths above the absorption maxima for blood hemoglobin (e.g., about 600 nm to about 1000 nm) would produce maximally effective scattering.

Without intending to be bound by any theory of invention, as ultrasound interacts with the optoacoustic membrane of the compositions of the invention, the compositions begin to oscillate with the ultrasound frequency. When tandem optical pulses are applied to the region containing the optoacoustic contrast agents, the optical signals emitted by the acoustically active contrast agents are modulated by the ultrasound. To a lesser extent the optical signals applied to the compositions may also modulate the acoustic signals which are reflected from the compositions.

As the optical signals resonating from the compositions are modulated by the ultrasound, the information received from optical transducer elements can be used to determine the precise spatial location of the optical signals. The ultrasound energy may be precisely focused to a position within a millimeter or less of the desired location. The ultrasound energy may be pulsed and if desired varied with respect to both amplitude and frequency. As the ultrasound energy is modulated, so are the optical signals received from the optoacoustic contrast agents. In so doing, a map of acoustic and optical information may be created which enables a high quality image to be obtained from the data.

Figure 8:
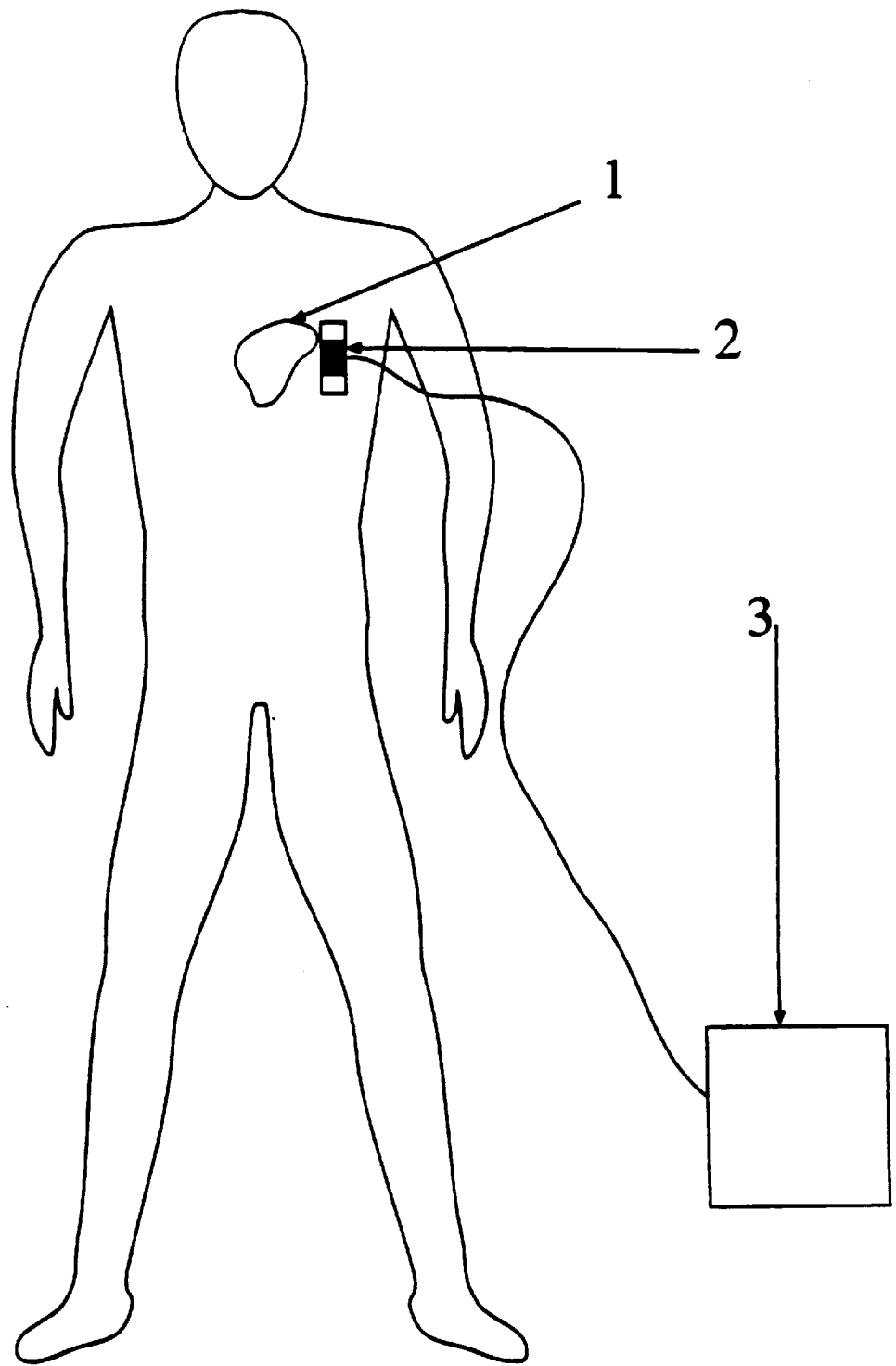
FIG. 8 illustrates one embodiment of the present invention where optoacoustic contrast agents are used for superficial or external therapy, i.e., where the combined ultrasound/optical transducer and scanners (2) are used outside the body and where the region of the patient to be treated (1) is inside the body. The combined ultrasound and optical transducers and scanners (2) are connected to the ultrasound and optical equipment (3).
Figure 9:
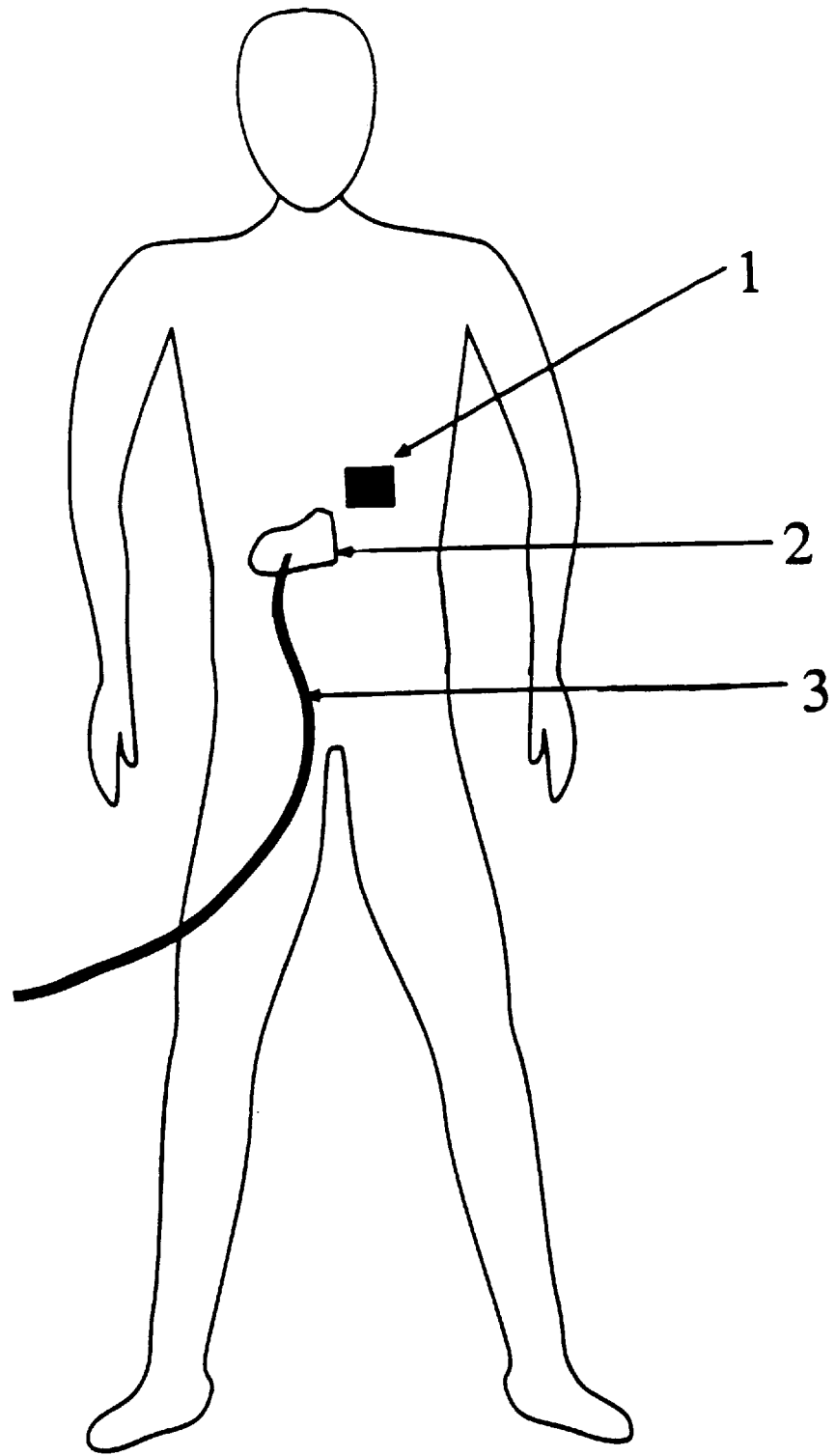
FIG. 9 illustrates one embodiment of the present invention where optoacoustic contrast agents are used in interstitial or surgical therapy, i.e., where the combined ultrasound and optical transducers and scanners (1) are surgically embedded in the body and where the region of the patient to be treated (2) is inside the body. The fiber optic bundle for endoscopic or surgical insertion (3) comes outside the body to the ultrasound and optical equipment (3).

FIGS. 8 and 9 exemplify two applications of the methods of the present invention. FIG. 8 illustrates an embodiment of the present invention where optoacoustic contrast agents are used for superficial or external therapy, i.e., where the combined ultrasound and optical transducers and scanners (2) are used outside the body and where the region of the patient to be treated (1) is inside the body. The combined ultrasound and optical transducers and scanners (2) are connected to the ultrasound and optical equipment (3).

FIG. 9 illustrates an embodiment of the present invention where optoacoustic contrast agents are used in interstitial or surgical therapy, i.e., where the combined ultrasound and optical transducers and scanners (1) are surgically included within the body and where the region of the patient to be treated (2) is inside the body. The fiber optic bundle for endoscopic or surgical insertion (3) comes outside the body to the ultrasound and optical equipment (3).

The optoacoustic contrast agents may also be used for oral or rectal applications. These contrast agents are generally used with probes which are equipped with both optical and acoustic elements. Such probes can be used transcutaneously or endoscopically for a variety of diagnostic and therapeutic applications, as will be apparent to one skilled in the art in view of the present disclosure.

In other embodiments, the optoacoustic contrast agents of the present invention may be used in conjunction with catheters or angioplasty balloons that are equipped with optical and/or ultrasound transducer elements.

A wide variety of lipids may be used as stabilizing materials and vesicles in the present invention. The lipids may be of either natural, synthetic or semi-synthetic origin, including for example, fatty acids, fluorinated lipids, neutral fats, phosphatides, oils, fluorinated oils, glycolipids, surface active agents (surfactants and fluorosurfactants), aliphatic alcohols, waxes, terpenes and steroids. Suitable lipids which may be used to prepare the stabilizing materials of the present invention include, for example, fatty acids, lysolipids, fluorinated lipids, phosphocholines, such as those associated with platelet activation factors (PAF) (Avanti Polar Lipids, Alabaster, Ala.), including 1-alkyl-2-acetoyl-sn-glycero 3-phosphocholines, and 1-alkyl-2-hydroxy-sn-glycero 3-phosphocholines, which target blood clots; phosphatidylcholine with both saturated and unsaturated lipids, including dioleoylphosphatidylcholine; dimyristoylphosphatidylcholine; dipentadecanoylphosphatidylcholine; dilauroylphosphatidylcholine; dipalmitoylphosphatidylcholine (DPPC); distearoylphosphatidylcholine (DSPC); and diarachidonylphosphatidylcholine (DAPC); phosphatidylethanolamines, such as dioleoylphosphatidylethanolamine, dipalmitoylphosphatidylethanolamine (DPPE) and distearoylphosphatidylethanolamine (DSPE); phosphatidylserine; phosphatidylglycerols, including distearoylphosphatidyl-glycerol (DSPG); phosphatidylinositol; sphingolipids such as sphingomyelin; glycolipids such as ganglioside GM1 and GM2; glucolipids; sulfatides; glycosphingolipids; phosphatidic acids, such as dipalmitoylphosphatidic acid (DPPA) and distearoylphosphatidic acid (DSPA); palmitic acid; stearic acid; arachidonic acid; oleic acid; lipids bearing polymers, such as chitin, hyaluronic acid, polyvinylpyrrolidone or polyethylene glycol (PEG), also referred to as "pegylated lipids" with preferred lipid bearing polymers including DPPE-PEG (DPPE-PEG), which refers to the lipid DPPE having a PEG polymer attached thereto, including, for example, DPPE-PEG5000, which refers to DPPE having attached thereto a PEG polymer having a mean average molecular weight of about 5000; lipids bearing sulfonated mono-, di-, oligo- or polysaccharides; cholesterol, cholesterol sulfate and cholesterol hemisuccinate; tocopherol hemisuccinate; lipids with ether and ester-linked fatty acids; polymerized lipids (a wide variety of which are well known in the art); diacetyl phosphate; dicetyl phosphate; stearylamine; cardiolipin; phospholipids with short chain fatty acids of about 6 to about 8 carbons in length; synthetic phospholipids with asymmetric acyl chains, such as, for example, one acyl chain of about 6 carbons and another acyl chain of about 12 carbons; ceramides; non-ionic liposomes including niosomes such as polyoxyalkylene (e.g., polyoxyethylene) fatty acid esters, polyoxy-alkylene (e.g., polyoxyethylene) fatty alcohols, polyoxyalkylene (e.g., polyoxyethylene) fatty alcohol ethers, polyoxyalkylene (e.g., polyoxyethylene) sorbitan fatty acid esters (such as, for example, the class of compounds referred to as TWEEN®, including, for example, TWEEN® 20, TWEEN®40 and TWEEN® 80, commercially available from ICI Americas, Inc., Wilmington, Del.), glycerol polyethylene glycol oxystearate, glycerol polyethylene glycol ricinoleate, alkyloxylated (e.g., ethoxylated) soybean sterols, alkyloxylated (e.g., ethoxylated) castor oil, polyoxyethylene-polyoxypropylene polymers, and polyoxyalkylene (e.g., polyoxyethylene) fatty acid stearates; sterol aliphatic acid esters including cholesterol sulfate, cholesterol butyrate, cholesterol isobutyrate, cholesterol palmitate, cholesterol stearate, lanosterol acetate, ergosterol palmitate, and phytosterol n-butyrate; sterol esters of sugar acids including cholesterol glucuronide, lanosterol glucuronide, 7-dehydrocholesterol glucuronide, ergosterol glucuronide, cholesterol gluconate, lanosterol gluconate, and ergosterol gluconate; esters of sugar acids and alcohols including lauryl glucuronide, stearoyl glucuronide, myristoyl glucuronide, lauryl gluconate, myristoyl gluconate, and stearoyl gluconate; esters of sugars and aliphatic acids including sucrose laurate, fructose laurate, sucrose palmitate, sucrose stearate, glucuronic acid, gluconic acid and polyuronic acid; saponins including sarsasapogenin, smilagenin, hederagenin, oleanolic acid, and digitoxigenin; glycerol dilaurate, glycerol trilaurate, glycerol dipalmitate, glycerol and glycerol esters including glycerol tripalmitate, glycerol distearate, glycerol tristearate, glycerol dimyristate, glycerol trimyristate; long chain alcohols including n-decyl alcohol, lauryl alcohol, myristyl alcohol, cetyl alcohol, and n-octadecyl alcohol; 6-(5-cholesten-3β-yloxy)-1-thio-β-D-galactopyranoside; digalactosyldiglyceride; 6-(5-cholesten-3β-yloxy)hexyl-6-amino-6-deoxy-1-thio-β-D-galactopyranoside; 6-(5-cholesten-3β-yloxy)hexyl-6-amino-6-deoxyl-1-thio-α-D-mannopyranoside; 12-(((7'-diethylaminocoumarin-3-yl) carbonyl)methylamino)-octadecanoic acid; N-[12-(((7'-diethylaminocoumarin-3-yl)carbonyl)methylamino)-octadecanoyl]-2-aminopalmitic acid; cholesteryl(4'-trimethylammonio)butanoate; N-succinyldioleoylphosphatidylethanolamine; 1,2-dioleoyl-sn-glycerol; 1,2-dipalmitoyl-sn-3-succinylglycerol; 1,3-dipalmitoyl-2-succinylglycerol; 1-hexadecyl-2-palmitoylglycerophosphoethanolamine and palmitoylhomocysteine, and/or any combinations thereof. In preferred embodiments, the stabilizing materials comprise phospholipids, including one or more of DPPC, DPPE, DPPA, DSPC, DSPE, DSPG, DSPA and DAPC.

Examples of polymerized lipids include unsaturated lipophilic chains, such as alkenyl or alkynyl, containing up to about 50 carbon atoms; phospholipids such as phosphoglycerides and sphingolipids carrying polymerizable groups; and saturated and unsaturated fatty acid derivatives with hydroxyl groups, such as triglycerides of d-12-hydroxyoleic acid, including castor oil and ergot oil. Polymerization may be designed to include hydrophilic substituents such as carboxyl or hydroxyl groups, to enhance dispersability so that the backbone residue resulting from biodegradation is water soluble. Suitable polymerizable lipids are also described, for example, by Klaveness et al, U.S. Pat. No. 5,536,490, the disclosure of which is hereby incorporated by reference herein in its entirety.

Suitable fluorinated lipids include, for example, compounds of the formula:

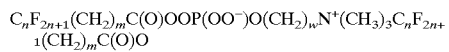

where m is 0 to about 18, n is 1 to about 12; and w is 1 to about 8. Examples of and methods for the synthesis of these, as well as other fluorinated lipids useful in the present invention, are set forth in U.S. application Ser. No. 08/465, 868, filed Jun. 6, 1995; Reiss et al, U.S. Pat. No. 5,344,930; Frezard et al., *Biochem Biophys Acta,* 1192:61–70 (1994); and Frezard et al, *Art. Cells Blood Subs and Immob Biotech.,*

22:1403–1408 (1994), the disclosures of each of which are incorporated herein by reference in their entirety. One specific example of a difluoroacylglycerylphosphatidylcholine, nonafluorinated diacylglycerylphosphatidylcholine, is represented by compound A, below. One skilled in the art will appreciate that analogous fluorinated derivatives of other common phospholipids (e.g., diacylphosphatidylserine, diacylphosphatidylethanolamine, diacylphosphatidylglycerol, diacylphosphatidylglycerol, and the like) as well as fluorinated derivatives of fatty acyl esters and free fatty acids may also function in accordance with the scope of the invention. Additionally lipid based and fluorinated (including perfluorinated) surfactants may be used as stabilizing materials in the present invention.

Exemplary polymerizable and/or fluorinated lipid compounds which may be used in the compositions of the present invention are illustrated below.

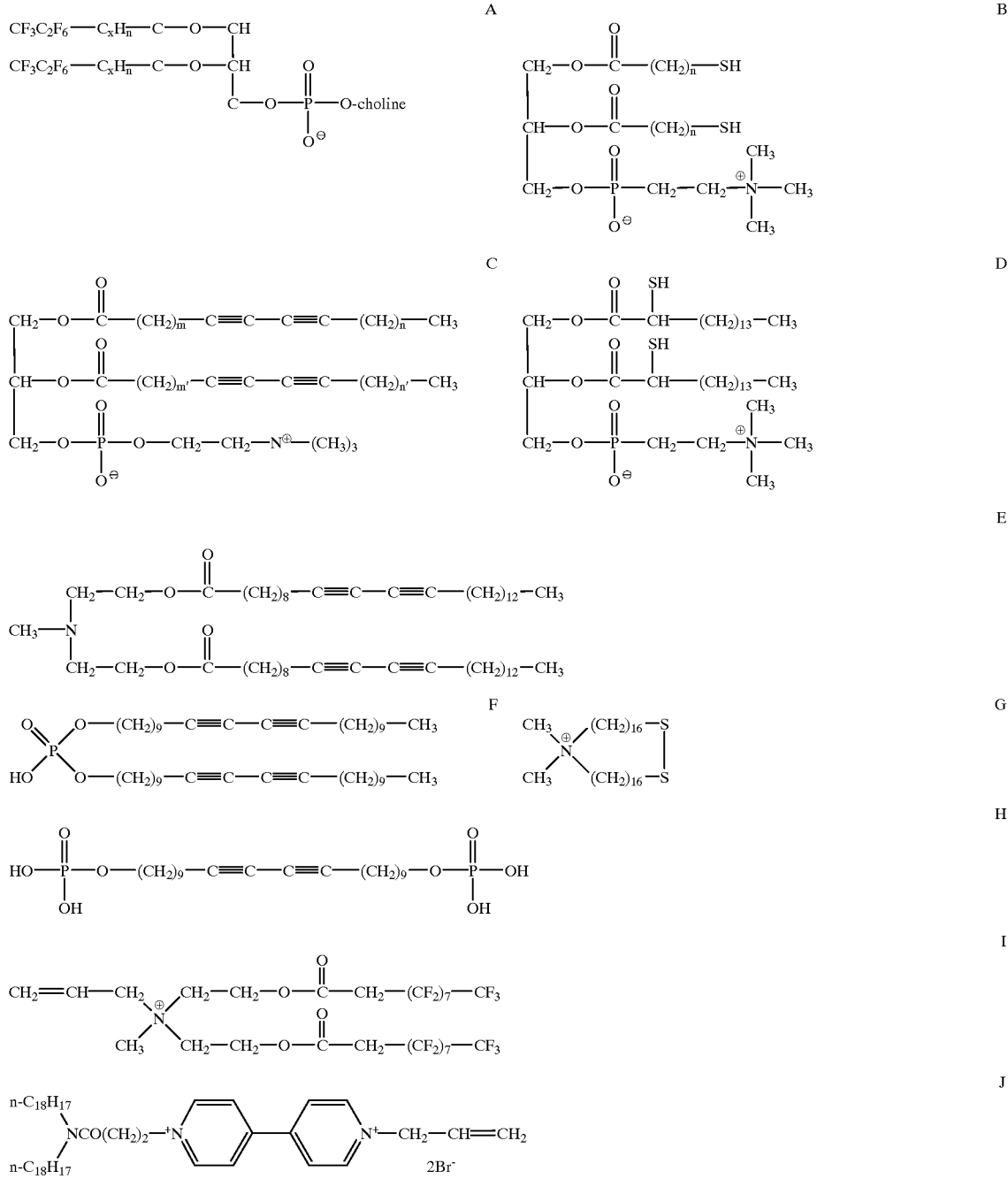

-continued

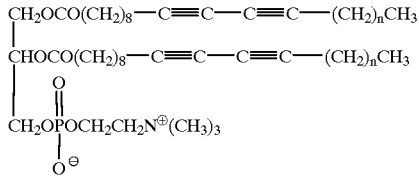
K

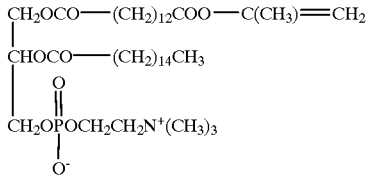
L

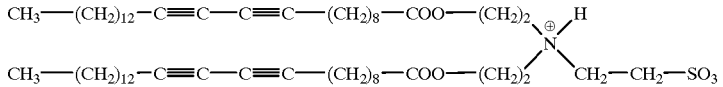
M

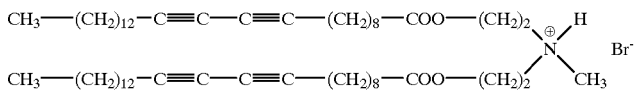
N

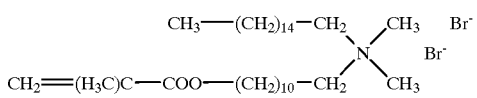
O

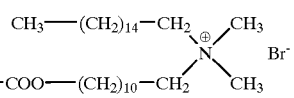
P

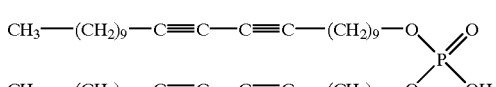
Q

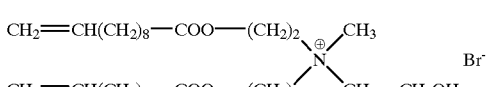
R

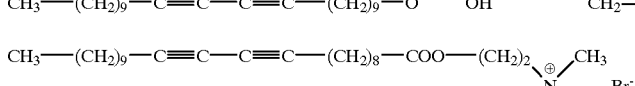
S

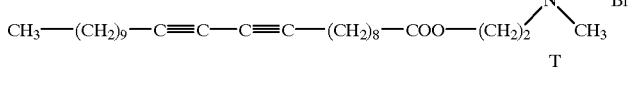
T

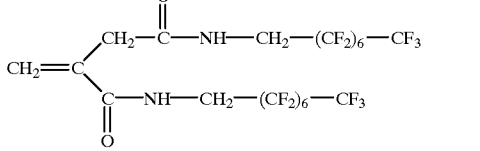
U

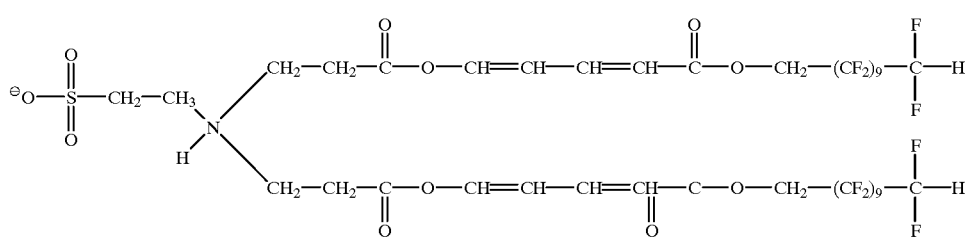
V

In formula A above, x is an integer from about 8 to about 18, and n is 2x. Most preferably x is 12 and n is 24. In formulas B, C, K and L above, m, n, m' and n' are, independently, an integer of from about 8 to about 18, preferably about 10 to about 14.

If desired, the stabilizing material may comprise a cationic lipid, such as, for example, N-[1-(2,3-dioleoyloxy)propyl]-N,N,N-trimethylammonium chloride (DOTMA), 1,2-dioleoyloxy-3-(trimethylammonio)propane (DOTAP); and 1,2-dioleoyl-3-(4'-trimethylammonio)butanoyl-sn-glycerol (DOTB). If a cationic lipid is used in the stabilizing materials, the molar ratio of cationic lipid to non-cationic lipid may be, for example, from about 1:1000 to about 1:100. Preferably, the molar ratio of cationic lipid to non-cationic lipid may be from about 1:2 to about 1:10, with a ratio of from about 1:1 to about 1:2.5 being preferred. Even more preferably, the molar ratio of cationic lipid to non-cationic lipid may be about 1:1.

If desired, aggregates or cochleates may be constructed of one or more charged lipids in association with one or more polymer bearing lipids, optionally in association with one or more neutral lipids. The charged lipids may either be anionic (i.e., negatively charged, that is, carrying a net negative charge) or cationic (i.e., positively charged, that is, carrying a net positive charge). Typically, the lipids are aggregated in the presence of a multivalent species, such as a counter ion, opposite in charge to the charged lipid.

Exemplary anionic lipids include phosphatidic acid and phosphatidyl glycerol and fatty acid esters thereof, amides of phosphatidyl ethanolamine such as anandamides and methanandamides, phosphatidyl serine, phosphatidyl inositol and fatty acid esters thereof, cardiolipin, phosphatidyl ethylene glycol, acidic lysolipids, sulfolipids, and sulfatides, free fatty acids, both saturated and unsaturated, and negatively charged derivatives thereof Phosphatidic acid and phosphatidyl glycerol and fatty acid esters thereof are preferred anionic lipids.

When the charged lipid is anionic, a multivalent (divalent, trivalent, etc.) cationic material may be used to form aggregates. Useful cations include, for example, cations derived from alkaline earth metals, such as beryllium ($Be^{+2}$), magnesium ($Mg^{+2}$), calcium ($Ca^{+2}$), strontium ($Sr^{+2}$), and barium ($Ba^{+2}$); amphoteric ions such as aluminum ($Al^{+3}$), gallium ($Ga^{+3}$), germanium ($Ge^{+3}$), tin ($Sn^{+4}$), and lead ($Pb^{+2}$ and $Pb^{+4}$); transition metals such as titanium ($Ti^{+3}$ and $Ti^{+4}$), vanadium ($V^{+2}$ and $V^{+3}$), chromium ($Cr^{+2}$ and $Cr^{+3}$), manganese ($Mn^{+2}$ and $Mn^{+3}$), iron ($Fe^{+2}$ and $Fe^{+3}$), cobalt ($Co^{+2}$ and $Co^{+3}$), nickel ($Ni^{+2}$ and $N^{+3}$), copper ($Cu^{\circ 2}$), zinc ($Zn^{+2}$), zirconium ($Zr^{+4}$), niobium ($Nb^{+3}$), molybdenum ($Mo^{+2}$ and $Mo^{+3}$), cadmium ($Cd^{+2}$), indium ($In^{+3}$), tungsten ($W^{+2}$ and $W^{+4}$), osmium ($OS^{+2}$, $Os^{+}3$ and $Os^{+4}$), iridium ($Ir^{+2}$, $Ir^{+}3$ and $Ir^{+4}$), mercury ($Hg^{+2}$), and bismuth ($Bi^{+3}$); and rare earth lanthanides, such as lanthanum ($La^{+3}$), and gadolinium ($Gd^{+3}$). Cations in all of their ordinary valence states will be suitable for forming aggregates and crosslinked lipids. Preferred cations include calcium ($Ca^{42}$), magnesium ($Mg^{+2}$), and zinc ($Zn^{+2}$) and paramagnetic cations such as manganese (preferably $Mn^{+2}$) and gadolinium ($Gd^{+3}$). Particularly preferred is calcium ($Ca^{+2}$). Some of the above ions (e.g., lead and nickel) may have associated toxicity and thus may be inappropriate for in vivo use.

When the charged lipid is cationic, an anionic material may be used to form aggregates. Preferably, the anionic material is multivalent, such as, for example, divalent. Examples of useful anionic materials include monatomic and polyatomic anions such as carboxylate ions, sulfide ion, sulfite ions, sulfate ions, oxide ions, nitride ions, carbonate ions, and phosphate ions. Anions of ethylene diamine tetraacetic acid (EDTA), diethylene triamine pentaacetic acid (DTPA), and 1,4,7,10-tetraazocyclododecane-N', N', N", N"'-tetraacetic acid (DOTA) may also be used. Other examples of useful anionic materials include anions of polymers and copolymers of acrylic acid, methacrylic acid, other polyacrylates and methacrylates, polymers with pendant $SO_3H$ groups, such as sulfonated polystyrene, and polystyrenes containing carboxylic acid groups.

Examples of cationic lipids include those listed above. A preferred cationic lipid for formation of aggregates is N-[1-(2,3-dioleoyloxy)propyl]-N,N,N-trimethylammonium chloride (DOTMA). Synthetic cationic lipids may also be used. Synthetic cationic lipids include common natural lipids derivatized to contain one or more basic functional groups.

Examples of lipids which can be so modified include dimethyl-dioctadecylammonium bromide, sphingolipids, sphingomyelin, lysolipids, glycolipids such as ganglioside GM1, sulfatides, glycosphingolipids, cholesterol and cholesterol esters and salts, N-succinyldioleoylphosphatidylethanolamine, 1,2,-dioleoyl-sn-glycerol, 1,3-dipalmitoyl-2-succinylglycerol, 1,2-dipalmitoyl-sn-3-succinylglycerol, 1-hexadecyl-2-palmitoylglycerophosphatidylethanolamine and palmitoylhomocystiene.

Specially synthesized cationic lipids also function in the embodiments of the invention, such as those described in U.S. patent application Ser. No. 08/391,938, filed Feb. 21, 1995, the disclosure of which is hereby incorporated herein by reference in its entirety, and include, for example, N,N'-bis (dodecyaminocarbonylmethylene)-N,N'-bis(β-N,N,N-trimethylammoniumethylami-nocarbonylmethyleneethylenediamine tetraiodide; N,N"-bis-hexadecylaminocarbonylmethylene)-N,N',N"-tris(β-N,N,N-trimethylammoniumethylaminocarbonylmethylenediethyle netriamine hexaiodide; N,N'-bis (dodecylaminocarbonylmethylene)-N,N"-bis(β-N,N,N-trimethylammoniumethylaminocarbonylmethylene)-cyclohexylene-1,4-diamine tetraiodide; 1,1,7,7-tetra-(β-N, N,N,N-tetramethylammoniumethylaminocarbonylmethylene)-3-hexadecylaminocarbonylmethylene-1,3,7-triaazaheptane heptaiodide; and N,N,N'N'-tetraphosphoethanolaminocarbonylmethylene) diethylenetriamine tetraiodide.

In the case of stabilizing materials which contain both cationic and non-cationic lipids, a wide variety of lipids, as described above, may be employed as the non-cationic lipid. Preferably, the non-cationic lipid comprises one or more phospholipids, such as DPPC, DPPE and dioleoylphosphatidylethanolamine. Instead of the cationic lipids listed above, lipids bearing cationic polymers, such as polylysine or polyarginine, as well as alkyl phosphonates, alkyl phosphinates, and alkyl phosphites, may be used in the stabilizing materials.

Saturated and unsaturated fatty acids which may be used in the present stabilizing materials include molecules that contain from about 12 carbon atoms to about 22 carbon atoms, in linear or branched form. Hydrocarbon groups consisting of isoprenoid units and/or prenyl groups can be used. Suitable saturated fatty acids include, for example, lauric, myristic, palmitic, and stearic acids. Suitable unsaturated fatty acids include, for example, lauroleic, physeteric, myristoleic, palmitoleic, petroselinic, and oleic acids. Suitable branched fatty acids include, for example, isolauric, isomyristic, isopalmitic, and isostearic acids.

Other useful lipids or combinations thereof apparent to one skilled in the art are also encompassed by the present invention. For example, carbohydrate-bearing lipids may be used, as described in U.S. Pat. No. 4,310,505, the disclosure of which is hereby incorporated herein by reference in its entirety.

In addition to stabilizing materials and/or vesicles formulated from lipids, embodiments of the present invention may involve vesicles formulated, in whole or in part, from proteins or derivatives thereof. Suitable proteins include, for example, albumin, hemoglobin, (α-1-antitrypsin, α-fetoprotein, aminotransferases, amylase, C-reactive protein, carcinoembryonic antigen, ceruloplasmin, complement, creatine phosphokinase, ferritin, fibrinogen, fibrin, transpeptidase, gastrin, serum globulins, myoglobin, immunoglobulins, lactate dehydrogenase, lipase, lipoproteins, acid phosphatase, alkaline phosphatase, a-1-serum protein fraction, α-2-serum protein fraction, β-protein fraction, γ-protein fraction and γ-glutamyl transferase. Other stabilizing materials and vesicles formulated from proteins that may be used in the present invention are described, for example, in U.S. Pat. Nos. 4,572,203, 4,718,433, 4,774,958, and 4,957,656, the disclosures of which are hereby incorporated herein by reference in their entirety. Other suitable protein-based stabilizing materials and vesicles would be apparent to one of ordinary skill in the art in view of the present disclosure.

In addition to stabilizing materials and/or vesicles formulated from lipids and/or proteins, embodiments of the present invention may also involve stabilizing materials or vesicles formulated from polymers which may be of natural, semi-synthetic (modified natural) or synthetic origin. Polymer denotes a compound comprised of two or more repeating monomeric units, and preferably 10 or more repeating monomeric units. Semi-synthetic polymer (or modified natural polymer) denotes a natural polymer that has been chemically modified in some fashion. Suitable natural polymers include naturally occurring polysaccharides, such as, for example, arabinans, fructans, fucans, galactans, galacturonans, glucans, mannans, xylans (such as, for example, insulin), levan, fucoidan, carrageenan, galatocarolose, pectic acid, pectins, including amylose, pullulan, glycogen, amylopectin, cellulose, dextran, dextrin, dextrose, glucose, polyglucose, polydextrose, pustulan, chitin, agarose, keratin, chondroitin, dermatan, hyaluronic acid, alginic acid, xanthin gum, starch and various other natural homopolymer or heteropolymers, such as those containing one or more of the following aldoses, ketoses, acids or amines: erythrose, threose, ribose, arabinose, xylose, lyxose, allose, altrose, glucose, dextrose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof. Accordingly, suitable polymers include, for example, proteins, such as albumin. Exemplary semi-synthetic polymers include carboxymethyl-cellulose, hydroxymethylcellulose, hydroxypropylmethylcellulose, methylcellulose, and methoxycellulose. Exemplary synthetic polymers include polyphosphazenes, polyalkylenes (e.g., polyethylene), such as, for example, polyethylene glycol (including, for example, the class of compounds referred to as PLURONICS®, commercially available from BASF, Parsippany, N.J.), polyoxyalkylenes (e.g., polyoxyethylene), and polyethylene terephthlate, polypropylenes (such as, for example, polypropylene glycol), polyurethanes (such as, for example, polyvinyl alcohol (PVA), polyvinyl chloride and polyvinyl-pyrrolidone), polyamides including nylon, polystyrene, polylactic acids, fluorinated hydrocarbon polymers, fluorinated carbon polymers (such as, for example, polytetrafluoroethylene), acrylate, methacrylate, and polymethylmeth-acrylate, and derivatives thereof. Preferred are synthetic polymers or copolymers prepared from monomers, such as acrylic acid, methacrylic acid, ethyleneimine, crotonic acid, acrylamide, ethyl acrylate, methyl methacrylate, 2-hydroxyethyl methacrylate (HEMA), lactic acid, glycolic acid, c-caprolactone, acrolein, cyanoacrylate, bisphenol A, epichlorhydrin, hydroxyalkylacrylates, siloxane, dimethylsiloxane, ethylene oxide, ethylene glycol, hydroxyalkyl-methacrylates, N-substituted acrylamides, N-substituted methacrylamides, N-vinyl-2-pyrrolidone, 2,4-pentadiene-1-ol, vinyl acetate, acrylonitrile, styrene, p-amino-styrene, p-amino-benzyl-styrene, sodium styrene sulfonate, sodium 2-sulfoxyethylmethacrylate, vinyl pyridine, aminoethyl methacrylates, 2-methacryloyloxytri-methylammonium chloride, and polyvinylidene, as well polyfunctional crosslinking monomers such as N,N'-methylenebis-acrylamide, ethylene glycol dimethacrylates, 2,2'-(p-phenylenedioxy)diethyl dimeth-acrylate, divinylbenzene, triallylamine and methylenebis(4-phenylisocyanate), including combinations thereof. Preferable polymers include polyacrylic acid, polyethyleneimine, poly-methacrylic acid, polymethylmethacrylate, polysiloxane, polydimethylsiloxane, polylactic acid, poly($\epsilon$-caprolactone), epoxy resin, poly(ethylene oxide), poly(ethylene glycol), and polyamide (nylon) polymers. Preferable copolymers include polyvinylidene-polyacrylonitrile, polyvinylidene-polyacrylonitrile-polymethyl-methacrylate, polystyrene-polyacrylonitrile and poly d-1, lactide co-glycolide poly-mers; most preferably polyvinylidene-polyacrylonitrile. Other suitable monomers and polymers will be apparent to one skilled in the art in view of the present disclosure.

Stabilizing materials and vesicles may be prepared from other materials. The materials may be basic and fundamental, and may form the primary basis for creating or establishing the stabilizing materials. For example, surfactants and fluorosurfactants may be basic and fundamental materials for preparing stabilizing materials and vesicles. On the other hand, the materials may be auxiliary, and act as subsidiary or supplementary agents which may enhance the functioning of the basic stabilizing material(s), or contribute some desired property in addition to that afforded by the basic stabilizing material(s), such as surfactants and/or polymers.

It is not always possible to determine whether a given material is a basic or an auxiliary agent, since the functioning of the material is determined empirically, for example, by the results produced with respect to producing stabilizing materials or vesicles. As an example of how the basic and auxiliary materials may function, it has been observed that the simple combination of a lipid and water or saline when shaken will often give a cloudy solution subsequent to autoclaving for sterilization. Such a cloudy solution may function as a contrast agent, but is aesthetically objectionable and may imply instability in the form of undissolved or undispersed lipid particles. Cloudy solutions may also be undesirable where the undissolved particulate matter has a diameter of greater than about 7 $\mu$m, and especially greater than about 10 $\mu$m. Manufacturing steps, such as sterile filtration, may also be problematic with solutions which contain undissolved particulate matter. Thus, propylene glycol may be added to remove this cloudiness by facilitating dispersion or dissolution of the lipid particles. Propylene glycol may also function as a wetting agent which can improve vesicle formation and stabilization by increasing the surface tension on the vesicle membrane or skin. It is possible that propylene glycol can also function as an additional layer that may coat the membrane or skin of the vesicle, thus providing additional stabilization. The surfactants described in U.S. Pat. Nos. 4,684,479, 5,215,680, and 5,562,893 the disclosures of each of which are hereby incorporated by reference herein in their entirety, may be used as basic or auxiliary stabilizing materials in the present invention.

Oils and fluorinated oils are auxiliary and basic stabilizing materials that may be used in the compositions of the present invention. Suitable oils include, for example, soybean oil, peanut oil, canola oil, olive oil, safflower oil, corn oil, mazola oil, cod liver oil, almond oil, cottonseed oil, ethyl oleate, isopropyl myristate, isopropyl palmitate, mineral oil, myristyl alcohol, octyldodecanol, persic oil, sesame oil, myristyl oleate, cetyl oleate, and myristyl palmitate. Other suitable oils include biocompatible oils consisting of saturated, unsaturated, and/or partially hydrogenated fatty acids, silicon-based oils including, for example, vinyl-terminated, hydride-terminated, silanol-terminated, amino-terminated, epoxy-terminated, carbinol-terminated fluids, and other silicon-based oils such as mercapto-modified silicon fluids and saturated, unsaturated, or aryl-alkyl- or alkyl-aryl-substituted silicon oils, synthetic oils such as triglycerides composed of saturated and unsaturated chains of $C_{12}$–$C_{24}$ fatty acids, such as for example the glycerol triglyceride ester of oleic acid, terpenes, linolene, squalene, squalamine, or any other oil commonly known to be ingestible which is suitable for use as a stabilizing compound in accordance with the teachings herein. The oils described herein may be fluorinated, such as triolein with a fluorine (F$_2$) gas. A "fluorinated oil" refers to an oil in which at least one hydrogen atom of the oil is replaced with a fluorine atom. Preferably, at least two or more of the hydrogen atoms in the oil are replaced with fluorine atoms. Fluorinated triglyceride oils may be prepared by reacting a reactive fluorinated species, such as, for example, a fluorine gas, with unsaturated triglyceride oils to produce the desired fluorinated triglyceride. Other oils described, for example, in U.S. Pat. No. 5,344,930, the disclosure of which is hereby incorporated by reference herein in its entirety.

Additional auxiliary and basic stabilizing materials which may be used in the present invention are described, for example, in U.S. application Ser. No. 08/444,754, filed May 19, 1995, the disclosure of which is hereby incorporated herein by reference in its entirety.

Compounds used to make mixed micelle systems may be used as basic or auxiliary stabilizing materials, and include, for example, sodium dodecyl sulfate, cetylammonium halides, cetylalkylammonium halides, lauryltrimethylammonium bromide (dodecyl-), cetyltrimethylammonium bromide (hexadecyl-), myristyltrimethylammonium bromide (tetradecyl-), alkyldimethylbenzylammonium chloride (where alkyl is C$_{12}$, C$_{14}$ or C$_{16}$,), benzyldimethyldodecylammonium bromide/chloride, benzyldimethyl hexadecylammonium bromide/chloride, benzyldimethyl tetradecylammonium halide (e.g, bromide/chloride, cetyldimethylethylammonium halide bromide/chloride, or cetylpyridinium bromide/chloride.

It may be possible to enhance the stability of stabilizing materials or vesicles by incorporating in the stabilizing materials and/or vesicles at least a minor amount, for example, about 1 to about 10 mole %, based on the total amount of lipid used, of a negatively charged lipid. Suitable negatively charged lipids include, for example, phosphatidylserine, phosphatidic acid, and fatty acids. Without intending to be bound by any theory of operation, it is believed that such negatively charged lipids provide added stability by counteracting the tendency of vesicles to rupture by fusing together. Thus, the negatively charged lipids may act to establish a uniform negatively charged layer on the outer surface of the vesicle, which will be repulsed by a similarly charged outer layer on other vesicles which are proximate thereto. In this way, the vesicles may be less prone to come into touching proximity with each other, which may lead to a rupture of the membrane or skin of the respective vesicles and consolidation of the contacting vesicles into a single, larger vesicle. A continuation of this process of consolidation will, of course, lead to significant degradation of the vesicles.

The lipids used, especially in connection with vesicles, are preferably flexible. This means, in the context of the present invention, that the vesicles can alter their shape, for example, to pass through an opening having a diameter that is smaller than the diameter of the vesicle.

In preferred embodiments, the stabilizing material and/or vesicle composition may contain, in whole or in part, a fluorinated (including perfluorinated) compound. Suitable fluorinated compounds include, for example, fluorinated surfactants, including alkyl surfactants, and fluorinated amphiphilic compounds. A wide variety of such compounds may be employed, including, for example, the class of compounds which are commercially available as ZONYL® fluorosurfactants (the DuPont Company, Wilmington, Del.), including ZONYL® phosphate salts (e.g., [F(CF$_2$CF$_2$)$_{3-8}$C$_2$CH$_2$O]$_{1,2}$P(O)(O$^-$NH$_4^+$)$_{2,1}$) which have terminal phosphate groups and ZONYL® sulfate salts which have terminal sulfate groups (e.g., F(CF$_2$CF$_2$)$_{3-8}$CH$_2$CH$_2$SCH$_2$CH$_2$N$^+$(CH$_3$)$_3$ $^-$OSO$_2$OCH$_3$). Suitable ZONYL® surfactants also include, for example, ZONYL® fluorosurfactants identified as Telomer B, including Telomer B fluorosurfactants which are pegylated (i.e., have at least one polyethylene glycol group attached thereto), also known as PEG-Telomer B, available from the DuPont Company. Other suitable fluorosurfactants are described in U.S. Pat. Nos. 5,276,146, 5,344,930 and 5,562,893, and U.S. application Ser. No. 08/465,868, filed Jun. 6, 1995, the disclosures of each of which are hereby incorporated by reference herein in their entirety.

Other suitable fluorinated surfactants and fluorinated lipid compounds for use as the stabilizing materials in the present invention are described in U.S. application Ser. No. 08/887,215, filed Jul. 2, 1997, the disclosure of which is hereby incorporated by reference herein in its entirety. Such fluorinated surfactants and fluorinated lipids include the compounds of formulas (I), (II), (III), (IV), (IVa), (V), (Va), (VI) and (VII).

For example, the stabilizing material may be a fluorinated fatty acyl derivative, such as, for example, that of formula (I):

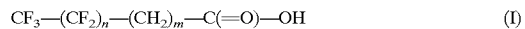

where n is an integer of from about 7 to about 13, preferably from about 9 to about 11; and m is an integer of from 1 to about 4, preferably 1 to about 2.

The stabilizing material may be a PEG Telomer compound of formula (II):

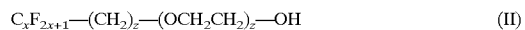

where x is an integer of from about 6 to about 12, preferably from about 8 to about 10, more preferably about 9; and z is an integer of from about 8 to about 20; preferably from about 8 to about 16; still more preferably from about 8 to about 12; even more preferably about 8 to about 10; most preferably about 9.

The stabilizing material may be a fluorinated carbohydrate derivative, such as, for example, that of formula (III):

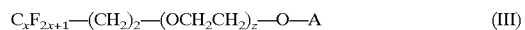

where x is an integer of from about 6 to about 12; preferably from about 8 to about 10; more preferably 9; z is an integer of from about 8 to about 20; preferably from about 8 to about 16; more preferably from about 8 to about 12; still more preferably from about 8 to about 10; most preferably about 9; and A is a monosaccharide or a disaccharide. Suitable monosaccharides and disaccharides include, for example, allose, altrose, glucose, dextrose, mannose, glycerose, gulose, idose, galactose, talose, fructose, psicose, sorbose, rhamnose, tagatose, ribose, arabinose, xylose, lyxose, ribulose, xylulose, erythrose, threose, erythrulose, fucose, sucrose, lactose, maltose, isomaltose, trehalose, cellobiose and the like. Preferably, the monosaccharide or disaccharide is glucose, dextrose, fructose, mannose, galactose, glucosamine, galactosamine, maltose, sucrose or lactose.

The stabilizing material may also be a fluorinated lipophilic derivative, such as, for example, that of formula (IV), which includes the compounds described in U.S. application Ser. No. 08/465,868, filed Jun. 6, 1995, the disclosure of which is hereby incorporated by reference herein in its entirety:

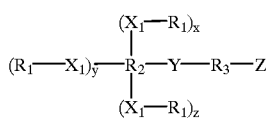

(IV)

where each of x, y and z is independently 0 or 1; each $X_1$ is independently —O—, —S—, —SO—, —SO$_2$—, —NR$_4$—, —C(=X$_2$)—, —C(=X$_2$)—O—, —O—C(=X$_2$)—, —C(=X$_2$)—NR$_4$— or —NR$_4$—C(=X$_2$)—; $X_2$ is O or S; Y is a direct bond or —X$_3$—M(=O)(OR$_5$)$_q$—O— where q is 1 or 2; $X_3$ is a direct bond or —O—; M is P or S; Z is hydrogen, the residue of a hydrophilic polymer, a saccharide residue or —N(R$_6$)$_r$, where r is 2 or 3; each $R_1$ is independently an alkyl group of 1 to about 30 carbon atoms or a fluorinated alkyl group of 1 to about 30 carbon atoms; $R_2$ is a direct bond or an alkylene linking group of 1 to about 10 carbon atoms; $R_3$ is a direct bond or an alkylene diradical of 1 to about 10 carbon atoms; each of $R_4$ and $R_5$ is independently hydrogen or an alkyl group of 1 to about 8 carbon atoms; and each $R_6$ is independently hydrogen, an alkyl group of 1 to about 8 carbon atoms or a residue of a hydrophilic polymer; provided that at least one of x, y and z is 1, at least one of $R_1$ is a fluorinated alkyl group of 1 to about 30 carbon atoms; provided that when $R_1$ is a direct bond, two of x, y and z are each 0.

In formula (IV), each of x, y and z is independently 0 or 1, provided that at least one of x, y and z is 1. In some embodiments, two of x, y and z are each 0. In other embodiments, one of x, y and z is 0 or 1 and the other two of x, y and z are each 1, with one of x, y and z being 0 and the other two of x, y and z being 1 being more preferred. In other embodiments, each of x, y and z is 1.

Each $X_1$ is independently —O—, —S—, —SO—, —SO$_2$—, —NR$_4$—, —C(=X$_2$)—, —C(=X$_2$)—O—, —O—C(=X$_2$)—, —C(=X$_2$)—NR$_4$— or —NR$_4$—C(=X$_2$)—. Preferably, each $X_1$ is independently —O—, —S—, —C(=X$_2$)—, —C(=X$_2$)—O—, —O—C(=X$_2$)—, —C(=X$_2$)—NR$_4$— or —NR$_4$—C(=X$_2$)—. More preferably, each $X_1$ is independently —C(=X$_2$)—O— or —O—C(=X$_2$)—, most preferably —C(=X$_2$)—O—.

Each $X_2$ is O or S, preferably O.

Y is a direct bond or —X$_3$—M(=O)(OR$_5$)q—O—, where q is 1 or 2. Preferably, Y is —X$_3$—M(=O)(OR$_5$)$_q$—O—. M is P or S, preferably P. $X_3$ is a direct bond or —O—, preferably, a direct bond.

Z is hydrogen atom, the residue of a hydrophilic polymer, a saccharide residue or —N(R$_6$)$_r$, where r is 2 or 3. In preferred embodiments, Z is —N(R$_6$)$_r$.

Each $R_1$ is independently an alkyl group of 1 to about 30 carbon atoms or a fluorinated alkyl group of 1 to about 30 carbon atoms, provided that at least one of $R_1$ is a fluorinated alkyl group of 1 to about 30 carbon atoms. Thus, when only one of x, y and z is 1, $R_1$ is necessarily a fluorinated alkyl group of 1 to about 30 carbon atoms. In preferred embodiments, where one or none of x, y and z is 0, and preferably where one of x, y and z is 0 and the other two of x, y and z are each 1, at least one of $R_1$ is an alkyl group of 1 to about 30 carbon atoms and at least one of $R_1$ is a fluorinated alkyl group of 1 to about 30 carbon atoms. In other embodiments, each $R_1$ is independently a fluorinated alkyl group of 1 to about 30 carbon atoms. When a fluorinated alkyl group of 1 to about 30 carbon atoms, $R_1$ is preferably a polyfluorinated alkyl group of 1 to about 30 carbon atoms, with a perfluorinated alkyl group of 1 to about 30 carbon atoms being more preferred. When a fluorinated alkyl group of 1 to about 30 carbon atoms, $R_1$ is preferably $C_nF_{2n+1}$—(CH$_2$)$_m$—, where n is 1 to about 16, preferably about 9 to about 14, and m is 0 to about 18, preferably 1 to about 10, more preferably 1 to about 4.

$R_2$ is a direct bond or an alkylene linking group of 1 to about 10 carbon atoms, provided that when $R_1$ is a direct bond, two of x, y and z are each 0. Preferably, $R_2$ is a direct bond or an alkylene linking group of 1 to about 4 carbon atoms. More preferably, $R_2$ is an alkylene linking group of about 3 carbons. Even more preferably, $R_2$ is —CH$_2$—CH$_2$—CH$_2$—.

$R_3$ is a direct bond or an alkylene diradical of 1 to about 1 carbons. Preferably, $R_3$ is a direct bond or an alkylene diradical of 1 to about 4 carbon atoms. More preferably, $R_3$ is an alkylene diradical of about 2 carbon atoms. Even more preferably, $R_3$ is —CH$_2$CH$_2$—.

Each of $R_4$ and $R_5$ is independently a hydrogen atom or an alkyl group of 1 to about 8 carbon atoms, preferably of 1 to about 4 carbon atoms. More preferably, each of $R_4$ and $R_5$ is a hydrogen atom.

$R_6$ is a hydrogen atom, an alkyl group of 1 to about 8 carbon atoms or a residue of a hydrophilic polymer. Preferably, $R_6$ is a hydrogen atom or an alkyl group of 1 to about 4 carbon atoms. More preferably, $R_6$ is a hydrogen atom or a methyl group, with a methyl group being even more preferred.

When any symbol appears more than once in a particular formula or substituent, such as, for example, in formula (IV), its meaning in each instance is independent of the other, unless otherwise indicated. This independence of meaning is subject to any of the stated provisos. Also, when each of two or more adjacent symbols is defined as being "a direct bond" to provide multiple, adjacent direct bonds, the multiple and adjacent direct bonds devolve into a single direct bond.

Z and $R_6$ in the definition of Z in formula (IV), can be the residue of a hydrophilic polymer. Exemplary polymers from which Z and/or $R_6$ can be derived include polymers in which the repeating units contain one or more hydroxy groups (polyhydroxy polymers), including, for example, poly(vinyl alcohol); polymers in which the repeating units contain one or more amino groups (polyamine polymers), including, for example, peptides, polypeptides, proteins and lipoproteins, such as albumin and natural lipoproteins; polymers in which the repeating units contain one or more carboxy groups (polycarboxy polymers), including, for example, carboxymethylcellulose, alginic acid and salts thereof, such as sodium and calcium alginate, glycosaminoglycans and salts thereof, including salts of hyaluronic acid, phosphorylated and sulfonated derivatives of carbohydrates, genetic material, such as interleukin-2 and interferon, and phosphorothioate oligomers; and polymers in which the repeating units contain one or more saccharide moieties (polysaccharide polymers), including, for example, carbohydrates. The molecular weight of the polymers from which Z and/or $R_6$ are derived may vary, and is generally about 50 to about 5,000,000, with polymers having a molecular weight of about 100 to about 50,000 being preferred. More preferred polymers have a molecular weight of about 150 to about 10,000, with molecular weights of 200 to about 8,000 being even more preferred.

Preferred polymers from which Z and/or $R_6$ are derived include, for example, poly(ethylene glycol) (PEG), poly (vinylpyrrolidine), polyoxomers, polysorbate and poly(vinyl alcohol), with PEG polymers being particularly preferred. Preferred among the PEG polymers are PEG polymers having a molecular weight of from about 100 to about 10,000. More preferably, the PEG polymers have a molecular weight of from about 200 to about 8,000, with PEG 2,000, PEG 5,000 and PEG 8,000, which have molecular weights of 2,000, 5,000 and 8,000, respectively, being even more preferred. Other suitable hydrophilic polymers, in addition to those exemplified above, will be readily apparent to one skilled in the art based on the present disclosure. Generally, polymers from which Z and/or $R_6$ are derived include polymers that can be incorporated in the fluorinated amphiphilic compounds via alkylation or acylation reactions.

As with the various polymers exemplified above, the polymeric residues can contain functional groups in addition, for example, to those typically involved in linking the polymeric residues to the fluorinated amphiphilic compounds. Such functionalities include, for example, carboxyl, amine, hydroxy and thiol groups. These functional groups on the polymeric residues can be further reacted, if desired, with materials which are generally reactive with such functional groups and which can assist in targeting specific tissues in the body including, for example, diseased tissue. Exemplary materials which can be reacted with the additional functional groups include, for example, proteins, including antibodies, carbohydrates, peptides, glycopeptides, glycolipids, lectins and nucleosides.

In addition to residues of hydrophilic polymers, Z in formula (IV) can be a saccharide residue. Exemplary saccharides from which Z can be derived include, for example, monosaccharides or sugar alcohols, such as erythrose, threose, ribose, arabinose, xylose, lyxose, fructose, sorbitol, mannitol and sedoheptulose, with preferred monosaccharides being fructose, mannose, xylose, arabinose, mannitol and sorbitol; and disaccharides, such as lactose, sucrose, maltose and cellobiose. Other saccharides include, for example, inositol and ganglioside head groups. Other suitable saccharides, in addition to those exemplified above, will be readily apparent to one skilled in the art based on the present disclosure. Generally, saccharides from which Z is derived include saccharides that can be incorporated in the fluorinated amphiphilic compounds via alkylation or acylation reactions.

Preferred fluorinated compounds that are within the scope of formula (IV) are the fluorinated compounds of the formula (IVa):

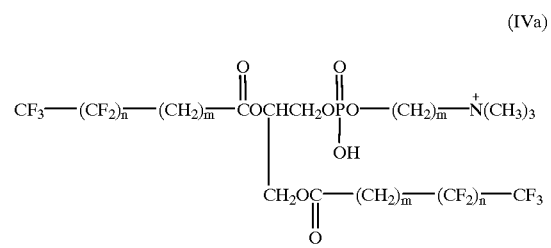

(IVa)

where n is an integer of from about 7 to about 13, preferably from about 9 to about 11; and m is an integer of from about 1 to about 4, preferably 1 to about 2.

The stabilizing material may also be a fluorinated amphiphilic moiety of formula (V):

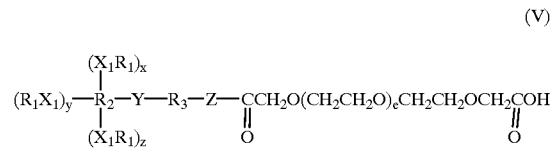

(V)

where $R_1$, $R_2$, $R_3$, $X_1$, Y, Z, x, y and z are as defined in formula (IV), including the preferred embodiments thereof; and where e is an integer of from 1 to about 30, preferably about 3 to about 20, more preferably about 4 to about 16, still more preferably about 4 to about 12, most preferably about 7 to about 9.

In a more preferred embodiment, the compound of formula (V) may be a compound of the formula (Va):

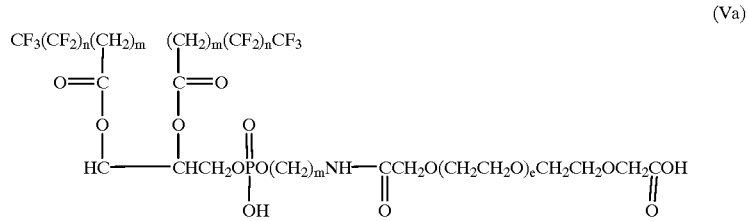

(Va)

where n and m are as defined above in formula (IVa) and where e is as defined above in formula (V).

The stabilizing material may also be a fluorinated fatty acyl derivative, such as, for example, that of formula (VI):

(VI)

Still further, the stabilizing material may be a fluorinated lipophilic derivative, such as, for example, that of formula (VII):

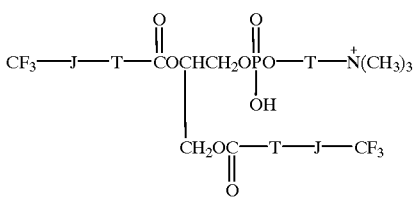

(VII)

In the above formulas (VI) and (VII), J is ($-(C=C)_{p1}-$($CF_2)_{p2}-(C=C)_{p3}-(CF_2)_{p4}-(C=C)_{p5}-(CF_2)_{p6}-(C=C)_{p7}-(CF_2)_{p8}-(C=C)_{p9}-(CF_2)_{p10}-(C=C)_{p11}-(CF_2)_{p12}-(C=C)_{p13}-$,), where p1, p2, p3, p4, p5, p6, p7, p8, p9, p10, p11, p12 and p13 are independently an integer of 0, 1 or 2; provided that the sum of (p1+p2+p3+p4+p5+p6+p7+p8+p9+p10+p11+p12+p13)is an integer of from about 7 to about 13, and provided that at least one of p2, p4, p6, p8, p10 or p12 is an integer of at least 1; and where T is ($-(C=C)_{t1}-(CH_2)_{t2}-(C=C)_{t3}-(CH_2)_{t4}-$), where t1, t2, t3, and t4 are independently an integer of 0, 1 or 2; provided that the sum of (t1+t2+t3+t4) is an integer of from 1 to about 4.

Other suitable fluorinated compounds that may be used as stabilizing materials and/or vesicles are described in U.S. Pat. No. 5,562,893, the disclosure of which is hereby incorporated by reference herein in its entirety. For example, synthetic organic monomeric repeating units may be used to form polymers suitable as stabilizing materials, including hydroxyacids, lactones, lactides, glycolides, acryl containing compounds, aminotriazol, orthoesters, anyhdrides, ester imides, imides, acetals, urethanes, vinyl alcohols, enolketones, and organosiloxanes.

The method of introducing fluorine into any of these materials is known in the art. For example, the introduction of perfluoro-t-butyl moieties is described in U.S. Pat. No. 5,234,680, the disclosure of which is hereby incorporated by reference herein in its entirety. These methods generally involve the reaction of perfluoroalkyl carbanions with host molecules as follows: $(CF_3)_3C^-+R-X \rightarrow (CF_3)_3C-R$, where R is a host molecule and X is a good leaving group, such as bromine, chlorine, iodine or a sulfonato group. After adding a leaving group to the foregoing stabilizing material using methods well known in the art, perfluoro-t-butyl moieties can then be easily introduced to these derivatized stabilizing materials as described above. Additional methods are known in the art for the introduction of trifluoromethyl groups into various organic compounds. For example, trifluoromethyl groups may be introduced by nucleophilic perfluoroalkylation using perfluoroalkyl-trialkylsilanes.

Fluorine can be introduced into any of the aforementioned stabilizing materials or vesicles either in their monomeric or polymeric form. Preferably, fluorine moieties are introduced into monomers, such as fatty acids, amino acids or polymerizable synthetic organic compounds, which are then polymerized for subsequent use as stabilizing materials and/or vesicles.

The introduction of fluorine into stabilizing materials and/or vesicles may also be accomplished by forming vesicles in the presence of a perfluorocarbon gas. For example, when vesicles are formed from proteins, such as human serum albumin in the presence of a perfluorocarbon gas, such as perfluoropropane, using mechanical cavitation, fluorine from the gas phase becomes bound to the protein vesicles during formation. The presence of fluorine in the vesicles and/or stabilizing materials can be detected by NMR of vesicle debris which has been purified from disrupted vesicles. Fluorine can also be introduced into stabilizing materials and/or vesicles using other methods, such as sonication, spray-drying or emulsification techniques.

Another way in which fluorine can be introduced into the stabilizing material and/or vesicle is by using a fluorine-containing reactive compound. The term "reactive compound" refers to compounds which are capable of interacting with the stabilizing material and/or vesicle in such a manner that fluorine moieties become covalently attached to the stabilizing material and/or vesicle. When the stabilizing material is a protein, preferred reactive compounds are either alkyl esters or acyl halides which are capable of reacting with the protein's amino groups to form an amide linkage via an acylation reaction. The reactive compound can be introduced at any stage during vesicle formation, but is preferably added to the gas phase prior to vesicle formation. For example, when vesicles are to be made using mechanical or ultrasound cavitation techniques, the reactive compound can be added to the gas phase by bubbling the gas to be used in the formation of the vesicles (starting gas) through a solution of the reactive compound into the gas phase. The resultant gas mixture, which now contains the starting gas and the reactive compound, is then used to form vesicles. The vesicles are preferably formed by sonication of human serum albumin in the presence of a gas mixture, as described in U.S. Pat. No. 4,957,656, the disclosure of which is hereby incorporated herein by reference in its entirety.

Suitable fluorine containing alkyl esters and acyl halides for use as stabilizing materials and/or vesicle forming materials in the present invention include, for example, diethyl hexafluoroglutarate, diethyl tetrafluorosuccinate, methyl heptafluorobutyrate, ethyl heptafluorobutyrate, ethyl pentafluoropropionate, methyl pentafluoropropionate, ethyl perfluorooctanoate, methyl perfluorooctanoate, nonafluoropentanoyl chloride, perfluoropropionyl chloride, hexafluoroglutaryl chloride and heptafluorobutyryl chloride.

Other fluorine containing reactive compounds can also be synthesized and used as the stabilizing materials and/or vesicle forming materials in the present invention, including, for example, aldehydes, isocyanates, isothiocyanates, epoxides, sulfonyl halides, anhydrides, acid halides and alkyl sulfonates, which contain perfluorocarbon moieties, including $-CF_3$, $-C_2F_5$, $-C_3F_4$ and $-C(CF_3)_3$. These reactive compounds can be used to introduce fluorine moieties into any of the aforementioned stabilizing materials by choosing a combination which is appropriate to achieve covalent attachment of the fluorine moiety.

Sufficient fluorine should be introduced to decrease the permeability of the vesicle to the aqueous environment. This will result in a slower rate of gas exchange with the aqueous environment which is evidenced by enhanced pressure resistance. Although the specific amount of fluorine necessary to stabilize the vesicle will depend on the components of the vesicle and the gas contained therein, after introduction of fluorine the vesicle will preferably contain 0.01 to 20% by weight, and more preferably about 1 to 10% by weight fluorine.

It may be desirable to use a fluorinated liquid, especially a liquid perfluorocarbon or a liquid perfluoroether, which are liquids at the temperature of use, including, for example, the in vivo temperature of the human body, to assist or enhance the stability of the compositions of the present invention. Suitable liquid perfluorocarbons and liquid perfluoroethers include, for example, perfluoroheptane, perfluorooctane, perfluorononane, perfluorodecane, perfluorodecalin, perfluorododecalin, perfluorooctyliodide, perfluorooctylbromide, perfluorotripropylamine, perfluorotributylamine, perfluorobutylethyl ether, bis (perfluoroisopropyl) ether and bis(perfluoropropyl) ether. Among these, perfluorooctylbromide is preferred. Although not intending to be bound by any theory of operation, in the case of vesicle compositions, the fluorinated liquid compound may be situated at the interface between the gas and the membrane or wall surface of the vesicle. Thus, an additional stabilizing layer of fluorinated liquid compound may be formed on the internal surface of the stabilizing composition which may also prevent any gas from diffusing through the vesicle membrane.

Other surfactants which may also be used in the compositions of the present invention are partially fluorinated phosphocholine surfactants. In these fluorinated surfactants, the dual alkyl compounds may be fluorinated at the terminal alkyl chains and the proximal carbons may be hydrogenated.

Still other suitable surfactants that may be used in the compositions of the present invention include, for example, compounds identified as TRITON-X® (e.g., octoxynols; available from Rohm & Haas, Philadelphia, Pa), BRIJ® (e.g., polyoxyethylene ethers; available from ICI-Americas, Wilmington, Del.), and FLUORADS® (e.g., fluorochemical surfactants; available from 3M, St. Paul, Minn.).

Preferred embodiments of the invention may involve vesicles which comprise three components: (1) a neutral lipid, for example, a nonionic or zwitterionic lipid, (2) a negatively charged lipid, and (3) a lipid bearing a stabilizing material, for example, a hydrophilic polymer. Preferably, the amount of the negatively charged lipid will be greater than about 1 mole % of the total lipid present, and the amount of lipid bearing a hydrophilic polymer will be greater than about 1 mole % of the total lipid present. Exemplary and preferred negatively charged lipids include phosphatidic acids. The lipid bearing a hydrophilic polymer will desirably be a lipid covalently linked to the polymer, and the polymer will preferably have a weight average molecular weight of from about 400 to about 100,000. Suitable hydrophilic polymers are preferably selected from the group consisting of polyethylene glycol (PEG), polypropylene glycol, polyvinyl alcohol, and polyvinyl pyrrolidone and copolymers thereof, with PEG polymers being preferred. Preferably, the PEG polymer has a molecular weight of from about 1000 to about 7500, with molecular weights of from about 2000 to about 5000 being more preferred. The PEG or other polymer may be bound to the lipid, for example, DPPE, through a covalent bond, such as an amide, carbamate or amine linkage. In addition, the PEG or other polymer may be linked to a targeting ligand, or other phospholipids, with a covalent bond including, for example, amide, ester, ether, thioester, thioamide or disulfide bonds. Where the hydrophilic polymer is PEG, a lipid bearing such a polymer will be said to be "pegylated." In preferred form, the lipid bearing a hydrophilic polymer may be DPPE-PEG, including, for example, DPPE-PEG5000, which refers to DPPE having a polyethylene glycol polymer of a mean weight average molecular weight of about 5000 attached thereto (DPPE-PEG5000). Another suitable pegylated lipid is distearoyl-phosphatidylethanolamine-polyethylene glycol 5000 (DSPE-PEG5000).

In preferred embodiments, the lipid compositions may include about 77.5 mole % DPPC, 12.5 mole % of DPPA, and 10 mole % of DPPE-PEG5000. Also preferred are compositions which comprise about 80 to about 90 mole % DPPC, about 5 to about 15 mole % DPPA and about 5 to about 15 mole % DPPE-PEG5000. Especially preferred are compositions which comprise DPPC, DPPA and DPPE-PEG5000 in a mole % ratio of 82:10:8, respectively. DPPC is substantially neutral, since the phosphatidyl portion is negatively charged and the choline portion is positively charged. Consequently, DPPA, which is negatively charged, may be added to enhance stabilization in accordance with the mechanism described above. DPPE-PEG provides a pegylated material bound to the lipid membrane or skin of the vesicle by the DPPE moiety, with the PEG moiety free to surround the vesicle membrane or skin, and thereby form a physical barrier to various enzymatic and other endogenous agents in the body whose function is to degrade such foreign materials. The DPPE-PEG may provide more vesicles of a smaller size which are safe and stable to pressure when combined with other lipids, such as DPPC and DPPA, in the given ratios. It is also theorized that the pegylated material, because of its structural similarity to water, may be able to defeat the action of the macrophages of the human immune system, which would otherwise tend to surround and remove the foreign object. The result is an increase in the time during which the stabilized vesicles may function as contrast media.

The terms "stable" or "stabilized" mean that the vesicles may be substantially resistant to degradation, including, for example, loss of vesicle structure or encapsulated photoactive agent, gas, gaseous precursor and/or targeting ligand, for a useful period of time. Typically, the vesicles employed in the present invention have a desirable shelf life, often retaining at least about 90% by volume of its original structure for a period of at least about two to three weeks under normal ambient conditions. In preferred form, the vesicles are desirably stable for a period of time of at least about 1 month, more preferably at least about 2 months, even more preferably at least about 6 months, still more preferably about 18 months, and yet more preferably up to about 3 years. The vesicles described herein, including gas and/or gaseous precursor filled vesicles, may also be stable even under adverse conditions, such as temperatures and pressures which are above or below those experienced under normal ambient conditions.

The stabilizing materials and/or vesicles used in the present invention may be controlled according to size, solubility and heat stability by choosing from among the various additional or auxiliary stabilizing materials described herein. These materials can affect the parameters of the vesicles, especially vesicles formulated from lipids, not only by their physical interaction with the membranes, but also by their ability to modify the viscosity and surface tension of the surface of the vesicle. Accordingly, the vesicles used in the present invention may be favorably modified and further stabilized, for example, by the addition of one or more of a wide variety of (i) viscosity modifiers, including, for example, carbohydrates and their phosphorylated and sulfonated derivatives; polyethers, preferably with molecular weight ranges between 400 and 100,000; and di- and trihydroxy alkanes and their polymers, preferably with molecular weight ranges between 200 and 50,000; (ii) emulsifying and/or solubilizing agents including, for example, acacia, cholesterol, diethanolamine, glyceryl monostearate, lanolin alcohols, lecithin, mono- and di-glycerides, mono-ethanolamine, oleic acid, oleyl alcohol, poloxamer, for example, poloxamer 188, poloxamer 184, poloxamer 181, PLURONICS® (BASF, Parsippany, N.J.), polyoxyethylene 50 stearate, polyoxyl 35 castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan mono-laurate, sorbitan mono-oleate, sorbitan mono-palmitate, sorbitan monostearate, stearic acid, trolamine, and emulsifying wax; (iii) suspending and/or viscosity-increasing agents, including, for example, acacia, agar, alginic acid, aluminum mono-stearate, bentonite, magma, carbomer 934P, carboxymethyl-cellulose, calcium and sodium and sodium 12, carrageenan, cellulose, dextran, gelatin, guar gum, locust bean gum, veegum, hydroxyethyl cellulose, hydroxypropyl methyl-cellulose, magnesium-aluminum-silicate, ZEOLITES®, methylcellulose, pectin, polyethylene oxide, povidone, propylene glycol alginate, silicon dioxide, sodium alginate, tragacanth, xanthan gum, α-d-gluconolactone, glycerol and mannitol; (iv) synthetic suspending agents, such as polyethylene glycol (PEG), polyvinylpyrrolidone (PVP), polyvinylalcohol (PVA), polypropylene glycol (PPG), and polysorbate; and (v) tonicity raising agents which stabilize and add tonicity, including, for example, sorbitol, mannitol, trehalose, sucrose, propylene glycol and glycerol.

The present stabilizing materials and/or vesicles are desirably formulated in an aqueous environment which can induce the stabilizing material (e.g., a lipid because of its hydrophobic-hydrophilic nature) to form vesicles, which may be the most stable configuration which can be achieved in such an environment. The diluents which can be employed to create such an aqueous environment include, for example, water, including deionized water, normal saline, physiological saline, or water containing one or more dissolved solutes, such as salts or sugars.

The present stabilizing materials or compositions preferably comprise a gas and/or a gaseous precursor. The gas provides the stabilizing materials or compositions with enhanced reflectivity, particularly when the gas is entrapped within the stabilizing materials or compositions. Preferred gases and gaseous precursors are inert and biocompatible, and include, for example, air, noble gases, such as helium, rubidium hyperpolarized xenon, hyperpolarized argon, hyperpolarized helium, neon, argon and xenon, carbon dioxide, nitrogen, fluorine, oxygen, sulfur-based gases, such as sulfur hexafluoride and sulfur tetrafluoride, fluorinated gases, including, for example, partially fluorinated gases or completely fluorinated gases, and mixtures thereof. Paramagnetic gases, such as $^{17}O_2$ may also be used in the stabilizing materials and vesicles. Gaseous precursors include materials that are capable of being converted to a gas in vivo.

A wide variety of materials can be used as gases and gaseous precursors in combination with the stabilizing materials and compositions of the present invention. For gaseous precursors, it is only required that the material be capable of undergoing a phase transition to the gas phase upon passing through the appropriate temperature. Suitable gases and/or gaseous precursors for use in the present invention include, for example, hexafluoroacetone, 1,3-dichlorotetrafluoroacetone, tetrafluoroallene, boron trifluoride, 1,2,3-trichloro-2-fluoro-1,3-butadiene, hexafluoro-1,3-butadiene, 1-fluorobutane, perfluorobutane, decafluorobutane, perfluoro-1-butene, perfluoro-2-butene, 2-chloro-1,1,1,4,4,4-hexafluorobutyne, 2-chloro-1,1,1,4,4,4-hexafluoro-2-butene, perfluoro-2-butyne, octafluorocyclobutane, perfluorocyclobutene, perfluorocyclobutane, perfluorocyclopentane, octafluorocyclopentene, perfluorocyclopropane, 1,1,1-trifluorodiazoethane, hexafluorodimethylamine, perfluoroethane, perfluoropropane, perfluoropentane, hexafluoroethane, hexafluoropropylene, 1,1,2,2,3,3,4,4-octafluorobutane, 1,1,1,3,3-pentafluorobutane, octafluoropropane, octafluorocyclopentene, 1,1-dichlorofluoroethane, hexafluoro-2-butyne, octafluoro-2-butene, hexafluorobuta-1,3-diene, perfluorodimethyl-amine, 4-methyl-1,1,1,2-tetrafluoroethane, 1,1,1-trifluoroethane, 1,1,2,2-tetrafluoroethane, 1,1,2-trichloro-1,2,2-trifluoroethane, 1,1,1-trichloro-2,2,2-trifluoroethane, 1,1-dichloro-1,2-difluoroethylene, 1,1-dichloro-1,2,2,2-tetrafluoroethane, 1-chloro-1,1,2,2,2-pentafluoroethane, 1,1-difluoro-2-chloroethane, 1,1-dichloro-2-fluoroethane, dichloro-1,1,2,2-tetrafluoroethane, 1-chloro-1,1,2,2-tetrafluoroethane, 2-chloro-1,1-difluoroethane, 1,1,2-trifluoro-2-chloroethane, 1,2-difluorochloroethane, chloropentafluoroethane, dichlorotrifluoroethane, fluoroethane, nitropentafluoroethane, nitrosopentafluoroethane, perfluoroethylamine, 1,2-dichloro-2,2-difluoroethane, 1,1-dichloro-1,2-difluoroethane, 1,2-dichloro-1,1,3-trifluoropropane, 1,2-difluoroethane, 1,2-difluoroethylene, trifluoromethanesulfonylchloride, trifluoromethanesulfenylchloride, (pentafluorothio)-trifluoromethane, trifluoromethanesulfonylfluoride, bromodifluoronitrosomethane, bromofluoromethane, bromochlorodifluoromethane, bromochlorofluoromethane, bromotrifluoromethane, bromotrifluoroethane, chlorodifluoronitromethane, chlorofluoromethane, chlorotrifluoromethane, chlorodifluoromethane, dibromofluoromethane, dibromodifluoromethane, dichlorodifluoromethane, dichlorofluoromethane, 1-bromoperfluorobutane, difluoromethane, difluoroiodomethane, fluoromethane, perfluoromethane, iodotrifluoromethane, iodotrifluoroethylene, nitrotrifluoromethane, nitrosotrifluoromethane, tetrafluoromethane, trichloro fluoromethane, trifluoromethane, perfluoropent-1-ene, 1,1,1,2,2,3-hexafluoropropane, 2,2-difluoropropane, heptafluoro-1-nitropropane, heptafluoro-1-nitrosopropane, heptafluoro-2-iodopropane, perfluoropropane, hexafluoropropane, 1,1,1,2,3,3-hexafluoro-2,3-dichloropropane, 1-bromo-1,1,2,3,3,3-hexafluoropropane, 1-bromoperfluoropropane, 2-chloropentafluoro-1,3-butadiene, 3-fluoropropane, 3-fluoropropylene, perfluoropropylene, perfluorotetrahydropyran, perfluoromethyltetrahydrofuran, perfluorobutylmethyl ether, perfluoromethyl-n-butyl ether, perfluoromethylisopropyl ether, perfluoromethyl-t-butyl ether, perfluorobutyl ethyl ether, perfluoromethylpentyl ether, 3,3,3-trifluoropropyne, 3-fluorostyrene, sulfur (di)-decafluoride ($S_2F_{10}$), sulfur hexafluoride, selenium hexafluoride, trifluoroacetonitrile, trifluoromethyl peroxide, trifluoromethyl sulfide, tungsten hexafluoride, 1-bromonona-fluorobutane, 1-chloro-1-fluoro-1-bromomethane, 1-bromo-2,4-difluorobenzene, 2-iodo-1,1,1-trifluoroethane, bromine pentafluoride, perfluoro-2-methyl-2-pentene, 1,1,1,3,3-pentafluoropentane, 3-fluorobenzaldehyde, 2-fluoro-5-nitrotoluene, 3-fluorostyrene, 3,5-difluoroaniline, 2,2,2-trifluoroethylacrylate, 3-(trifluoromethoxy)-acetophenone, bis-(perfluoroisopropyl) ether, bis(perfluoropropyl) ether, perfluoroisobutylmethyl ether, perfluoro n-propylethyl ether, perfluorocyclobutyl methyl ether, perfluorocyclopropylethyl ether, perfluoroisopropylmethyl ether, perfluoro n-propylmethyl ether, perfluorodiethyl ether, perfluorocyclopropylmethyl ether, perfluoromethylethyl ether, perfluorodimethyl ether, air, noble gases, such as helium, rubidium hyperpolarized xenon, hyperpolarized argon, hyperpolarized helium, neon, argon, xenon, carbon dioxide, nitrogen, isopropyl acetylene, allene, 1,2-butadiene, 2,3-butadiene, 1,3-butadiene, 2-methyl-1,3-butadiene, butadiene, 2-methylbutane, 1-butene, 2-butene, 2-methyl-1-butene, 3-methyl-1-butene, 4-phenyl-3-butene-2-one, 2-methyl-1-butene-3-yne, butyl nitrate, 1-butyne, 2-butyne, 3-methyl-1-butyne, 2-bromobutyraldehyde, carbonyl sulfide, crotononitrile, cyclobutane, methylcyclobutane, cyclopropane, 3-chlorocyclopentene, dimethylamine, 1,2-dimethyl-cyclopropane, 1,1-dimethylcyclopropane, 1,2-dimethylcyclopropane, ethylcyclopropane, methylcyclopropane, diacetylene, 3-ethyl-3-methyl diaziridine, dimethylethylamine, bis-(dimethylphosphine) amine, dimethyloxonium chloride, 2,3-dimethyl-2-norbomane, 1,3-dioxolane-2-one, 1,1-dichloroethane, 1,1-dichloroethylene, chloroethane, 1,1-dichloro-ethane, methane, chlorodinitromethane, iodomethane, disilanomethane, 2-methylbutane, methyl ether, methyl isopropyl ether, methyllactate, methylnitrite, methylsulfide, methyl vinyl ether, neon, neopentane, nitrogen, nitrous oxide, 1,2,3-nonadecanetricarboxylic acid 2-hydroxytrimethyl ester, 1-nonene-3-yne, 1,4-pentadiene, n-pentane, 4-amino-4-methyl-pentan-2-one, 1-pentene, 2-pentene (cis and trans), 3-bromopent-1-ene, 2-chloropropane, tetrachlorophthalic acid, 2,3,6-trimethyl-piperidine, propane, 1-chloropropane, 1-chloro-propylene, chloro-propylene-(trans), chloropropane-(trans), 2-chloropropylene, 2-amino-propane, 1,2-epoxypropane, propene, propyne, 2,4-diaminotoluene, vinyl acetylene, vinyl ether, ethyl vinyl ether, 5-bromovaleryl chloride, 1-bromoethane, 6-bromo-1-hexene, 2-bromo-2-nitropropane, 2-bromo-5-nitrothiophene, 2-bromopropene, 3-chloro-5,5-dimethyl-2-cylohexene, 2-chloro-2-methylpropane and mixtures thereof One skilled in the art could readily determine whether any of the above compounds are a gas or a gaseous precursor at any given temperature.

Preferred gases and gaseous precursors are compounds which are sparingly soluble in water but which may, in some cases, be liposoluble, such as low molecular weight alkanes and their fluorinated analogs. In preferred embodiments, the gas and gaseous precursor comprise a fluorinated compound, which includes compounds containing one or more fluorine atoms. Preferred compounds contain more than one fluorine atom, with perfluorocarbons being more preferred. Preferred gases and gaseous precursors include, for example, fluorinated carbons, perfluorocarbons, sulfur hexafluoride, perfluoro ethers and combinations thereof.

Preferred perfluorocarbons may be saturated, unsaturated or cyclic, including, for example, perfluoromethane, perfluoroethane, perfluoropropane, perfluorocyclopropane, perfluorobutane, perfluorocyclobutane, perfluoropentane, perfluorocylcopentane, perfluorohexane, perfluorocyclohexane and mixtures thereof. More preferably, the perfluorocarbon is perfluorohexane, perfluoropentane, perfluoropropane or perfluorobutane, with perfluoropropane being particularly preferred.

Preferred ethers include partially or fully fluorinated ethers, preferably having a boiling point of from about 36° C. to about 60° C. Fluorinated ethers are ethers in which one or more hydrogen atoms is replaced by a fluorine atom. Fluorinated ethers may have the general formula $CX_3(CX_2)_n$—O—$(CX_2)_nCX_3$, wherein X is a hydrogen atom, a fluorine atom or another halogen atom provided that at least one of X is a fluorine atom. Preferred fluorinated ethers include, for example, perfluorotetrahydropyran, perfluoro-methyltetrahydrofuran, perfluorobutylmethyl ether (e.g., perfluoro t-butylmethyl ether, perfluoro isobutyl methyl ether, perfluoro n-butyl methyl ether), perfluoropropylethyl ether (e.g., perfluoro isopropyl ethyl ether, perfluoro n-propyl ethyl ether), perfluoro-cyclobutylmethyl ether, perfluorocyclopropyl ethyl ether, perfluoropropyl methyl ether (e.g., perfluoro isopropyl methyl ether, perfluoro n-propyl methyl ether), perfluorodiethyl ether, perfluorocyclopropylmethyl ether, perfluoromethylethyl ether and perfluorodimethyl ether.

Other preferred fluoroether compounds contain between 4 and 6 carbon atoms, and optionally contain one halide ion, preferably $Br^{1-}$. For example, compounds having the structure $C_nF_yH_xOBr$, where n is an integer of from 1 to about 6, y is an integer of from 0 to about 13, and x is an integer of from 0 to about 13, are useful as gaseous precursors. Examples of gaseous precursors having this formula include perfluoropropyl-oxylbromide and 2-bromooxyperfluoropropane.

Other preferable gases are sulfur hexafluoride and selenium hexafluoride. Yet another preferable gas is heptafluoropropane, including 1,1,1,2,3,3,3-heptafluoropropane and its isomer, 1,1,2,2,3,3,3-heptafluoropropane. Other compounds that may be used as gases and/or gaseous precursors include compounds comprising a sulfur atom, including compounds of the formula $CF_3$—$(CF_2)_n$—$SF_5$ or $SF_5$—$(CF_2)_n$—$SF_5$, where n is an integer of from 1 to about 10.

Mixtures of different types of gases and/or gaseous precursors, such as mixtures of a perfluorocarbon or a perfluoro ether and another type of gas and/or gaseous precursor, such as, for example, air or nitrogen, can also be used in the compositions of the present invention. Other suitable gases and gaseous precursors would be apparent to one skilled in the art in view of the present disclosure.

Preferably, the gaseous precursor materials comprise compounds that are sensitive to changes in temperature. Exemplary of suitable gaseous precursors which are sensitive to changes in temperature are the perfluorocarbons and perfluoro ethers. As the skilled artisan will appreciate, a particular perfluorocarbon or perfluoro ether may exist in the liquid state when the stabilizing materials are first made, and are thus used as a gaseous precursor. Alternatively, the perfluorocarbon or perfluoro ether may exist in the gaseous state when the stabilizing materials are made, and are thus used directly as a gas. Whether the perfluorocarbon or perfluoro ether is used as a liquid or a gas generally depends on its liquid/gas phase transition temperature, or boiling point. For example, a preferred perfluorocarbon, perfluoropentane, has a liquid/gas phase transition temperature (boiling point) of 29.5° C. This means that perfluoropentane is generally a liquid at room temperature (about 25° C.), but is converted to a gas within the human body, the normal temperature of which is about 37° C., which is above the transition temperature of perfluoropentane. Thus, under normal circumstances, perfluoropentane is a gaseous precursor. As known to one of ordinary skill in the art, the effective boiling point of a substance may be related to the pressure to which that substance is exposed. This relationship is exemplified by the ideal gas law: PV=nRT, where P is pressure, V is volume, n is moles of substance, R is the gas constant, and T is temperature. The ideal gas law indicates that as pressure increases, the effective boiling point increases also. Conversely, as pressure decreases, the effective boiling point decreases.

Additionally, one skilled in the art will recognize that the phase transition temperature of a compound may be affected by local conditions within the tissue, such as, for example, local pressure (for example, interstitial, interfacial, or other pressures in the region). If the pressure within the tissues is higher than ambient pressure, this will be expected to raise the phase transition temperature. The extent of such effects may be estimated using standard gas law predictions, such as Charles' Law and Boyle's Law. As an approximation, compounds having a liquid-to-gas phase transition temperature between about 30° C. and about 50° C. can be expected to exhibit about a 1° C. increase in the phase transition temperature for every 25 mm Hg increase in pressure. For example, the liquid-to-gas phase transition temperature (boiling point) of perfluoropentane is 29.5° C. at a standard pressure of about 760 mm Hg, but the boiling point is about 30.5° C. at an interstitial pressure of 795 mm Hg.

Other gaseous precursors which are suitable for use in the stabilizing materials and compositions described herein are agents which are sensitive to pH. These agents include materials that are capable of evolving gas, for example, upon being exposed to a pH that is neutral or acidic. Examples of such pH sensitive agents include salts of an acid which is selected from the group consisting of inorganic acids, organic acids and mixtures thereof. Carbonic acid ($H_2CO_3$) is an example of a suitable inorganic acid, and aminomalonic acid is an example of a suitable organic acid. Other suitable inorganic and organic acids would be apparent to one skilled in the art in view of the present disclosure.

Gaseous precursors derived from salts are preferably alkali metal salts, ammonium salts and mixtures thereof. More preferably, the salt is a carbonate, a bicarbonate, a sesquecarbonate, an aminomalonate and mixtures thereof. Suitable gaseous precursor materials which are derived from salts include, for example, lithium carbonate, sodium carbonate, potassium carbonate, lithium bicarbonate, sodium bicarbonate, potassium bicarbonate, magnesium carbonate, calcium carbonate, magnesium bicarbonate, ammonium carbonate, ammonium bicarbonate, ammonium sesquecarbonate, sodium sesquecarbonate, sodium aminomalonate and ammonium aminomalonate. Aminomalonate is well known in the art, and its preparation is described, for example, in Thanassi, *Biochemistry*, 9(3):525 (1970); Fitzpatrick et al., *Inorganic Chemistry*, 13(3):568 (1974); and Stelmashok et al., *Koordinatsionnaya Khimiya*, 3(4):524 (1977), the disclosures of each of these publications are hereby incorporated herein by reference in their entirety.

The gaseous precursor materials may be also photoactivated materials, such as a diazonium ion and aminomalonate. As discussed more fully hereinafter, certain stabilizing materials and/or vesicles, particularly vesicles, may be formulated so that gas is formed at the target tissue or by the action of sound on the stabilizing materials. Examples of gaseous precursors are described, for example, in U.S. Pat. Nos. 5,088,499 and 5,149,319, the disclosures of each of which are hereby incorporated herein by reference in their entirety. Other gaseous precursors, in addition to those exemplified above, will be apparent to one skilled in the art in view of the present disclosure.

The gases and/or gaseous precursors are preferably incorporated in the stabilizing materials and/or compositions irrespective of the physical nature of the composition. Thus, the gases and/or gaseous precursors may be incorporated, for example, in stabilizing materials in which the stabilizing materials are aggregated randomly, such as emulsions, dispersions or suspensions, as well as in vesicles, including vesicles such as cochleates, micelles and liposomes. Incorporation of the gases and/or gaseous precursors in the stabilizing materials and/or compositions may be achieved by a number of methods. For example, gas filled compositions can be produced by shaking or otherwise agitating an aqueous mixture which comprises a gas and/or gaseous precursor and one or more lipids. This promotes the formation of stabilized compositions within which the gas and/or gaseous precursor is encapsulated.

In addition, a gas may be bubbled directly into an aqueous mixture of stabilizing materials and/or vesicle-forming compounds. Alternatively, a gas instillation method can be used as described, for example, in U.S. Pat. Nos. 5,352,435 and 5,228,446, the disclosures of each of which are hereby incorporated herein by reference in their entirety. Other suitable methods for incorporating the gas and/or gaseous precursor in cationic lipid compositions are described in U.S. Pat. No. 4,865,836, the disclosure of which is hereby incorporated herein by reference in its entirety. Other methods would be apparent to one skilled in the art based on the present disclosure. Preferably, the gas may be instilled in the stabilizing materials and/or other compositions after or during the addition of the stabilizing material and/or during formation of vesicles.

It is preferred that the stabilizing materials, and especially the vesicles, be formulated from lipids and optional stabilizing compounds to promote the formation of stable vesicles. Additionally, it is preferred that the stabilizing materials and/or vesicles comprise a highly stable gas as well. The phrase "highly stable gas" refers to a gas which has limited solubility and diffusability in aqueous media. Exemplary highly stable gases include perfluorocarbons since they are generally less diffusible and relatively insoluble in aqueous media. Thus, their use may promote the formation of highly stable vesicles.

Compositions employed herein may also include, with respect to their preparation, formation and use, gaseous precursors that can be activated to change from a liquid or solid into a gas by temperature, pH, light, and energy (such as ultrasound). The gaseous precursors may be made into gas by storing the precursors at reduced pressure. For example, a vial stored under reduced pressure may create a headspace of perfluoro-pentane or perfluorohexane gas, useful for creating a preformed gas prior to injection. Preferably, the gaseous precursors may be activated by temperature. Set forth below is a table listing a series of gaseous precursors which undergo phase transitions from liquid to gaseous states at relatively close to normal body temperature (37° C.) or below, and the size of the emulsified droplets that would be required to form a vesicle of a maximum size of 10 μm.

TABLE 1

Physical Characteristics of Gaseous Precursors and Diameter of Emulsified Droplet to Form a 10 μm Vesicle

| Compound | Molecular Weight | Boiling Point (° C.) | Density | Diameter (μm) of emulsified droplet to make 10 μm vesicle |
|---|---|---|---|---|
| perfluoropentane | 288.04 | 28.5 | 1.7326 | 2.9 |
| 1-fluorobutane | 76.11 | 32.5 | 0.67789 | 1.2 |
| 2-methyl butane | 72.15 | 27.8 | 0.6201 | 2.6 |
| 2-methyl 1-butene | 70.13 | 31.2 | 0.6504 | 2.5 |
| 2-methyl-2-butene | 70.13 | 38.6 | 0.6623 | 2.5 |
| 1-butene-3-yne-2-methyl | 66.10 | 34.0 | 0.6801 | 2.4 |
| 3-methyl-1-butyne | 68.12 | 29.5 | 0.6660 | 2.5 |
| octafluorocyclobutane | 200.04 | −5.8 | 1.48 | 2.8 |
| decafluorobutane | 238.04 | −2 | 1.517 | 3.0 |
| hexafluoroethane | 138.01 | −78.1 | 1.607 | 2.7 |

As noted above, it is preferred to optimize the utility of the stabilizing materials and/or vesicles, especially vesicles formulated from lipids, by using gases of limited solubility. The phrase "limited solubility" refers to the ability of the gas to diffuse out of the vesicles by virtue of its solubility in the surrounding aqueous medium. A greater solubility in the aqueous medium imposes a gradient with the gas in the vesicle such that the gas may have a tendency to diffuse out of the vesicle. A lesser solubility in the aqueous milieu may, on the other hand, decrease or eliminate the gradient between the vesicle and the interface such that diffusion of the gas out of the vesicle may be impeded. Preferably, the gas entrapped in the vesicle has a solubility less than that of oxygen, that is, about 1 part gas in about 32 parts water. See *Matheson Gas Data Book,* 1966, Matheson Company Inc. More preferably, the gas entrapped in the vesicle possesses a solubility in water less than that of air; and even more preferably, the gas entrapped in the vesicle possesses a solubility in water less than that of nitrogen.

The compositions and stabilizing materials of the present invention may also comprise a targeting moiety, such as a targeting ligand. Targeting ligands are preferably associated with the stabilizing materials and/or vesicles covalently or non-covalently. In the case of stabilizing materials, the targeting ligand may be bound, for example, via a covalent or non-covalent bond, to at least one of the lipids, proteins, polymers or surfactants incorporated in the stabilizing materials. Preferably, the targeting ligand is bound to the stabilizing materials and/or vesicles covalently. In the case of lipid compositions which comprise cholesterol, the targeting ligand is preferably bound to the cholesterol substantially only non-covalently, and/or the targeting ligand is bound covalently to a component of the composition, for example, another lipid, such as a phospholipid, other than the cholesterol. If desired, the targeting ligands may also be bound to other stabilizing materials, for example, lipids, polymers, proteins or surfactants, which may be present in the compositions. The targeting ligands which are incorporated in the compositions of the present invention are preferably substances which are capable of targeting receptors and/or tissues in vivo or in vitro. The compositions of the present invention may comprise a single type or class of targeting ligand, as well as two, three, four, five, six, seven or more different types or classes of targeting ligands.

With respect to the targeting of tissue, the targeting ligands are desirably capable of targeting, for example, heart tissue and membranous tissues, including endothelial and epithelial cells. In the case of receptors, the targeting ligands are desirably capable of targeting GPIIbIIIa receptors or lymphocyte receptors, such as T-cells, B-cells or interleukin-2 receptors.

Suitable targeting ligands for use in targeting tissues and/or receptors, include, for example, proteins, including antibodies, antibody fragments, hormones, hormone analogues, glycoproteins, lipoproteins and lectins, peptides, polypeptides, amino acids, sugars, such as saccharides including monosaccharides and polysaccharides, and carbohydrates, glycolipids, vitamins, steroids, steroid analogs, hormones, cofactors, and genetic material, including nucleosides, nucleotides, nucleotide acid constructs and polynucleotides, with peptides being particularly preferred.

Genetic material that may be used as targeting ligands include, for example, nucleic acids, RNA and DNA, of either natural or synthetic origin, recombinant RNA, recombinant DNA, sense RNA, sense DNA, antisense RNA, antisense DNA, hammerhead RNA, ribozymes, hammerhead ribozymes, antigene nucleic acids, single stranded RNA, double stranded RNA, single stranded DNA, double stranded DNA, ribooligonucleotides, deoxyribooligonucleotides, antisense ribooligonucleotides, and antisense deoxyribooligonucleotides, and analogs of any of the above.

Protein A, which is produced by most strains of *Staphylococcus aureus,* is an example of a protein that may be used as a targeting ligand in the present invention. Protein A is commercially available, for example, from Sigma Chemical Co. (St. Louis, Mo.). Protein A may then be used for binding a variety of IgG antibodies. Generally, peptides which are particularly useful as targeting ligands include natural, modified natural, or synthetic peptides that incorporate additional modes of resistance to degradation by vascularly circulating esterases, amidases, or peptidases. One very useful method of stabilization of peptide moieties incorporates the use of cyclization techniques. As an example, the end-to-end cyclization whereby the carboxy terminus is covalently linked to the amine terminus via an amide bond may be useful to inhibit peptide degradation and increase circulating half-life. Additionally, a side chain-to-side chain cyclization or an end-to-side chain cyclization is also particularly useful in inducing stability. In addition, the substitution of an L-amino acid for a D-amino acid in a strategic region of the peptide may offer resistance to biological degradation.

Preferred targeting ligands in the present invention include cell adhesion molecules (CAM), among which are, for example, cytokines, integrins, cadherins, immunoglobulins and selectins, all of which are discussed in detail below.

In connection with the targeting of endothelial cells, suitable targeting ligands include, for example, one or more of the following: oligosaccharides terminating in the Sialyl Lewis X (Slex) sequence: $\alpha$-Sialic-acid $(2\rightarrow 3)$pGal $(1\rightarrow 4)$ [$\alpha$Fuc$(1\rightarrow 3)$]$\beta$Glc-NAc-OR; MAdCAM-1, CD34, GlyCAM-1, PSGL-1, LFA-1; PECAM-1; growth factors, including, for example, basic fibroblast growth factor (bFGF), acidic fibroblast growth factor (aFGF), transforming growth factor-alpha (TGF-$\alpha$), transforming growth factor-beta (TGF-$\beta$), platelet-derived endothelial cell growth factor (PD-ECGF) vascular endothelial growth factor (VEGF) and human growth factor (HGF); angiogenin; tumor necrosis factors, including tumor necrosis factor-alpha (TNF-$\alpha$) and tumor necrosis factor-beta (TNF-$\beta$), and receptor antibodies and fragments thereof to tumor necrosis factor (TNF) receptor 1 or 2 family, including, for example, TNF-R1, TNF-R2, FAS, TNFR-RP, NGF-R, CD30, CD40, CD27, OX40 and 4-1BB; copper-containing polyribonucleotide angiotropin with a molecular weight of about 4,500, as well as low molecular weight non-peptide angiogenic factors, such as 1-butyryl glycerol; the prostaglandins, including, for example, prostaglandin $E_1$ (PGE$_1$) and prostaglandin $E_2$ (PGE$_2$); nicotinamide; adenosine; dipyridamole; dobutamine; hyaluronic acid degradation products, such as, for example, degradation products resulting from hydrolysis of $\beta$ linkages, including hyalobiuronic acid; angiogenesis inhibitors, including, for example, collagenase inhibitors; minocycline; medroxy-progesterone; chitin chemically modified with 6-O-sulfate and 6-O-carboxy-methyl groups; angiostatic steroids, such as tetrahydrocortisol; acidic and basic fibroblast growth factor (FGF, which can bind heparin), and heparin, including low molecular weight fragments of heparin or analogues of heparin, such as, for example, fragments having a molecular weight of about 6,000, admixed with steroids, such as, for example, cortisone or hydrocortisone; angiogenesis inhibitors, including angioinhibin (AGM-1470 an angiostatic antibiotic); platelet factor 4; protamine; sulfated polysaccharide peptidoglycan complexes derived from the bacterial wall of an Arthobacter species; fungal-derived angiogenesis inhibitors, such as fumagillin derived from *Aspergillus fumigatus*; D-penicillamine; gold thiomalate;

thrombospondin; vitamin $D_3$ analogues, including, for example, 1-α, 25-dihydroxy vitamin $D_3$ and a synthetic analogue 22-oxa-1-α, 25-dihydroxy-vitamin $D_3$; interferons, including, for example, α-interferon, β-interferon and γ-interferon; cytokines and cytokine fragments, such as the interleukins, including, for example, interleukin-1 (IL-1, IL-1α, IL-1β, IL-1ra), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), interleukin-13 (IL-13), interleukin-14 (IL-14); erythropoietin; a 20-mer peptide or smaller for binding to receptor or antagonists to native cytokines; granulocyte macrophage colony stimulating factor (GMCSF); $LTB_4$ leukocyte receptor antagonists; simple sulfated polysaccharides, such as cyclodextrins, including α-cyclodextrin, β-cyclodextrin, and γ-cyclodextrin; tetradecasulfate; transferrin; ferritin; platelet factor 4; protamine; Gly-His-Lys complexed to copper; ceruloplasmin; (12R)-hydroxyeicosatrienoic acid; okadaic acid; lectins; antibodies; CD11a/CD18; Very Late Activation Integrins, VLA-11, VLA-2, VLA-3, VLA-4, VLA-5, VLA-6, $β1α7$, $β1α8$, $β1αv$, the LEUCAM family, LFA-1, Mac-1, p150.95, the cytoadhesion family, CD41a, vitronectin receptor, $β_4α_6$, $β_5α_v$, $β_6α_v$, $β_7α_4$, LPAM-1, $β_7α_{IEL}$, $β_8α_8$. Other suitable peptides which may serve as CAM ligands in the present invention include those described in EP 0 727 225 A2, WO 94/07918, WO 94/19024, WO 93/25244, WO 93/23085 and WO 94/28942, the disclosures of which are hereby incorporated by reference herein in their entirety.

In another embodiment, small peptides which bind the interluekin-1(IL-1) receptor may be used. For example, peptides generated by phage display core sequences of QPY have been shown to be essential for peptide binding, including, for example, AF12198, a 15-mer with a core sequence of WYQJY (SEQ ID NO:1), where J is azetidine; and IL-1 antagonists with $K_d 10^{-10}$ to $10^{-12}$M, such as AcPhe-Glu, Trp-Pro-Gly-Trp-Tyr-Gln-Aze-Tyr-Ala-Leu-Pro-Leu-$CONH_2$ SEQ ID NO:2 or Ac-Phe-Glu-Trp-Pro-Gly-Trp-Tyr-Gln-Aze-Tyr-Ala-Leu-Pro-Leu SEQ ID NO:3.

Endothelial-leukocyte adhesion molecules (ELAM's) are antigens which are expressed by endothelial cells under conditions of stress which then facilitate the migration of the leukocytes across the endothelium lining the vasculature into the surrounding tissues. These same endothelial-leukocyte adhesion molecules may be advantageously exploited as receptors for targeting of vesicles. These endothelial cell adhesion molecules belong to a family known as selectins in which the known members, such as GMP-140, all participate in endothelial-leukocyte adhesion and include ELAM-1, LAM-1 and the granule membrane protein 140 (GMP-140) also known as platelet activation-dependent granule-external membrane protein (PADGEM), VCAM-1/INCAM-110 (Vascular Adhesion Molecule/Inducible Adhesion Molecule) and ICAM-1 (Intercellular Adhesion Molecule).

The cadherin family of cell adhesion molecules may also be used as targeting ligands, including for example, the E-, N-, and P-cadherins, cadherin-4, cadherin-5, cadherin-6, cadherin-7, cadherin-8, cadherin-9, cadherin-10, and cadherin-11; most preferably cadherin C-5. Antibodies directed to cadherins, such as, for example, the monoclonal antibody Ec6C10, may be used to recognize cadherins expressed locally by specific endothelial cells.

A wide variety of different targeting ligands can be selected to bind to the cytoplasmic domains of the ELAM molecules. Targeting ligands in this regard may include lectins, a wide variety of carbohydrate or sugar moieties, antibodies, antibody fragments, Fab fragments, such as, for example, Fab'2, and synthetic peptides, including, for example, Arginine-Glycine-Aspartic Acid (R-G-D) which may be targeted to wound healing. While many of these materials may be derived from natural sources, some may be synthesized by molecular biological recombinant techniques and others may be synthetic in origin. Peptides may be prepared by a variety of techniques known in the art. Targeting ligands derived or modified from human leukocyte origin, such as CD11a/CD18, and leukocyte cell surface glycoprotein (LFA-1), may also be used as these are known to bind to the endothelial cell receptor ICAM-1. The cytokine inducible member of the immunoglobulin superfamily, VCAM-1, which is mononuclear leukocyte-selective, may also be used as a targeting ligand. VLA-4, derived from human monocytes, may be used to target VCAM-1. Antibodies and other targeting ligands may be employed to target endoglin, which is an endothelial cell proliferation marker. Endoglin is upregulated on endothelial cells in miscellaneous solid tumors. A targeting ligand which may be used to target endoglin is the antibody TEC-11. Thorpe et al, *Breast Cancer Research and Treatment*, 36:237–51 (1995).

Endothelial cell activation in the setting of atherosclerosis is used in this invention to target the compositions to regions of arteriosclerosis including, for example, atherosclerotic plaque. One such target that can be used is the inducible mononuclear leukocyte endothelial adhesion molecule recognized by Rb1/9 as an ATHERO-ELAM. The monoclonal antibodies, H4/18 and H18/7, may be used to target endothelial cell surface antigens which are induced by cytokine mediators. As a preferred embodiment, gaseous precursor filled vesicles are targeted to atherosclerotic plaque to non-invasively detect diseased blood vessels before severe damage has occurred, for example, prior to stroke or myocardial infarction, so that appropriate medical or surgical intervention may be implemented. ATHERO-ELAM is a preferred target and ligands, such as antibodies, peptides, or lectins or combinations thereof may be used to target this cell surface epitope expressed on endothelial cells in the context of atherosclerosis. Alternatively, lipoproteins or lipoprotein fragments derived from low or high density lipoprotein proteins may be used as targeting ligands. Additionally, cholesterol may be used to target the endothelial cells and localize the stabilizing materials, emulsions, vesicles and the like, to regions of atherosclerotic plaque. In embodiments involving the use of cholesterol as a targeting ligand, the cholesterol is preferably unmodified (non-derivatized) with other chemical groups, moieties, ligands and the like.

A targeting ligand directed toward thrombotic material in the plaque may be used to differentiate between active and inactive regions of atherosclerotic plaque. Active plaques in the process of generating thrombi are more dangerous as these plaques may ultimately occlude a vessel or result in emboli. In this regard, in addition to low molecular weight heparin fragments, other targeting ligands, such as, for example, anti-fibrin antibody, tissue plasminogen activator (t-PA), anti-thrombin antibody and fibrin antibodies directed to platelet activation factions, may be used to target active plaque with evolving clots. Preferred targeting ligands are those which will target a plasma membrane associated GPIIbIIIa in activated platelets in addition to targeting P-selectin, and an antibody or associated antibody fragment directed to GPIIbIIIa. The present invention is also useful for detecting regions of acute myocardial infarction. By attaching anti-myosin (particularly cardiomyosin) antibody or anti-actin antibodies to the lipids, polymers or stabilizing materials, infarcted myocardium may be detected by the methods of the present invention. For targeting to granulation tissue (healing wounds), many of the above targeting ligands may be useful. The wound healing tripeptide, arginine-glycine-aspartic acid (RGD), may also be used as a targeting ligand in this regard.

As with the endothelial cells discussed above, a wide variety of peptides, proteins and antibodies may be employed as targeting ligands for targeting epithelial cells. Preferably, a peptide, including synthetic, semi-synthetic or naturally-occurring peptides, with high affinity to the epithelial cell target receptor may be selected, with synthetic peptides being more preferred. In connection with these preferred embodiments, peptides having from about 5 to about 15 amino acid residues are preferred. Antibodies may be used as whole antibody or antibody fragments, for example, Fab or Fab'2, either of natural or recombinant origin. The antibodies of natural origin may be of animal or human origin, or may be chimeric (mouse/human). Human recombinant or chimeric antibodies are preferred and fragments are preferred to whole antibody.

Examples of monoclonal antibodies which may be employed as targeting ligands in the present compositions include CALAM 27, which is formed by immunizing BALB/c mice with whole human squamous cell carcinoma of the tongue and forming hybridomas by crossing extracted spleen cells with those of an NS1 syngeneic myeloma cell line. Gioanni et al., *Cancer Research,* 47:4417–4424 (1987). CALAM 27 is directed to surface epitopes of both normal and malignant epithelial cells. Normal lymph nodes generally do not contain cells expressing these epitopes. See *Cancer Research,* 47:4417–4424 (1987). Accordingly, lipid and/or vesicle compositions comprising this antibody can be used to target metastases in the lymph nodes. The monoclonal antibody 3C2 may be employed as a targeting ligand for targeting malignant epithelial cells of serious ovarian carcinoma and endometrioid carcinoma. Another exemplary targeting ligand is Mab 4C7 (see Cancer Research, 45:2358–2362 (1985)), which may be used to target mucinous carcinoma, endometriod carcinoma and mesonephroid carcinoma. For targeting squamous cell carcinoma in head and neck cancer, Mab E48 (Biological Abstract, Vol. 099 Issue. 066 Ref. 082748) may be used as a targeting ligand. For targeting malignant melanoma, the monoclonal antibody 225.28s (*Pathol. Biol.,* 38 (8):866–869 (1990)) may be employed. The monoclonal antibody mAb2E$_1$, which is targeted to EPR-1 (effector cell protease 1), may also be used.

Targeting ligands may be selected for targeting antigens, including antigens associated with breast cancer, such as epidermal growth factor receptor (EGFR), fibroblast growth factor receptor, erbB2/HER-2 and tumor associated carbohydrate antigens (Cancer, 74(3):1006–12 (1994)). CTA 16.88, homologous to cytokeratins 8, 18 and 19, is expressed by most epithelial-derived tumors, including carcinomas of the colon, pancreas, breast, ovary and lung. Thus, antibodies directed to these cytokeratins, such as 16.88 (IgM) and 88BV59 (IgG3k), which recognize different epitopes on CTA 16.88 (*Semin. Nucl. Med.,* 23(2):165–79 (1993)), may be employed as targeting ligands. For targeting colon cancer, anti-CEA IgG Fab' fragments may be employed as targeting ligands. Chemically conjugated bispecific anti-cell surface antigen, anti-hapten Fab'-Fab antibodies may also be used as targeting ligands. The MG series monoclonal antibodies may be selected for targeting, for example, gastric cancer (Chin. Med. Sci. J, 6(1):56 (1991)).

There are a variety of cell surface epitopes on epithelial cells for which targeting ligands may be selected. For example, the protein human papilloma virus (HPV) has been associated with benign and malignant epithelial proliferations in skin and mucosa. Two HPV oncogenic proteins, E6 and E7, may be targeted as these may be expressed in certain epithelial derived cancers, such as cervical carcinoma. See *Curr. Opin. Immunol.,* 6(5):746 (1994). Membrane receptors for peptide growth factors (PGF-R), which are involved in cancer cell proliferation, may also be selected as tumor antigens. Anticancer Drugs, 5(4):379 (1994). Also, epidermal growth factor (EGF) and interleukin-2 may be targeted with suitable targeting ligands, including peptides, which bind these receptors. Certain melanoma associated antigens (MAA), such as epidermal growth factor receptor (EGFR) and adhesion molecules (*Tumor Biol.,* 15 (4):188 (1994)), which are expressed by malignant melanoma cells, can be targeted with the compositions provided herein. The tumor associated antigen FAB-72 on the surface of carcinoma cells may also be selected as a target.

A wide variety of targeting ligands may be selected for targeting myocardial cells. Suitable targeting ligands include, for example, anticardiomyosin antibody, which may comprise polyclonal antibody, Fab'2 fragments, or be of human origin, animal origin, for example, mouse origin, or of chimeric origin. Additional targeting ligands include dipyridamole; digitalis; nifedipine; apolipoprotein; low density lipoproteins (LDL), including α-LDL, vLDI, and methyl LDL; ryanodine; endothelin; complement receptor type 1; IgG Fc; beta 1-adrenergic; dihydropyridine; adenosine; mineralocorticoid; nicotinic acetylcholine and muscarinic acetylcholine; antibodies to the human alpha 1A-adrenergic receptor; pharmaceuticals, such as drugs, including the alpha 1-antagonist prazosin; antibodies to the anti-beta-receptor; drugs which bind to the anti-beta-receptor; anti-cardiac RyR antibodies; endothelin-1, which is an endothelial cell-derived vasoconstrictor peptide that exerts a potent positive inotropic effect on cardiac tissue (endothelin-1 binds to cardiac sarcolemmal vesicles); monoclonal antibodies which may be generated to the T-cell receptor (x -P receptor and thereby employed to generate targeting ligands; the complement inhibitor sCRI; drugs, peptides or antibodies which are generated to the dihydropyridine receptor; monoclonal antibodies directed towards the anti-interleukin-2 receptor may be used as targeting ligands to direct the present compositions to areas of myocardial tissue which express this receptor and which may be up-regulated in conditions of inflammation; cyclosporine for directing similarly the compositions to areas of inflamed myocardial tissue; methylisobutyl isonitrile; lectins which bind to specific sugars on membranes of cardiac myocytes and cardiac endothelial cells; adrenomedullin (ADM), which is an endogenous hypotensive and vasorelaxing peptide; atrial natriuretic peptide (ANP); C-type natriuretic peptide (CNP), which is a 22 amino acid peptide of endothelial cell origin and is structurally related to atrial natriuretic peptide but genetically distinct, and possesses vasoactive and antimitogenic activity; vasonatrin peptide (VNP) which is a chimera of atrial natriuretic peptide (ANP) and C-type natriuretic peptide (CNP) and comprises 27 amino acids; thrombin; endothelium-derived relaxing factor (EDRF); neutral endopeptidase 1 (NEP-1); competitive inhibitors to EDRF, including, for example, NG-monomethyl-L-arginine (L-NMMA); potassium channel antagonists, such as charybdotoxin and glibenclamide; antiheart antibodies, which may be identified in patients with idiopathic dilated cardiomyopathy but which preferably do not elicit cytolysis in the myocardium; antibodies directed against the adenine nucleotide translocator, the branched-chain keto acid dehydrogenase or cardiac myosin; specific antagonists for the endothelin-A receptor, which may be referred to as BQ-123; and antibodies to the angiotensin II receptor.

Two of the major antigens of heart sarcolemmal are calcium binding glycoproteins which copurify with the dihydropyridine receptor. Antisera may be raised, including polyclonal or monoclonal antibodies, against purified sarcolemma. These antibodies may also be employed as targeted ligands. Purified fractions of the calcium binding glycoproteins may be isolated from the plasma membranes of the sarcolemma and then used to generate antibodies. ANP, which may be used as a targeting ligand, can be obtained from cultures of human aortic endothelial cells. ANP is generally localized in endothelium, but also may localize to the endothelial or myocardial tissue. ANP may be prepared, for example, using recombinant techniques, as well as by synthesis of the peptide using peptide synthesis techniques well known to one skilled in the art. It is also possible to use an antibody, either polyclonal or monoclonal, directed towards ANP. Similarly, a peptide directed to ANP may be used for targeting endothelial and/or myocardial cells. Both the β and α forms of atrial natriuretic factor may be used as potential targeting ligands for directing the present compositions to myocardial tissue.

A wide variety of targeting ligands may be employed to direct the present compositions, and particularly vesicle compositions, to the GPIIbIIIa receptor. Compositions which are directed to the GPIIbIIIa receptor are highly useful for targeting vascular thromboses or clots, and are useful for diagnosing, as well as treating such clots. Included among such targeting ligands are, for example, peptides, such as Arg-Gly-Asp-Ser (RGDS) SEQ ID NO:4, Gly-Arg-Gly-Asp-Ser-Pro (GRGDSP) SEQ ID NO:5, and Gly-Pro-Arg-Pro (GPRP) SEQ ID NO:6. Pentapeptides containing the sequence Arg-Gly-Asp (RGD) are also useful including, for example, G4120, which is a cyclic peptide containing the amino acid sequence Arg-Gly-Asp (RGD). Also useful are peptides derived from human coagulation Factor XIIIA including, for example, fragments such as NKLIVRRGQS FYVQIDFSRPYDPRRDL FRVEYVIGRYPQENKGTY-IPVPIVSELQSGKWGAKIVMRE DRSVRLSIQSSPK-CIVGKFRMYVAVWTPYGVLRTSRNPETD-TYILFNPWCEDDAVYLDN EKEREEYVLNDIGVIFYGEVNDIKTRSWSYGQF-R' SEQ ID NO:7 where R' is —CONH$_2$ or —NH$_2$. In addition, peptides which are fragments of the Factor XIIIA fragment, which include in their sequence the sequence NKLIVRR-GOSFYVQIDFSRPYDPRRD SEQ ID NO:8 or DDAVYLDNEKEREEYV LNDIGVIFYGEVNDIKTR-SWSYGQF SEQ ID NO:9.

Additional peptides which may be useful as targeting ligands for targeting the GPIIbIIIa receptor include, for example, peptides comprising the tripeptide sequence of arginine-tyrosine-aspartic acid (Arg-Tyr-Asp; also abbreviated RGD), linked from amino-to-carboxy-terminus and which may bind to the GPIIbIIIa binding region on activated platelets.

Exemplary of such peptides include, for example, peptides of the general formula $R^1$—$(X^1)_n$—Arg—Tyr—Asp—$(Y)_o$—$(X^2)_m$—$R^2$, wherein each of $X^1$, $X^2$ and Y may independently be one or more amino acid residues while, in certain cases, it is preferred that Y is other than a serine or alanine residue, and each of m, n and o is independently 0 or 1, provided, in certain cases, that when m is 1, then o is 1, and $R^1$ is a protected or unprotected terminal amino group and $R^2$ is a protected or unprotected terminal carboxy group.

In a preferred embodiment, $X^1$ is the peptide Ala-Arg-Arg-Ser-Ser-Pro-Ser-Tyr-Tyr SEQ ID NO:10 and $X^2$ is the peptide Gly-Ala-Gly-Pro-Tyr-Tyr-Ala-Met-Asp-Tyr SEQ ID NO:11. Useful peptides include Arg-Ser-Pro-Ser-Tyr-Tyr-Arg-Tyr-Asp-Gly-Ala-Gly-Pro-Tyr-Tyr-Ala-Met-Asp-Tyr SEQ ID NO:12 and Ala-Arg-Arg-Ser-Pro-Ser-Tyr-Tyr-Arg-Tyr-Asp-Gly-Ala-Gly-Pro-Tyr-Tyr-Ala-Met-Asp-Tyr SEQ ID NO:13.

Synthetic compounds which combine a natural amino acid sequence with synthetic amino acids can also be used as the targeting ligand, such as a fibrinogen receptor antagonist compound which comprises the sequence XX-Gly-Asp, wherein XX is a synthetic α-amino acid containing a linear side chain, such as

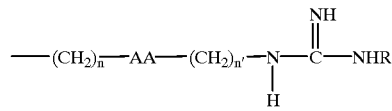

wherein n+n' is 3; AA is a single bond; and R is phenyl or benzyl;

or —(CH$_2$)$_n$—AA—(CH$_2$)$_{n'}$—NHR, wherein n is an integer of 1 to 4; n' is an integer of 2 to 4; AA is oxygen, sulfur or a single bond; and R is H, C$_{1-6}$ alkyl, optionally substituted aryl, optionally substituted arylmethyl or optionally substituted cycloalkyl, provided, in certain cases, that when AA is a single bond and R is H, then n+n' is other than 3 or 4.

Another such compound comprises a fibrinogen receptor antagonist of the formula:

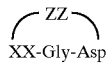

wherein XX is a synthetic α-amino acid containing a linear side chain having the formula

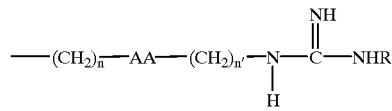

wherein n+n' is 3; AA is a single bond; and R is phenyl or benzyl; or

—(CH$_2$)$_n$—AA—(CH$_2$)$_{n'}$—NHR, wherein n is an integer of 1 to 4; n' is an integer of 2 to 4; AA is oxygen, sulfur or a single bond; and R is H, C$_{1-6}$ alkyl, optionally substituted cycloalkyl, provided that, in certain cases, when AA is a single bond and R is H, then n+n' is other than 3 or 4, and ZZ is a sequence of 1 to 4 optionally substituted amino acids.

Other useful peptides for use as targeting ligands include, for example, "Elegantin," which has the following sequence: Gly-Glu-Glu-Cys-Asp-Cys-Gly-Ser-Pro-Glu-Asn-Pro-Cys-Cys-Asp-Ala-Ala-Thr-Cys-Lys-Leu-Arg-Pro-Gly-Ala-Gln-Cys-Ala-Asp-Gly-Leu-Cys-Cys-Asp-Gln-Cys-Arg-Phe-Lys-R-R'-Arg-Thr-Ile-Cys-Arg-Arg-Ala-Arg-Gly-Asp-Asn-Pro-Asp-Asp-Arg-Cys-Thr-Gly-Gln-Ser-Ala-Asp-Cys-Pro-Arg-Asn-Gly-Tyr SEQ ID NO:14, wherein each of R and R' is independently any amino acid; "Albolabrin," which has the following sequence: Glu-Ala-Gly-Glu-Asp-Cys-Asp-Cys-Gly-Ser-Pro-Ala-Asn-Pro-Cys-Cys-Asp-Ala-Ala-Thr-Cys-Lys-Leu-Leu-Pro-Gly-Ala-Gln-Cys-Gly-Glu-Gly-Leu-Cys-Cys-Asp-Gln-Cys-Ser-Phe-Met-Lys-Lys-Gly-Thr-Ile-Cys-Arg-Arg-Ala-Arg-Gly-Asp-Asp-Leu-Asp-Asp-Tyr-Cys-Asn-Gly-Ile-Ser-Ala-Gly-Cys-Pro-Arg-Asn-Pro-Leu- His-Ala SEQ ID NO:15; "Batroxostatin," which has the following sequence: Glu-Ala-Gly-Glu-Glu-Cys-Asp-Cys-Gly-Thr-Pro-Glu-Asn-Pro-Cys-Cys-Asp-Ala-Ala-Thr-Cys-Lys-Leu-Arg-Pro-Gly-Ala-Gln-Cys-Ala-Glu-Gly-Leu-Cys-Cys-Asp-Gln-Cys-Arg-Phe-Lys-Gly-Ala-Gly-Lys-Ile-Cys-Arg-Arg-Ala-Arg-Gly-Asp-Asn-Pro-Asp-Asp-Cys-Thr-Gly-Gln-Ser-Ala-Asp-Cys-Pro-Arg-Phe SEQ ID NO:16; and "Flavoridin," which has the following sequence: Gly-Gly-Glu-Cys-Asp-Cys-Gly-Ser-Pro-Glu-Asn-Pro-Cys-Cys-Asp-Ala-Ala-Thr-Cys-Lys-Leu-Arg-Pro-Gly-Ala-Gln-Cys-Ala-Asp-Gly-Leu-Cys-Cys-Asp-Gln-Cys-Arg-Phe-Lys-R-R'-Arg-Thr-Ile-Cys-Arg-Ile-Ala-Arg-Gly-Asp-Phe-Pro-Asp-Asp-Arg-Cys-Thr-Gly-Leu-Ser-Ala-Asp-Cys-Pro-Arg-R-Asn-Asp-Leu SEQ ID NO:17, wherein each of R and R' is independently any amino acid.

Other ligands useful for targeting the GPIIbIIIa receptor include synthetic compounds, such as Ac-(D)Phe-Pro-boroArg and the cyclic peptidomimetic cyclo(D-2-aminobutyrate-N-Methyl-L-Arginyl-Glycyl-L-Aspartyl-3-amino-methyl-benzoic acid) methanesulfonate salt. Peptides that can also be used include a library of hexapeptides flanked by cysteine residues (capable of forming cyclic disulfides) and cyclic, disulfide-bonded forms of peptides with the sequence Arg-Gly-Asp or Lys-Gly-Asp, as well as the carboxyl-terminal derived peptide, REYVVMWK (SEQ ID NO:18). Certain matrix glycoproteins such as Thrombospondin are also useful in this regard. Members of the serpin family of serine protease inhibitors, such as Plasminogen activator inhibitor type I (PAI-1) are other useful ligands.

Generally, it is preferred to employ as targeting ligands for the GPIIbIIIa receptor a peptide having from about 3 to about 20 amino acids, with peptides having from about 4 to about 15 amino acids being more preferred. Even more preferably, targeting ligands for the GPIIbIIIa receptor may comprise peptides having from about 4 to about 8 amino acids, with peptides having from about 4 to about 6 amino acids or about 5 amino acids being still more preferred. If desired, the peptides may be cyclized, for example, by (1) side chain-to-side chain covalent linkages, including, for example, by the formation of a disulfide linkage via the oxidation of two thiol containing amino acids or analogs thereof, including, for example, cysteine or penicillamine; (2) end-to-side chain covalent linkages, including, for example, by the use of the amino terminus of the amino acid sequence and a side chain carboxylate group, such as, for example, a non-critical glutamic acid or aspartic acid group. Alternatively, the end-to-side chain covalent linkage may involve the carboxylate terminus of the amino acid sequence and a side chain amino, amidine, guanidine, or other group in the sidechain which contains a nucleophilic nitrogen atom, such sidechain groups including, for example, lysine, arginine, homoarginine, homolysine, or the like; (3) end-to-end covalent linkages that are covalent amide linkages, or the like. Such processes are well known to those skilled in the art. In addition, "pseudocyclization" may be employed, in which cyclization occurs via non-covalent interactions, such as electrostatic interactions, which induces a folding of the secondary structure to form a type of cyclic moiety. It is contemplated that metal ions may aid the induction of a "pseudocyclic" formation. This type of pseudocyclic formation may be analogous to "zinc fingers." As known to one of ordinary skill in the art, zinc fingers involve the formation due to electrostatic interactions between a zinc ion ($Zn^{2+}$) and cysteine, penicillamine and/or homocysteine, of a region in the shape of a loop (the finger). In the case of homocysteine, the RGD sequence would reside at the tip of the finger. Of course, it is recognized that, in the context of the present invention, any type of stabilizing cyclization would be suitable as long the recognition and binding peptide ligand, such as, for example, RGD, maintains the proper conformation and/or topography to bind to the appropriate receptor in clots with a reasonable Michaelis-Menten constant ($k_m$) or binding constant. As used herein, the term "conformation" refers to the three-dimensional organization of the backbone of the peptide, peptoid, or pseudopeptide, and the term "topography" refers to the three-dimensional organization of the sidechain of the peptide, peptoid, or pseudopeptide.

Other suitable targeting ligands include: Ac-Cys-Arg-Gly-Asp-Met-Phe-Gly-Cys-$CONH_2$ SEQ ID NO:19; Ac-Cys-Arg-Gly-Asp-Met-Leu-Arg-Cys-$CONH_2$ SEQ ID NO:20; Ac-Cys-Arg-Gly-Asp-Phe-Leu-Asn-Cys-$CONH_2$ SEQ ID NO:21; Ac-Cys-Asn-Thr-Leu-Lys-Gly-Asp-Cys-$CONH_2$ SEQ ID NO:22; Ac-Cys-Asn-Trp-Lys-Arg-Gly-Asp-Cys-$CONH_2$ SEQ ID NO:23; and Ac-Cys-N-methyl-Arg-Gly-Asp-Pen-$CONH_2$ SEQ ID NO:24, where "Pen" refers to penicillamine (β,β-dimethylcysteine).

Other compounds which may be used as targeting ligands include peptides, or derivatives thereof, represented by the formula:

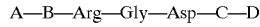

where A is proline, thioproline, hydroxyproline, dehydroproline, 2-oxo-4-thiazolidine carboxylic acid, N-alkyl glycine or an amino acid derivative of the formula

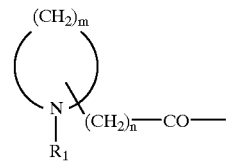

tryptophan, or a tryptophan derivative of the formula

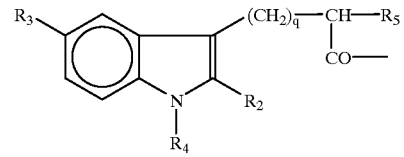

pyroglutamic acid or 2-azetidinone-4-carboxylic acid; B is serine, glycine, valine, alanine, threonine or β-alanine; C is an amino acid group having a hydrophobic functional group; and D is hydroxy or amino; wherein $R_1$ is hydrogen, —$(CH_2)_pCH_3$ or —CO—$(CH_2)_pCH_3$; $R_2$ is hydrogen or alkyl; $R_3$ is hydrogen or alkoxy; $R_4$ is hydrogen or alkyl; $R_5$ is hydrogen, amino or acylamino; m is an integer of 2 to 5; n is an integer of 0 to 2; p is an integer of 0 to 5; and q is an integer of 0 to 3.

Other suitable targeting ligands include peptides, peptide derivatives, or salts thereof having the formula:

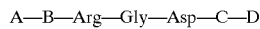

where A is arotic acid or hydroorotic acid; B is an amino acid; C is an amino acid having a hydrophobic functional group; and D is hydroxy or amino. In the above compounds, amino acids having hydrophobic functional groups in the definition of "C" include, for example, tryptophan and phenylalanine.

Various peptides which would be suitable for use as a targeting ligand in connection with the present invention, especially for targeting GPIIbIIIa, are described, for example, in U.S. Pat. No. 5,498,601 and European Patent Applications: 0 368 486 A2, 0 382 451 A2, and 0 422 938 B1, the disclosures of which are hereby incorporated by reference herein in their entirety. Other suitable targeting ligands include, for example, conjugated peptides, such as, for example, glycoconjugates and lectins, which are peptides attached to sugar moieties. Other targeting ligands which may be used in the compositions of the present invention, in addition to those exemplified above, would be apparent to one skilled in the art in view of the present disclosure.

The targeting ligand is preferably covalently bound to the surface of the stabilizing material or vesicle by a spacer including, for example, hydrophilic polymers, such as the hydrophilic polymers described herein, preferably polyethylene glycol. Preferred molecular weights of the polymers are from 1000 da to 10,000 da, with 500 da being most preferred. Preferably the polymer is bifunctional with the targeting ligand bound to a terminus of the polymer. Generally, the targeting ligand will range from about 0.1 to about 20 mole % of the exterior components of the vesicle. In the case of gas-filled lipid vesicles, this amount is preferably between about 0.5 and about 10 mole % with about 1 to about 10 mole % being most preferred. The exact ratio will depend upon the particular targeting ligand.

In one embodiment of the invention, the targeting ligands are directed toward lymphocytes which may be T-cells or B-cells, with T-cells being the preferred target. Depending on the targeting ligand, the composition may be targeted to one or more classes or clones of T-cells. To select a class of targeted lymphocytes, a targeting ligand having specific affinity for that class is employed. For example, an anti CD-4 antibody can be used for selecting the class of T-cells harboring CD-4 receptors, an anti CD-8 antibody can be used for selecting the class of T-cells harboring CD-8 receptors, an anti CD-34 antibody can be used for selecting the class of T-cells harboring CD-34 receptors, etc. A lower molecular weight ligand is preferably employed, e.g., Fab or a peptide fragment. For example, an OKT3 antibody or OKT3 antibody fragment may be used. When a receptor for a class of T-cells or clones of T-cells is selected, the composition will be delivered to that class of cells. Using HLA-derived peptides, for example, will allow selection of targeted clones of cells expressing reactivity to HLA proteins. Other suitable compositions and targeting ligands for targeting B-cells and T-cells are described in U.S. Pat. No. 5,620,689, the disclosure of which is hereby incorporated by reference herein in its entirety.

The following table illustrate ligands from the major histocompatability complex (MHC) and their receptors in the class of T-cells for which they have affinity. All the ligands, T-cell receptors and peptide sequences in the table below may be used in the present invention.

TABLE 2

MHC LIGANDS AND T-CELL RECEPTORS

| T-Cell Receptor | Ligand | Peptide Sequence |
|---|---|---|
| HTB157.7 | K$^b$ (Q10b hybrid) | Heterogeneous |
| HTB157.7 | pK$^b$163–174 | NA |
| 2C | L$^d$/p2Ca | LSPFPFDL* SEQ ID NO: 25 |
| 2C | L$^d$/p2Ca-A5 | LSPFAFDL SEQ ID NO: 26 |
| 2C | L$^d$/p2Ca-A3 | LSAFPFDL SEQ ID NO: 27 |
| 2C | L$^d$/p2Ca-A8 | LSPFPFDA SEQ ID NO: 28 |

TABLE 2-continued

MHC LIGANDS AND T-CELL RECEPTORS

| T-Cell Receptor | Ligand | Peptide Sequence |
|---|---|---|
| 2C | L$^d$/SL9 | SPFPFDLLL SEQ ID NO: 29 |
| 2C | K$^b$/p2Ca | LSPFPFDL SEQ ID NO: 30 |
| 2C | L$^d$/QL9 | QLSPSPDL SEQ ID NO: 31 |
| 4G3 | K$^b$/pOV8 | SIINFEKL SEQ ID NO: 32 |
| 2C | L$^d$/p2Ca-Y4 | LSPYPFDL SEQ ID NO: 33 |
| 2C | L$^d$/p2Ca-A1 | ASPFPFDL SEQ ID NO: 34 |
| Clone 30 | K$^b$/ IgG (bivalent) | Heterogeneous |
| 14.3d | 1-E$^d$/pHA | SSFGAFGIFPK SEQ ID NO: 35 |
| 5C.C7 | 1-E$^k$/MCC | ANERADLIAYLKQATK SEQ ID NO: 36 |
| 228.4 | 1-E$^k$/ MCC-K99A | ANERADLIAYLKQATK SEQ ID NO: 37 |
| 2B4 | 1-E$^k$/MCC | ANERADLIAYLKQATK SEQ ID NO: 38 |
| 2B4 | 1-E$^k$/PCC | ANERADLIAYLKQATAK SEQ ID NO: 39 |
| 2B4 | 1-E$^k$/ MCC-T102S | ANERADLIAYLKQASK SEQ ID NO: 40 |
| HA1.7 | SEB | |
| 14.3dβ | SEC1 | |
| 14.3dβ | SEC2 | |
| 14.3dβ | SEC3 | |
| 14.3dβ | SEB | |
| 14.3dβ | SPEA | |

*Single-letter code for amino acids. Summarized from Fremont et al, Current Opinion In Immunology, (1996) 8:93–100, page 96, Table 2, the disclosure of which is hereby incorporated herein by reference in its entirety.

Another major area for targeted delivery involves the interlekin-2 (IL-2) system. IL-2 is a t-cell growth factor that is produced following antigen or mitogen induced stimulation of lymphoid cells. Among the cell types which produce IL-2 are CD4$^+$ and CD8$^+$t-cells and large granular lymphocytes, as well as certain t-cell tumors. IL-2 receptors are glycoproteins expressed on responsive cells. They are notable in connection with the present invention because they are readily endocytosed into lysosomal inclusions when bound to IL-2. The ultimate effect of this endocytosis depends on the target cell, but among the notable in vivo effects are regression of transplantable murine tumors, human melanoma or renal cell cancer. IL-2 has also been implicated in antibacterial and antiviral therapies and plays a role in allograft rejection. In addition to IL-2 receptors, preferred targets include the anti-IL-2 receptor antibody, natural IL-2 and an IL-2 fragment of a 20-mer peptide or smaller generated by phage display which binds to the IL-2 receptor.

Additionally, an IL-2 peptide fragment which has binding affinity for IL-2 receptors can be incorporated either by direct attachment to a reactive moiety on the stabilizing material or via a spacer or linker molecule with a reactive end such as an amine, hydroxyl, or carboxylic acid functional group. Such linkers are well known in the art and may comprise from 3 to 20 amino acid residues. Alternatively, D-amino acids or derivatized amino acids may be used which avoid proteolysis in the target tissue.

Still other systems which can be used in the present invention include IgM-mediated endocytosis in B-cells or a variant of the ligand-receptor interactions described above wherein the T-cell receptor is CD2 and the ligand is lymphocyte function-associated antigen 3 (LFA-3), as described, for example, by Wallner et al, *J. Experimental Med.*, 166:923 (1987), the disclosure of which is hereby incorporated by reference herein in its entirety.

The targeting ligand may be incorporated in the present stabilizing materials in a variety of ways. Generally, the targeting ligand may be incorporated in the present stabilizing materials by being associated covalently or non-covalently with one or more of the stabilizing materials which are included in the compositions including, for example, the lipids, proteins, polymers, surfactants, and/or auxiliary stabilizing materials. In preferred form, the targeting ligand may be associated covalently with one or more of the aforementioned materials contained in the present stabilizing materials. Preferred stabilizing materials of the present invention comprise lipid, protein, polymer or surfactant compounds. In these compositions, the targeting ligands are preferably associated covalently with the stabilizing materials.

Exemplary covalent bonds by which the targeting ligands are associated with the stabilizing materials include, for example, maleimide; amide (—CONH—); thioamide (—CSNH—); ether (ROR'), where R and R' may be the same or different and are other than hydrogen); ester (—COO—); thioester (—COS—); —O—; —S—; —S$_n$—, where n is greater than 1, preferably about 2 to about 8, and more preferably about 2; carbamates; -NH-; -NR-, where R is alkyl, for example, alkyl of from 1 to about 4 carbons; urethane; and substituted imidate; and combinations of two or more of these. Covalent bonds between targeting ligands and, for example, lipids, may be achieved through the use of molecules that may act as spacers to increase the conformational and topographical flexibility of the ligand. Such spacers include, for example, succinic acid, 1,6-hexanedioic acid, 1,8-octanedioic acid, and the like, as well as modified amino acids, such as, for example, 6-aminohexanoic acid, 4-aminobutanoic acid, and the like. In addition, in the case of targeting ligands which comprise peptide moieties, side chain-to-side chain crosslinking may be complemented with side chain-to-end crosslinking and/or end-to-end crosslinking. Also, small spacer molecules, such as dimethylsuberimidate, may be used to accomplish similar objectives. The use of agents, including those used in Schiffs base-type reactions, such as gluteraldehyde, may also be employed. The Schiffs base linkages, which may be reversible linkages, can be rendered more permanent covalent linkages via the use of reductive amination procedures. This may involve, for example, chemical reducing agents, such as lithium aluminum hydride reducing agents or their milder analogs, including lithium aluminum diisobutyl hydride (DIBAL), sodium borohydride (NaBH$_4$) or sodium cyanoborohydride (NaBH$_3$CN).

The covalent linking of the targeting ligands to the stabilizing materials in the present compositions may be accomplished using synthetic organic techniques which would be apparent to one of ordinary skill in the art in view of the present disclosure. For example, the targeting ligands may be linked to the stabilizing materials via the use of well known coupling or activation agents. As known to the skilled artisan, activating agents are generally electrophilic, which can be employed to elicit the formation of a covalent bond. Suitable activating agents which may be used include, for example, carbonyldi-imidazole (CDI), dicyclohexylcarbodiimide (DCC), diisopropylcarbodiimide (DIC), methyl sulfonyl chloride, Castro's Reagent, and diphenyl phosphoryl chloride.

The covalent bonds may involve crosslinking and/or polymerization. Crosslinking preferably refers to the attachment of two chains of polymer molecules by bridges, composed of either an element, a group, or a compound, which join certain carbon atoms of the chains by covalent chemical bonds. For example, crosslinking may occur in polypeptides which are joined by the disulfide bonds of the cystine residue. Crosslinking may be achieved, for example, by (1) adding a chemical substance (crosslinking agent) and exposing the mixture to heat, or (2) subjecting a polymer to high energy radiation. A variety of crosslinking agents, or "tethers," of different lengths and/or functionalities are described, for example, by Lunbland, *Techniques in Protein Modification*, CRC Press, Inc., Ann Arbor, MI, pp. 249–68 (1995), the disclosures of which is hereby incorporated herein by reference in its entirety. Exemplary crosslinkers include, for example, 3,3'-dithiobis (succinimidylpropionate), dimethyl suberimidate, and variations thereof, based on hydrocarbon length, and bis-N-maleimido-1,8-octane.

Additionally, the targeting ligands may be linked or attached to the lipids, proteins, polymers, or surfactants or other stabilizing materials via a linking group. A variety of linking groups are available and would be apparent to one skilled in the art in view of the present disclosure. Preferably, the linking group comprises a hydrophilic polymer. Suitable hydrophilic polymers include, for example, polyalkyleneoxides such as, for example, polyethylene glycol (PEG) and polypropylene glycol (PPG), polyvinylpyrrolidones, polyvinylmethylethers, polyacrylamides, such as, for example, polymethacrylamides, polydimethylacrylamides and polyhydroxypropyl-methacrylamides, polyhydroxyethyl acrylates, polyhydroxypropyl methacrylates, polymethyl-oxazolines, polyethyloxazolines, polyhydroxyethyl-oxazolines, polyhyhydroxypropyl-oxazolines, polyvinyl alcohols, polyphosphazenes, poly (hydroxyalkylcarboxylic acids), polyoxazolidines, polyaspartamide, and polymers of sialic acid (polysialics). The hydrophilic polymers are preferably selected from the group consisting of PEG, PPG, polyvinylalcohol and polyvinylpyrrolidone and copolymers thereof, with PEG and PPG polymers being more preferred and PEG polymers being even more prefered.

Thus, in embodiments involving lipid compositions which comprise lipids bearing polymers including, for example, DPPE-PEG, the targeting ligand may be linked directly to the polymer which is attached to the lipid to provide, for example, a conjugate of DPPE-PEG-TL, where TL is a targeting ligand. Thus, using the example DPPE-PEG, such as, for example, DPPE-PEG5000, the aforementioned conjugate may be represented as DPPE-PEG5000-TL. The hydrophilic polymer used as a linking group is preferably a bifunctional polymer, for example, bifunctional PEG, such as diamino-PEG. In this case, one end of the PEG group is linked, for example, to a lipid compound, and is bound at the free end to the targeting ligand via an amide linkage. A hydrophilic polymer, for example, PEG, substituted with a terminal carboxylate group on one end and a terminal amino group on the other end, may also be used. These latter bifunctional hydrophilic polymer may be preferred since they possess various similarities to amino acids.

Standard peptide methodology may be used to link the targeting ligand to the lipid when utilizing linker groups having two unique terminal functional groups. Bifunctional hydrophilic polymers, and especially bifunctional PEGs, may be synthesized using standard organic synthetic methodologies. In addition, many of these materials are available commercially, such as, for example, α-amino-ω-carboxy-PEG which is commercially available from Shearwater Polymers (Huntsville, Ala.). An advantage of using a PEG material as the linking group is that the size of the PEG can be varied such that the number of monomeric subunits of ethylene glycol may be as few as, for example, about 5, or as many as, for example, about 500 or even greater. Accordingly, the "tether" or length of the linkage may be varied, as desired. This may be important depending, for example, on the particular targeting ligand employed. For example, a targeting ligand which comprises a large protein molecule may require a short tether, such that it will simulate a membrane bound protein. A short tether would also allow for a vesicle to maintain a close proximity to the cell.

Another suitable linking group which may provide a short tether is glyceraldehyde. Glyceraldehyde may be bound, for example, to DPPE via a Schiff's base reaction. Subsequent Amadori rearrangement can provide a substantially short linking group. The P carbonyl of the Schiff's base may then react with a lysine or arginine of the targeting protein or peptide to form the targeted lipid.

Additionally, the compounds employed in the present stabilizing materials may contain various functional groups, such as, for example, hydroxy, thio and amine groups, which can react with a carboxylic acid or carboxylic acid derivative of the hydrophilic polymeric linker using suitable coupling conditions which would be apparent to one of ordinary skill in the art in view of the present disclosure. After the carboxylic acid group (or derivative thereof) reacts with the functional group, for example, hydroxy, thio or amine group to form an ester, thioester or amide group, any protected functional group may be deprotected utilizing procedures which would be well known to one skilled in the art. The term protecting group refers to any moiety which may be used to block the reaction of a functional group and which may be removed, as desired, to afford the unprotected functional group. Any of a variety of protecting groups may be employed and these will vary depending, for example, as to whether the group to be protected is an amine, hydroxyl or carboxyl moiety. If the functional group is a hydroxyl group, suitable protecting groups include, for example, certain ethers, esters and carbonates. Such protecting groups are described, for example, in Greene, TW and Wuts, PGM "Protective Groups in Organic Synthesis" John Wiley, New York, 2nd Edition (1991), the disclosure of which is hereby incorporated herein by reference in its entirety. Protecting groups for amine groups include, for example, t-butyloxycarbonyl (Boc), allyloxycarbonyl (Alloc), benzyloxycarbonyl (Cbz), o-nitrobenzyloxycarbonyl and and trifluoroacetate (TFA).

Amine groups which may be present, for example, on a backbone of a polymer which is included in the vesicles, may be coupled to amine groups on a hydrophilic linking polymer by forming a Schiff's base, for example, by using coupling agents, such as glutaraldehyde. An example of this coupling is described by Allcock et al, *Macromolecules*, 19(6):1502 (1986), the disclosure of which is hereby incorporated herein by reference in its entirety. If, for example, vesicles are formulated from polylysine, free amino groups may be exposed on the surface of the vesicles, and these free amine groups may be activated as described above. The activated amine groups can be used, in turn, to couple to a functionalized hydrophilic polymer, such as, for example, α-amino-ω-hydroxy-PEG in which the ω-hydroxy group has been protected with a carbonate group. After the reaction is completed, the carbonate group can be cleaved, thereby enabling the terminal hydroxy group to be activated for reaction to a suitable targeting ligand. In certain embodiments, the surface of a vesicle may be activated, for example, by displacing chlorine atoms in chlorine-containing phosphazene residues, such as polydichlorophosphazene. Subsequent addition of a targeting ligand and quenching of the remaining chloride groups with water or aqueous methanol will yield the coupled product.

In addition, poly(diphenoxyphosphazene) can be synthesized (Allcock et al., *Macromolecules*, 19(6):1502–1508 (1986)) and immobilized, for example, on DPPE, followed by nitration of the phenoxy moieties by the addition of a mixture of nitric acid and acetic anhydride. The subsequent nitro groups may then be activated, for example, by (1) treatment with cyanogen bromide in 0.1 M phosphate buffer (pH 11), followed by addition of a targeting ligand containing a free amino moiety to generate a coupled urea analog, (2) formation of a diazonium salt using sodium nitrite/HCl, followed by addition of the targeting ligand to form a coupled ligand, and/or (3) the use of a dialdehyde, for example, glutaraldehyde as described above, to form a Schiff's base. After linking the DPPE to the hydrophilic polymer and the targeting ligand, the vesicles may be formulated utilizing the procedures described herein.

Aldehyde groups on polymers can be coupled with amines as described above by forming a Schiff's base. An example of this coupling procedure is described by Allcock et al, *Macromolecules*, 14:1616 (1981), the disclosure of which is hereby incorporated herein by reference in its entirety.

In the above procedures, the polymer or terminus of the lipid, for example, phosphatidylglycerol or phosphatidylethanolamine, is preferably activated and coupled to the hydrophilic polymeric linker, the terminus of which has been blocked in a suitable manner. As an example of this strategy, α-amino-ω-carboxy-PEG4000 having a t-Boc protected terminal amino group and a free carboxylate end, may be activated with 1,1'-carbonyldiimidazole in the presence of hydroxybenzo-triazole in N-methyl-pyrrolidone. After the addition of phosphatidylethanolamine, the t-Boc group may be removed by using trifluoroacetic acid (TFA), leaving the free amine. The amine may then be reacted with a targeting ligand which may comprise, for example, a peptide, protein, alkaloid, or other moiety, by similar activation of the ligand, to provide the lipid-linker-targeting ligand conjugate. Other strategies, in addition to those exemplified above, may be utilized to prepare the lipid-linker-targeting ligand conjugates. Generally, these methods employ synthetic strategies which are known to one skilled in the art of synthetic organic chemistry.

As known to one of ordinary skill in the art, immunoglobulins typically comprise a flexible region which is identified as the "hinge" region. See, e.g., "Concise Encyclopedia of Biochemistry", Second Edition, Walter de Gruyter & Co., pp. 282–283 (1988). Fab' fragments can be linked to the lipids, polymers, proteins and/or vesicles using the well-defined sites of the thiols of the hinge region. This is a preferred region for coupling Fab' fragments as the potential binding site is remote from the antigen-recognition site. Generally, it may be difficult to utilize the thiols of the hinge group unless they are adequately prepared. In particular, as outlined by Shahinian et al, *Biochimica et Biophysica Acta*, 1239:157–167 (1995), the disclosure of which is hereby incorporated by reference herein in its entirety, it may be important to reduce the thiol groups so that they are available for coupling, for example, to maleimide derivatized linking groups. Examples of reducing agents commonly used are ethanedithiol, mercapto-ethanol, mercaptoethylamine or the more commonly used dithiothreitol, commonly referred to as Cleland's reagent. It should be noted that care should be exercised when utilizing certain reducing agents, such as dithiothreitol, as overreduction may result. Discriminating use of reducing agents may be necessary in connection with proteins whose activity or binding capacity may be compromised due to overreduction and subsequent denaturation or conformational change.

F(ab')₂ antibody fragments may be prepared by incubating the antibodies with pepsin (60 μg/ml) in 0.1 M sodium acetate (pH 4.2) for 4 h at 37° C. Digestion may be terminated by adding 2 M Tris (pH 8.8) to a final concentration of 80 mM. The F(ab')₂ fragments may then be obtained by centrifugation (10,000× g. 30 min. 4° C.). The supernatant may then be dialyzed at 4° C. against 150 mM NaCl, 20 mM phosphate at pH 7.0. This then may be chromatographed on a column of Protein A-Sepharose CL-4B to remove any undigested IgG. The Fab' fragments may then be prepared by extensively degassing the solutions and purging with nitrogen prior to use. The F(ab')₂ fragments may be provided at a concentration of 5 mg/ml and reduced under argon in 30 mM cysteine.

Alternatively, cysteamine may be employed. 100 mM Tris, pH 7.6 may be used as a buffer for 15 min at 37° C. The solutions may then be diluted 2-fold with an equal volume of the appropriate experimental buffer and spun through a 0.4 ml spin column of Bio-Gel P-6DG. The resulting Fab' fragments may be more efficient in their coupling to maleimide linkers.

The same procedure may be employed with other macromolecules containing cysteine residues for coupling, for example, to the maleimide spacers. Also, peptides may be utilized provided that they contain a cysteine residue. If the peptides have not been made fresh and there is a possibility of oxidation of cysteine residues within the peptide structure, it may be necessary to regenerate the thiol group using the approach outlined above.

Additional linkers would include other derivatives of lipids useful for coupling to a bifunctional spacer. For example, phosphatidylethanolamine (PE) may be coupled to a bifunctional agent. For example N-succinimidyl 4-(p-maleimidophenyl)-butyrate (SMPB) and N-succinimidyl 3-(2-pyridyldithiol) propionate (SPDP), N-succinimidyl trans-4-(N-maleimidylmethyl)cyclohexane-1-carboxylate (SMCC), and N-succinimidyl 3-maleimidyl-benzoate (SMB) may be used among others, to produce, for example, the functionalized lipids MPB-PE and PDP-PE.

The free end of the hydrophilic spacer, such as polyethylene glycol ethylamine, which contains a reactive group, such as an amine or hydroxyl group, may be used to bind a cofactor or other targeting ligand. For example, polyethylene glycol ethylamine may be reacted with N-succinimidylbiotin or p-nitrophenylbiotin to introduce a coupling group onto the spacer. For example, biotin may be coupled to the spacer, which will non-covalently bind proteins. As an example, MPB-PEG-DPPE may be synthesized as follows. DPPE-PEG with a free amino group at the terminus of the PEG will be provided as described previously. Synthesis of the SMPB:PEG-DPPE may then be carried out with 1 equivalent of triethylamine in chloroform at a molar ratio of 1:5 SMPB:DPPE-PEG. After 3 hours, the reaction mixture will be evaporated to dryness under argon. Excess unreacted SMPB and major by products will be removed by preparative thin layer chromatography (TLC, silica gel developed with 50% acetone in chloroform). The upper portion of the lipid band can be extracted from the silica with about 20–30% methanol in chloroform (V:V) resulting in the isolation of pure intact MPB-Peg-DPPE. Streptavidin may then be coupled to proteins so that the proteins in turn may then be coupled to the MPB-PEG-DPPE. Briefly SPDP would be incubated with streptavidin at room temperature for 30 minutes and chromatography employed to remove unreacted SPDP. Dithiothreitol (DTT) was added to the reaction mixture and 10 minutes later 2-thiopyridone at a concentration of 343 nM. The remainder of the reaction mixture is reduced with DTT (25 mM for 10 min.). The thiolated product is isolated by gel exclusion. The resulting streptavidin labeled proteins may be used to bind to the biotinylated spacers affixed to the lipid moieties.

Other suitable methods for linking the targeting ligand to the stabilizing materials of the present invention and for activating the free end of the stabilizing materials are described by Allen et al, U.S. Pat. No. 5,620,689, the disclosure of which is hereby incorporated by reference herein in its entirety.

The targeted compounds of the present invention are incorporated in compositions which may be used to form targeted emulsions and/or targeted vesicles, including, for example, targeted emulsions, targeted micelles, targeted liposomes, targeted albumin coated microspheres, targeted polymer coated microspheres, targeted cochleates and the like. The targeting ligand which is attached to the compounds from which the vesicles are prepared may be directed, for example, outwardly from the surface of the vesicle. Thus, there is provided a targeted vesicle which can be used to target receptors and tissues.

In certain embodiments, the targeting ligands may be incorporated in the present stabilizing materials via non-covalent associations. As known to one skilled in the art, non-covalent association is generally a function of a variety of factors, including, for example, the polarity of the involved molecules, the charge (positive or negative), if any, of the involved molecules, the extent of hydrogen bonding through the molecular network, and the like. Non-covalent bonds are preferably selected from the group consisting of ionic interaction, dipole—dipole interaction, hydrogen bonds, hydrophilic interactions, van der Waal's forces, and any combinations thereof. Non-covalent interactions may be employed to bind the targeting ligand to the lipid, or directly to the surface of a vesicle. For example, the amino acid sequence Gly-Gly-His may be bound to the surface of a vesicle, preferably by a linker, such as PEG, and copper, iron or vanadyl ion may then be added. Proteins, such as antibodies which contain histidine residues, may then bind to the vesicle via an ionic bridge with the copper ion, as described in U.S. Pat. No. 5,466,467, the disclosure of which is hereby incorporated herein by reference in its entirety. An example of hydrogen bonding involves cardiolipin lipids which can be incorporated into the lipid compositions.

In preferred embodiments of the present invention, which may involve vesicles, changes, for example, in pH and/or temperature in vivo, may be employed to promote a change in location in the targeting ligands, for example, from a location within the vesicle, to a location external to the outer wall of the vesicle. This may promote binding of the targeting ligands to targeting sites, for example, receptors, such as lymphocytes, and tissues, including myocardial, endothelial and epithelial cells, since the targeting ligand has a greater likelihood of exposure to such targeting sites. In addition, high energy ultrasound can be used to promote rupturing of the vesicles. This can also expose the targeting ligand to the desired binding site.

As an example, a targeting ligand incorporated into the compositions of the present invention may be of the formula:

wherein L is a lipid, protein, polymer, carbohydrate, surfactant, photoactive agent or the like; P is a hydrophilic polymer; and T is a targeting ligand.

In a preferred embodiment, L is a lipid selected from the group consisting of lecithins, phosphatidylcholines, phosphatidylserines, phosphatidyl-inositols, cardiolipins, cholesterols, cholesterolamines, lysophosphatides, erythro-sphingosines, sphingomyelins, ceramides, cerebrosides, saturated phospholipids, unsaturated phospholipids, and krill phospholipids. More preferably, L is a lipid is selected from the group consisting of lecithins, phosphatidylcholines, phosphatidyl-serines and phosphatidylinositols. In other preferred embodiments, L is a lipid selected from the group consisting of 1,2-diacyl-sn-glycero-3-phosphocholines, 1,2-diacyl-sn-glycero-3-phosphoethanolamines, 1,2-diacyl-sn-glycero-3-[phospho-rac-(1-glycerols)], 1,2-diacyl-sn-glycero-3-phosphates, 1,2-diacyl-sn-glycero-3-[phosphoserines], lyso-phosphatidylcholines, lysophosphatidylglycerols, 1,2-diacyl-sn-glycerols, 1,2-diacyl-ethylene glycols, N-(n-caproylamine)-1,2-diacyl-sn-glycero-3-phosphoethanolamines, N-dodecanylamine-1,2-diacyl-sn-glycero-3-phosphoethanolamines, N-succinyl-1,2-diacyl-sn-glycero-3-phosphoethanolamines, N-glutaryl-1,2-diacyl-sn-glycero-3-phosphoethanolamincs and N-dodecanyl-1,2-diacyl-sn-glycero-3-phosphoethanol-amines. More preferably, L is a lipid selected from the group consisting of 1,2-diacyl-sn-glycero-3-phosphocholines, 1,2-diacyl-sn-glycero-3-phosphoethanolamines, 1,2-diacyl-sn-glycero-3-[phospho-rac-(1-glycerols)], 1,2-diacyl-sn-glycero-3-phosphates, 1,2-diacyl-sn-glycero-3-[phosphoserines], lysophosphatidylcholines, lysophosphatidyl-glycerols and 1,2-diacyl-sn-glycerols.

In other embodiments, L is a protein which comprises albumin.

In still other embodiments, L is a polymer which comprises synthetic polymers or copolymers prepared from monomers selected from the group consisting of acrylic acid, methacrylic acid, ethyleneimine, crotonic acid, acrylamide, ethyl acrylate, methyl methacrylate, 2-hydroxyethyl methacrylate, lactic acid, glycolic acid, ε-caprolactone, acrolein, cyanoacrylate, bisphenol A, epichlorhydrin, hydroxyalkyl-acrylates, siloxane, dimethylsiloxane, ethylene oxide, propylene oxide, ethylene glycol, hydroxyalkylmeth-acrylates, N-substituted acrylamides, N-substituted methacrylamides, N-vinyl-2-pyrrolidone, 2,4-pentadiene-1-ol, vinyl acetate, acrylonitrile, styrene, p-aminostyrene, p-aminobenzylstyrene, sodium styrene sulfonate, sodium 2-sulfoxyethylmeth-acrylate, vinyl pyridine, aminoethyl methacrylates, 2-methacryloyloxytrimethylammonium chloride and polyphosphazene. Also preferred are compounds where L is a polymer which comprises synthetic polymers or copolymers selected from the group consisting of polyacrylic acid, polyethyleneimine, polymethacrylic acid, polymethylmethacrylate, polysiloxane, polydimethylsiloxane, polylactic acid, poly(ε-caprolactone), epoxy resin, poly(ethylene oxide), poly(propylene oxide), poly(ethylene glycol), polyamide, polyvinylidene-polyacrylonitrile, polyvinylidene-polyacrylonitrile-polymethylmethacrylate and polystyrene-polyacrylonitrile. Preferred among these polymers is polyvinylidene-polyacrylonitrile copolymer.

In other embodiments, L is a surfactant, preferably a fluorosurfactant.

In the above compounds, P is a hydrophilic polymer. Preferably, P is a hydrophilic polymer selected from the group consisting of polyalkyleneoxides, polyvinyl alcohol, polyvinylpyrrolidones, polyacrylamides, polymethacrylamides, polyphosphazenes, phosphazene, poly(hydroxyalkylcarboxylic acids) and polyoxazolidines. More preferably, P is a polyalkyleneoxide polymer, with polyethylene glycol and polypropylene glycol being even more preferred and polyethylene glycol being particularly preferred.

In the above formula, T is a targeting ligand. Preferably, T is a targeting ligand described herein, including proteins, lipoproteins, glycolipids, antibodies, peptides, saccharides, steroids, steroid analogs and genetic material, with proteins, peptides and saccharides being more preferred.

In the case of targeting ligands which comprise saccharide groups, suitable saccharide moieties include, for example, monosaccharides, disaccharides and polysaccharides. Exemplary monosaccharides may have six carbon atoms and these saccharides include allose, altrose, glucose, dextrose, mannose, gulose, idose, galactose, talose, fructose, psicose, verbose and tagatose. Five carbon saccharides include ribose, arabinose, xylose, lyxose, ribulose and xylulose. Four carbon saccharides include erythrose, threose and erythrulose. Disaccharides include sucrose, lactose, maltose, isomaltose and cellobiose. Saccharide bearing targeting lipids may be synthesized through a multistep organic synthesis approach, as described more fully hereinafter. For example, lipids bearing targeting glucose moieties may be prepared by reacting, for example, α-glucopyranosyl bromide tetrabenzyl with ω-trifluoroacetyl-aminopoly-ethyleneglycol to obtain ω-glucopyranosyl tetrabenzyl-ω'-trifluoroacetyl-aminopolyethyleneglycol. This may then be hydrolyzed in a sodium carbonate or potassium carbonate solution and then hydrogenated to obtain ω-glucopyranpsyl-ω'amino-polyethyleneglycol. Aminoglyco-pyranosyl terminated polyethyleneglycol may then react with N-DPGS-succinimide to form the lipid bearing saccharide DPGS-NH-PEG-Glucose. In certain embodiments, the targeting ligands target cancer cells or tumor cells.

In another embodiment, the targeting ligand incorporated into the compositions of the present invention may be of the formula:

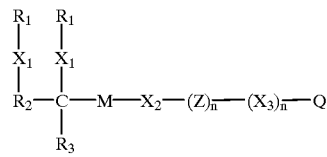

where each $X_1$ is independently —O—, —S—, —SO—, —SO$_2$—, —NR$_4$—, —X$_4$—C(=X$_5$)—, —C(=X$_5$)—X$_4$— or —C(=X$_5$)—; each of $X_2$ and $X_3$ is independently a direct bond, —R$_5$—X$_4$—C(=X$_5$)—, —R$_5$—C(=X$_5$)—X$_4$, —X$_4$—C(=X$_5$)—R$_5$—, —C(=X$_5$)—X$_4$—R$_5$—, —X$_4$—R$_5$—C(=X$_5$)—X$_4$—, —R$_5$—X$_4$—C(=X$_5$)—R$_5$—C(=X$_5$)—X$_4$— or —R$_5$—C(=X$_5$)—X$_4$—R$_5$—X$_4$—C(=X$_5$)—; each $X_4$ is independently —O—, —NR$_4$— or —S—; each $X_5$ is independently O or S; M is —R$_5$—X$_4$—C(=X$_5$)—, —R$_5$—C(=X$_5$)—X$_4$—, —R$_5$—X$_4$—(YX$_5$)P(=X$_5$)—X$_4$— or —X$_4$—(YX$_5$)P(=X$_5$)—X$_4$—R$_5$—; each n is, independently, 0 or 1; Y is hydrogen or a pharmaceutically acceptable counter ion; Z is a hydrophilic polymer; Q is a targeting ligand or a precursor to a targeting ligand; each $R_1$ is independently an alkyl group of 1 to about 50 carbons that may optionally be substituted with one or more halogen atoms; each $R_2$ is independently an alkylene group of 1 to about 30 carbons that may optionally be substituted with one or more halogen atoms; each of $R_3$ and $R_4$ is independently hydrogen or alkyl of 1 to about 10 carbons; and each $R_5$ is independently a direct bond or alkylene of 1 to about 30 carbons.

In the above formula, when any symbol appears more than once in a particular formula or substituent, its meaning in each instance is independent of the other. Also in the above formula, it is intended that when each of two or more adjacent symbols is defined as being a "direct bond" to provide multiple, adjacent direct bonds, the multiple and adjacent direct bonds devolve into a single direct bond.

In preferred embodiments, each $X_1$ is independently —$X_4$—C(=$X_5$)—, —C(=$X_5$)—$X_4$— or —C(=$X_5$)—. More preferably, each $X_1$ is independently —$X_4$—C(=$X_5$)— or —C(=$X_5$)—$X_4$—. Even more preferably, $X_1$ is —C(=$X_5$)—$X_4$—, for example, —C(=O)—O—.

In preferred embodiments, each of $X_2$ and $X_3$ is independently a direct bond, —$R_5$—$X_4$—C(=$X_5$)—, —$R_5$—C(=$X_5$)—$X_4$, —$X_4$—C(=$X_5$)—$R_5$—, —C(=$X_5$)—$X_4$—$R_5$—, —$X_4$—$R_5$—C(=$X_5$)—$X_4$—or —$R_5$—$X_4$—C(=$X_5$)—$R_5$—C(=$X_5$)—$X_4$—. More preferably, $X_2$ is —$CH_2CH_2$—C(=O)—NH— or —$CH_2CH_2$NH—C(=O)—$CH_2CH_2$—C(=O)—NH— and $X_3$ is a direct bond, —C(=O)—NH—, —NH—C(=O)—, —NH—C(=O)—$CH_2$—, —NH$CH_2$—C(=O)—NH— or —NH—C(=O)—$CH_2CH_2$.

Preferably, each $X_4$ is independently —O— or —N$R_4$—. Preferably, $X_5$ is O.

In certain preferred embodiments, M is —$R_5$—$X_4$—C(=$X_5$)— or —$R_5$—$X_4$—(Y$X_5$)P(=$X_5$)—$X_4$—, with M more preferably being —$CH_2$O—C(=O) or —$CH_2$O—(HO)P(=O)—O—. In other preferred embodiments, M is —$R_5$—$X_4$—C(=$X_5$)— or —$R_5$—C(=$X_5$)—$X_4$—. In yet other preferred embodiments, M is —$R_5$—$X_4$—(Y$X_5$)P(=$X_5$)—$X_4$— or —$X_4$—(Y$X_5$)P(=$X_5$)—$X_4$—$R_5$—. where at least one of $X_4$ or $X_5$ is S.

In the above formula, Z is a hydrophilic polymer. Preferably, Z is selected from the group consisting of polyalkyleneoxides, polyvinyl alcohol, polyvinylpyrrolidones, polyacrylamides, polymethacrylamides, polyphosphazenes, poly(hydroxyalkyl-carboxylic acids) and polyoxazolidines. More preferably, Z comprises a polyalkylene-oxide. Even more preferably, Z is a polyalkyleneoxide selected from the group consisting of polyethylene glycol and polypropylene glycol, with polyethylene glycol being still more preferred. In certain other preferred embodiments, Z is a hydrophilic polymer other than polyalkylene-oxides, including polyethylene glycol and polypropylene glycol. The molecular weight of Z may vary, depending, for example, on the particular end-use of the compounds. Preferably, Z is a polymer having a molecular weight which ranges from about 100 to about 10,000, and all combinations and subcombinations of ranges therein. More preferably, Z is a polymer having a molecular weight of from about 1,000 to about 5,000. Also preferred are polymers which exhibit polydispersities ranging from greater than about 1 to about 3, and all combinations and subcombinations of ranges therein. More preferably, Z is a polymer having a polydispersity of from greater than about 1 to about 2, with polydispersities of from greater than about 1 to about 1.5 being even more preferred, and polydispersities of from greater than about 1 to about 1.2 being still more preferred.

In the above formula, Q is a targeting ligand or a precursor thereto. Q is preferably a targeting ligand described herein, including proteins, lipoproteins, glycolipids, antibodies, peptides, saccharides, steroids, steroid analogs and genetic material, more preferably proteins, peptides and saccharides.

In the above formula, each $R_1$ is independently alkyl which ranges from 1 to about 50 carbons, and all combinations and subcombinations of ranges therein, or alkenyl of from about 2 to about 50 carbons, and all combinations and subcombinations of ranges therein. Preferably, each $R_1$ is independently alkyl of greater than 1 to about 40 carbons. More preferably, each $R_1$ is independently alkyl of about 5 to about 30 carbons. Even more preferably, each $R_1$ is independently alkyl of about 10 to about 20 carbons, with alkyl of about 15 carbons being still more preferred. In certain preferred embodiments, $R_1$ is a shorter chain alkyl of from 1 to about 20 carbons. In certain other preferred embodiments, $R_1$ is a longer chain alkyl of from about 20 to about 50 carbons, or about 30 to about 50 carbons. In other preferred embodiments, the alkyl group in $R_1$ may be substituted with one or more fluorine atoms, and may be perfluorinated.

In the above formula, each $R_2$ is independently alkylene which ranges from 1 to about 30 carbons, and all combinations and subcombinations of ranges therein. Preferably, each $R_2$ is independently alkylene of 1 to about 20 carbons. More preferably, each $R_2$ is independently alkylene of 1 to about 10 carbons. Even more preferably, each $R_2$ is independently alkylene of 1 to about 5 carbons, with methylene being especially preferred. In other preferred embodiments, the alkylene group in $R_2$ may be substituted with one or more fluorine atoms, and may be perfluorinated.

In the above formula, each of $R_3$ and $R_4$ is independently hydrogen or alkyl which ranges from 1 to about 10 carbons, and all combinations and subcombinations of ranges therein. Preferably, each of $R_3$ and $R_4$ is hydrogen or alkyl of 1 to about 5 carbons. More preferably, each of $R_3$ and $R_4$ is hydrogen.

In the above formula, each $R_5$ is independently a direct bond or alkylene which ranges from 1 to about 30 carbons, and all combinations and subcombinations of ranges therein. Preferably, each $R_5$ is independently a direct bond or alkylene of 1 to about 20 carbons. More preferably, each $R_5$ is independently a direct bond or alkylene of 1 to about 10 carbons. Even more preferably, each $R_5$ is independently a direct bond or alkylene of 1 to about 5 carbons. Still more preferably, each $R_5$ is a direct bond or —$(CH_2)_x$—, where x is 1 or 2.

The compositions and stabilizing materials of the present invention may also comprise or be used in combination with a bioactive agent. Suitable bioactive agents include, for example, antineoplastic agents, blood products, biological response modifiers, anti-fungal agents, hormones, steroids, vitamins, peptides, peptide analogs, enzymes, anti-allergenic agents, anti-coagulation agents, circulatory agents, anti-tubercular agents, anti-viral agents, anti-anginal agents, antibiotics, anti-inflammatory agents, analgesics, anti-protozoan agents, anti-rheumatic agents, narcotics, cardiac glycoside agents, chelates, neuromuscular blocking agents, sedatives (hypnotics), local anesthetic agents, general anesthetic agents, radioactive particles, radioactive ions, X-ray contrast agents, monoclonal antibodies, polyclonal antibodies and genetic material.

Exemplary bioactive agents are listed below; however, the list is exemplary only and is not intended to limit the bioactive agents that may be used in the present invention.

Antineoplastic agents, include, for example, platinum compounds (e.g., spiroplatin, cisplatin, and carboplatin), methotrexate, adriamycin, mitomycin c, ansamitocin, bleomycin, bleomycin sulfate, cytosine arabinoside, arabinosyl adenine, mercaptopolylysine, vincristine, busulfan, chlorambucil, melphalan (e.g., PAM, L-PAM or phenylalanine mustard), mercaptopurine, mitotane, procarbazine hydrochloride, dactinomycin (actinomycin D), daunorubicin hydrochloride, doxorubicin hydrochloride, taxol, plicamycin (mithramycin), aminoglutethimide, estramustine phosphate sodium, flutamide, leuprolide acetate, megestrol acetate, tamoxifen citrate, testolactone, trilostane, amsacrine (m-AMSA), asparaginase (L-asparaginase), Erwina asparaginase, etoposide (VP-16), interferon α-2a, interferon α-2b, teniposide (VM-26), vinblastine sulfate (VLB), vincristine sulfate, and carzelesin.

Blood products, include, for example, erythropoietin, parenteral iron, hemin, and hematoporphyrins and their derivatives.

Biological response modifiers, include, for example, muramyldipeptide, muramyltripeptide, microbial cell wall components, lymphokines (e.g., bacterial endotoxin such as lipopolysaccharide, macrophage activation factor), sub-units of bacteria (such as Mycobacteria, Corynebacteria), the synthetic dipeptide, N-acetyl-muramyl-L-alanyl-D-isoglutamine, and prostaglandins.

Anti-fungal agents, include, for example, ketoconazole, nystatin, griseofulvin, flucytosine (5-fc), miconazole, amphotericin B, ricin, and β-lactam antibiotics (e.g., sulfazecin).

Hormones and steroids, include, for example, growth hormone, melanocyte stimulating hormone, adrenocorticotropic hormone, dexamethasone, dexamethasone acetate, dexamethasone sodium phosphate, cortisone, cortisone acetate, hydrocortisone, hydrocortisone acetate, hydrocortisone cypionate, hydrocortisone sodium phosphate, hydrocortisone sodium succinate, prednisone, prednisolone, prednisolone acetate, prednisolone sodium phosphate, prednisolone tebutate, prednisolone pivalate, triamcinolone, triamcinolone acetonide, triamcinolone hexacetonide, triamcinolone diacetate, methylprednisolone, methylprednisolone acetate, methylprednisolone sodium succinate, flunsolide, beclomethasone dipropionate, betamethasone sodium phosphate, betamethasone, vetamethasone disodium phosphate, vetamethasone sodium phosphate, betamethasone acetate, betamethasone disodium phosphate, chloroprednisone acetate, corticosterone, desoxycorticosterone, desoxycorticosterone acetate, desoxycortico-sterone pivalate, desoximethasone, estradiol, fludrocortisone, fludrocortisone acetate, dichlorisone acetate, fluorohydrocortisone, fluorometholone, fluprednisolone, paramethasone, paramethasone acetate, androsterone, fluoxymesterone, aldosterone, methandrostenolone, methylandrostenediol, methyl testosterone, norethandrolone, testosterone, testosterone enanthate, testosterone propionate, equilenin, equilin, estradiol benzoate, estradiol dipropionate, estriol, estrone, estrone benzoate, acetoxy-pregnenolone, anagestone acetate, chlormadinone acetate, flurogestone acetate, hydroxymethylprogesterone, hydroxymethylprogesterone acetate, hydroxy-progesterone, hydroxyprogesterone acetate, hydroxyprogesterone caproate, melengestrol acetate, normethisterone, pregnenolone, progesterone, ethynyl estradiol, mestranol, dimethisterone, ethisterone, ethynodiol diacetate, norethindrone, norethindrone acetate, norethisterone, fluocinolone acetonide, flurandrenolone, flunisolide, hydrocortisone sodium succinate, methylprednisolone sodium succinate, prednisolone phosphate sodium, triamcinolone acetonide, hydroxydione sodium, spironolactone, oxandrolone, oxymetholone, prometholone, testosterone cypionate, testosterone phenylacetate, estradiol cypionate, and norethynodrel.

Vitamins, include, for example, cyanocobalamin neinoic acid, retinoids and derivatives thereof such as retinol palmitate, oc-tocopherol, naphthoquinone, cholecalciferol, folic acid and tetrahydrofolate.

Peptides and peptide analogs, include, for example, manganese super oxide dismutase, tissue plasminogen activator (t-PA), glutathione, insulin, dopamine, peptide ligands containing RGD, AGD, RGE, KGD, KGE or KQAGDV (Peptides with affinity for the GPIIBIIIa receptor), opiate peptides, enkephalins, endorphins and their analogs, human chorionic gonadotropin (HCG), corticotropin release factor (CRF), cholecystokinins and their analogs, bradykinins and their analogs and promoters and inhibitors, elastins, vasopressins, pepsins, glucagon, substance P, integrins, captopril, enalapril, lisinopril and other ACE inhibitors, adrenocorticotropic hormone (ACTH), oxytocin, calcitonins, IgG or fragments thereof, IgA or fragments thereof, IgM or fragments thereof, ligands for Effector Cell Protease Receptors (all subtypes), thrombin, streptokinase, urokinase, t-PA and all active fragments or analogs, Protein Kinase C and its binding ligands, interferons (α-interferon, β-interferon, γ-interferon), colony stimulating factors (CSF), granulocyte colony stimulating factors (GCSF), granulocyte-macrophage colony stimulating factors (GM-CSF), tumor necrosis factors (TNF), nerve growth factors (NGF), platelet derived growth factors, lymphotoxin, epidermal growth factors, fibroblast growth factors, vascular endothelial cell growth factors, erythropoietin, transforming growth factors, oncostatin M, interleukins (1, 2, 3, 4, 5, 6, 7, 8, 9, 10, 11 and 12), metalloprotein kinase ligands, collagenases and agonists and antagonists.

Enzymes, include, for example, alkaline phosphatase, cyclooxygenase type I and agonists and antagonists.

Anti-allergenic agents, include, for example, amelexanox.

Anti-coagulation agents, include, for example, phenprocoumon and heparin.

Circulatory drugs, include, for example, propranolol.

Anti-tubercular agents, include, for example, para-aminosalicylic acid, isoniazid, capreomycin sulfate cycloserine, ethambutol hydrochloride ethionamide, pyrazinamide, rifampin, and streptomycin sulfate.

Anti-viral agents, include, for example, acyclovir, amantadine azidothymidine (AZT or Zidovudine), ribavirin, and vidarabine monohydrate (adenine arabinoside, ara-A).

Anti-anginal agents, include, for example, diltiazem, nifedipine, verapamil, erythritol tetranitrate, isosorbide dinitrate, nitroglycerin (glyceryl trinitrate), and pentaerythritol tetranitrate.

Antibiotics, include, for example, dapsone, chloramphenicol, neomycin, cefaclor, cefadroxil, cephalexin, cephradine erythromycin, clindamycin, lincomycin, amoxicillin, ampicillin, bacampicillin, carbenicillin, dicloxacillin, cyclacillin, picloxacillin, hetacillin, methicillin, nafcillin, oxacillin, penicillin G, penicillin V, ticarcillin, rifampin, and tetracycline.

Anti-inflammatory agents and analgesics, include, for example, diflunisal, ibuprofen, indomethacin, meclofenamate, mefenamic acid, naproxen, oxyphenbutazone, phenylbutazone, piroxicam, sulindac, tolmetin, aspirin and salicylates.

Anti-protozoan agents, include, for example, chloroquine, metronidazole, hydroxychloroquine, quinine, and meglumine antimonate.

Anti-rheumatic agents, include, for example, penicillamine.

Narcotics, include, for example, paregoric and opiates, such as codeine, heroin, methadone, morphine and opium.

Cardiac glycoside agents, include, for example, deslanoside, digitoxin, digoxin, digitalin and digitalis.

Chelates, include, for example, diethylene triamine pentaacetic acid (DTPA) and 1,4,7,1 0-tetraazocyclododecane-N',N',N'',N''-tetraacetic acid (DOTA). Any chelate that is generally used in conjunction with paramagnetic or radioactive metal ions may be used.

Neuromuscular blocking agents, include, for example, atracurium mesylate, gallamine triethiodide, hexafluorenium bromide, metocurine iodide, pancuronium bromide, succinylcholine chloride (suxamethonium chloride), tubocurarine chloride, and vecuronium bromide.

Sedatives (hypnotics), include, for example, amobarbital, amobarbital sodium, aprobarbital, butabarbital sodium, chloral hydrate, ethchlorvynol, ethinamate, flurazepam hydrochloride, glutethimide, methotrimeprazine hydrochloride, methyprylon, midazolam hydrochloride paraldehyde, pentobarbital, pentobarbital sodium, phenobarbital sodium, secobarbital sodium, talbutal, temazepam, and triazolam.

Local anesthetic agents, include, for example, bupivacaine hydrochloride, chloroprocaine hydrochloride, etidocaine hydrochloride, lidocaine hydrochloride, mepivacaine hydrochloride, procaine hydrochloride, and tetracaine hydrochloride.

General anesthetic agents, include, for example, droperidol, etomidate, fentanyl citrate with droperidol, ketamine hydrochloride, methohexital sodium, and thiopental sodium.

Radioactive particles or radioactive ions, include, for example, strontium, rhenium, yttrium, technetium, and cobalt.

X-ray contrast agents, include, for example, X-ray contrast agents known in the art that contain heavy metals such as yttrium, ytterbium, lanthanides in chelates or other iodinated materials, such as iothalamate.

Genetic material, includes, for example, nucleic acids, RNA and DNA, of either natural or synthetic origin, including recombinant RNA and DNA and antisense RNA and DNA; hammerhead RNA, ribozymes, hammerhead ribozymes, antigene nucleic acids, both single and double stranded RNA and DNA and analogs thereof, ribooligonucleotides, antisense ribooligonucleotides, deoxyribooligonucleotides, and antisense deoxyribooligonucleotides. Other types of genetic material that may be used include, for example, genes carried on expression vectors such as plasmids, phagemids, cosmids, yeast artificial chromosomes (YACs), and defective or "helper" viruses, antigene nucleic acids, both single and double stranded RNA and DNA and analogs thereof, such as phosphorothioate and phosphorodithioate oligodeoxynucleotides. Additionally, the genetic material may be combined, for example, with proteins or other polymers. Other examples of genetic material include, for example, DNA encoding at least a portion of LFA-3, DNA encoding at least a portion of an HLA gene, DNA encoding at least a portion of dystrophin, DNA encoding at least a portion of CFTR, DNA encoding at least a portion of IL-2, DNA encoding at least a portion of TNF, and an antisense oligonucleotide capable of binding the DNA encoding at least a portion of Ras. DNA encoding certain proteins may be used in the treatment of many different types of diseases. For example, adenosine deaminase may be provided to treat ADA deficiency; tumor necrosis factor and/or interleukin-2 may be provided to treat advanced cancers; HDL receptor may be provided to treat liver disease; thymidine kinase may be provided to treat ovarian cancer, brain tumors, or HIV infection; HLA-B7 may be provided to treat malignant melanoma; interleukin-2 may be provided to treat neuroblastoma, malignant melanoma, or kidney cancer; interleukin-4 may be provided to treat cancer; HIV env may be provided to treat HIV infection; antisense ras/p53 may be provided to treat lung cancer; and Factor VIII may be provided to treat Hemophilia B. See, for example, *Science* 258:744–746.

The bioactive agent may be a prodrug, including the prodrugs described, for example, by Sinkyla et al., *J. Pharm.*

*Sci.*, 64:181–210 (1975), in U.S. application Ser. No. 08/851,780 filed May 6, 1997, and in U.S. application Ser. No. 08/887,215 filed Jul. 2, 1997, the disclosures of which are hereby incorporated by reference herein in their entirety.

The bioactive agents used in the present invention are preferably highly active in low concentrations. The targeting aspects of the invention further enable lower dosages to be used for therapy, since the effective concentration at the therapeutic site remains undiluted in the body. The amount of bioactive agent to be administered to a patient depends, for example, on the particular bioactive agent, the method in which the bioactive agent is being administered, and the age, sex, weight and physical condition of the patient. Generally, treatment is initiated with small dosages, which can then be increased by small increments, until the desired effect under the circumstances is achieved. Additionally, one skilled in the art may rely on reference materials, such as the *Physician's Desk Reference*, published by Medical Economics Company at Montvale, N.J. 07645-1742, to determine the appropriate amount of a particular bioactive agent that may be administered to a patient. In a preferred embodiment, the bioactive agent is delivered by applying ultrasound to the patient (e.g., in a region of the patient and/or to diseased tissue in the patient) for the purpose, for example, of treating a condition (i.e., a disease state, malady, disorder, etc.) in the patient.

The stabilizing materials and/or vesicles of the present invention may be prepared using any of a variety of suitable methods. These are described below separately for the embodiments involving stabilizing materials and a gas, including gas filled vesicles, and embodiments involving stabilizing materials and a gaseous precursor, including gaseous precursor filled vesicles, although stabilizing materials comprising both a gas and a gaseous precursor are a part of the present invention.

A wide variety of methods are available for the preparation of the stabilizing materials, including vesicles, such as micelles and/or liposomes. Included among these methods are, for example, shaking, drying, gas-installation and spray drying. Suitable methods for preparing vesicle compositions are described, for example, in U.S. Pat. No. 5,469,854, the disclosure of which is hereby incorporated herein by reference in its entirety. The vesicles are preferably prepared from lipids which remain in the gel state.

Micelles may be prepared using any one of a variety of conventional micellar preparatory methods which will be apparent to one skilled in the art. These methods typically involve suspension of the stabilizing material, such as a lipid compound, in an organic solvent, evaporation of the solvent, resuspension in an aqueous medium, sonication and centrifugation. The foregoing methods, as well as others, are discussed, for example, in Canfield et al, *Methods in Enzymology*, 189:418 (1990); El-Gorab et al, *Biochem. Biophys. Acta*, 306:58 (1973); *Colloidal Surfaciant*, Shinoda, K., Nakagana, Tamamushi and Isejura, Academic Press, NY (1963) (especially "The Formation of Micelles," Shinoda, Chapter 1, pp. 1–88); Catalysis in Micellar and Macromolecular Systems, Fendler and Fendler, Academic Press, NY (1975). The disclosures of each of the foregoing publications are hereby incorporated herein by reference in their entirety.

In liposomes, the lipid compound(s) may be in the form of a monolayer or bilayer, and the monolayer or bilayer lipids may be used to form one or more monolayers or bilayers. In the case of more than one monolayer or bilayer, the monolayers or bilayers are generally concentric. Thus, lipids may be used to form unilamellar liposomes (comprised of one monolayer or bilayer), oligolamellar liposomes (comprised of two or three monolayers or bilayers) or multilamellar liposomes (comprised of more than three monolayers or bilayers).

A wide variety of methods are available in connection with the preparation of vesicles, including liposomes. Accordingly, liposomes may be prepared using any one of a variety of conventional liposomal preparatory techniques which will be apparent to one skilled in the art, including, for example, solvent dialysis, French press, extrusion (with or without freeze-thaw), reverse phase evaporation, simple freeze-thaw, sonication, chelate dialysis, homogenization, solvent infusion, microemulsification, spontaneous formation, solvent vaporization, solvent dialysis, French pressure cell technique, controlled detergent dialysis, and others, each involving the preparation of the vesicles in various fashions. See, e.g., Madden et al., *Chemistry and Physics of Lipids,* 53:37 (1990), the disclosure of which is hereby incorporated herein by reference in its entirety. Suitable freeze-thaw techniques are described, for example, in International Application Serial No. PCT/US89/05040, filed Nov. 8, 1989, the disclosure of which is hereby incorporated herein by reference in its entirety. Methods which involve freeze-thaw techniques are preferred in connection with the preparation of liposomes. Preparation of the liposomes may be carried out in a solution, such as an aqueous saline solution, aqueous phosphate buffer solution, or sterile water. The liposomes may also be prepared by various processes which involve shaking or vortexing, which may be achieved, for example, by the use of a mechanical shaking device, such as a Wig-L-Bug™ (Crescent Dental, Lyons, Ill.), a Mixomat (Degussa AG, Frankfurt, Germany), a Capmix (Espe Fabrik Pharmazeutischer Praeparate GMBH & Co., Seefeld, Oberay Germany), a Silamat Plus (Vivadent, Lechtenstein), or a Vibros (Quayle Dental, Sussex, England). Conventional microemulsification equipment, such as a Microfluidizer™ (Microfluidics, Woburn, Mass.) may also be used.

Spray drying may be employed to prepare gas filled vesicles. Utilizing this procedure, the stabilizing materials, such as lipids, may be pre-mixed in an aqueous environment and then spray dried to produce gas filled vesicles. The vesicles may be stored under a headspace of a desired gas.

Many liposomal preparatory techniques which may be adapted for use in the preparation of vesicle compositions are discussed, for example, in U.S. Pat. Nos. 4,728,578, 4,728,575, 4,737,323, 4,533,254, 4,162,282, 4,310,505, and 4,921,706; U.K. Patent Application GB 2193095 A; International Application Nos. PCT/US85/01161 and PCT/US89/05040 Mayer et al., *Biochimica et Biophysica Acta,* 858:161 (1986); Hope et al., *Biochimica et Biophysica Acta,* 812:55 (1985); Mayhew et al., *Methods in Enzymology,* 149:64 (1987); Mayhew et al., *Biochimica et Biophysica Acta,* 755:169 (1984); Cheng et al, *Investigative Radiology,* 22:47 (1987); and *Liposome Technology,* Gregoriadis, ed., Vol. 1, pp. 29–31, 51–67 and 79–108 (CRC Press Inc., 1984), the disclosures of which are hereby incorporated by reference herein in their entirety.

In connection with stabilizing materials, and especially lipid compositions in the form of vesicles, it may be advantageous to prepare the lipid compositions at a temperature below the gel to liquid crystalline phase transition temperature of the lipids. This phase transition temperature is the temperature at which a lipid bilayer will convert from a gel state to a liquid crystalline state. See, for example, Chapman et al, J. Biol. Chem., 249:2512 (1974), the disclosure of which is hereby incorporated by reference herein in its entirety. It is believed that vesicles which are prepared from lipids that possess higher gel state to liquid crystalline state phase transition temperatures tend to have enhanced impermeability at any given temperature. See Marsh, CRC Handbook of Lipid Bilayers (CRC Press, Boca Raton, Fla. 1990), at p. 139 (the disclosure of which is hereby incorporated by reference herein in its entirey) for main chain melting transitions of saturated diacyl-sn-glycero-3-phosphocholines. The gel state to liquid crystalline state phase transition temperatures of various lipids will be readily apparent to one skilled in the art and are described, for example, by Gregoriadis, ed., *Liposome Technology,* Vol. I, 1–18 (CRC Press, 1984).

Stabilizing materials, such as lipids, comprising a gas can be prepared by agitating an aqueous solution containing, if desired, a stabilizing material, in the presence of a gas. The term "agitating" means any shaking motion of an aqueous solution such that gas is introduced from the local ambient environment into the aqueous solution. This agitation is preferably conducted at a temperature below the gel to liquid crystalline phase transition temperature of the lipid. The shaking involved in the agitation of the solutions is preferably of sufficient force to result in the formation of a lipid composition, including vesicle compositions, and particularly vesicle compositions comprising gas filled vesicles. The shaking may be by swirling, such as by vortexing, side-to-side, or up and down motion. Different types of motion may be combined. Also, the shaking may occur by shaking the container holding the aqueous lipid solution, or by shaking the aqueous solution within the container without shaking the container itself.

The shaking may occur manually or by machine. Mechanical shakers that may be used include, for example, a shaker table such as a VWR Scientific (Cerritos, Calif.) shaker table, as well as any of the shaking devices described hereinbefore, with the Capmix (Espe Fabrik Pharmazeutischer Praeparate GMBH & Co., Seefeld, Oberay, Germany) being preferred. It has been found that certain modes of shaking or vortexing can be used to make vesicles within a preferred size range. Shaking is preferred, and it is preferred that the shaking be carried out using the Espe Capmix mechanical shaker. In accordance with this preferred method, it is preferred that a reciprocating motion be utilized to generate the lipid compositions, and particularly vesicles. It is even more preferred that the motion be reciprocating in the form of an arc. It is contemplated that the rate of reciprocation, as well as the arc thereof, is particularly important in connection with the formation of vesicles. Preferably, the number of reciprocations or full cycle oscillations is from about 1,000 to about 20,000 per minute, more preferably from about 2,500 to about 8,000 per minute, most preferably from about 3,300 to about 5,000 per minute. Of course, the number of oscillations can be dependent upon the mass of the contents being agitated. Generally, a larger mass requires fewer oscillations. Another means for producing shaking includes the action of gas emitted under high velocity or pressure.

It will also be understood that preferably, with a larger volume of aqueous solution, the total amount of force will be correspondingly increased. Vigorous shaking is defined as at least about 60 shaking motions per minute, and is preferred. Vortexing occurs at about 60 to about 300 revolutions per minute, more preferably at about 300 to about 1,800 revolutions per minute.

In addition to the simple shaking methods described above, more elaborate methods can also be employed. Such elaborate methods include, for example, liquid crystalline shaking gas instillation processes and vacuum drying gas instillation processes, such as those described in U.S. Pat. Nos. 5,469,854, 5,580,575, 5,585,112, and 5,542,935, and U.S. application Ser. No. 08/307,305, filed Sep. 16, 1994, the disclosures of each of which are incorporated herein by reference in their entirety. Emulsion processes may also be employed in the preparation of compositions in accordance with the present invention. Such emulsification processes are described, for example, in Quay, U.S. Pat. Nos. 5,558,094, 5,558,853, 5,558,854, and 5,573,751, the disclosures of each of which are hereby incorporated herein by reference in their entirety. Spray drying may be also employed to prepare the gaseous precursor filled vesicles. Utilizing this procedure, the lipids may be pre-mixed in an aqueous environment and then spray dried to produce gaseous precursor filled vesicles. The vesicles may be stored under a headspace of a desired gas. Although any of a number of varying techniques can be used, the vesicle compositions employed in the present invention are preferably prepared using a shaking technique. Preferably, the shaking technique involves agitation with a mechanical shaking apparatus, such as an Espe Capmix (Seefeld, Oberay, Germany), using, for example, the techniques described in U.S. Pat. No. 5,542,935, the disclosure of which is hereby incorporated by reference herein in its entirety. In addition, after extrusion and sterilization procedures, which are discussed in detail below, agitation or shaking may provide vesicle compositions which can contain substantially no or minimal residual anhydrous lipid phase in the remainder of the solution. (Bangham et al, *J. Mol. Biol.* 13:238 (1965)). Other preparatory techniques include those described in Unger, U.S. Pat. No. 5,205,290, the disclosure of which is hereby incorporated herein by reference in its entirety.

Foams comprise an additional embodiment of the invention. Foams have biomedical applications in tissue augmentation, wound healing, and prevention of peritoneal adhesions. Phospholipid foams can be created by increasing the concentration of the phospholipids as well as by mixing with materials such as cetyl alcohol, surfactants, simethicone or polymers, such as methylcellulose. Fluorinated phospholipids may also be used to create stable, long-lasting foams. The most stable foams are generally prepared from materials which are polymerized or crosslinked, such as polymerizable phospholipids. Since foaming is also a function of surface tension reduction, detergents are generally useful foaming agents.

Foams can also be produced by shaking gas filled vesicles, where the foam appears on the top of the aqueous solution, and is coupled with a decrease in the volume of the aqueous solution upon the formation of foam. Preferably, the final volume of the foam is at least about two times the initial volume of the aqueous stabilizing material solution; more preferably, the final volume of the foam is at least about three times the initial volume of the aqueous solution; even more preferably, the final volume of the foam is at least about four times the initial volume of the aqueous solution; and most preferably, all of the aqueous stabilizing material solution is converted to foam.

The required duration of shaking time may be determined by detection of the formation of foam. For example, 10 ml of lipid solution in a 50 ml centrifuge tube may be vortexed for about 15–20 minutes or until the viscosity of the gas filled liposomes becomes sufficiently thick so that it no longer clings to the side walls as it is swirled. At this time, the foam may cause the solution containing the gas filled liposomes to raise to a level of about 30 to about 35 ml.

The concentration of lipid required to form a preferred foam level will vary depending upon the type of lipid used, and may be readily determined by one skilled in the art, in view of the present disclosure. For example, the concentration of 1,2-dipalmitoylphosphatidylcholine (DPPC) used to form gas filled liposomes by the methods of the present invention is about 20 mg/ml to about 30 mg/ml saline solution. The concentration of distearoylphosphatidylcholine (DSPC) used is about 5 mg/ml to about 10 mg/ml saline solution. Specifically, DPPC in a concentration of 20 mg/ml to 30 mg/ml, upon shaking, yields a total suspension and entrapped gas volume four times greater than the suspension volume alone. DSPC in a concentration of 10 mg/ml, upon shaking, yields a total volume completely devoid of any liquid suspension volume and contains entirely foam.

Microemulsification is a common method of preparing an emulsion of a foam precursor. Temperature increases and/or lowered pressures will cause foaming as gas bubbles form in the liquid. As discussed above, the foam may be stabilized by, for example, surfactants, detergents or polymers.

The size of gas filled vesicles can be adjusted, if desired, by a variety of procedures, including, for example, microemulsification, vortexing, extrusion, filtration, sonication, homogenization, repeated freezing and thawing cycles, extrusion under pressure through pores of defined size, and similar methods. Gas filled vesicles prepared in accordance with the methods described herein can range in size from less than about 1 $\mu$m to greater than about 100 $\mu$m. In addition, after extrusion and sterilization procedures, which are discussed in detail below, agitation or shaking provides vesicle compositions which provide substantially no or minimal residual anhydrous lipid phase in the remainder of the solution. (Bangham, et al, *J. Mol. Biol.*, 13:238 (1965)). If desired, the vesicles of the present invention may be used as they are formed, without any attempt at further modification of the size thereof. For intravascular use, the vesicles preferably have diameters of less than about 30 $\mu$m, and more preferably, less than about 12 $\mu$m. For targeted intravascular use including, for example, binding to certain tissue, such as cancerous tissue, the vesicles can be significantly smaller, for example, less than about 100 nm in diameter. For enteric or gastrointestinal use, the vesicles can be significantly larger, for example, up to a millimeter in size. Preferably, the vesicles are sized to have diameters of from about 2 $\mu$m to about 100 $\mu$m.

The gas filled vesicles may be sized by a simple process of extrusion through filters wherein the filter pore sizes control the size distribution of the resulting gas filled vesicles. By using two or more cascaded or stacked sets of filters, for example, a 10 $\mu$m filter followed by an 8 $\mu$m filter, the gas filled vesicles can be selected to have a very narrow size distribution around 7 to 9 $\mu$m. After filtration, these gas filled vesicles can remain stable for over 24 hours.

The sizing or filtration step may be accomplished by the use, for example, of a filter assembly when the composition is removed from a sterile vial prior to use, or more preferably, the filter assembly may be incorporated into a syringe during use. The method of sizing the vesicles will then comprise using a syringe comprising a barrel, at least one filter, and a needle; and will be carried out by an extraction step which comprises extruding the vesicles from the barrel through the filter fitted to the syringe between the barrel and the needle, thereby sizing the vesicles before they are administered to a patient. The extraction step may also comprise drawing the vesicles into the syringe, where the filter will function in the same way to size the vesicles upon entrance into the syringe. Another alternative is to fill such a syringe with vesicles which have already been sized by some other means, in which case the filter now functions to ensure that only vesicles within the desired size range, or of the desired maximum size, are subsequently administered by extrusion from the syringe.

In other embodiments, the vesicle compositions may be heat sterilized or filter sterilized and extruded through a filter prior to shaking. Generally, vesicle compositions comprising a gas may be heat sterilized, and vesicle compositions comprising gaseous precursors may be filter sterilized. Once gas filled vesicles are formed, they may be filtered for sizing as described above. Performing these steps prior to the formation of gas and/or gaseous precursor filled vesicles provide sterile gas and/or gaseous precursor filled vesicles ready for administration to a patient. For example, a mixing vessel such as a vial or syringe may be filled with a filtered lipid composition, and the composition may be sterilized within the mixing vessel, for example, by autoclaving. Gas may be instilled into the composition to form gas filled vesicles by shaking the sterile vessel. Preferably, the sterile vessel is equipped with a filter positioned such that the gas filled vesicles pass through the filter before contacting a patient.

The step of extruding the solution of lipid compound through a filter decreases the amount of unhydrated material by breaking up any dried materials and exposing a greater surface area for hydration. Preferably, the filter has a pore size of about 0.1 to about 5 $\mu$m, more preferably, about 0.1 to about 4 $\mu$m, even more preferably, about 0.1 to about 2 $\mu$m, and still more preferably, about 1 $\mu$m. Unhydrated compound, which is generally undesirable, appears as amorphous clumps of non-uniform size.

The sterilization step provides a composition that may be readily administered to a patient for diagnostic imaging. In certain embodiments, sterilization may be accomplished by heat sterilization, preferably, by autoclaving the solution at a temperature of at least about 100° C., and more preferably, by autoclaving at about 100° C. to about 130° C., even more preferably about 110° C. to about 130° C., still more preferably about 120° C. to about 130° C., and even more preferably about 130° C. Preferably, heating occurs for at least about 1 minute, more preferably about 1 to about 30 minutes, even more preferably about 10 to about 20 minutes, and still more preferably about 15 minutes. If desired, the extrusion and heating steps, as outlined above, may be reversed, or only one of the two steps can be used. Other modes of sterilization may be used, including, for example, exposure to gamma radiation.

In addition to the above embodiments, gaseous precursors contained in vesicles can be formulated which, upon activation, for example, by exposure to elevated temperature, varying pH, or light, undergo a phase transition from, for example, a liquid, including a liquid entrapped in a vesicle, to a gas, expanding to create the gas filled vesicles described herein. This technique is described in U.S. Pat. Nos. 5,542,935 and 5,585,112, the disclosures of which are hereby incorporated by reference herein in their entirety. The preferred method of activating the gaseous precursor is by exposure to elevated temperature. Activation or transition temperature, and like terms, refer to the boiling point of the gaseous precursor and is the temperature at which the liquid to gaseous phase transition of the gaseous precursor takes place. Useful gaseous precursors are those materials which have boiling points in the range of about −100° C. to about 70° C. The activation temperature is particular to each gaseous precursor, and can be readily determined by one skilled in the art.

The methods of preparing the gaseous precursor filled vesicles may be carried out below the boiling point of the gaseous precursor such that a liquid is incorporated, for example, into a vesicle. In addition, the methods may be conducted at the boiling point of the gaseous precursor, such that a gas is incorporated, for example, into a vesicle. For gaseous precursors having low temperature boiling points, liquid precursors may be emulsified using a microfluidizer device chilled to a low temperature. The boiling points may also be depressed using solvents in liquid media to utilize a precursor in liquid form. Further, the methods may be performed where the temperature is increased throughout the process, whereby the process starts with a gaseous precursor as a liquid and ends with a gas.

The methods of producing the temperature activated gaseous precursor filled vesicles may be carried out at a temperature below the boiling point of the gaseous precursor. In this embodiment, the gaseous precursor is entrapped within a vesicle such that the phase transition does not occur during manufacture. Instead, the gaseous precursor filled vesicles are manufactured in the liquid phase of the gaseous precursor. Activation of the phase transition may take place at any time as the temperature is allowed to exceed the boiling point of the precursor. Also, knowing the amount of liquid in a droplet of liquid gaseous precursor, the size of the vesicles upon attaining the gaseous state may be determined.

Alternatively, the gaseous precursors may be utilized to create stable gas filled vesicles which are pre-formed prior to use. In this embodiment, the gaseous precursor is added to a container housing a lipid composition at a temperature below the liquid-gaseous phase transition temperature of the respective gaseous precursor. As the temperature is increased, and an emulsion is formed between the gaseous precursor and liquid solution, the gaseous precursor undergoes transition from the liquid to the gaseous state. As a result of this heating and gas formation, the gas displaces the air in the head space above the liquid mixture so as to form gas filled vesicles which entrap the gas of the gaseous precursor, ambient gas (e.g. air), or coentrap gas state gaseous precursor and ambient air. This phase transition can be used for optimal mixing and formation of the contrast agent. For example, the gaseous precursor, perfluorobutane, can be entrapped in the lipid vesicles and as the temperature is raised beyond the boiling point of perfluorobutane (4° C.), perfluorobutane gas is entrapped in the vesicles. Accordingly, the gaseous precursors may be selected to form gas filled vesicles in vivo or may be designed to produce the gas filled vesicles in situ, during the manufacturing process, on storage, or at some time prior to use. A water bath, sonicator or hydrodynamic activation by pulling back the plunger of a syringe against a closed stopcock may be used to activate targeted gas filled vesicles from temperature-sensitive gaseous precursors prior to intravenous injection or infusion.

As a further embodiment of this invention, by pre-forming the gaseous precursor in the liquid state into an aqueous emulsion, the maximum size of the vesicle may be estimated by using the ideal gas law, once the transition to the gaseous state is effectuated. For the purpose of making gas filled vesicles from gaseous precursors, the gas phase is assumed to form instantaneously and substantially no gas in the newly formed vesicle has been depleted due to diffusion into the liquid, which is generally aqueous in nature. Hence, from a known liquid volume in the emulsion, one would be able to predict an upper limit to the size of the gas filled vesicle.

In the present invention, a mixture of a lipid compound and a gaseous precursor, containing liquid droplets of defined size, may be formulated such that upon reaching a specific temperature, for example, the boiling point of the gaseous precursor, the droplets will expand into gas filled vesicles of defined size. The defined size represents an upper limit to the actual size because the ideal gas law cannot account for such factors as gas diffusion into solution, loss of gas to the atmosphere, and the effects of increased pressure.

The ideal gas law, which can be used for calculating the increase in the volume of the gas bubbles upon transitioning from liquid to gaseous states, is PV=nRT, where P is pressure in atmospheres (atm); V is volume in liters (L); n is moles of gas; T is temperature in degrees Kelvin (K); and R is the ideal gas constant (22.4 L-atm/K-mole). With knowledge of volume, density, and temperature of the liquid in the mixture of liquids, the amount, for example, in moles, and volume of liquid precursor may be calculated which, when converted to a gas, will expand into a vesicle of known volume. The calculated volume will reflect an upper limit to the size of the gas filled vesicle, assuming instantaneous expansion into a gas filled vesicle and negligible diffusion of the gas over the time of the expansion.

Thus, for stabilization of the precursor in the liquid state in a mixture wherein the precursor droplet is spherical, the volume of the precursor droplet may be determined by the equation: Volume (spherical vesicle)=$4/3\pi r^3$, where r is the radius of the sphere.

Once the volume is predicted, and knowing the density of the liquid at the desired temperature, the amount of liquid gaseous precursor in the droplet may be determined. In more descriptive terms, the following can be applied: $V_{gas}=4/3\pi (r_{gas})^3$, by the ideal gas law, PV=nRT, substituting reveals, $V_{gas}=nRT/P_{gas}$, or, (A) $n=4/3 [\pi r_{gas}^3]$ P/RT, amount $n=4/3 [\pi r_{gas}^3 P/RT] \cdot MW_n$. Converting back to a liquid volume (B) $V_{liq}=[4/3[\pi r_{gas}^3]P/RT]\cdot MW_n/D]$, where D is the density of the precursor. Solving for the diameter of the liquid droplet, (C) diameter/2=$[3/4\pi[4/3 \cdot [\pi r_{gas}^3]P/RT]MW_n/D]^{1/3}$, which reduces to Diameter=$2[[r_{gas}^3]P/RT [MW_n/D]]^{1/3}$.

As a further means of preparing vesicles of the desired size for use in the methods of the present invention, and with a knowledge of the volume and especially the radius of the liquid droplets, one can use appropriately sized filters to size the gaseous precursor droplets to the appropriate diameter sphere.

A representative gaseous precursor may be used to form a vesicle of defined size, for example, 10 μm diameter. In this example, the vesicle is formed in the bloodstream of a human being, thus the typical temperature would be 37° C. or 310 K. At a pressure of I atmosphere and using the equation in (A), $7.54 \times 10^{-17}$ moles of gaseous precursor would be required to fill the volume of a 10 μm diameter vesicle.

Using the above calculated amount of gaseous precursor and 1-fluoro-butane, which possesses a molecular weight of 76.11, a boiling point of 32.5° C. and a density of 0.7789 g/mL at 20° C., further calculations predict that $5.74 \times 10^{-5}$ grams of this precursor would be required for a 10 μm vesicle. Extrapolating further, and with the knowledge of the density, equation (B) further predicts that $8.47 \times 10^{-16}$ mL of liquid precursor is necessary to form a vesicle with an upper limit of 10 μm. Finally, using equation (C), a mixture, for example, an emulsion containing droplets with a radius of 0.0272 μm or a corresponding diameter of 0.0544 μm, is formed to make a gaseous precursor filled vesicle with an upper limit of a 10 μm vesicle.

An emulsion of this particular size could be easily achieved by the use of an appropriately sized filter. In addition, as seen by the size of the filter necessary to form gaseous precursor droplets of defined size, the size of the filter would also suffice to remove any possible bacterial contaminants and, hence, can be used as a sterile filtration as well.

This embodiment for preparing gas filled vesicles may be applied to all gaseous precursors activated by temperature. In fact, depression of the freezing point of the solvent system allows the use of gaseous precursors which would undergo liquid-to-gas phase transitions at temperatures below 0° C. The solvent system can be selected to provide a medium for suspension of the gaseous precursor. For example, 20% propylene glycol miscible in buffered saline exhibits a freezing point depression well below the freezing point of water alone. By increasing the amount of propylene glycol or adding materials such as sodium chloride, the freezing point can be depressed even further.

The selection of appropriate solvent systems may be determined by physical methods as well. When substances, solid or liquid, herein referred to as solutes, are dissolved in a solvent, such as water based buffers, the freezing point is lowered by an amount that is dependent upon the composition of the solution. Thus, as defined by Wall, one can express the freezing point depression of the solvent by the following equation: $\ln x_a = \ln(1-x_b) = \Delta H_{fus}/R(1/T_o - 1/T)$, where $x_a$ is the mole fraction of the solvent; $x_b$ is the mole fraction of the solute; $\Delta H_{fus}$ is the heat of fusion of the solvent; and $T_o$ is the normal freezing point of the solvent.

The normal freezing point of the solvent can be obtained by solving the equation. If $x_b$ is small relative to $x_a$, then the above equation may be rewritten as: $x_b = \Delta H_{fus}/R[T-T_o/T_oT] \approx \Delta H_{fus}/\Delta T/RT_o^2$. The above equation assumes the change in temperature $\Delta T$ is small compared to $T_2$. This equation can be simplified by expressing the concentration of the solute in terms of molality, m (moles of solute per thousand grams of solvent). Thus, the equation can be rewritten as $X_b=m/[m+1000/m_a] \approx mMa/1000$, where Ma is the molecular weight of the solvent. Thus, substituting for the fraction $x_b$: $\Delta T=[M_aRT_o^2/1000\Delta H_{fus}]m$ or $\Delta T=K_f m$, where $K_f=M_aRT_o^2/1000\Delta H_{fus}$. $K_f$ is the molal freezing point and is equal to 1.86 degrees per unit of molal concentration for water at one atmosphere pressure. The above equation may be used to accurately determine the molal freezing point of solutions of gaseous precursor filled vesicles. Accordingly, the above equation can be applied to estimate freezing point depressions and to determine the appropriate concentrations of liquid or solid solute necessary to depress the solvent freezing temperature to an appropriate value.

Methods of preparing the temperature activated gaseous precursor filled vesicles include: (a) vortexing and/or shaking an aqueous mixture of gaseous precursor and additional materials as desired, including, for example, stabilizing materials, thickening agents and/or dispersing agents. Optional variations of this method include autoclaving before vortexing or shaking; heating an aqueous mixture of gaseous precursor; venting the vessel containing the mixture/suspension; shaking or permitting the gaseous precursor filled vesicle to form spontaneously and cooling down the suspension of gaseous precursor filled vesicles; and extruding an aqueous suspension of gaseous precursor through a filter of about 0.22 μm. Alternatively, filtering may be performed during in vivo administration of the vesicles such that a filter of about 0.22 μm is employed; (b) microemulsification whereby an aqueous mixture of gaseous precursor is emulsified by agitation and heated to form, for example, vesicles prior to administration to a patient; (c) heating a gaseous precursor in a mixture, with or without agitation, whereby the less dense gaseous precursor filled vesicles float to the top of the solution by expanding and displacing other vesicles in the vessel and venting the vessel to release air; and (d) utilizing in any of the above methods a sealed vessel to hold the aqueous suspension of gaseous precursor and maintaining the suspension at a temperature below the phase transition temperature of the gaseous precursor, followed by autoclaving to raise the temperature above the phase transition temperature, optionally with shaking, or permitting the gaseous precursor vesicle to form spontaneously, whereby the expanded gaseous precursor in the sealed vessel increases the pressure in the vessel, and cooling down the gas filled vesicle suspension, after which shaking may also take place.

Freeze drying is useful to remove water and organic materials prior to the shaking installation method. Drying installation methods may be used to remove water from vesicles. By pre-entrapping the gaseous precursor in the dried vesicles (i.e. prior to drying) after warming, the gaseous precursor may expand to fill the vesicle. Gaseous precursors can also be used to fill dried vesicles after they have been subjected to vacuum. As the dried vesicles are kept at a temperature below their gel state to liquid crystalline temperature, the drying chamber can be slowly filled with the gaseous precursor in its gaseous state.

Preferred methods for preparing the temperature activated gaseous precursor filled vesicles comprise shaking an aqueous solution having a lipid compound in the presence of a gaseous precursor at a temperature below the liquid state to gas state phase transition temperature of the gaseous precursor. This is preferably conducted at a temperature below the gel state to liquid crystalline state phase transition temperature of the lipid. The mixture is then heated to a temperature above the liquid state to gas state phase transition temperature of the gaseous precursor which causes the precursor to volatilize and expand. Heating is then discontinued, and the temperature of the mixture is then allowed to drop below the liquid state to gas state phase transition temperature of the gaseous precursor. Shaking of the mixture may take place during the heating step, or subsequently after the mixture is allowed to cool. Other methods for preparing gaseous precursor filled vesicles can involve shaking an aqueous solution of, for example, a lipid and a gaseous precursor, and separating the resulting gaseous precursor filled vesicles.

Conventional, aqueous-filled liposomes of the prior art are routinely formed at a temperature above the phase transition temperature of the lipids used to make them, since they are more flexible and thus useful in biological systems in the liquid crystalline state. See, for example, Szoka and Papahadjopoulos, *Proc. Natl. Acad. Sci.,* 75:4194–4198 (1978). In contrast, the vesicles made according to embodiments described herein are gaseous precursor filled, which imparts greater flexibility, since gaseous precursors after gas formation are more compressible and compliant than an aqueous solution.

The methods contemplated by the present invention provide for shaking an aqueous solution comprising a lipid, in the presence of a temperature activatable gaseous precursor. Preferably, the shaking is of sufficient force such that a foam is formed within a short period of time, such as about 30 minutes, preferably within about 20 minutes, and more preferably within about 10 minutes. The shaking may involve microemulsifying, microfluidizing, swirling (such as by vortexing), side-to-side, or up and down motion. In the case of the addition of gaseous precursor in the liquid state, sonication may be used in addition to the shaking methods set forth above. Further, different types of motion may be combined. Also, the shaking may occur by shaking the container holding the aqueous lipid solution, or by shaking the aqueous solution within the container without shaking the container itself. Further, the shaking may occur manually or by machine. Mechanical shakers that may be used include, for example, the mechanical shakers described hereinbefore, with an Espe Capmix (Seefeld, Oberay Germany) being preferred. Another means for producing shaking includes the action of gaseous precursor emitted under high velocity or pressure.

According to the methods described herein, in addition to a gaseous precursor, a gas may be provided by the local ambient atmosphere. The local ambient atmosphere can include the atmosphere within a sealed container, as well as the external environment. Alternatively, for example, a gas may be injected into or otherwise added to the container having the aqueous lipid solution or into the aqueous lipid solution itself to provide a gas other than air. Gases that are lighter than air are generally added to a sealed container, while gases heavier than air can be added to a sealed or an unsealed container. Thus, the present invention includes co-entrapment of air and/or other gases along with the gaseous precursors described herein.

The gaseous precursor filled vesicles can be used in substantially the same manner as the gas filled vesicles described herein, once activated by application to the tissues of a host, where such factors as temperature or p I may be used to cause generation of the gas. The gaseous precursors may undergo phase transitions from liquid to gaseous states at or near the normal body temperature of the host, and can be activated, for example, by the in vivo temperature of the host so as to undergo transition to the gaseous phase therein. In the preferred methods of the present invention, activation prior to administration to a patient is used, for example, by thermal, mechanical or optical means. This activation can occur where, for example, the host tissue is human tissue having a normal temperature of about 37° C. and the gaseous precursors undergo phase transitions from liquid to gaseous states up to about 60° C. or about 70° C.

In any of the techniques described above for preparing lipid-based vesicles, photoactive agents, bioactive agents and/or targeting ligands may be incorporated with the lipids before, during or after formation of the vesicles, as would be apparent to one of ordinary skill in the art in view of the present disclosure.

Conjugates of targeting ligands and fluorinated surfactants, bioactive agents and fluorinated surfactants or photoactive agents and fluorinated surfactants can be synthesized by variations on a theme suggested by the reaction sequence set forth in the present disclosure and according to methods known to one skilled in the art, as disclosed, for example, by Quay, et al, European Patent Publication EP 0 727 225 A2, the disclosure of which is hereby incorporated herein by reference in its entirety. For example, targeting ligand and fluorinated surfactant conjugates, bioactive agent and fluorinated surfactant conjugates or photoactive agent and fluorinated surfactant conjugates can be prepared by the reaction schemes below, where "LIG" refers to a targeting ligand, bioactive agent or a photoactive agent and "$R_f$" refers to a fluorinated surfactant or fluorinated lipid. For example, "$R_f$" may be $(C_nF_{2n+1})$.

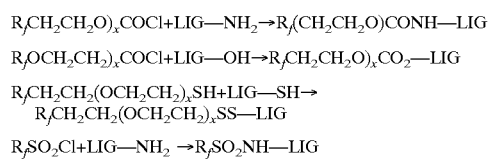

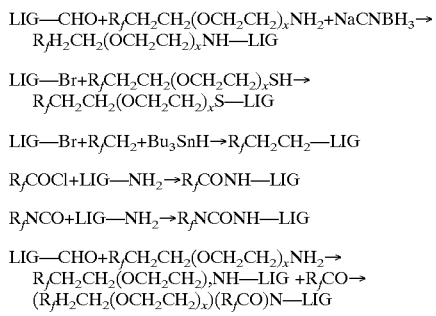

With respect to polyethylene glycol containing fragments, the following can be used, for example, PEG2-NHS ester, NHS-PEG-VS, NHS-PEG-MAL, methoxy-PEG-vinylsulfone, PEG-(VS)$_2$, methoxy-PEG-ald, PEG-(ald)$_2$, methoxy-PEG-epx, PEG-(epx)$_2$, methoxy-PEG-Tres, PEG-(Tres)$_2$, methoxy-PEG-NPC, PEG-(NPC)$_2$, methoxy-PEG-CDI, PEG-(CDI)$_2$, mPEG-Gly-OSu, mPEG-NLe-OSu, methoxy-SPA-PEG, (SPA)$_2$-PEG, methoxy-SS-PEG, (SS)$_2$-PEG all of which are available from Shearwater Polymers, Inc. (Huntsville, Ala.). Where these types of fragments are used, i.e., where the fragments may not themselves have surfactant properties adequate for a given ultrasound contrast formulation, or act only weakly as surfactants, the conjugate formed can be used in conjunction with other surfactants in the final formulation.

Vesicle compositions which comprise vesicles formulated from proteins, such as albumin vesicles, may be prepared by various processes, as will be apparent to one skilled in the art in view of the present disclosure. Suitable methods include those described, for example, in U.S. Pat. Nos. 4,572,203, 4,718,433, 4,774,958, and 4,957,656, the disclosures of each of which are hereby incorporated herein by reference in their entirety. Included among the methods are those which involve sonicating a solution of a protein. In preferred form, the starting material may be an aqueous solution of a heat-denaturable, water-soluble biocompatible protein. The encapsulating protein is preferably heat-sensitive so that it can be partially insolubilized by heating during sonication. Suitable heat-sensitive proteins include, for example, albumin, hemoglobin, and collagen, preferably, the protein is a human protein, with human serum albumin (HSA) being more preferred. HSA is available commercially as a sterile 5% aqueous solution, which is suitable for use in the preparation of protein-based vesicles. As would be apparent to one of ordinary skill in the art, other concentrations of albumin, as well as other proteins which are heat-denaturable, can be used to prepare the vesicles. Generally speaking, the concentration of HSA can vary and may range from about 0.1 to about 25% by weight, and all combinations and subcombinations of ranges therein. It may be preferable, in connection with certain methods for the preparation of protein-based vesicles, to utilize the protein in the form of a dilute aqueous solution. For albumin, it may be preferred to utilize an aqueous solution containing from about 0.5 to about 7.5% by weight albumin, with concentrations of less than about 5% by weight being preferred, for example, from about 0.5 to about 3% by weight.

Protein-based vesicles may be prepared using equipment which is commercially available. For example, in connection with a feed perparation operation as disclosed, for example, in U.S. Pat. No. 4,957,656, stainless steel tanks which are commercially available from Walker Stainless Equipment Co. (New Lisbon, Wis.), and process filters which are commercially available from Millipore (Bedford, MA), may be utilized.

The sonication operation may utilize both a heat exchanger and a flow through sonciating vessel, in series. Heat exhanger equipment of this type may be obtained from ITT Standard (Buffalo, N.Y.). The heat exchanger maintains operating temperature for the sonciation process, with temperature controls ranging from about 65° C. to about 80° C., depending on the makeup of the media. The vibration frequency of the sonication equipment may vary over a wide range, for example, from about 5 to about 40 kilohertz (kHz), with a majority of the commerically available sonicators operating at about 10 or 20 kHz. Suitable sonicating equipment include, for example, a Sonics & Materials Vibra-Cell, equipped with a flat-tipped sonicator horn, available from Sonics & Materials, Inc. (Danbury, Conn.). The power applied to the sonicator horn can be varied over power settings scaled from 1 to 10 by the manufacturer, as with Sonics & Materials Vibra-Cell Model V1500. An intermediate power setting, for example, from 5 to 9, can be used. It is preferred that the vibrational frequency and the power supplied be sufficeint to produce cavitation in the liquid being sonicated. Feed flow rates may range from about 50 mL/min to about 1000 mL/min, and all combinations and subcombinations of ranges therein. Residence times in the sonication vessel can range from about 1 second to about 4 minutes, and gaseous fluid addition rates may range from about 10 cubic centimeters (cc) per minute to about 100 cc/min, or 5% to 25% of the feed flow rate, and all combinations and subcombinations of ranges therein.

It may be preferable to carry out the sonication in such a manner to produce foaming, and especially intense foaming, of the solution. Generally, intense foaming and aerosolating are important for obtaining a contrast agent having enhanced concentration and stability. To promote foaming, the power input to the sonicator horn may be increased, and the process may be operated under mild pressure, for example, about 1 to about 5 psi. Foaming may be easily detected by the cloudy appearance of the solution, and by the foam produced.

Suitable methods for the preparation of protein-based vesicles may also involve physically or chemically altering the protein or protein derivative in aqueous solution to denature or fix the material. For example, protein-based vesicles may be prepared from a 5% aqueous solution of HSA by heating after formation or during formation of the contrast agent via sonication. Chemical alteration may involve chemically denaturing or fixing by binding the protein with a difunctional aldehyde, such as gluteraldehyde. For example, the vesicles may be reacted with 0.25 grams of 50% aqueous gluteradehyde per gram of protein at pH 4.5 for 6 hours. The unreacted gluteraldehyde may then be washed away from the protein.

In any of the techniques described above for preparing protein-based stabilizing materials and/or vesicles, photoactive agents, bioactive agents and/or targeting ligands may be incorporated with the proteins before, during or after formation of the vesicles, as would be apparent to one of ordinary skill in the art in view of the present disclosure.

Vesicle compositions which comprise vesicles formulated from polymers may be prepared by various processes, as will be apparent to one skilled in the art in view of the present disclosure. Suitable processes include, for example, interfacial polymerization, phase separation and coacervation, multiorifice centrifugal preparation, and solvent evaporation. Suitable procedures which may be employed or modified in accordance with the present disclosure to prepare vesicles from polymers include those procedures described in U.S. Pat. Nos. 4,179,546, 3,945, 956, 4,108,806, 3,293,114, 3,401,475, 3,479,811, 3,488,714, 3,615,972, 4,549,892, 4,540,629, 4,421,562, 4,420,442, 4,898,734, 4,822,534, 3,732,172, 3,594,326, and 3,015,128; Japan Kokai Tokkyo Koho 62 286534, British Patent No. 1,044,680, Deasy, *Microencapsulation and Related Drug Processes,* 20:195–240 (Marcel Dekker, Inc., N.Y., 1984), Chang et al., *Canadian J. of Physiology and Pharmacology,* 4:115–129 (1966), and Chang, *Science,* 146:524–525 (1964), the disclosures of each of which are hereby incorporated herein by reference in their entirety. In a preferred method, the vesicles may be prepared using a heat expansion process described, for example, in U.S. Pat. Nos. 4,179,546, 3,945,956, and 4,108,806, British Patent No. 1,044,680, and Japan Kokai Tokkyo Koho 62 286534. Generally, the heat expansion process may be carried out by preparing vesicles of an expandable polymer or copolymer which may contain in their void (cavity) a volatile liquid (gaseous precursor). The vesicle is then heated, plasticising the vesicle and converting the volatile liquid into a gas, causing the vesicle to expand to up to about several times its original size. When the heat is removed, the thermoplastic polymer retains at least some of its expanded shape. Vesicles produced by this process tend to be of particularly low density.

Polymers useful in the heat expansion process will be readily apparent to one skilled in the art and include thermoplastic polymers or copolymers, including polymers or copolymers of many of the monomers described above. Preferable of the polymers and copolymers described above include polyvinylidene-polyacrylonitrile, polyvinylidene-polyacrylonitrile-polymethylmethacrylate, and polystyrene-polyacrylonitrile. A most preferred copolymer is polyvinylidene-polyacrylonitrile.

Volatile liquids useful in the heat expansion process are known to one skilled in the art and include aliphatic hydrocarbons such as ethane, ethylene, propane, propene, butane, isobutane, neopentane, acetylene, hexane, heptane; chlorofluoro-carbons such as $CCl_3F$, $CCl_2F_3$, $CClF_3$, $CClF_2$—$CCl_2 1F_2$, chloroheptafluorocyclobutane, and 1,2-dichlorohexafluorocyclobutane; tetraalkyl silanes, such as tetramethyl silane, trimethylethyl silane, trimethylisopropyl silane, and trimethyl n-propyl silane; as well as perfluorocarbons, including the perfluorocarbons described above. It is important that the volatile liquid not be a solvent for the polymer or copolymer being utilized. It is also preferred that the volatile liquid have a boiling point that is below the softening point of the involved polymer or copolymer. Boiling points of various volatile liquids and softening points of various polymers and copolymers will be readily ascertainable to one skilled in the art, and suitable combinations of polymers or copolymers and volatile liquids will be apparent to the skilled artisan. By way of guidance, and as one skilled in the art would recognize, generally as the length of the carbon chain of the volatile liquid increases, the boiling point of that liquid increases also. Also, mildly preheating the vesicles in water in the presence of hydrogen peroxide prior to definitive heating and expansion may pre-soften the vesicle to allow expansion to occur more readily.

For example, to produce vesicles from synthetic polymers, vinylidene and acrylonitrile may be copolymerized in a medium of isobutane liquid using one or more of the foregoing modified or unmodified literature procedures, such that isobutane becomes entrapped within the vesicles. When such vesicles are then heated to a temperature of from about 80° C. to about 120° C., the isobutane gas expands, which in turn expands the vesicles.

After heat is removed, the expanded polyvinylidene and acrylonitrile copolymer vesicles remain substantially fixed in their expanded position. The resulting low density vesicles are extremely stable both dry and suspended in an aqueous media. Isobutane is utilized herein merely as an illustrative liquid, with the understanding that other liquids which undergo liquid/gas transitions at temperatures useful for the synthesis of these vesicles and formation of the very low density vesicles upon heating can be substituted for isobutane. Similarly, monomers other than vinylidene and acrylonitrile may be employed in preparing the vesicles.

In preferred embodiments, the vesicles which are formulated from synthetic polymers and which may be employed in the methods of the present invention are commercially available from Expancel, Nobel Industries (Sundsvall, Sweden), including EXPANCEL 551 DE™ microspheres. The EXPANCEL 551 DE™ microspheres are composed of a copolymer of vinylidene and acrylonitrile which have isobutane liquid encapsulated therein. Such microspheres are sold as a dry composition and are about 50 $\mu$m in size. The EXPANCEL 551 DE™ microspheres have a specific gravity of only 0.02 to 0.05, which is between one-fiftieth and one-twentieth the density of water.

In any of the techniques described above for preparing polymer-based stabilizing materials and/or vesicles, photoactive agents, bioactive agents and/or targeting ligands may be incorporated with the polymers before, during or after formation of the vesicles, as would be apparent to one skilled in the art in view of the present disclosure.

As with the preparation of stabilizing materials and/or vesicles, a wide variety of techniques are available for the preparation of stabilizing materials comprising photoactive agents, bioactive agents and/or targeting ligands. For example, the stabilizing materials and/or vesicle compositions may be prepared from a mixture of lipid compounds, photoactive agents, bioactive agents and/or targeting ligands and gases and/or gaseous precursors. In this case, lipid compositions are prepared as described above in which the compositions also comprise photoactive agents, bioactive agents and/or targeting ligands. Thus, for example, micelles can be prepared in the presence of a photoactive agent, bioactive agent and/or targeting ligand. In connection with lipid compositions which comprise a gas, the preparation can involve, for example, bubbling a gas directly into a mixture of the lipid compounds and one or more additional materials. Alternatively, the lipid compositions may be preformed from lipid compounds and gas and/or gaseous precursors. In the latter case, the photoactive agent, bioactive agent and/or targeting ligand is then added to the lipid composition prior to use. For example, an aqueous mixture of liposomes and gas may be prepared to which the photoactive agent, bioactive agent and/or targeting ligand is added and which is agitated to provide the liposome composition. The liposome composition can be readily isolated since the gas and/or photoactive agent, bioactive agent and/or targeting ligand filled liposome vesicles generally float to the top of the aqueous solution. Excess photoactive agent, bioactive agent and/or targeting ligand can be recovered from the remaining aqueous solution.

As one skilled in the art will recognize, any of the stabilizing materials and/or vesicle compositions may be lyophilized for storage, and reconstituted or rehydrated, for example, with an aqueous medium (such as sterile water, phosphate buffered solution, or aqueous saline solution), with the aid of vigorous agitation. Lyophilized preparations generally have the advantage of greater shelf life. To prevent agglutination or fusion of the lipids and/or vesicles as a result of lyophilization, it may be useful to include additives which prevent such fusion or agglutination from occurring.

Additives which may be useful include sorbitol, mannitol, sodium chloride, glucose, dextrose, trehalose, polyvinylpyrrolidone and poly(ethylene glycol) (PEG), for example, PEG 400. These and other additives are described in the literature, such as in the U.S. Pharmacopeia, USP XXII, NF XVII, The United States Pharmacopeia, The National Formulary, United States Pharmacopeial Convention Inc., 12601 Twinbrook Parkway, Rockville, Md. 20852, the disclosure of which is hereby incorporated herein by reference in its entirety.

The concentration of lipid required to form a desired stabilized vesicle level will vary depending upon the type of lipid used, and may be readily determined by routine experimentation. For example, in preferred embodiments, the concentration of 1,2-dipalmitoylphosphatidylcholine (DPPC) used to form stabilized vesicles according to the methods of the present invention is about 0.1 mg/ml to about 30 mg/ml of saline solution, more preferably from about 0.5 mg/ml to about 20 mg/ml of saline solution, and most preferably from about 1 mg/ml to about 10 mg/ml of saline solution. The concentration of distearoylphosphatidylcholine (DSPC) used in preferred embodiments is about 0.1 mg/ml to about 30 mg/ml of saline solution, more preferably from about 0.5 mg/ml to about 20 mg/ml of saline solution, and most preferably from about 1 mg/ml to about 10 mg/ml of saline solution. The amount of composition which is administered to a patient can vary. Typically, the intravenous dose may be less than about 10 ml for a 70 kg patient, with lower doses being preferred.

Another embodiment of preparing a targeted therapeutic composition comprises combining at least one lipid and a gaseous precursor; agitating until gas filled vesicles are formed; adding a photoactive agent, bioactive agent and/or targeting ligand to the gas filled vesicles such that the photoactive agent, bioactive agent and/or targeting ligand binds to the gas filled vesicle by a covalent bond or non-covalent bond; and agitating until a delivery vehicle comprising gas filled vesicles and a photoactive agent, bioactive agent and/or targeting ligand result. Rather than agitating until gas filled vesicles are formed before adding the photoactive agent, bioactive agent and/or targeting ligand, the gaseous I 0 precursor may remain a gaseous precursor until the time of use.

Alternatively, a method of preparing targeted therapeutic compositions may comprise combining at least one lipid and a photoactive agent, bioactive agent and/or targeting ligand such that the photoactive agent, bioactive agent and/or targeting ligand binds to the lipid by a covalent bond or non-covalent bond, adding a gaseous precursor and agitating until a delivery vehicle comprising gas-filled vesicles and a photoactive agent, bioactive agent and/or targeting ligand result. The gaseous precursor may be added and remain a gaseous precursor until the time of use.

Alternatively, the gaseous precursors may be utilized to create stable gas filled vesicles with photoactive agents, bioactive agents and/or targeting ligands which are preformed prior to use. In this embodiment, the gaseous precursor and photoactive agent, bioactive agent and/or targeting ligand are added to a container housing a suspending and/or stabilizing medium at a temperature below the liquid-gaseous phase transition temperature of the respective gaseous precursor. As the temperature is then exceeded, and an emulsion is formed between the gaseous precursor and liquid solution, the gaseous precursor undergoes transition from the liquid to the gaseous state. As a result of this heating and gas formation, the gas displaces the air in the head space above the liquid suspension so as to form gas filled lipid spheres which entrap the gas of the gaseous precursor, ambient gas for example, air, or coentrap gas state gaseous precursor and ambient air. This phase transition can be used for optimal mixing and stabilization of the delivery vehicle. For example, the gaseous precursor, perfluorobutane, can be entrapped in the lipid or other stabilizing compound, and as the temperature is raised beyond the boiling point of perfluorobutane (4° C.), stabilizing compound entrapped fluorobutane gas results. As an additional example, the gaseous precursor fluorobutane, can be suspended in an aqueous suspension containing emulsifying and stabilizing agents such as glycerol or propylene glycol and vortexed on a commercial vortexer. Vortexing is commenced at a temperature low enough that the gaseous precursor is liquid and is continued as the temperature of the sample is raised past the phase transition temperature from the liquid to gaseous state. In so doing, the precursor converts to the gaseous state during the microemulsification process. In the presence of the appropriate stabilizing agents, surprisingly stable gas filled vesicles and photoactive agents, bioactive agents and/or targeting ligands result.

All of the above embodiments involving preparations of the stabilized gas filled vesicles used in the present invention, may be sterilized by autoclave or sterile filtration if these processes are performed before either the gas instillation step or prior to temperature mediated gas conversion of the temperature sensitive gaseous precursors within the suspension. Alternatively, one or more antibactericidal agents and/or preservatives may be included in the formulation of the compositions including, for example, sodium benzoate, all quaternary ammonium salts, sodium azide, methyl paraben, propyl paraben, sorbic acid, ascorbylpalmitate, butylated hydroxyanisole, butylated hydroxytoluene, chlorobutanol, dehydroacetic acid, ethylenediamine, monothioglycerol, potassium benzoate, potassium metabisulfite, potassium sorbate, sodium bisulfite, sulfur dioxide, and organic mercurial salts. Such sterilization, which may also be achieved by other conventional means, such as by irradiation, will be necessary where the stabilized microspheres are used for imaging under invasive circumstances, for example, intravascularly or intraperitoneally. The appropriate means of sterilization will be apparent to the artisan instructed by the present description of the stabilized gas filled vesicles and their use. The compositions are generally stored as an aqueous suspension but in the case of dried or lyophilized vesicles or dried or lyophilized lipidic spheres the compositions may be stored as a dried or lyophilized powder ready to be reconstituted or rehydrated prior to use.

Additionally, the compositions of the present invention may be in the form of a solid porous matrix. A solid porous matrix may be prepared with a solvent, a surfactant, a gas and/or gaseous precursor, a photoactive agent, bioactive agent and/or a targeting ligand. The targeting ligand may be attached to the surfactant of the solid porous matrix by bonding to one or more of the materials employed in the compositions from which they are made, including the lipids, proteins, polymers, and/or auxiliary stabilizing materials.

A solid porous matrix comprising a solvent, a surfactant and a photoactive agent, a targeting ligand and/or bioactive agent may be processed by controlled agitation or controlled drying by a number of methods known in the art. The methods of drying include, for example, spray drying, lyophilization, and vacuum drying. Agitation methods include, for example, shaking, vortexing, and ball milling.

Most preferably a solid porous matrix comprising a surfactant and a photoactive agent, a targeting ligand and/or bioactive agent is prepared such that a solvent, a surfactant, and a photoactive agent, a targeting ligand and/or bioactive agent are combined to form an emulsion in the form of a random aggregate. In the case of spray drying, the emulsion, or colloidal suspension, is placed into association with a blowing agent such as methylene chloride, for example. Each of the ingredients of the solid porous matrix, the solvent, surfactant, and photoactive agent, targeting ligand and/or bioactive agent, may be combined and the blowing agent subsequently added thereto. Alternatively, the ingredients may be separated and combined in a stream of air together with the blowing agent. The blowing agent is stabilized by the surfactant, such as a phospholipid or a fluorosurfactant, within aqueous or organic media, the former being preferred. Additionally, some nonpolar photoactive agent emulsions may contain an oil to effect solubilization. As the suspension or emulsion is then spray dried, the photoactive agent and/or bioactive agent dries and the blowing agent and solvent are removed tending to form microcavities within the crystals of the photoactive agent and/or bioactive agent. The surfactants typically tend to adsorb to the surface of the porous crystal lattice of the photoactive agent and/or bioactive agent. The resulting powdered crystalline material may then be stored under a head space of the desired gas. Preferably an insoluble gas is selected such as perfluorobutane. This results in crystalline matrices imbibing insoluble gas. When the matrices are resuspended, the result is crystalline matrices of photoactive agent and/or bioactive agent surrounded by a film of gas/gaseous precursor material and surfactant, and, optionally, a targeting ligand.

As an alternative to spray drying, the crystalline matrices of photoactive agents and/or bioactive agents may be prepared by lyophilization. Another alternative, agitation, by ball milling, for example, may be performed in place of or in combination with spray drying, and/or lyophilization. A bulk quantity of the composition of the present invention may be prepared with a ball mill or a colloid mill device. The appropriate sized crystalline particles are prepared, generally under 10 $\mu$m, preferably under 5 $\mu$m and still more preferably under 1 $\mu$m by subjecting the bulk crystals to sufficient energy and duration of the ball milling process. The surfactants may be incorporated into the bulk crystalline matrix prior to or during the ball milling process. Alternatively, the surfactant may be incorporated into the crystalline matrix after the preparation of the microparticles. In this latter case the crystalline microparticles or nanoparticles may be suspended in a solvent (generally organic) within which the photoactive agent and/or bioactive agent is insoluble. The surfactant is added to the suspension and mixed with agitation. The organic solvent may be removed by lyophilization or spray drying. The resulting dried surfactant micro- or nano-crystalline solid matrix of a surfactant and photoactive agent and/or bioactive agent is then stored within a head space of the appropriate gas and hydrated prior to use.

The solvent of the solid porous matrix may be an aqueous solvent or an organic solvent. Suitable solvents include alkylated alcohols, ethers, acetone, alkanes, dimethyl sulfoxide, toluene, cyclic hydrocarbons, benzene, and gaseous precursors. The ethers may be methoxylated ethers, alkylated ethers, diether, triethers, oligo ethers, polyethers, cyclic ethers, and crown ethers; the alkylated alcohol may be methanol; and the alkane may be hexane. The solvent may be partially or fully fluorinated. The solvent is a suspending medium for associating the surfactant with the photoactive agent in the preparation of a solid porous matrix. The photoactive agent and/or bioactive agent is typically only marginally soluble in the solvent.

In preparing a solid porous matrix, the surfactants, gases, gaseous precursors, photoactive agents, bioactive agents and/or targeting ligands may be any of those described herein.

The solvent useful in the preparation of solid porous matrix may be removed during the processing of the matrix. During spray drying, for example, the solvent, the surfactant, and the photoactive agent, may be combined together with a blowing agent into a gaseous stream such that a substantial portion of the solvent is evaporated during spray drying. As a result, a solid porous matrix of a surfactant and a photoactive agent, a bioactive agent and/or a targeting ligand is prepared. Additional details regarding solid porous matrix systems are described in U.S. Provisional application Ser. No. 60/046,379, filed May 13, 1997, the disclosure of which is hereby incorporated by reference herein in its entirety.

As discussed above, the optoacoustic contrast agents of the present invention are particularly useful in conjunction with both ultrasound imaging and optical imaging. Diagnostic ultrasound may be used to visualize the vesicles or stabilizing materials, verify the localization of the vesicles or stabilizing materials in certain tissue and/or resonate the vesicles or stabilizing materials. Therapeutic ultrasound may be used to promote rupture of the vesicles or stabilizing materials once the vesicles or stabilizing materials reach the intended target, including tissue and/or receptor destinations.

The contrast medium of the present invention may be useful in providing images of tissue, such as myocardial, endothelial, and/or epithelial tissue, as well as the gastrointestinal, pulmonary and cardiovascular regions, but can also be employed more broadly, such as in imaging the vasculature, or in other ways as will be readily apparent to one skilled in the art. Diseased tissue includes, for example, endothelial tissue which results from vasculature that supports diseased tissue. As a result, the localization and visualization of endothelial tissue to a region of a patient which under normal circumstances is not associated with endothelial tissue provides an indication of diseased tissue in the region. The present methods can also be used in connection with delivery of targeting ligands to internal regions of a patient.

Additionally, the present invention teaches methods of delivering a therapeutic photoactive agent to a patient and/or treating a condition in a patient by administering the optoacoustic contrast agents of the present invention to a patient, applying ultrasound to the patient or a region of the patient to deliver the photoactive agent and/or bioactive agent and then applying light energy to the patient or a region of the patient. Preferably, substantially all of the optoacoustic contrast agents, stabilizing materials and/or vesicles rupture when delivering the photoactive agent and/or bioactive agent to the patient or a region of the patient. Optionally, the compositions may be monitored with ultrasound imaging and/or optical imaging to determine the location of the compositions prior to applying ultrasound to deliver the photoactive agent and/or bioactive agent to the patient or a region of the patient. These methods may be particularly useful in treating cancer with therapeutic photoactive agents. Irradiation of light for this method may be applied interstitially, superficially, intravascularly or with the aid of light conductors, such as fiber optics.

The present invention describes methods of imaging a patient and/or diagnosing the presence of diseased tissue in a patient by administering the optoacoustic contrast agents to a patient, and scanning the patient using ultrasound imaging and/or optical imaging to obtain visible images of a region of a patient and/or of any diseased tissue in a region of a patient. In a preferred embodiment, the patient is scanned using both ultrasound imaging and optical imaging to obtain visible images of a region of a patient and/or of any diseased tissue in a region of a patient. When obtaining visible images of a region of a patient and/or of any diseased tissue in a region of a patient, substantially all of the stabilizing materials and/or vesicles do not rupture.

For example, ultrasound may be applied to the patient or a region of the patient to resonate the optoacoustic contrast agents, wherein substantially all of the stabilizing materials and/or vesicles do not rupture, and then ultrasound imaging and optical imaging may both be used to obtain visible images of a region of a patient and/or of any diseased tissue in a region of a patient. The term "substantially" in this context means that more than about 50% of the stabilizing materials and/or vesicles do not rupture, preferably at least about 60%, about 70% or about 80% of the stabilizing materials and/or vesicles do not rupture, more preferably at least about 90%, about 95%, about 99% or about 100% of the stabilizing materials and/or vesicles do not rupture.

In another embodiment of the invention, ultrasound may be used to resonate the optoacoustic contrast agents, and then optical imaging may be used, without ultrasound imaging, to obtain visible images of a region of a patient and/or of any diseased tissue in a region of a patient. Preferably in this embodiment, substantially all of the optoacoustic contrast agents do not rupture when ultrasound is used to resonate the optoacoustic contrast agents, where "substantially" is defined above in the context of stabilizing materials and/or vesicles that do not rupture.

In another embodiment of the invention, ultrasound may be used to resonate the optoacoustic contrast agents, and then ultrasound imaging may be used, without optical imaging, to obtain visible images of a region of a patient and/or of any diseased tissue in a region of a patient. In this embodiment, the photoactive agent in the optoacoustic contrast agent may provide a different ultrasound image when compared to ultrasound contrast agents that do not contain a photoactive agent. In this embodiment, substantially all of the stabilizing materials and/or vesicles do not rupture, where "substantially" is defined above in the context of stabilizing materials and/or vesicles that do not rupture.

In another embodiment of the invention, when the stabilizing materials and/or vesicles also comprise a bioactive agent, ultrasound may be applied to deliver the bioactive agent and/or photoactive agent after visible images of the region of the patient and/or of any diseased tissue in the region of the patient are obtained. In this embodiment, substantially all of the stabilizing materials and/or vesicles rupture to deliver the bioactive agent and/or photoactive agent. The term "substantially" in this context means that more than about 50% of the stabilizing materials and/or vesicles rupture, preferably at least about 60%, about 70% or about 80% of the stabilizing materials and/or vesicles rupture, more preferably at least about 90%, about 95%, about 99% or about 100% of the stabilizing materials and/or vesicles rupture.

In yet another embodiment of the invention, ultrasound may be used to rupture substantially all of the stabilizing materials and/or vesicles to deliver the photoactive agent and/or bioactive agent, and ultrasound imaging and optical imaging may both be used to obtain images of a region of a patient and/or of any diseased tissue in the patient. If ultrasound is used to rupture substantially all of the stabilizing materials and/or vesicles, the optoacoustic contrast agents may be monitored with ultrasound imaging and/or optical imaging to determine the location of the compositions prior to applying ultrasound to rupture substantially all of the stabilizing materials and/or vesicles. After delivery, light energy is applied to activate or irradiate the photoactive agents. In this embodiment, the term "substantially" is as defined above with respect to stabilizing materials and/or vesicles that rupture.

In yet another embodiment, ultrasound may be used to rupture substantially all of the stabilizing materials and/or vesicles to deliver the photoactive agent and/or bioactive agent, and then ultrasound imaging, without optical imaging, may be used to obtain images of a region of a patient and/or of any diseased tissue in a region of a patient. After delivery, light energy is applied to activate or irradiate the photoactive agents. The term "substantially" is as defined above with respect to stabilizing materials and/or vesicles that rupture.

In yet another embodiment, ultrasound may be used to rupture substantially all of the stabilizing materials and/or vesicles to deliver the photoactive agent and/or bioactive agent, and then optical imaging, without ultrasound imaging, may be used to obtain images of a region of a patient and/or of any diseased tissue in a region of a patient. After delivery, light energy is applied to activate or irradiate the photoactive agents. The term "substantially" is as defined above with respect to stabilizing materials and/or vesicles that rupture.

The amount of the optoacoustic contrast agents of the present invention to be administered to a patient depends, for example, on the method in which the compositions are being administered, and the age, sex, weight and physical condition of the patient. Generally, treatment is initiated with small dosages, which can then be increased by small increments, until the desired effect under the circumstances is achieved. The targeting aspects of the invention further enable lower dosages of the optoacoustic contrast agents to be used for therapy, since the effective concentration of the contrast agents at the therapeutic site remains undiluted in the body.

The compositions of the invention may be administered to a patient by a variety of different means. The means of administration will vary depending upon the intended application. As one skilled in the art would recognize, administration of the compositions, stabilizing materials and/or vesicles of the present invention can be carried out in various fashions, for example, topically, including ophthalmic, dermal, ocular and rectal, intrarectally, transdermally, orally, intraperitoneally, parenterally, intravenously, intravascularly, intralymphatically, intratumorly, intramuscularly, interstitially, intraarterially, subcutaneously, intraocularly, intrasynovially, transepithelially, pulmonarily via inhalation, ophthalmically, sublingually, buccally, or via nasal inhalation via insufflation or nebulization.

The stabilizing materials and/or vesicles of the present invention may be administered as an infusion. "Infusion" refers to intravascular or intra-arterial administration at a rate of, for example, less than about 1 cc/second, more preferably less than about 0.5 cc/second or less than about 30 cc/minute, even more preferably at about 0.1 cc/minute to about 30 cc/minute, most preferably at about 0.1 cc/minute to about 5.0 cc/minute. Varying the rate of infusion is also desirable. For example, infusion may initially be started at a rate of about 1.0 to about 4.0 cc/second, followed by a more sustained infusion rate of about 0.1 cc/second. The fast infusion rate initially achieves the optimal level of the stabilizing material and/or vesicle in the blood, while the slow infusion rate is better tolerated hemodynamically.

The delivery of photoactive agents and/or bioactive agents from the stabilizing materials of the present invention using ultrasound is best accomplished for tissues which have a good acoustic window for the transmission of ultrasonic energy. This is the case for most tissues in the body such as muscle, the heart, the lungs, the liver and most other vital structures. In the brain, in order to direct the ultrasonic energy past the skull, a surgical window may be necessary.

The compositions, stabilizing materials and/or vesicles of the present invention are especially useful for targeting ligands that may be degraded in aqueous media or upon exposure to oxygen and/or atmospheric air. For example, vesicles may be filled with an inert gas for use with labile targeting ligands. Additionally, the compositions may be filled with an inert gas and used to encapsulate a labile targeting ligand for use in a region of a patient that would normally cause the targeting ligand to be exposed to atmospheric air, such as cutaneous and ophthalmic applications.

For topical applications, the stabilizing materials and/or vesicles may be used alone, may be mixed with one or more solubilizing agents, such as dimethylsulfoxide (DMSO), or may be used with a delivery vehicle, and applied to the skin or mucosal membranes. Penetrating and/or solubilizing agents useful for the topical application of the stabilizing materials and/or vesicles are well known in the art. Stabilizing materials and/or vesicles formulated with penetration enhancing agents may be administered transdermally in a patch or reservoir with a permeable membrane applied to the skin. The use of rupturing ultrasound may increase transdermal delivery of photoactive agents. Further, a mechanism may be used to monitor and modulate delivery of the photoactive agents. For example, ultrasound may be used to visually monitor the bursting of the gas filled vesicles and modulate delivery of the photoactive agents and/or bioactive agents and/or a hydrophone may be used to detect the sound of the bursting of the gas filled vesicles and modulate delivery of the photoactive agents and/or bioactive agents.

The invention is useful in delivering compositions to a patient's lungs. For pulmonary applications, dried or lyophilized powdered compositions may be administered via inhaler. Aqueous suspensions of liposomes, micelles or other vesicles, preferably gas/gaseous precursor filled, may be administered via nebulization. The compositions of the present invention are lighter than, for example, conventional liquid filled liposomes which generally deposit in the central proximal airway rather than reaching the periphery of the lungs. Therefore, improved delivery of the compositions of the invention to the periphery of the lungs, including the terminal airways and the alveoli, may be provided.

For application to the lungs, the compositions may be applied through nebulization. In applications such as the targeting of the lungs, which are lined with lipids, the photoactive agent and/or bioactive agent may be released upon aggregation of the gas and/or gaseous precursor filled liposomes with the lipids lining the targeted tissue. Additionally, the gas and/or gaseous precursor filled liposomes may burst after administration without the use of ultrasound. Thus, ultrasound need not be applied to release the photoactive agent and/or bioactive agent in this type of administration. Of course, it may still be necessary to apply light energy to activate the photoactive agent and to induce its therapeutic capabilities.

The release of the photoactive agents, bioactive agents and/or vesicle rupture may be monitored ultrasonically by several different mechanisms. As bubbles are destroyed, it results in eventual dissolution of the ultrasound signal. Prior to signal dissolution, however, the vesicles provide an initial burst of signal. In other words, as increasing levels of ultrasound energy are applied to the treatment zone containing the vesicles, there is a transient increase in signal. This transient increase in signal may be recorded at the fundamental frequency, the harmonic, the odd harmonic or the ultraharmonic frequence.

Generally, the compositions of the invention are administered in the form of an aqueous suspension such as in water or a saline solution (e.g., phosphate buffered saline). Preferably, the water is sterile. Also, preferably the saline solution is an isotonic saline solution, although, if desired, the saline solution may be hypotonic (e.g., about 0.3 to about 0.5% NaCl). The solution may be buffered, if desired, to provide a pH range of about 5 to about 7.4. Preferably, dextrose or glucose is included in the media. Other solutions that may be used for administration of the compositions of the present invention include oils, such as, for example, almond oil, corn oil, cottonseed oil, ethyl oleate, isopropyl myristate, isopropyl palmitate, mineral oil, myristyl alcohol, octyldodecanol, olive oil, peanut oil, persic oil, sesame oil, soybean oil, squalene and fluorinated oils. Suitable fluorinated oils are described in U.S. Pat. No. 5,344,930, the disclosure of which is hereby incorporated by reference herein in its entirety.

The size of the stabilizing materials and/or vesicles of the present invention will depend upon the intended use. With smaller vesicles, resonant frequency ultrasound will generally be higher than for larger vesicles. Sizing also serves to modulate resultant vesicular biodistribution and clearance. In addition to filtration, the size of the vesicles can be adjusted, if desired, by procedures known to one skilled in the art, such as shaking, microemulsification, vortexing, filtration, repeated freezing and thawing cycles, extrusion, extrusion under pressure through pores of a defined size, sonication, homogenization, the use of a laminar stream of a core of liquid introduced into an immiscible sheath of liquid. Extrusion under pressure through pores of defined size is a preferred method of adjusting the size of the vesicles. See, for example, U.S. Pat. Nos. 4,728,578, 4,728,575, 4,737,323, 4,533,254, 4,162,282, 4,310,505 and 4,921,706; U.K. Patent Application GB 2193095 A; International Applications PCT/US85/01161 and PCT/US89/05040; Mayer et al., *Biochimica et Biophysica Acta,* 858:161–168 (1986); Hope et al., *Biochimica et Biophysica Acta,* 812:55–65 (1985); Mayhew et al., *Methods in Enzymology,* 149:64–77 (1987); Mayhew et al., *Biochimica et Biophysica Acta,* 755:169–74 (1984); Cheng et al, *Investigative Radiology,* 22:47–55 (1987); and *Liposomes Technology,* Gregoriadis, ed., Vol. I, pp. 29–37, 51–67 and 79–108 (CRC Press Inc, Boca Raton, Fla., 1984). The disclosures of each of the foregoing patents, publications and patent applications are hereby incorporated by reference herein in their entirety.

Since vesicle size influences biodistribution, different size vesicles may be selected for various purposes. For example, for intravascular application, the preferred size range is a mean outside diameter between about 30 nm and about 10 $\mu$m, with the preferable mean outside diameter being about 5 $\mu$m. More specifically, for intravascular application, the size of the vesicles is preferably about 10 $\mu$m or less in mean outside diameter, and preferably less than about 7 $\mu$m, and more preferably less than about 5 $\mu$m in mean outside diameter. Preferably, the vesicles are no smaller than about 30 nm in mean outside diameter. To provide therapeutic delivery to organs such as the liver and to allow differentiation of tumor from normal tissue, smaller vesicles, between about 30 nm and about 100 nm in mean outside diameter, are preferred. For embolization of a tissue such as the kidney or the lung, the vesicles are preferably less than about 200 μm in mean outside diameter. For intranasal, intrarectal or topical administration, the vesicles are preferably less than about 100 μm in mean outside diameter. Large vesicles, between 1 and about 10 μm in size, will generally be confined to the intravascular space until they are cleared by phagocytic elements lining the vessels, such as the macrophages and Kupffer cells lining capillary sinusoids. For passage to the cells beyond the sinusoids, smaller vesicles, for example, less than about 1 μm in mean outside diameter, e.g., less than about 300 nm in size, may be utilized. In preferred embodiments, the vesicles are administered individually, rather than embedded in a matrix, for example.

For in vitro use, such as cell culture applications, the stabilizing materials and/or vesicles may be added to the cells in cultures and then incubated. Subsequently, ultrasound imaging and optical imaging can be applied to the culture media containing the cells and stabilizing materials and/or vesicles.

In carrying out the imaging methods of the present invention, the stabilizing materials and/or vesicle compositions can be used alone, or in combination with diagnostic agents, bioactive agents or other agents, including excipients such as flavoring or coloring materials, which are well known to one skilled in the art.

In the case of diagnostic applications, ultrasound energy and optical imaging are applied to at least a portion of the patient to image the target tissue. Ultrasonic imaging techniques, including second harmonic imaging, and gated imaging, are well known in the art, and are described, for example, in Uhlendorf, *IEEE Transactions on Ultrasonics, Ferroelectrics, and Frequency Control*, 14(1):70–79 (1994) and Sutherland, et al., *Journal of the American Society of Echocardiography*, 7(5):441–458 (1994), the disclosures of each of which are hereby incorporated by reference herein in their entirety.

Ultrasound can be used for both diagnostic and therapeutic purposes. In diagnostic ultrasound, ultrasound waves or a train of pulses of ultrasound may be applied with a transducer. The ultrasound is generally pulsed rather than continuous, although it may be continuous, if desired. Diagnostic ultrasound generally involves the application of a pulse of echoes, after which, during a listening period, the ultrasound transducer receives reflected signals. Harmonics, ultraharmonics or subharmonics may be used. The second harmonic mode may be beneficially used, in which the 2x frequency is received, where x is the incidental frequency. This may decrease the signal from the background material and enhance the signal from the transducer using the contrast media of the present invention, which may be targeted to the desired site, for example, blood clots. Other harmonic signals, such as odd harmonics signals, for example, 3x or 5x, may be similarly received using this method. Subharmonic signals, for example, x/2 and x/3, may also be received and processed to form an image.

In addition to the pulsed method, continuous wave ultrasound, for example, Power Doppler, may be applied. This may be particularly useful where rigid vesicles, for example, vesicles formulated from polymethyl methacrylate, are used. In this case, the relatively higher energy of the Power Doppler may be made to resonate the vesicles and, if desired, promote their rupture. This can create acoustic emissions which may be in the subharmonic or ultraharmonic range or, in some cases, in the same frequency as the applied ultrasound. There may be a spectrum of acoustic signatures released in this process and the transducer being used may receive the acoustic emissions to detect, for example, the presence of a clot. In addition, the process of vesicle rupture may be used to transfer kinetic energy to the surface, for example of a clot to promote clot lysis. Thus, therapeutic thrombolysis may be achieved with a combination of diagnostic and therapeutic ultrasound. Spectral Doppler may also be used.

Generally, energy levels from diagnostic ultrasound do not rupture stabilizing materials and/or vesicles. As noted above, diagnostic ultrasound may involve the application of one or more pulses of sound. Pauses between pulses permits the reflected sonic signals to be received and analyzed. The limited number of pulses used in diagnostic ultrasound limits the effective energy which is delivered to the tissue that is being studied.

Higher energy ultrasound, for example, ultrasound which is generated by therapeutic ultrasound equipment, can generally rupture stabilizing materials and/or vesicles. Devices for therapeutic ultrasound use from about 10 to about 100% duty cycles, depending on the area of tissue to be treated with the ultrasound. Areas of the body which are generally characterized by larger amounts of muscle mass, for example, the back and thighs, as well as highly vascularized tissues, such as heart tissue, may require a larger duty cycle, for example, up to about 100%.

In therapeutic ultrasound, continuous wave ultrasound is used to deliver higher energy levels. For the rupture of vesicles, continuous wave ultrasound is preferred, although the sound energy may also be pulsed. If pulsed sound energy is used, the sound will generally be pulsed in echo train lengths of from about 8 to about 20 or more pulses at a time. Preferably, the echo train lengths are about 20 pulses at a time. In addition, the frequency of the sound used may vary from about 0.025 to about 100 megahertz (MHz). The frequency for therapeutic ultrasound ranges between about 0.75 and about 3 MHz, preferably between about 1 and about 2 MHz. In addition, energy levels may vary from about 0.5 Watt (W) per square centimeter ($cm^2$) to about 5.0 $W/cm^2$, preferably from about 0.5 to about 2.5 $W/cm^2$. Energy levels for therapeutic ultrasound involving hyperthermia are generally from about 5 $W/cm^2$ to about 50 $W/cm^2$. For very small vesicles, for example, vesicles having a diameter of less than about 0.5 μm, higher frequencies of sound are generally preferred because smaller vesicles are capable of absorbing sonic energy more effectively at higher frequencies of sound. When very high frequencies are used, for example, greater than about 10 MHz, the sonic energy will generally penetrate fluids and tissues to a limited depth only. Thus, external application of the sonic energy may be suitable for skin and other superficial tissues. For deep structures, it is generally necessary to focus the ultrasonic energy so that it is preferentially directed within a focal zone. Alternatively, ultrasonic energy may be applied via interstitial probes, intravascular ultrasound catheters or endoluminal catheters. In addition to the therapeutic uses discussed above, the present compositions can be employed in connection with esophageal carcinoma or in the coronary arteries for the treatment of atherosclerosis, as well as the therapeutic uses described, for example, in U.S. Pat. No. 5,149,319, the disclosure of which is hereby incorporated by reference herein in its entirety.

A therapeutic ultrasound device may be used which employs two frequencies of ultrasound. The first frequency may be x, and the second frequency may be 2x. Preferably, the device would be designed so that the focal zones of the first and second frequencies converge to a single focal zone. The focal zone of the device may then be directed to the compositions, for example, stabilizing materials and/or targeted vesicle compositions, within the targeted tissue. The ultrasound device may provide second harmonic therapy with simultaneous application of the x and 2x frequencies of ultrasound energy. In the case of ultrasound used in conjunction with vesicles, the second harmonic therapy may provide improved rupturing of vesicles as compared to ultrasound energy involving a single frequency. The preferred frequency range may reside within the fundamental harmonic frequencies of the vesicles. Lower energy may also be used with this device. An ultrasound device which may be used in connection with the aforementioned second harmonic therapy is described, for example, by Kawabata, et al, *Ultrasonics Sonochemistry*, 3:1–5 (1996), the disclosure of which is hereby incorporated by reference herein in its entirety.

In ultrasonic imaging, the vesicles of the invention preferably possess a reflectivity of greater than 2 dB, more preferably between about 4 dB and about 20 dB. Within these ranges, the highest reflectivity for the vesicles is exhibited by the larger vesicles, by higher concentrations of vesicles, and/or when higher ultrasound frequencies are used.

For therapeutic delivery of photoactive agents and/or bioactive agents, rupturing the vesicles and/or stabilizing materials is carried out by applying ultrasound of a certian frequency to the region of the patient where therapy is desired after the stabilizing materials and/or vesicles have been administered or have otherwise reached the desired region, e.g., via delivery with targeting ligands. Specifically, it has been found that when ultrasound is applied at a frequency corresponding to the peak resonant frequency of the vesicles and/or stabilizing materials, the vesicles and/or stabilizing materals will rupture and release their contents, e.g., the photoactive agents and/or bioactive agents. The peak resonant frequency can be determined either in vivo or in vitro, preferably in vivo by exposing the stabilizing materials and/or vesicles to ultrasound, receiving the reflected resonant frequency signals and analyzing the spectrum of signals received to determine the peak, using conventional means. The peak, as determined, corresponds to the peak resonant frequency or second harmonic.

Preferably, the compositions of the invention that are used for the therapeutic delivery of photoactive agents have a peak resonant frequency of between about 0.5 MHz and about 10 MHz. Of course, the peak resonant frequency will vary depending on the outside diameter and, to some extent, the elasticity or flexibility of the vesicles, with the larger and more elastic or flexible vesicles having a lower resonant frequency than the smaller and less elastic or flexible vesicles.

The vesicles will also rupture when exposed to non-peak resonant frequency ultrasound in combination with a higher intensity (wattage) and duration (time). This higher energy, however, results in greatly increased heating, which may not be desirable. By adjusting the frequency of the energy to match the peak resonant frequency, the efficiency of rupture and release of the photoactive agent is improved, appreciable tissue heating does not generally occur (frequently no increase in temperature above about 2° C.) and less overall energy is required. Thus, application of ultrasound at the peak resonant frequency, while not required, is preferred.

For diagnostic or therapeutic ultrasound, any of the various types of diagnostic ultrasound imaging devices may be used in the methods of the invention, the particular type or model of the device not being critical. Other suitable devices designed for administering ultrasonic hyperthermia are described in U.S. Pat. Nos. 4,620,546, 4,658,828, and 4,586,512, the disclosures of each of which are hereby incorporated herein by reference in their entirety. Preferably, the device employs a resonant frequency (RF) spectral analyzer. The transducer probes may be applied externally or may be implanted. Ultrasound is generally initiated at lower intensity and duration, and then intensity, time, and/or resonant frequency increased until the vesicle is visualized on ultrasound (e.g., for diagnostic ultrasound applications).

Although application of the various principles will be readily apparent to one skilled in the art in view of the present disclosure, by way of general guidance, for gas filled vesicles of about 1.5 to about 10 $\mu$m in mean outside diameter, the resonant frequency will generally be in the range of about 1 to about 10 MHz. By adjusting the focal zone to the center of the target tissue (e.g., a tumor) the vesicles can be visualized under real time ultrasound as they accumulate within the target tissue. Using the 7.5 MHz curved array transducer as an example, adjusting the power delivered to the transducer to maximum and adjusting the focal zone within the target tissue, the spatial peak temporal average (SPTA) power will then be a maximum of approximately 5.31 mW/cm$^2$ in water. This power will cause some release of the photoactive agents from the vesicles, but much greater release can be accomplished using a higher power. Similarly, preventing the release of photoactive agents can be accomplished using a lower power.

By switching the transducer to the doppler mode, higher power outputs are available, up to 2.5 W/cm$^2$ from the same transducer. With the machine operating in doppler mode, the power can be delivered to a selected focal zone within the target tissue and the vesicles can be made to release the photoactive agent. Selecting the transducer to match the resonant frequency of the vesicles will make this process of photoactive agent release even more efficient.

For larger diameter vesicles, e.g., greater than 3 $\mu$m in mean outside diameter, a lower frequency transducer may be more effective in accomplishing therapeutic release. For example, a lower frequency transducer of 3.5 MHz (20 mm curved array model) may be selected to correspond to the resonant frequency of the gas filled vesicles. Using this transducer, 101.6 milliwatts per cm$^2$ may be delivered to the focal spot, and switching to doppler mode will increase the power output (SPTA) to 1.02 Wcm$^2$.

To use the phenomenon of cavitation to release and/or activate the photoactive agents within the stabilizing materials and/or vesicles, lower frequency energies may be used, as cavitation occurs more effectively at lower frequencies. Using a 0.757 MHz transducer driven with higher voltages (as high as 300 volts) cavitation of solutions of vesicles will occur at thresholds of about 5.2 atmospheres. Ultrasound-induced cavitation will change the optical signature of photoactive materials that have been incorporated in the stabilizing materials and/or vesicles.

The table below shows the ranges of energies transmitted to tissues from diagnostic ultrasound on commonly used instruments such as the Piconics Inc. (Tyngsboro, Mass.) Portascan general purpose scanner with receiver pulser 1966 Model 661; the Picker (Cleveland, Ohio) Echoview 8L Scanner including 80C System or the Medisonics (Mountain View, Calif.) Model D-9 Versatone Bidirectional Doppler. In general, the energy ranges in pulse repetition are useful for diagnosis and monitoring stabilizing materials and/or vesicles, but are insufficient to rupture the vesicles.

TABLE 3

Power and Intensities Produced by Diagnostic Equipment*

| Pulse repetition rate (Hz) | Total ultrasonic power output P (mW) | Average Intensity at transducer face $I_{ID}$ (W/m$^2$) |
| --- | --- | --- |
| 520 | 4.2 | 32 |
| 676 | 9.4 | 71 |
| 806 | 6.8 | 24 |
| 1000 | 14.4 | 51 |
| 1538 | 2.4 | 8.5 |

*Values obtained from Carson et al., Ultrasound in Med & Biol., 3:341–350 (1978), the disclosure of which is hereby incorporated herein by reference in its entirety.

Either fixed frequency or modulated frequency ultrasound may be used in diagnostic and therapeutic applications. Fixed frequency is defined wherein the frequency of the sound wave is constant over time. A modulated frequency is one in which the wave frequency changes over time, for example, from high to low (PRICH) or from low to high (CHIRP). For example, a PRICH pulse with an initial frequency of 10 MHz of sonic energy is swept to 1 MHz with increasing power from about 1 to about 5 watts. Focused, frequency modulated, high energy ultrasound may increase the rate of local gaseous expansion within the compositions and rupturing to provide local delivery of therapeutic photoactive agents.

The frequency of the sound used may range from about 0.025 to about 100 MHz, preferably between about 0.75 and about 3 MHz, more preferably between about 1 and about 2 MHz. Commonly used therapeutic frequencies of about 0.75 to about 1.5 MHz may be used. Commonly used diagnostic frequencies of about 3 to about 7.5 MHz may be used.

For very small vesicles, e.g., below 0.5 μm in mean outside diameter, higher frequencies of sound may be preferred as these smaller vesicles will absorb sonic energy more effectively at higher frequencies of sound. When very high frequencies are used, e.g., over 10 MHz, the sonic energy will generally have limited depth penetration into fluids and tissues. External application may be preferred for the skin and other superficial tissues, but for deep structures, the application of sonic energy via interstitial probes or intravascular ultrasound catheters may be preferred.

For optical imaging, optically active gases, such as argon or neon, may also be incorporated in the compositions of the invention. The wavelength and intensity of irradiation to be applied to activate photoactive agent will depend upon the particular photoactive agents being used, since different photoactive agents have different optimal wavelengths of response. Thus, the requisite wavelength and intensity of irradiation may be readily determined by one skilled in the art based upon the particular photoactive agents being used. Suitable wavelengths are generally about 500 nm to about 1400 nm, and suitable intensities are generally about 1 mW/cm$^2$ to about 1,000 mW/cm$^2$. Photodynamic therapy using optical imaging is described, for example, by Bergstrom et al, *J. Photochem. Photobiol. B.*, 24(1):17–23 (1994), Gatenby et al, *Radiology*, 163(1):172–5 (1987), Gatenby et al, *Radiology*, 163 (1):167–71 (1987).

As discussed above, the stabilizing materials and compositions of the present invention may be used in connection with diagnostic imaging and therapeutic imaging, including, for example, ultrasound, optical imaging, magnetic resonance imaging (MRI), nuclear magnetic resonance (NMR), computed tomography (CT), electron spin resonance (ESR), nuclear medical imaging, elastography, drug delivery with ultrasound, radiofrequency (RF) and microwave laser. Preferably, the stabilizing materials and compositions of the present invention are used with ultrasound imaging and optical imaging. The stabilizing materials and compositions of the present invention may be used in combination with various contrast agents, including conventional contrast agents, which may serve to increase their effectiveness as contrast agents for diagnostic and therapeutic imaging.

Examples of suitable contrast agents for use in combination with the present stabilizing materials include, for example, stable free radicals, such as, stable nitroxides, as well as compounds comprising transition, lanthanide and actinide elements, which may, if desired, be in the form of a salt or may be covalently or non-covalently bound to complexing agents, including lipophilic derivatives thereof, or to proteinaceous macromolecules. Preferable transition, lanthanide and actinide elements include, for example, Gd(III), Mn(II), Cu(II), Cr(III), Fe(II), Fe(III), Co(II), Er(II), Ni(II), Eu(III) and Dy(III). More preferably, the elements may be Gd(III), Mn(II), Cu(II), Fe(II), Fe(III), Eu(III) and Dy(III), most preferably Mn(II) and Gd(III). The foregoing elements may be in the form of a salt, including inorganic salts, such as a manganese salt, for example, manganese chloride, manganese carbonate, manganese acetate, and organic salts, such as manganese gluconate and manganese hydroxylapatite. Other exemplary salts include salts of iron, such as iron sulfides, and ferric salts, such as ferric chloride.

The above elements may also be bound, for example, through covalent or noncovalent association, to complexing agents, including lipophilic derivatives thereof, or to proteinaceous macromolecules. Preferable complexing agents include, for example, texaphyrins, diethylenetriaminepentaacetic acid (DTPA), ethylene-diaminetetraacetic acid (EDTA), 1,4,7,10-tetraazacyclododecane-N,N',N',N'''-tetraacetic acid (DOTA), 1,4,7,10 -tetraazacyclododecane-N,N',N''-triacetic acid (DOTA), 3,6,9-triaza-12-oxa-3,6,9-tricarboxymethylene-10-carboxy-13-phenyltri-decanoic acid (B-19036), hydroxybenzylethylenediamine diacetic acid (HBED), N,N'-bis(pyridoxyl-5-phosphate)ethylene diamine, N,N'-diacetate (DPDP), 1,4,7-triazacyclo-nonane-N,N',N''-triacetic acid (NOTA), 1,4,8,11-tetraazacyclotetradecane-N,N',N'',N'''-tetraacetic acid (TETA), kryptands (macrocyclic complexes), and desferrioxamine. More preferably, the complexing agents are EDTA, DTPA, DOTA, DO3A and kryptands, most preferably DTPA. Preferable lipophilic complexes include alkylated derivatives of the complexing agents EDTA, DOTA, for example, N,N'-bis-(carboxy-decylamidomethyl-N-2,3-dihydroxypropyl)ethylenediamine-N,N'-diacetate (EDTA-DDP); N,N'-bis-(carboxyoctadecylamidomethyl-N-2,3-dihydroxypropyl)-ethylene-diamine-N,N'-diacetate (EDTA-ODP); and N,N'-Bis(carboxylaurylamidomethyl-N-2,3-dihydroxypropyl)ethylenediamine-N,N'-diacetate (EDTA-LDP); including those described in U.S. Pat. No. 5,312,617, the disclosure of which is hereby incorporated herein by reference in its entirety. Preferable proteinaceous macromolecules include, for example, albumin, collagen, polyarginine, polylysine, polyhistidine, γ-globulin and β-globulin, with albumin, polyarginine, polylysine, and polyhistidine being more preferred. Suitable complexes therefore include Mn(II)-DTPA, Mn(II)-EDTA, Mn(II)-DOTA, Mn(II)-DO3A, Mn(II)-kryptands, Gd(III)-DTPA, Gd(III)-DOTA, Gd(III)-DO3A, Gd(III)-kryptands, Cr(III)-EDTA, Cu(II)-EDTA, or iron-desferrioxamine, more preferably Mn(II)-DTPA or Gd(III)-DTPA.

Nitroxides are paramagnetic contrast agents which increase both T1 and T2 relaxation rates on MRI by virtue of the presence of an unpaired electron in the nitroxide molecule. As known to one of ordinary skill in the art, the paramagnetic effectiveness of a given compound as an MRI contrast agent may be related, at least in part, to the number of unpaired electrons in the paramagnetic nucleus or molecule, and specifically, to the square of the number of unpaired electrons. For example, gadolinium has seven unpaired electrons whereas a nitroxide molecule has one unpaired electron. Thus, gadolinium is generally a much stronger MRI contrast agent than a nitroxide. However, effective correlation time, another important parameter for assessing the effectiveness of contrast agents, confers potential increased relaxivity to the nitroxides. When the tumbling rate is slowed, for example, by attaching the paramagnetic contrast agent to a large molecule, it will tumble more slowly and thereby more effectively transfer energy to hasten relaxation of the water protons. In gadolinium, however, the electron spin relaxation time is rapid and will limit the extent to which slow rotational correlation times can increase relaxivity. For nitroxides, however, the electron spin correlation times are more favorable and tremendous increases in relaxivity may be attained by slowing the rotational correlation time of these molecules. The gas filled vesicles of the present invention are ideal for attaining the goals of slowed rotational correlation times and resultant improvement in relaxivity. Although not intending to be bound by any particular theory of operation, it is contemplated that since the nitroxides may be designed to coat the perimeters of the vesicles, for example, by making alkyl derivatives thereof, the resulting correlation times can be optimized. Moreover, the resulting contrast medium of the present invention may be viewed as a magnetic sphere, a geometric configuration which maximizes relaxivity.

Exemplary superparamagnetic contrast agents suitable for use in the compositions of the present invention include metal oxides and sulfides which experience a magnetic domain, ferro- or ferrimagnetic compounds, such as pure iron, magnetic iron oxide, such as magnetite, $\gamma$-$Fe_2O_3$, $Fe_3O_4$, manganese ferrite, cobalt ferrite and nickel ferrite. Paramagnetic gases can also be employed in the present compositions, such as oxygen 17 gas ($^{17}O_2$). In addition, hyperpolarized xenon, neon, or helium gas may also be employed. MR whole body imaging may then be employed to rapidly screen the body, for example, for thrombosis, and ultrasound may be applied, if desired, to aid in thrombolysis.

The contrast agents, such as the paramagnetic and superparamagnetic contrast agents described above, may be employed as a component within the delivery vehicles and/or stabilizing materials. With respect to vesicles, the contrast agents may be entrapped within the internal void thereof, administered as a solution with the vesicles, incorporated with any additional stabilizing materials, or coated onto the surface or membrane of the vesicle. Mixtures of any one or more of the paramagnetic agents and/or superparamagnetic agents in the present compositions may be used. The paramagnetic and superparamagnetic agents may also be coadministered separately, if desired.

If desired, the paramagnetic or superparamagnetic agents may be delivered as alkylated or other derivatives incorporated into the compositions, especially the lipidic walls of the vesicles. In particular, the nitroxides 2,2,5,5-tetramethyl-1-pyrrolidinyloxy, free radical and 2,2,6,6-tetramethyl-1-piperidinyloxy, free radical, can form adducts with long chain fatty acids at the positions of the ring which are not occupied by the methyl groups via a variety of linkages, including, for example, an acetyloxy linkage. Such adducts are very amenable to incorporation into the lipid and/or vesicle compositions of the present invention.

The stabilizing materials and/or vesicles of the present invention, and especially the vesicles, may serve not only as effective carriers of the superparamagnetic agents described above, but also may improve the effect of the susceptibility contrast agents. Superparamagnetic contrast agents include metal oxides, particularly iron oxides but including manganese oxides, and as iron oxides, containing varying amounts of manganese, cobalt and nickel which experience a magnetic domain. These agents are nano or microparticles and have very high bulk susceptibilities and transverse relaxation rates. The larger particles, for example, particles having diameters of about 100 nm, have much higher P2 relaxivities as compared to R1 relaxivities. The smaller particles, for example, particles having diameters of about 10 to about 15 nm, have somewhat lower R2 relaxivities, but much more balanced $R_1$ and R2 values. Much smaller particles, for example, monocrystalline iron oxide particles having diameters of about 3 to about 5 nm, have lower R2 relaxivities, but probably the most balanced $R_1$ and R2 relaxation rates. Ferritin can also be formulated to encapsulate a core of very high relaxation rate superparamagnetic iron. It has been discovered that the lipid and/or vesicle compositions, especially vesicle compositions, including gas filled vesicles, can increase the efficacy and safety of these conventional iron oxide based MRI contrast agents.

The iron oxides may simply be incorporated into the stabilizing materials and/or vesicles. Preferably, in the case of vesicles formulated from lipids, the iron oxides may be incorporated into the walls of the vesicles, for example, by being adsorbed onto the surfaces of the vesicles, or entrapped within the interior of the vesicles.

Without being bound to any particular theory of operation, it is believed that the vesicles of the present invention increase the efficacy of the superparamagnetic contrast agents by several mechanisms. First, it is believed that the vesicles function to increase the apparent magnetic concentration of the iron oxide particles. Also, it is believed that the vesicles increase the apparent rotational correlation time of the MRI contrast agents, including paramagnetic and superparamagnetic agents, so that relaxation rates are increased. In addition, the vesicles appear to increase the apparent magnetic domain of the contrast medium according to the manner described hereinafter.

Certain of the vesicles of the present invention, and especially vesicles formulated from lipids, may be visualized as flexible spherical domains of differing susceptibility from the suspending medium, including, for example, the aqueous suspension of the contrast medium or blood or other body fluids, for example, in the case of intravascular injection or injection into other body locations. In the case of ferrites or iron oxide particles, it should be noted that the contrast provided by these agents is dependent on particle size. This phenomenon is very common and is often referred to as the "secular" relaxation of the water molecules. Described in more physical terms, this relaxation mechanism is dependent upon the effective size of the molecular complex in which a paramagnetic atom, or paramagnetic molecule, or molecules, may reside. One physical explanation may be described in the following Solomon-Bloembergen equations which define the paramagnetic contributions as a function of the $T_1$ and $T_2$ relaxation times of a spin ½ nucleus with gyromagnetic ratio g perturbed by a paramagnetic ion: $1/T_1M = (2/15)S(S+1)\gamma^2 g^2 \beta^2/r^6[3\tau_c/(1+\omega_I^2\tau_c^2)+7\tau_c/(1+\omega_s^2\tau_c^2)] + (2/3)S(S+1)A^2/h^2 [\tau_e/(1+\omega_s 2\tau_e^2)]$ and $1/T_2M = (1/15)S(S+1)\gamma^2 g^2 \beta^2/r^6[4\tau_c+3\tau_c/(1+\omega_I^2\tau_c^2)+13\tau_c/(1+w_s^2\tau_c^2)]+(1/3)S(S+1)A^2/h^2[\tau_e/(1+\omega_s 2\tau_e^2)]$ where S is the electron spin quantum number; g is the electronic g factor;

P is the Bohr magneton; $\omega_I$ and $\omega_s$ (657 $w_I$) is the Larrnor angular precession frequencies for the nuclear spins and electron spins; r is the ion-nucleus distance; A is the hyperfine coupling constant; $\tau_c$ and $\tau_e$ are the correlation times for the dipolar and scalar interactions, respectively; and h is Planck's constant.

A few large particles may have a much greater effect than a larger number of much smaller particles, primarily due to a larger correlation time. If one were to make the iron oxide particles very large however, increased toxicity may result, and the lungs may be embolized or the complement cascade system may be activated. Furthermore, it is believed that the total size of the particle is not as important as the diameter of the particle at its edge or outer surface. The domain of magnetization or susceptibility effect falls off exponentially from the surface of the particle. Generally speaking, in the case of dipolar (through space) relaxation mechanisms, this exponential fall off exhibits an $r^6$ dependence for a paramagnetic dipole—dipole interaction. Interpreted literally, a water molecule that is 4 angstroms away from a paramagnetic surface will be influenced 64 times less than a water molecule that is 2 angstroms away from the same paramagnetic surface. The ideal situation in terms of maximizing the contrast effect would be to make the iron oxide particles hollow, flexible and as large as possible. It has not been possible to achieve this heretofore and it is believed that the benefits have been unrecognized heretofore also. By coating the inner or outer surfaces of the vesicles with the contrast agents, even though the individual contrast agents, for example, iron oxide nanoparticles or paramagnetic ions, are relatively small structures, the effectiveness of the contrast agents may be greatly enhanced. In so doing, the contrast agents may function as an effectively much larger sphere wherein the effective domain of magnetization is determined by the diameter of the vesicle and is maximal at the surface of the vesicle. These agents afford the advantage of flexibility, namely, compliance. While rigid vesicles might lodge in the lungs or other organs and cause toxic reactions, these flexible vesicles slide through the capillaries much more easily.

In contrast to the flexible vesicles described above, it may be desirable, in certain circumstances, to formulate vesicles from substantially impermeable polymeric materials including, for example, polymethyl methacrylate. This would generally result in the formation of vesicles which may be substantially impermeable and relatively inelastic and brittle. In embodiments involving diagnostic imaging, for example, ultrasound, contrast media which comprise such brittle vesicles would generally not provide the desirable reflectivity that the flexible vesicles may provide. However, by increasing the power output on ultrasound, the brittle microspheres can be made to rupture, thereby causing acoustic emissions which can be detected by an ultrasound transducer.

Nuclear Medicine Imaging (NMI) may also be used in connection with the diagnostic and therapeutic method aspects of the present invention. For example, NMI may be used to detect radioactive gases, such as $Xe^{133}$, which may be incorporated in the present compositions in addition to, or instead of, the gases discussed above. Such radioactive gases may be entrapped within vesicles for use in detecting, for example, thrombosis. Preferably, bifunctional chelate derivatives are incorporated in the walls of vesicles, and the resulting vesicles may be employed in both NMI and ultrasound. In this case, high energy, high quality nuclear medicine imaging isotopes, such as technetium$^{99m}$ or indium$^{111}$ can be incorporated in the walls of vesicles. Whole body gamma scanning cameras can then be employed to rapidly localize regions of vesicle uptake in vivo. If desired, ultrasound may also be used to confirm the presence, for example, of a clot within the blood vessels, since ultrasound generally provides improved resolution as compared to nuclear medicine techniques. NMI may also be used to screen the entire body of the patient to detect areas of vascular thrombosis, and ultrasound can be applied to these areas locally to promote rupture of the vesicles and treat the clot.

Elastography is an imaging technique which generally employs much lower frequency sound, for example, about 60 kHz, as compared to ultrasound which can involve frequencies of over 1 MHz. In elastography, the sound energy or vibratory energy is generally applied to the tissue and the elasticity of the tissue may then be determined. In connection with preferred embodiments of the invention, which involve highly elastic vesicles, the deposition of such vesicles onto, for example, a clot, increases the local elasticity of the tissue and/or the space surrounding the clot. This increased elasticity may then be detected with elastography. If desired, elastography can be used in conjunction with other imaging techniques, such as MRI and ultrasound.

EXAMPLES

The invention is further demonstrated in the following examples. Examples 1–4 are for purposes of illustration only and are not intended to limit the scope of the present invention. Examples 1–3 are actual examples, while Example 4 is a prophetic example.

Example 1

Perfluoropropane encapsulated lipid bilayers were formed with a lipid formulation comprising 5 mg/ml of a mixture comprising 82 mole % dipalmitoylphosphatidylcholine, 10 mole % dipalmitoylphosphatidic acid, and 8 mole % dipalmitoylphosphatidylethanolamine-PEG 5,000 (Avanti Polar Lipids, Alabaster, Ala.) in a vehicle comprising 8:1:1 of v:v:v normal saline:propylene glycol:glycerol, yielding a foam and a lower vehicle layer that was predominantly devoid of any particulate. To this mixture was added 1 mg/ml of dipalmitoylphosphatidylethanol-amine derivatized with lissamine rhodamine B (Avanti Polar Lipids, Alabaster, Ala.), at about 25 mole percent (e.g., generally about 1 to about 50 mole percent). Dipalmitoylphosphatidylethanolamine is derivatized with lissamine rhodamine B by methods known in the art, including those described by Leenhouts et al, *Biochim. Biophys. Acta,* 1237(2)121–126 (1995) and MacDonald, *J. Biol. Chem.,* 265:13533–13539 (1990), the disclosures of which are hereby incorporated by reference herein in their entirety. The maximum to be used is determined by which concentration will still allow formation of stable lipid coated bubbles. Preferably, this will be at 10 to 20 mole percent.

The optoacoustic liposomes were formed by shaking the mixture on an ESPE Capmix for two minutes at 4,500 rpm. Variations of the vehicle yielded varying degrees of clarity to the lower vehicle layer. Prior to filtration, the gas-filled microspheres were sized on a Particle Sizing SYstems Model 770 optical sizer (Particle Sizing Systems, Santa Barbara, Calif.). Sizing resulted in 99% of all particles residing below 34 $\mu$m. The resultant product ws then filtered through an 8 $\mu$m filter to yield microspheres of uniform size. Sizing of the subsequent microspheres resulted in 99.5% of all particles residing below 10 $\mu$m. The photoactive lipid was optimally excited with 550 nm (yellow-green) light and the fluorescence emission peak was 590 nm.

Example 2

1.5 g of a fluorescein-derivatized diacylphosphatidyl ethanolamine and 3 g of soybean oil were agitated in a vortex mixer. Diacylphosphatidyl ethanolamine was derivatized with fluorescein by methods known in the art including those described by Ahlers et al, *Biophys. J*, 63:823–838 (1992), the disclosure of which is hereby incorporated by reference herein in its entirety. To this mixture was added 1.0 g of a lipid blend comprising 82 mol % dipalmitoylphosphatidylcholine, 10 mol % dipalmitoylphosphatidic acid and 8 mol % dipalmitoylphosphatidylethanolamine-PEG5000 (all phospholipids from Avanti Polar Lipids, Alabaster, Ala.). The mixture was stirred for 10 minutes at 50° C. then transferred into a container with 200 mls normal saline plus 1% w/v Pluronic F-65 and emulsified with a Microfluidizer (10×) at 16,000 psi while the temperature was maintained at 50° C. The material was then subdivided into 1.0 ml aliquots in 1.5 ml vials. The vials were vacuum-evacuated, and the headspace was filled with perfluorobutane. The vials were sealed and shaken on an ESPE Capmix for 60 seconds at 4,500 rpm (alternatively, the vials may be placed on a Wig-L-Bug (Crescent Dental, Lyons Ill.) and agitated at 2800 rpm for 2 minutes). The resulting product was a suspension of a fluorescent lipid in oil filled liposomes or lipospheres (i.e., vesicles) containing about 0.45% by weight fluorophore and 0.45% by weight other lipids. The final product comprised acoustically and optically active lipospheres instilled with perfluorobutane gas, with a mean diameter under 10 $\mu$m.

The product can be injected into a patient in this form or filtered to eliminate particles over 2 $\mu$m just prior to injection. For optoacoustic imaging, the fluorophore is excited at 497 nm and fluorescence emission is maximal at 521 nm.

Example 3

The targeted formulation disclosed in Example 11 of commonly owned U.S. application Ser. No. 08/851,780, filed May 6, 1997 (the disclosure of which is incorporated herein by reference), was prepared in the following manner: to a cooled (0 to 5° C.) solution of 1,2-dipalmitoyl-sn-glycero-3-succinate 66.8 mg, N-hydroxy-succinimide 11.5 mg, dimethylaminopyridine (DMAP) 2 mg and acetonitrile 40 mL in a 100 mL round bottom flask was added dropwise to a solution of dicyclohexyl carbodiimide (DCC) 20.6 mg in acetonitrile 10 mL. The resulting mixture was stirred for 5 hours. The solid material which formed during the reaction (dicyclohexylurea) was removed by filtration, and the filtrate was concentrated in vacuo to yield 78 mg of a white product of N-DPGS-succinimide.

To a cooled (0 to 5° C.) solution of the above N-DPGS-succinimide (78 mg) and CHCl$_3$ (10 mL) (Mallinckrodt, St. Louis, Mo.) in a 100 mL round bottom flask was added dropwise a solution of $\omega$-amino-$\omega'$-carboxy-polyethyleneglycol (0.3 g) and triethylamine (40 mg) in CHCl$_3$ (20 mL). The resulting mixture was stirred for 5 hours at 10° C. After stirring overnight, the reaction mixture was poured into ice water and neutralized with 10% HCl to a pH of about 3 or less. The lower organic layer was removed using a separatory funnel and washed three times with water. The organic layer was collected and dried (NaSO$_4$). Filtration and concentration in vacuo yielded 0.34 g of a white solid of 3-$\omega$-carboxy-polyethyleneglycol-imino-succinat-1,2-dipalmitoyl-sn-glycerol (DPGS-$\omega$-carboxy-PEG).

To a cooled (0 to 5° C.) solution of DPGS-w-carboxy-PEG (200 mg) from Step B, N-hydroxysuccinimide (6 mg), dimethylaminopyridine (DMAP) (2 mg) and acetonitrile (40 mL) in a 250 mL round bottom flask was added dropwise a solution of dicyclohexyl carbodiimide (DCC) (12 mg) in acetonitrile (10 mL). The resulting mixture was stirred for 5 hours and the white solid which formed (dicyclohexylurea) was removed by filtration. The filtrate was concentrated in vacuo to yield 200 mg of a white solid of 3-succinamoyl-oxycarbonyl-polyethyleneglycol-imino-succinate-1,2-dipalmitoyl-sn-glycerol (DPGS-$\omega$-carboxy-PEG-succinimide).

To a cooled (5 to 10° C.), stirred solution of human IL-2 (20 mg) (Sigma Chemical Co., St. Louis, Mo.) in an aqueous buffer (20 mL) at a pH of 8.5 was added dropwise a solution of DPGS-$\omega$-carboxy-PEG-succinimide from Step C (4 mg) and acetonitrile (10 mL). The temperature of the resulting mixture was equilibrated to room temperature and the reaction mixture was stirred for about 48 hours. The mixture was concentrated in vacuo and the residual salts were dialyzed away using a dialysis bag having a molecular weight cutoff of about 3500, equilibrated against water. The resulting dialyzed solution was frozen and lyophilized to yield 12 mg of a white solid of a N-(1,2-dipalmitoyl-sn-glycero-3-succinyl)-PEG-Interleukin-2 (DPGS-PEG-IL-2) conjugate targeting moiety.

The targeted vesicle formulation described above was modified in that 15 mole percent of the fluorescent lipid NBD-diacylphosphatidyl ethanolamine (Avanti Polar Lipids, Alabaster, Ala.) was substituted for the DPPA component and a portion of the DPPC component. The final lipid composition of the optoacoustic agent comprised 72 mole % DPPC, 8 mole % DPPE-PEG5000, 5 mole % DPGS-PEG-IL-2 and 15% NBD-diacylphosphatidyl ethanolamine. The lipid mix was then subdivided into 1.0 ml aliquots in 1.5 ml vials. The vials were vacuum-evacuated, and the headspace was filled with perfluoropentane gas and shaken on an ESPE Capmix for 60 seconds at 4500 rpm.

The formulation is injectible for thrombus imaging (acoustic and/or optical) and thrombolysis. Optical imaging is best performed with incident radiation of 460 nm and fluorescence detection at 534 nm.

Example 4

As shown in Figures, the form of the delivery vehicle can be a solid matrix drug (as illustrated in FIG. 5) or acoustically active liposphere (as illustrated in FIG. 4) or a lipid vesicle (as illustrated in FIG. 7). The delivery vehicles entrap an echogenic gas or gaseous precursor and present targeting ligands for delivery to receptors at the site requiring therapy. The vehicles incorporate a photoactive agent which may be a drug (e.g., a bioactive agent) or accompany a drug.

Photofrin (Quadra Logic Technologies, Vancouver BC), a photoactive agent that is a purified hematoporphyrin derivative, is converted into a lipid-solubilized dried drug and targeted to human melanoma cells with microbubble containing an optionally-fluorinated lipid conjugate of anti-interleukin-2 fab fragment (AB5 (APC))(avaible from Oncogene Research, Cambridge, Mass.). The synthesis of the conjugate is described in detail below.

To a cooled (0 to 5° C.) solution of 1,2-dipalmitoyl-sn-glycero-3-succinate 66.8 mg, N-hydroxy-succinimide 11.5 mg, dimethylaminopyridine (DMAP) 2 mg and acetonitrile 40 mL in a 100 mL round bottom flask was added dropwise to a solution of dicyclohexyl carbodiimide (DCC) 20.6 mg in acetonitrile 10 mL. The resulting mixture was stirred for 5 hours. The solid material which formed during the reaction (dicyclohexylurea) was removed by filtration, and the filtrate was concentrated in vacuo to yield 78 mg of a white product of N-DPGS-succinimide.

To a cooled (0 to 5° C.) solution of the N-DPGS-succinimide (78 mg) and CHCl$_3$ (10 mL) (Mallinckrodt, St. Louis, Mo.) in a 100 ml round bottom flask was added dropwise a solution of ω-amino-ω'-carboxy-polyethyleneglycol (0.3 g) and triethylamine (40 mg) in CHCl$_3$ (20 mL). The resulting mixture was stirred for 5 hours at 10° C. After stirring overnight, the reaction mixture was poured into ice water and neutralized with 10% HCl to a pH of about 3 or less. The lower organic layer was removed using a separatory funnel and washed three times with water. The organic layer was collected and dried (NaSO$_4$). Filtration and concentration in vacuo yielded 0.34 g of a white solid of 3-ω-carboxypolyethyleneglycol-imino-succinat-1,2-dipalmitoyl-sn-glycerol (DPGS-6-carboxy-PEG).

To a cooled (0 to 5° C.) solution of DPGS-ω-carboxy-PEG (200 mg), N-hydroxy-succinimide (6 mg), dimethylaminopyridine (DMAP) (2 mg) and acetonitrile (40 mL) in a 250 mL round bottom flask was added dropwise a solution of dicyclohexyl carbodiimide (DCC) (12 mg) in acetonitrile (10 mL). The resulting mixture was stirred for 5 hours and the white solid which formed (dicyclohexylurea) was removed by filtration. The filtrate was concentrated in vacuo to yield 200 mg of a white solid of 3-succinamoyl-oxycarbonyl-polyethyleneglycol-imino-succinate-1,2-dipalmitoyl-sn-glycerol (DPGS-ω-carboxy-PEG-succinimide).

To a cooled (5 to 10° C.), stirred solution of human IL1-2 (20 mg) (Sigma Chemical Co., St. Louis, Mo.) in an aqueous buffer (20 mL) at a pH of 8.5 was added dropwise a solution of DPGS-ω-carboxy-PEG-succinimide (4 mg) and acetonitrile (10 mL). The temperature of the resulting mixture was equilibrated to room temperature and the reaction mixture was stirred for about 48 hours. The mixture was concentrated in vacuo and the residual salts were dialyzed away using a dialysis bag having a molecular weight cutoff of about 3500, equilibrated against water. The resulting dialyzed solution was frozen and lyophilized to yield 12 mg of a white solid of a N-(1,2-dipalmitoyl-sn-glycero-3-succinyl)-PEG-Interleukin-2 (DPGS-PEG-IL-2). Additional details regarding this reaction are set forth in U.S. application Ser. No. 08/851,780, filed May 6, 1997, the disclosure of which is hereby incorporated by reference herein in its entirety.

Since Photofrin is water soluble, it is best used as a methanol-soluble dried drug, with the methanol solution added to a lipid mixture of DPPC/DPPA/DPPE-PEG5000 (8:1:1 w/w/w). The mixture is placed in a ball mill so that particles of the drug of a uniform size are formed and filtered to exclude those over 0.5 μm. This material is then transferred to a lyophilizer and dried to obtain a lipid-coated drug aggregate. It may then be reconstituted in normal saline in a shaker with the headspace replaced with perfluorobutane.

Each patent, patent application and publication cited in the present disclosure is hereby incorporated by reference herein in its entirety.

Although the invention has been set forth in considerable detail, one skilled in the art will appreciate that numerous changes and modifications can be made to the preferred embodiments of the invention and that such changes and modifications may be made without departing from the sprit and scope of the invention.

What is claimed is:

1. A method of providing an image of a region of a patient comprising:

administering to the patient a composition comprising a stabilizing material, a photoactive agent, and a gas, a gaseous precursor or a gas and a gaseous precursor; and scanning the patient using ultrasound imaging and optical imaging wherein optical signals resonating from the composition are modulated by the ultrasound to obtain visible images of the region of the patient, wherein the gas and gaseous precursor comprise a fluorinated compound.

2. The method of claim 1, wherein the stabilizing material is in a vesicular form.

3. The method of claim 1, wherein the stabilizing material is in a non-vesicular form.

4. The method of claim 1, wherein the stabilizing material comprises a lipid, a protein or a polymer.

5. The method of claim 4, wherein the stabilizing material comprises a lipid.

6. The method of claim 1, wherein the stabilizing material comprises a surfactant.

7. The method of claim 6, wherein the stabilizing material comprises a fluorinated surfactant.

8. The method of claim 1, wherein the photoactive agent is active in a wavelength of from about 500 nm to about 1400 nm.

9. The method of claim 1, wherein the photoactive agent is active in an infrared wavelength.

10. The method of claim 1, wherein the photoactive agent is a fluorescent material.

11. The method of claim 1, wherein the photoactive agent is a photosensitizer.

12. The method of claim 1, wherein the photoactive agent is at least one selected from the group consisting of fluoresceins, indocyanine green, rhodamine, triphenylamines, polymethines, cyanines, phthalocyanines, naphthocyanines, merocyanines, fullerenes, oxatellurazoles, verdins, rhodins, perphycenes, sapphyrins, rubyrins, metalloporphyrins, cholesteryl 4,4-difluoro-5,7-dimethyl-4-bora-3a,4a-diaza-s-indacene-3-dodecanoate, cholesteryl 12-(N-methyl-N-(7-nitrobenz-2-oxa-1,3-diazol-4-yl)amino)-dodecanate, cholesteryl cis-parinarate, cholesteryl 3-((6-phenyl)-1,3,5-hexatrienyl)phenylproprionate, cholesteryl 1-pyrenebutyrate, cholesteryl 1-pyrenedecanoate, cholesteryl 1-pyrenehexanoate, 22-(N-(7-nitrobenz-2-oxa-1,3-diazol-4-yl)amino)-23,24-bisnor-5-cholen-3β-ol, 22-(N-(7-nitrobenz-2-oxa-1,3-diazol-4-yl)amino)-23,24-bisnor-5-cholen-3β-yl cis-9-octadecenoate, 1-pyrenemethyl 3-(hydroxy-22,23-bisnor-5-cholenate, 1-pyrenemethyl 3β-(cis-9-octadecenoyloxy)-22,23-bisnor-5-cholenate, acridine orange 10-dodecyl bromide, acridine orange 10-nonyl bromide, 4-(N,N-dimethyl-N-tetradecylammonium)methyl-7-hydroxycoumarin) chloride, 2-dodecylresorufin, 4-heptadecyl-7-hydroxycoumarin, 5-hexadecanoyl-aminoeosin, N-octadecyl-N'-(5-(fluoresceinyl))-thiourea, octadecyl rhodamine B chloride, 2-(3-(diphenylhexatrienyl) propanoyl)-1-hexadecanoyl-sn-glycero-3-phosphocholine, 6-N-(7-nitrobenz-2-oxa-1,3-diazol-4-yl)amino)hexanoic acid, 1-hexadecanoyl-2-(1-pyrenedecanoyl)-sn-glycero-3-phosphocholine, 1,1'-dioctadecyl-3,3,3',3'-tetramethylindocarbocyanine perchlorate, 12-(9-anthroyloxy)oleic acid, 5-butyl-4,4-difluoro-4-bora-3a,4a-diaza-s-indacene-3-nonanoic acid, N-(lissamine rhodamine B sulfonyl)-1,2-dihexadecanoyl-sn-glycero-3-phosphoethanolamine, triethylammonium salt, phenylglyoxal monohydrate, naphthalene-2,3-dicarbox-aldehyde, 8-bromomethyl-4,4-difluoro-1,3,5,7-tetramethyl-4-bora-3a, 4a-diaza-s-indacene, o-phthaldialdehyde, lissamine rhodamine B sulfonyl chloride, 9-anthronitrile, 1-pyrenesulfonyl chloride, 4-(4-(dihexadecylamino)styryl)-N-methylpyridinium iodide, texaphyrins, texaphyrin-metal chelates, chlorins, chlorin e6, bonellin, mono-L-aspartyl chlorin e6, mesochlorin, mesotetraphenylisobacteriochlorin, mesotetraphenyl-bacteriochlorin, hypocrellin B, purpurins, octaethylpurpurin, zinc(II) etiopurpurin, tin(IV) etiopurpurin, tin ethyl etiopurpurin, lutetium texaphyrin, photofrin, protoporphyrin IX, tin protoporphyrin, porphyrins, benzoporphyrins, haematoporphyrin, methyl pheophorbide-α-(hexyl-ether), porphycenes, ketochlorins, sulfonated tetraphenylporphines, δ-aminolevulinic acid, chlorophyll, carotenoids, flavonoids, bilins, phytochromes, phycobilins, phycoerythrin, phycocyanines, retinoic acid, retinoins and retinates.

13. The method of claim 12, wherein the photoactive agent is conjugated to the stabilizing material.

14. The method of claim 12, wherein the photoactive agent is conjugated to an antibody.

15. The method of claim 1, wherein the fluorinated compound is sulfur hexafluoride, a perfluorocarbon or a perfluoroether.

16. The method of claim 15, wherein the fluorinated compound is selected from the group consisting of sulfur hexafluoride, perfluoromethane, perfluoroethane, perfluoropropane, perfluorocyclopropane, perfluorobutane, perfluorocyclobutane, perfluoropentane, perfluorocyclopentane, perfluorohexane, perfluorocyclohexane, perfluorotetrahydropyran, perfluoromethyltetrahydrofuran, perfluorobutylmethyl ether, perfluoropropylethyl ether, perfluorocyclobutylmethyl ether, perfluorocyclopropylethyl ether, perfluoropropylmethyl ether, perfluorodiethyl ether, perfluorocyclopropylmethyl ether, perfluoromethylethyl ether and perfluorodimethyl ether.

17. The method of claim 1, wherein the composition further comprises a fluorinated liquid.

18. The method of claim 17, wherein the fluorinated liquid is selected from the group consisting of perfluoroheptane, perfluorooctane, perfluorononane, perfluorodecane, perfluorododecane, perfluorodecalin, perfluorododecalin, perfluorooctyliodide, perfluorooctylbromide, perfluorotripropylamine, perfluorotributylamine, perfluorobutylethyl ether, bis(perfluoroisopropyl) ether and bis (perfluoropropyl) ether.

19. The method of claim 1, wherein the composition further comprises a targeting ligand.

20. The method of claimed, wherein the targeting ligand is selected from the group consisting of a protein, a peptide and a saccharide.

21. The method of claim 19, wherein the targeting ligand is selected from the group consisting of a glycolipid, a lipoprotein and an antibody.

22. The method of claim 19, wherein the targeting ligand is genetic material.

23. The method of claim 22, wherein the genetic material is selected from the group consisting of RNA, DNA, sense RNA, sense DNA, antisense RNA, antisense DNA, hammerhead RNA, ribozymes, hammerhead ribozymes, antigene nucleic acids, ribooligonucleotides, deoxyribooligonucleotides, antisense ribooligonucleotides and antisense deoxyribooligonucleotides.

24. The method of claim 1, wherein the composition further comprises a bioactive agent.

25. The method of claim 24, further comprising applying ultrasound to deliver the bioactive agent to the region of the patient.

26. The method of claim 1, wherein the composition further comprises an oil.

27. The method of claim 1, wherein the composition is a solid porous matrix.

28. A method of diagnosing the presence of diseased tissue in a patient comprising:
administering to the patient a composition comprising a stabilizing material, a photoactive agent, and a gas, a gaseous precursor or a gas and a gaseous precursor; and
scanning the patient using ultrasound imaging and optical imaging wherein optical signals resonating from the composition are modulated by the ultrasound to obtain a visible image of any diseased tissue in the patient, wherein the gas and gaseous precursor comprise a fluorinated compound.

29. The method of claim 28, wherein the stabilizing material is in a vesicular form.

30. The method of claim 28, wherein the stabilizing material is in a non-vesicular form.

31. The method of claim 28, wherein the stabilizing material comprises a lipid, a protein or a polymer.

32. The method of claim 31, wherein the stabilizing material comprises a lipid.

33. The method of claim 28, wherein the stabilizing material comprises a surfactant.

34. The method of claim 33, wherein the stabilizing material comprises a fluorinated surfactant.

35. The method of claim 28, wherein the photoactive agent is active in a wavelength of from about 500 nm to about 1400 nm.

36. The method of claim 28, wherein the photoactive agent is active in an infrared wavelength.

37. The method of claim 28, wherein the photoactive agent is a fluorescent material.

38. The method of claim 28, wherein the photoactive agent is a photosensitizer.

39. The method of claim 25, wherein the photoactive agent is at least one selected from the group consisting of fluoresceins, indocyanine green, rhodamine, triphenylamines, polymethines, cyanines, phthalocyanines, naphthocyanines, merocyanines, fullerenes, oxatellurazoles, verdins, rhodins, perphycenes, sapphyrins, rubyrins, metalloporphyrins, cholesteryl 4,4-difluoro-5,7-dimethyl-4-bora-3a,4a-diaza-s-indacene-3-dodecanoate, cholesteryl 12-(N-methyl-N-(7-nitrobenz-2-oxa-1,3-diazol-4-yl)amino)-dodecanate, cholesteryl cis-parinarate, cholesteryl 3-((6-phenyl)-1,3,5-hexatrienyl)phenylproprionate, cholesteryl 1-pyrenebutyrate, cholesteryl 1-pyrenedecanoate, cholesteryl 1-pyrenehexanoate, 22-(N-(7-nitrobenz-2-oxa-1,3-diazol-4-yl)amino)-23,24-bisnor-5-cholen-3β-ol, 22-(N-(7-nitrobenz-2-oxa-1,3-diazol-4-yl)amino)-23,24-bisnor-5-cholen-3β-yl cis-9-octadecenoate, 1-pyrenemethyl 3-(hydroxy-22,23-bisnor-5-cholenate, 1-pyrenemethyl 3β-(cis-9-octadecenoyloxy)-22,23-bisnor-5-cholenate, acridine orange 10-dodecyl bromide, acridine orange 10-nonyl bromide, 4-(N,N-dimethyl-N-tetradecylammonium)methyl-7-hydroxycoumarin) chloride,, 2-dodecylresorufin, 4-heptadecyl-7-hydroxycoumarin, 5-hexadecanoyl-aminoeosin, N-octadecyl-N'-(5-(fluoresceinyl))-thiourea, octadecyl rhodamine B chloride, 2-(3-(diphenylhexatrienyl) propanoyl)-1-hexadecanoyl-sn-glycero-3-phosphocholine, 6-N-(7-nitrobenz-2-oxa-1,3-diazol-4-yl)amino)hexanoic acid, 1-hexadecanoyl-2-(1-pyrenedecanoyl)-sn-glycero-3-phosphocholine, 1,1'-dioctadecyl-3,3,3',3'-tetramethylindocarbocyanine perchlorate, 12-(9-anthroyloxy)oleic acid, 5-butyl-4,4-difluoro-4-bora-3a,4a-diaza-s-indacene-3-nonanoic acid, N-(lissamine rhodamine B sulfonyl)-1,2-dihexadecanoyl-sn-glycero-3-phosphoethanolamine, triethylammonium salt, phenylglyoxal monohydrate, naphthalene-2,3-dicarbox-aldehyde, 8-bromomethyl-4,4-difluoro-1,3,5,7-tetramethyl-4-bora-3a, 4a-diaza-s-indacene, o-phthaldialdehyde, lissamine rhodamine B sulfonyl chloride, 9-anthronitrile, 1-pyrenesulfonyl chloride, 4-(4-(dihexadecylamino)styryl)-N-methylpyridinium iodide, texaphyrins, texaphyrin-metal chelates, chlorins, chlorin e6, bonellin, mono-L-aspartyl chlorin e6, mesochlorin, mesotetraphenylisobacteriochlorin, mesotetraphenyl-bacteriochlorin, hypocrellin B, purpurins, octaethylpurpurin, zinc(II) etiopurpurin, tin(IV) etiopurpurin, tin ethyl etiopurpurin, lutetium texaphyrin, photofrin, protoporphyrin IX, tin protoporphyrin, porphyrins, benzoporphyrins, haematoporphyrin, methyl pheophorbide-α-(hexyl-ether), porphycenes, ketochlorins, sulfonated tetraphenylporphines, δ-aminolevulinic acid, chlorophyll, carotenoids, flavonoids, bilins, phytochromes, phycobilins, phycoerythrin, phycocyanines, retinoic acid, retinoins and retinates.

40. The method of claim 39, wherein the photoactive agent is conjugated to the stabilizing material.

41. The method of claim 39, wherein the photoactive agent is conjugated to an antibody.

42. The method of claim 28, wherein the fluorinated compound is sulfur hexafluoride, a perfluorocarbon or a perfluoroether.

43. The method of claim 42, wherein the fluorinated compound is selected from the group consisting of sulfur hexafluoride, perfluoromethane, perfluoroethane, perfluoropropane, perfluorocyclopropane, perfluorobutane, perfluorocyclobutane, perfluoropentane, perfluorocyclopentane, perfluorohexane, perfluorocyclohexane, perfluorotetrahydropyran, perfluoromethyltetrahydrofuran, perfluorobutylmethyl ether, perfluoropropylethyl ether, perfluorocyclobutylmethyl ether, perfluorocyclopropylethyl ether, perfluoropropylmethyl ether, perfluorodiethyl ether, perfluorocyclopropylmethyl ether, perfluoromethylethyl ether and perfluorodimethyl ether.

44. The method of claim 28, wherein the composition further comprises a fluorinated liquid.

45. The method of claim 44, wherein the fluorinated liquid is selected from the group consisting of perfluoroheptane, perfluorooctane, perfluorononane, perfluorodecane, perfluorododecane, perfluorodecalin, perfluorododecalin, perfluorooctyliodide, perfluorooctylbromide, perfluorotripropylamine, perfluorotributylamine, perfluorobutylethyl ether, bis(perfluoroisopropyl) ether and bis(perfluoropropyl) ether.

46. The method of claim 28, wherein the composition further comprises a targeting ligand.

47. The method of claim 46, wherein the targeting ligand is selected from the group consisting of a protein, a peptide and a saccharide.

48. The method of claim 46, wherein the targeting ligand is selected from the group consisting of a glycolipid, a lipoprotein and an antibody.

49. The method of claim 46, wherein the targeting ligand is genetic material.

50. The method of claim 49, wherein the genetic material is selected from the group consisting of RNA, DNA, sense RNA, sense DNA. antisense RNA, antisense DNA, hammerhead RNA, ribozymes, hammerhead ribozymes, antigene nucleic acids, ribooligonucleotides, deoxyribooligonucleotides, antisense ribooligonucleotides and antisense deoxyribooligonucleotides.

51. The method of claim 28, wherein the composition further comprises a bioactive agent.

52. The method of claim 51, further comprising applying ultrasound to deliver the bioactive agent to the diseased tissue in the patient.

53. The method of claim 28, wherein the composition further comprises an oil.

54. The method of claim 28, wherein the composition is a solid porous matrix.

* * * * *

UNITED STATES PATENT AND TRADEMARK OFFICE
CERTIFICATE OF CORRECTION

PATENT NO. : 6,123,923
DATED : September 26, 2000
INVENTOR(S) : Evan C. Unger and Yunqiu Wu It is certified that error appears in the above-identified patent and that said Letters Patent is hereby corrected as shown below:

Title Page,
Item [73], Assingee, please delete "Imarx" and insert -- ImaRx -- therefor.
Item [56], References Cited, FOREIGN PATENT DOCUMENTS, please delete "WO 84/02909" and insert -- WO 94/02909 -- therefor.
OTHER PUBLICATIONS,
"Fukuda et al.," please delete "Diotadecyldimethylammonium" and insert
-- Dioctadecyldimethylammonium -- therefor.
"Shiina et al.," please delete "Hyperthermiably" and insert -- Hyperthermia by -- therefor.
"Ter-Pogossian," please delete" *Tomography*, Kee, et al., n,", and, in second line thereof, after "*Computed Body*", please insert --*Tomography*, Lee et al.,--.
"Aronberg," please delete "Kee" and insert -- Lee -- therefor.
"Freézard et al.," please delete " Freézard" and insert -- Frézard -- therefor.
"Villanueva et al.," please delete "Patters" and insert --Patterns -- therefor.
"Reddi et al.," please delete "Lipsome–" and insert -- Liposome– -- therefor.
"Yang et al.," please delete "Facture" and insert -- Fracture -- therefor.

Column 8,
Line 24, please delete "ore" and insert -- or -- therefor.

Column 13,
Line 24, please delete "pheophorbide-α-" and insert -- pheophorbide-a- -- therefor
Lines 55 and 59, please delete "tridecaene" and insert -- tridecane -- therefor Column 15,
Line 22, please delete "(-pyrenedecanoyl)" and insert -- (1-pyrenedecanoyl) -- therefor Column 16,
Line 20, please delete "2.0," and insert -- 2.0$\lambda$ -- therefor.

Column 23,
Line 55, please delete "homocystiene" and insert -- homocysteine -- therefor.
Line 61, please delete "(dodecyaminocarbonylmethylene)" and insert
-- (dodecylaminocarbonylmethylene) -- therefor.

Column 24,
Line 47, please delete " a-1- " and insert -- α-1- -- therefor.

Column 29,
Line 41, please delete "each X, is" and insert -- each $X_1$ is --, and, please delete "–C(=X,)" and insert -- –C(=$X_2$) -- therefor.

UNITED STATES PATENT AND TRADEMARK OFFICE
CERTIFICATE OF CORRECTION

PATENT NO. : 6,123,923
DATED : September 26, 2000
INVENTOR(S) : Evan C. Unger and Yunqiu Wu It is certified that error appears in the above-identified patent and that said Letters Patent is hereby corrected as shown below:

Column 30,
Line 13, please delete "1 carbons" and insert -- 10 carbons -- therefor.

Column 39,
Line 12, please delete "norbomane" and insert -- norbornane -- therefor.

Column 44,
Line 29, please delete "(2→3)pGal" and insert -- (2→3)βGal -- therefor.

Column 45,
Line 39, please delete " SEQ ID NO:2" and insert -- (SEQ ID NO:2) -- therefor.
Line 40, please delete " SEQ ID NO:3" and insert -- (SEQ ID NO:3) -- therefor.

Column 48,
Line 39, please delete "x-P" and insert -- α-β -- therefor.

Column 49,
Line 33, please delete "SEQ ID NO:4" and insert -- (SEQ ID NO:4) -- therefor.
Line 34, please delete "SEQ ID NO:5" and insert -- (SEQ ID NO:5) -- therefor.
Line 35, please delete "SEQ ID NO:6" and insert -- (SEQ ID NO:6) -- therefor.
Line 46, please delete "SEQ ID NO:7" and insert -- (SEQ ID NO:7) -- therefor.

Column 49,
Line 49, please delete "SEQ ID NO:8" and insert -- (SEQ ID NO:8) -- therefor.
Line 51, please delete "SEQ ID NO:9" and insert -- (SEQ ID NO:9) -- therefor.

Column 50,
Line 2, please delete "SEQ ID NO:10" and insert -- (SEQ ID NO:10) -- therefor.
Lines 3-4, please delete "SEQ ID NO:11" and insert -- (SEQ ID NO:11) -- therefor.
Line 6, please delete " SEQ ID NO:12" and insert -- (SEQ ID NO:12) -- therefor.
Line 8, please delete " SEQ ID NO:13" and insert -- (SEQ ID NO:13) -- therefor.
Line 60, please delete "SEQ ID NO:14" and insert -- (SEQ ID NO:14) -- therefor.

Column 51,:
Line 1, please delete "SEQ ID NO:15" and insert -- (SEQ ID NO:15) -- therefor.
Line 7, please delete "SEQ ID NO:16" and insert -- (SEQ ID NO:16) -- therefor.
Line 14, please delete "SEQ ID NO:17" and insert -- (SEQ ID NO:17) -- therefor.

UNITED STATES PATENT AND TRADEMARK OFFICE
CERTIFICATE OF CORRECTION

PATENT NO.    : 6,123,923                                           Page 3 of 5
DATED         : September 26, 2000
INVENTOR(S)   : Evan C. Unger and Yunqiu Wu It is certified that error appears in the above-identified patent and that said Letters Patent is hereby corrected as shown below:

Column 52,
Line 13, please delete "SEQ ID NO:19" and insert -- (SEQ ID NO:19) -- therefor.
Lines 14-15, please delete "SEQ ID NO:20" and insert -- (SEQ ID NO:20) -- therefor.
Line 16, please delete "SEQ ID NO:21" and insert -- (SEQ ID NO:21) -- therefor.
Line 17, please delete "SEQ ID NO:22" and insert -- (SEQ ID NO:22) -- therefor.
Line 18, please delete "SEQ ID NO:23" and insert -- (SEQ ID NO:23) -- therefor.
Line 19, please delete "SEQ ID NO:24" and insert -- (SEQ ID NO:24) -- therefor.

Column 53, Table 2,
Line 63, please delete "SEQ ID NO:25" and insert -- (SEQ ID NO:25) -- therefor.
Line 64, please delete "SEQ ID NO:26" and insert -- (SEQ ID NO:26) -- therefor.
Line 65, please delete "SEQ ID NO:27" and insert -- (SEQ ID NO:27) -- therefor.
Line 66, please delete "SEQ ID NO:28" and insert -- (SEQ ID NO:28) -- therefor.

Column 54, Table 2,
Line 7, please delete "SEQ ID NO:29" and insert -- (SEQ ID NO:29) -- therefor.
Line 8, please delete "SEQ ID NO:30" and insert -- (SEQ ID NO:30) -- therefor.
Line 9, please delete "SEQ ID NO:31" and insert -- (SEQ ID NO:31) -- therefor.
Line 10, please delete "SEQ ID NO:32" and insert -- (SEQ ID NO:32) -- therefor.
Line 11, please delete "SEQ ID NO:33" and insert -- (SEQ ID NO:33) -- therefor.
Line 12, please delete "SEQ ID NO:34" and insert -- (SEQ ID NO:34) -- therefor.
Line 14, please delete "SEQ ID NO:35" and insert -- (SEQ ID NO:35) -- therefor.
Line 15, please delete "SEQ ID NO:36" and insert -- (SEQ ID NO:36) -- therefor.
Line 16, please delete "SEQ ID NO:37" and insert -- (SEQ ID NO:37) -- therefor.
Line 18, please delete "SEQ ID NO:38" and insert -- (SEQ ID NO:38) -- therefor.
Line 19, please delete "SEQ ID NO:39" and insert -- (SEQ ID NO:39) -- therefor.
Line 20, please delete "SEQ ID NO:40" and insert -- (SEQ ID NO:40) -- therefor.

Column 62,
Line 24, please delete "ω-glucopyranpsyl" and insert -- ω-glucopyranosyl -- therefor.

Column 65,
Line 19, please delete "adrenocortio-" and insert -- adrenocortico- -- therefor.

Column 67,
Line 55, please delete "interlcukin-2" and insert -- interleukin-2 --therefor.
Line 67, please delete "Sinkyla" and insert -- Sinkula -- therefor.

Column 75,
Line 55, please delete " $5.74 \times 10^{-5}$" and insert -- $5.74 \times 10^{-15}$ -- therefor.

UNITED STATES PATENT AND TRADEMARK OFFICE
CERTIFICATE OF CORRECTION

PATENT NO.    : 6,123,923
DATED         : September 26, 2000
INVENTOR(S)   : Evan C. Unger and Yunqiu Wu It is certified that error appears in the above-identified patent and that said Letters Patent is hereby corrected as shown below:

Column 79,
Line 2, please delete "R$_f$H$_2$CH$_2$ . . ." and insert -- R$_f$CH$_2$CH$_2$ . . . -- therefor.
Line 62, please delete "perparation" and insert -- preparation -- therefor.

Column 80,
Line 20, please delete "sufficeint" and insert -- sufficient -- therefor.

Column 83,
Line 42, please delete "I 0".

Column 94,
Line 1, please delete "typc" and insert -- type -- therefor.

Column 98,
Lines 16 and 19, please delete "R$_1$" and insert -- R1 -- therefor.

Column 99,
Line 1, please delete "P is" and insert -- β is -- therefor.

Column 100,
Line 62, please delete "ws" and insert -- was -- therefor.

Column 101,
Line 66, please delete "...w-carboxy-" and insert -- ... ω-carboxy- -- therefor.

Column 102,
Line 58, please delete "avaible" and insert -- available -- therefor.

Column 122,
Line 44, please delete "pheophorbide-α-" and insert -- pheophorbide-a -- therefor.

Column 123,
Line 13, please delete "claimed" and insert -- claim 19 -- therefor.

UNITED STATES PATENT AND TRADEMARK OFFICE
CERTIFICATE OF CORRECTION

PATENT NO. : 6,123,923
DATED : September 26, 2000
INVENTOR(S) : Evan C. Unger and Yunqiu Wu It is certified that error appears in the above-identified patent and that said Letters Patent is hereby corrected as shown below:

Column 124,
Line 47, please delete "pheophorbide-α-" and insert -- pheophorbide-a -- therefor.

Signed and Sealed this

Thirtieth Day of March, 2004

JON W. DUDAS
*Acting Director of the United States Patent and Trademark Office*

SEQUENCE LISTING

```
<160> NUMBER OF SEQ ID NOS: 40

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Novel
      Sequence
<220> FEATURE:
<221> NAME/KEY: UNSURE
<222> LOCATION: (4)
<223> OTHER INFORMATION: X = aze: azetidine

<400> SEQUENCE: 1

Trp Tyr Gln Xaa Tyr
 1               5

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Novel
      Sequence
<220> FEATURE:
<221> NAME/KEY: UNSURE
<222> LOCATION: (7)
<223> OTHER INFORMATION: X = aze: azetidine

<400> SEQUENCE: 2
```

```
Trp Pro Gly Trp Tyr Gln Xaa Tyr Ala Leu Pro Leu
 1               5                  10
```

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Novel
      Sequence
<220> FEATURE:
<221> NAME/KEY: UNSURE
<222> LOCATION: (9)
<223> OTHER INFORMATION: X = aze: azetidine

<400> SEQUENCE: 3

```
Phe Glu Trp Pro Gly Trp Tyr Gln Xaa Tyr Ala Leu Pro Leu
 1               5                  10
```

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 4

```
Arg Gly Asp Ser
 1
```

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 5

```
Gly Arg Gly Asp Ser Pro
 1               5
```

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 6

```
Gly Pro Arg Pro
 1
```

<210> SEQ ID NO 7
<211> LENGTH: 159
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 7

```
Asn Lys Leu Ile Val Arg Arg Gly Gln Ser Phe Tyr Val Gln Ile Asp
 1               5                  10                  15

Phe Ser Arg Pro Tyr Asp Pro Arg Arg Asp Leu Phe Arg Val Glu Tyr
```

-continued

```
                    20                  25                  30
Val Ile Gly Arg Tyr Pro Gln Glu Asn Lys Gly Thr Tyr Ile Pro Val
            35                  40                  45
Pro Ile Val Ser Glu Leu Gln Ser Gly Lys Trp Gly Ala Lys Ile Val
        50                  55                  60
Met Arg Glu Asp Arg Ser Val Arg Leu Ser Ile Gln Ser Ser Pro Lys
 65                  70                  75                  80
Cys Ile Val Gly Lys Phe Arg Met Tyr Val Ala Val Trp Thr Pro Tyr
                85                  90                  95
Gly Val Leu Arg Thr Ser Arg Asn Pro Glu Thr Asp Thr Tyr Ile Leu
            100                 105                 110
Phe Asn Pro Trp Cys Glu Asp Asp Ala Val Tyr Leu Asp Asn Glu Lys
        115                 120                 125
Glu Arg Glu Glu Tyr Val Leu Asn Asp Ile Gly Val Ile Phe Tyr Gly
    130                 135                 140
Glu Val Asn Asp Ile Lys Thr Arg Ser Trp Ser Tyr Gly Gln Phe
145                 150                 155
```

<210> SEQ ID NO 8
<211> LENGTH: 26
<212> TYPE: PRT
<213> ORGANISM: Artificial Sequence
<220> FEATURE:
<223> OTHER INFORMATION: Description of Artificial Sequence: Novel
      Sequence <400> SEQUENCE: 8

```
Asn Lys Leu Ile Val Arg Arg Gly Gln Ser Phe Tyr Val Gln Ile Asp
 1               5                  10                  15
Phe Ser Arg Pro Tyr Asp Pro Arg Arg Asp
            20                  25
```

<210> SEQ ID NO 9
<211> LENGTH: 41
<212> TYPE: PRT
<213> ORGANISM: Artificial Sequence
<220> FEATURE:
<223> OTHER INFORMATION: Description of Artificial Sequence: Novel
      Sequence <400> SEQUENCE: 9

```
Asp Asp Ala Val Tyr Leu Asp Asn Glu Lys Glu Arg Glu Glu Tyr Val
 1               5                  10                  15
Leu Asn Asp Ile Gly Val Ile Phe Tyr Gly Glu Val Asn Asp Ile Lys
            20                  25                  30
Thr Arg Ser Trp Ser Tyr Gly Gln Phe
        35                  40
```

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Novel
      Sequence <400> SEQUENCE: 10

```
Ala Arg Arg Ser Ser Pro Ser Tyr Tyr
 1               5
```

<210> SEQ ID NO 11

```
<211> LENGTH: 10
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 11

Gly Ala Gly Pro Tyr Tyr Ala Met Asp Tyr
 1               5                  10

<210> SEQ ID NO 12
<211> LENGTH: 19
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 12

Arg Ser Pro Ser Tyr Tyr Arg Tyr Asp Gly Ala Gly Pro Tyr Tyr Ala
 1               5                  10                  15

Met Asp Tyr

<210> SEQ ID NO 13
<211> LENGTH: 21
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 13

Ala Arg Arg Ser Pro Ser Tyr Tyr Arg Tyr Asp Gly Ala Gly Pro Tyr
 1               5                  10                  15

Tyr Ala Met Asp Tyr
             20

<210> SEQ ID NO 14
<211> LENGTH: 69
<212> TYPE: PRT
<213> ORGANISM: Artificial Sequence
<220> FEATURE:
<223> OTHER INFORMATION: Description of Artificial Sequence: Novel
      Sequence
<220> FEATURE:
<221> NAME/KEY: UNSURE
<222> LOCATION: (40)..(41)
<223> OTHER INFORMATION: X = any amino acid

<400> SEQUENCE: 14

Gly Glu Glu Cys Asp Cys Gly Ser Pro Glu Asn Pro Cys Cys Asp Ala
 1               5                  10                  15

Ala Thr Cys Lys Leu Arg Pro Gly Ala Gln Cys Ala Asp Gly Leu Cys
                20                  25                  30

Cys Asp Gln Cys Arg Phe Lys Xaa Xaa Arg Thr Ile Cys Arg Arg Ala
            35                  40                  45

Arg Gly Asp Asn Pro Asp Asp Arg Cys Thr Gly Gln Ser Ala Asp Cys
        50                  55                  60

Pro Arg Asn Gly Tyr
 65

<210> SEQ ID NO 15
<211> LENGTH: 73
<212> TYPE: PRT
```

<213> ORGANISM: Artificial Sequence
<220> FEATURE:
<223> OTHER INFORMATION: Description of Artificial Sequence: Novel
      Sequence

<400> SEQUENCE: 15

Glu Ala Gly Glu Asp Cys Asp Cys Gly Ser Pro Ala Asn Pro Cys Cys
 1               5                  10                  15

Asp Ala Ala Thr Cys Lys Leu Leu Pro Gly Ala Gln Cys Gly Glu Gly
            20                  25                  30

Leu Cys Cys Asp Gln Cys Ser Phe Met Lys Lys Gly Thr Ile Cys Arg
        35                  40                  45

Arg Ala Arg Gly Asp Asp Leu Asp Asp Tyr Cys Asn Gly Ile Ser Ala
    50                  55                  60

Gly Cys Pro Arg Asn Pro Leu His Ala
65                  70

<210> SEQ ID NO 16
<211> LENGTH: 68
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 16

Glu Ala Gly Glu Glu Cys Asp Cys Gly Thr Pro Glu Asn Pro Cys Cys
 1               5                  10                  15

Asp Ala Ala Thr Cys Lys Leu Arg Pro Gly Ala Gln Cys Ala Glu Gly
            20                  25                  30

Leu Cys Cys Asp Gln Cys Arg Phe Lys Gly Ala Gly Lys Ile Cys Arg
        35                  40                  45

Arg Ala Arg Gly Asp Asn Pro Asp Asp Cys Thr Gly Gln Ser Ala Asp
    50                  55                  60

Cys Pro Arg Phe
65

<210> SEQ ID NO 17
<211> LENGTH: 70
<212> TYPE: PRT
<213> ORGANISM: Artificial Sequence
<220> FEATURE:
<223> OTHER INFORMATION: Description of Artificial Sequence: Novel
      Sequence
<220> FEATURE:
<221> NAME/KEY: UNSURE
<222> LOCATION: (40)..(41)
<223> OTHER INFORMATION: X= any amino acid
<220> FEATURE:
<221> NAME/KEY: UNSURE
<222> LOCATION: (67)
<223> OTHER INFORMATION: X = any amino acid

<400> SEQUENCE: 17

Gly Gly Glu Cys Asp Cys Gly Ser Pro Glu Asn Pro Cys Cys Asp Ala
 1               5                  10                  15

Ala Thr Cys Lys Leu Arg Pro Gly Ala Gln Cys Ala Asp Gly Leu Cys
            20                  25                  30

Cys Asp Gln Cys Arg Phe Lys Xaa Xaa Arg Thr Ile Cys Arg Ile Ala
        35                  40                  45

Arg Gly Asp Phe Pro Asp Asp Arg Cys Thr Gly Leu Ser Ala Asp Cys
    50                  55                  60

```
Pro Arg Xaa Asn Asp Leu
 65                  70

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 18

Arg Glu Tyr Val Val Met Trp Lys
 1               5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 19

Cys Arg Gly Asp Met Phe Gly Cys
 1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 20

Cys Arg Gly Asp Met Leu Arg Cys
 1               5

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 21

Cys Arg Gly Asp Phe Leu Asn Cys
 1               5

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 22

Cys Asn Thr Leu Lys Gly Asp Cys
 1               5

<210> SEQ ID NO 23
<211> LENGTH: 8
<212> TYPE: PRT
<213> ORGANISM: Artificial Sequence
<220> FEATURE:
```

<223> OTHER INFORMATION: Description of Artificial Sequence: Novel
      Sequence

<400> SEQUENCE: 23

Cys Asn Trp Lys Arg Gly Asp Cys
 1               5

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence: Novel
      Sequence
<220> FEATURE:
<221> NAME/KEY: UNSURE
<222> LOCATION: (4)
<223> OTHER INFORMATION: x is penicillamine (beta,beta-dimethylcysteine)

<400> SEQUENCE: 24

Arg Gly Asp Xaa
 1

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 25

Leu Ser Pro Phe Pro Phe Asp Leu
 1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 26

Leu Ser Pro Phe Ala Phe Asp Leu
 1               5

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 27

Leu Ser Ala Phe Pro Phe Asp Leu
 1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 28

```
Leu Ser Pro Phe Pro Phe Asp Ala
 1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 29

Ser Pro Phe Pro Phe Asp Leu Leu Leu
 1               5

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 30

Leu Ser Pro Phe Pro Phe Asp Leu
 1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 31

Gln Leu Ser Pro Ser Pro Asp Leu
 1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 32

Ser Ile Ile Asn Phe Glu Lys Leu
 1               5

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 33

Leu Ser Pro Tyr Pro Phe Asp Leu
 1               5

<210> SEQ ID NO 34
<211> LENGTH: 8
<212> TYPE: PRT
<213> ORGANISM: Artificial Sequence
<220> FEATURE:
```

```
<223> OTHER INFORMATION: Description of Artificial Sequence: Novel
      Sequence

<400> SEQUENCE: 34

Ala Ser Pro Phe Pro Phe Asp Leu
  1               5

<210> SEQ ID NO 35
<211> LENGTH: 11
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 35

Ser Ser Phe Gly Ala Phe Gly Ile Phe Pro Lys
  1               5                  10

<210> SEQ ID NO 36
<211> LENGTH: 16
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 36

Ala Asn Glu Arg Ala Asp Leu Ile Ala Tyr Leu Lys Gln Ala Thr Lys
  1               5                  10                  15

<210> SEQ ID NO 37
<211> LENGTH: 16
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 37

Ala Asn Glu Arg Ala Asp Leu Ile Ala Tyr Leu Lys Gln Ala Thr Lys
  1               5                  10                  15

<210> SEQ ID NO 38
<211> LENGTH: 16
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 38

Ala Asn Glu Arg Ala Asp Leu Ile Ala Tyr Leu Lys Gln Ala Thr Lys
  1               5                  10                  15

<210> SEQ ID NO 39
<211> LENGTH: 17
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 39

Ala Asn Glu Arg Ala Asp Leu Ile Ala Tyr Leu Lys Gln Ala Thr Ala
  1               5                  10                  15
Lys
```

-continued

```
<210> SEQ ID NO 40
<211> LENGTH: 16
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 40

Ala Asn Glu Arg Ala Asp Leu Ile Ala Tyr Leu Lys Gln Ala Ser Lys
 1               5                  10                  15
```